(12) United States Patent
Sanders

(10) Patent No.: US 8,981,057 B2
(45) Date of Patent: Mar. 17, 2015

(54) B-CELL STIMULATING FUSION PROTEINS OF AN ANTIGEN WITH BAFF OR APRIL

(75) Inventor: Rogier Willem Sanders, Amsterdam (NL)

(73) Assignee: Academisch Medisch Centrum Bij De Universiteit Van Amsterdam, Amsterdamn (NL)

( * ) Notice: Subject to any disclaimer, the term of this patent is extended or adjusted under 35 U.S.C. 154(b) by 40 days.

(21) Appl. No.: 13/582,364

(22) PCT Filed: Mar. 7, 2011

(86) PCT No.: PCT/NL2011/050159
§ 371 (c)(1),
(2), (4) Date: Dec. 21, 2012

(87) PCT Pub. No.: WO2011/108937
PCT Pub. Date: Sep. 9, 2011

(65) Prior Publication Data
US 2013/0139274 A1 May 30, 2013

(30) Foreign Application Priority Data
Mar. 5, 2010 (EP) .................................. 10155702

(51) Int. Cl.
| | | |
|---|---|---|
| *C07K 14/54* | (2006.01) | |
| *C12N 15/62* | (2006.01) | |
| *A61K 38/17* | (2006.01) | |
| *A61K 38/19* | (2006.01) | |
| *A61K 39/00* | (2006.01) | |
| *A61K 39/12* | (2006.01) | |
| *A61K 39/21* | (2006.01) | |
| *C07K 14/47* | (2006.01) | |
| *C07K 14/705* | (2006.01) | |
| *C07K 14/005* | (2006.01) | |
| *C07K 14/11* | (2006.01) | |
| *C07K 14/16* | (2006.01) | |
| *C07K 14/435* | (2006.01) | |
| *C07K 14/535* | (2006.01) | |

(52) U.S. Cl.
CPC ............... *C07K 14/54* (2013.01); *A61K 38/191* (2013.01); *A61K 39/00* (2013.01); *A61K 39/12* (2013.01); *A61K 39/21* (2013.01); *C07K 14/4705* (2013.01); *C07K 14/70575* (2013.01); *C12N 15/62* (2013.01); *C07K 14/005* (2013.01); *C07K 14/11* (2013.01); *C07K 14/16* (2013.01); *C07K 14/435* (2013.01); *C07K 14/535* (2013.01); *A61K 2039/55516* (2013.01); *C07K 2319/735* (2013.01); *C12N 2740/16034* (2013.01); *C12N 2740/16022* (2013.01); *C12N 2740/16122* (2013.01); *C12N 2760/16122* (2013.01); *C12N 2760/16134* (2013.01)
USPC .................... 530/350; 536/23.4; 514/21.2

(58) Field of Classification Search
CPC ........... C07K 14/70575; A61K 38/191; A61K 2039/55516; A61K 39/12
See application file for complete search history.

(56) References Cited

U.S. PATENT DOCUMENTS

| | | | | |
|---|---|---|---|---|
| 6,248,329 B1 * | 6/2001 | Chandrashekar et al. | . | 424/191.1 |
| 2004/0013674 A1 * | 1/2004 | Ambrose et al. | ........... | 424/178.1 |
| 2005/0186637 A1 * | 8/2005 | Yu et al. | ......................... | 435/7.1 |
| 2006/0003407 A1 * | 1/2006 | Rennert et al. | ............... | 435/69.1 |
| 2006/0084148 A1 * | 4/2006 | Tschopp | ...................... | 435/69.3 |
| 2009/0291080 A1 * | 11/2009 | Gottenberg et al. | ....... | 424/134.1 |
| 2009/0297504 A1 * | 12/2009 | Kelley et al. | ............... | 424/130.1 |

FOREIGN PATENT DOCUMENTS

| | | |
|---|---|---|
| WO | 2007030803 | 3/2007 |
| WO | 2007067681 | 6/2007 |

OTHER PUBLICATIONS

Marsters et al. (Current Biology 2000, 10: 785-788).*
Pradet-Balade et al. (EMBO J. 2002, 21: 5711-5720).*
Rickert et al., Immunol Rev. 2011, 244: 115-133.*
Rentero et al., Chimia 2011, 65: 843-845.*
Colman P.M., Research in Immunology 1994, 145: 33-36.*
Day et al. (Biochemistry 2005, 44: 1919-1931).*
Lederman et al., Molecular Immunology 1991, 28: 1171-1181.*
Li et al., PNAS 1990, 77: 3211-3214.*
Ellis, R.W. ("Vaccines" Plotkin, et al. (eds), W. B. Saunders (publisher) 1988, Chapter 29. p. 568-575.*
Duttagupta et al. (Crit. Rev. Immunol., 2009, 29: 469-486).*
Singh et al., Nature Biotechnology, 1999, 17: 1075-1081.*
Euler et al., The Journal of Infectious Diseases 2010; 201: 1045-1053.*
Ryu et al., Mol. Cells 2012; 34: 231-237.*
Verkoczy et al. (Current Opinion in Immunology 2011, 23:383-390).*
Yu et al. (Protein Expression and Purification 2009, 68: 49-53).*
International Search Report for PCT/NL2011/050159 Mailed Aug. 25, 2011.

* cited by examiner

*Primary Examiner* — Ilia Ouspenski
(74) *Attorney, Agent, or Firm* — Miles & Stockbridge PC

(57) ABSTRACT

The invention relates to the fields of molecular biology, medicine, virology and vaccine development. Because the different forms of the presently available vaccines all have their specific drawbacks, there is a need for alternative vaccine strategies. The current invention provides means and methods for such alternative vaccine strategies.

11 Claims, 63 Drawing Sheets

| Antigen | Animal | Virus | | |
|---|---|---|---|---|
| | | MN | SF162.LS | BaL.26 |
| Env | A289 | 2218 | 2203 | 177 |
| Env | A290 | 111 | 207 | <20 |
| Env | A323 | 519 | 54 | <20 |
| Env | A292 | 65 | 33 | <20 |
| Env-APRIL | B293 | 421 | 2003 | 117 |
| Env-APRIL | B294 | 112 | 176 | 57 |
| Env-APRIL | B295 | 1647 | 2170 | 164 |
| Env-APRIL | B296 | 4093 | 3105 | 191 |
| Env-BAFF | C297 | 6764 | 589 | 347 |
| Env-BAFF | C299 | 241 | <20 | <20 |
| Env-BAFF | C300 | 53 | 817 | <20 |
| Env-CD40L | D301 | 68 | 2056 | 170 |
| Env-CD40L | D302 | 122 | 281 | 23 |
| Env-CD40L | D303 | <20 | 76 | <20 |
| Env-CD40L | D304 | 1438 | 2000 | 109 |
| gp120 protein | H317 | 29 | <20 | <20 |
| gp120 protein | H318 | <20 | 66 | <20 |
| gp120 protein | H319 | 64 | 250 | <20 |
| gp120 protein | H320 | 23 | <20 | <20 |

ALIGNMENT MOUSE AND HUMAN SURFACTANT PROTEIN A

```
mSP-A   MSLGSLAFTL FLTVAGIRC NGTEVCAGSP GIPGTPGSHG GIPGTPGSHG LPGRDGRDGI KGDPGPPGPM GPPGGMPGLP GRDGLPGAPG APGEHGDKGE PGERGLPGFP
hSP-A1  MWLCPLALNL ILMAASGAVC EVKDVCVGSP GIPGTPSHG  GIPGTPSHG  LPGRDGRDGL KGDPGPPGPM KGDPGPPGPM GPPGEMPGPP GNEHLPGAPG IPGECGEKGE PGERGPPGLP
hSP-A2  MWLCPLALTL ILMAASGAAC EVKDVCVGSP GIPGTPSHG  GIPGTPSHG  LPGRDRDGV  KGDPGPPGPM GPPGETPGPP GNNGLPGAPG VPGERGEKGE AGERGPPGLP mSP-A   AVLDEELQTA SYETEHQILQ TMGVLSLAGS MLSVGEKVFS TKGGSVNFDT IREMCTRAGG HIAAPRNPEE NEAIASITKK YNTYPYLGVI EGQTPGDFHY
hSP-A1  AHLDEELQAT LHDFRHQILQ TRGALSLQGS INTVGEKVFS SNGQSITFDA IQEACARAGG RIAVPRNPEE NEAIASFVKK YNTYAYVGLT EGPSPGDFRY
hSP-A2  AHLDEELQAT LHDFRHQILQ TRGALSLQGS INTVGEKVFS SNGQSITFDA IQEACARAGG RIAVPRNPEE NEAIASFVKK YNTYAYVGLT EGPSPGDFRY mSP-A   LDGASVNYTN WYPGEPRGRG REKCVEMYTD GQWNDRACLQ YRLAICEF
hSP-A1  SDGTPVNYTN WYRGEPAGRG KEQCVEMYTD GQWNDRACLY SRLTI
hSP-A2  SDGTPVNYTN WYRGEPAGRG KEQCVEMYTD GQWNDRACLY SRLTICEF
```

JT-FL SOSIP.R6-mSPA-CD40L-H9

```
MDAMKRGLCC VLLLCGAVFV SPSQEIHARF RRGAAVEKLW VTVYYGVPVW KEATTTLFCA SDAKAYDTEV HNVWATHACV
PTDPNPQEVV LENVTEHFNM WKNNMVEQMQ EDIISLWDQS LKPCVKLTPL CVTLNCKDVN ATNTNDSEG TMERGEIKNC
SFNITTSIRD EVQKEYALFY KLDVVPIDNN NTSYRLISCD TSVITQACPK ISFEPIPIHY CAPAGFAILK CNDKTFNGKG
PCKNVSTVQC THGIRPVVST QLLLNGSLAE EEVVIRSDNF TNNAKTIIVQ LKESVEINCT RPNNNTRKSI HIGPGRAFYT
TGEIIGDIRQ AKCNISRAKW NQTLKQIVIK LREQFGNKTI VFMHSSGGDP EIVMHSFNCG GEFFYCNSTQ LFNSTWNNI
EGSNNTEGNT ITLPCRIKQI INMWQEVGKA MYAPPIRGQI RCSSNITGLL LTRDGGINEN GTEIFRPGGG DMRDNWRSEL
YKYKVKIEP LGVAPTKCKR RVVQRERRR AVGIGAVFLG FLGAAGSTMG AASMTLTVQA RLLSGIVQQ QNNLLRAPEA
QQRMLQLTVW GIKQLQARVL AVERYLGDQQ LLGIWGCSGK LICCTAVPWN ASWSNKSLIDK IWNNMTWMEW EREIDNYTSE
IYTLIEESQN QQEKNEQELL ELDKWASLWN WFDITNWLWI LGGGCTGGGG GEPGERGLPG FPAILDEELQ TALYEIKHQI LQTMGVLSLQ
GIKGDPGPPG PMGPPGEMPG LPGRDGLPGA PGAPGEHGDK GEFGGGGRSG VHLGVFELQ AGASVFNVT EASQVIHRVG PSSQRPFIVG
GGRGCGDPQI AAHVSEANS NAASVLQWAK KGYTWKSNL VMLENGKQLT VKREGLYVYV TQVTFCSNRE FSSFGLLKLH HHHHH
LWLRPSSGSE RILKAANTH SSSQLCEQQS VHLGVFELQ AGASVFNVT EASQVIHRVG FSSFGLLKLH HHHHH
```

Figure 28

Improvement gp140-mSPA-mCD40L octadecamer (bouquet)
TEMP  DITKWLWLLSGGTGGGTG----------NGTEVCAGSPGIP----------GTPGNHGLPGRDGRDGIKGPPGPPGPMGPPGGMPGLPGRD
DWIWY DITK--------GGGTGGGTG----------NGTEVCAGSPGIP----------GTPGNHGLPGRDGRDGIKGDPGPPGPMGPPGGMPGLPGRD
1.    DITK--------GGGTGGGTG----------NGTEVCAGSPGIP----------GTPGNHGLPGRDGRDGIKGDPGPPGPMGPPGGMPGLPGRD
1A.   DITK--------GGGTGGGTG----------KCNGTEVCAGSPGIP--------GTPGNHGLPGRDGRDGIKGDPGPPGPMGPPGGMPGLPGRD
1B.   DITK--------GGGTGGGTG----------IKCNGTEVCAGSPGIP--------GTPGNHGLPGRDGRDGIKGDPGPPGPMGPPGGMPGLPGRD
2.    DITK--------GGGTGGGTG----------EVRDVCVGSPGIP----------GTPGNHGLPGRDGRDGIKGDPGPPGPMGPPGGMPGLPGRD
2A.   DITK--------GGGTGGGTG----------VCEVRDVCVGSPGIP--------GTPGNHGLPGRDGRDGIKGDPGPPGPMGPPGGMPGLPGRD
2B.   DITK--------GGGTGGGTG----------AVCEVRDVCVGSPGIP--------GTPGNHGLPGRDGRDGIKGDPGPPGPMGPPGGMPGLPGRD
3.    DITK--------GGGTGGGTGCGGTCSGSQTCEDTLKTCSVIACGSPGIP-----GTPGNHGLPGRDGRDGIKGDPGPPGPMGPPGGMPGLPGRD
4.    DITK--------GGGTGGGTG----------NGTEVCAGSPGIP----------GTPGNHGLPGRDGRBGIKGDPGPPGPMGPPGFMPGLPGRD
5.    DITK--------GGGTGGGTG----------NGTEVCAGSPGIPGRDGRBGPKGTPGNHGLPGRDGRBGIKGDPGPPGPMGPPGGMPGLPGRD Make dWIWI (dWIWY) variant by qc (primers present) or cloning Asp718/agel- MOUSE SURFACTANT PROTEIN A
MSLGSLAFTL FLTVAGIKC NGTEVCAGSP GIPGTPGNHG LPGRDGRDGI KGDPGPPGPM GPPGGMPGLP GRDGLPGAPG APGEKGDKGE PGERGLPGFP
AYLDEELQTA SYETKKQILQ TWGVLSLQGS MLSVGDKVFS TNGQSVNFDT IREMCTRAGG HIAAPRNPEE NEAIASITKK YNTYPYLGVI EQTPGDFFHY
LDGASVNYTN WYPGEPRGRG KEKCVEMYTD GKWNDKGCLQ YRLAICEF MOUSE ADIPONECTIN
VLLQALLFL LILPSHAEDD VTTTEELAPA LVPPPKGTCA GWMAGIPGHP GHNGTPGRDG RGGTPGERGE KGDAGLLGPK GETGDVGMTG AEGPRGFPGT
PGRKGEPGEA AYVYRSAFSV GLETRVTVPN VPIRFTKIFY MQQNHYDGST GKFYCNIPGL YYFSYHITVY MKDVKVSLFK KDKAVLFTYD QYQENVDQA
SGSVLHLEV GDQWLQVYG DGDRNGLYAD NVNDSTFTGF LLYHDTN MOUSE C1Q CHAIN A
METSGGWLVA CVLTMTLVWT VAEDVCRAPN GRDGAPGNPG RPGRPGLKGE RGEPGAAGIR TGIRGFKGDP GESGPPGKPG NVGLPGPSGP LGDSGPQGLA
GVKGNPGNIR DQPRPAFSAI RQNPWTLGNV VIFDKVLTNQ ESPYQNHTGR FICAVPGFYY FNFQVISRWD LCLFIKSSSG GQPRDSLSFS NTNNKGLFQV
LAGGTVLGLR RGDEVWIEKD PAKGRIYQGI EADSIFSGFL IPPSA MOUSE C1Q CHAIN B
MKTGWGEWT HLLLLLGFL HVSWAQSSCT GPPGLPGIPG VPGVPGSDGQ PGTPGIKGEK GLPGLAGDLG EPGEKGBPGI PGTPGKVGPK GPVGPKGTPG
PSGPRGPKGD SGDYCATGKV AFSALRTING PLRPNQVIRF EKVITNANEN YEPRNGKFTC KVPGLYFFTY HASSRGVLCV NLVRGRDRDS MGRVVTFCDY
AQNIFQVTTG GVVLKLEQEE VVHLQATDKN SLLGIEGANS IFTGFLLFPD MDA MOUSE C1Q CHAIN C
MNVGPSCQFG CGLCLLLFL LALPLRSQAS AGCYGIPGMP GMPGAPGKDG HDGLQGPKGE PGIPAVPGTQ GPKGQKGEPG MPGHRGKNGP RGTSGLPGDP
GRPPGEPG VEGRYKQHQ SVFTVTRQTT QYPEAVALVR FNSVVTNPQG HVNPSTGKFT CEVPGLYYFV YTSHTANLC VHLNLNLARV ASFCDHMPNS
KQYSSGGALL RLGRGDEVWL SVNDYNGMWL IEGSNSVFSG FLLFPD

Figure 32

MOUSE MANNOSE-BINDING LECTIN (PROTEIN C)
MSIFTSFLLL CVVTVYAET LTEGVQNSCP VVTCSSPGLN GFPGKDGRDG AKGEKGEPGQ GLRGLQGPPG KVGPTGPPGN PGLKGAVGPK GDRGDRAEFD
TSEIDSEIAA LRSELRALRN WVLFSLSERV GKYFVSSVK RMSLDRVKAL CSETQGSVAT PRNABENSAI QKVAKDIAYL GITDVRVBGS FEDLTGNRVR
YTNWMDGEPN NTGDGEDCVV ILGNGKWNDV PCSDSFLAIC EFSD

MOUSE MANNOSE-BINDING LECTIN (PROTEIN A)
MLLPLLPVL LCVVSVSSSG SQTCEDTLKT CSVIACGRDG RDGPRGDKGE PGQRLRGLQG PPEKLGPPGS VGSPGSPGPK GQKGDHGDNR AIEEKLANME
AEIRILKSKL QLTNKLHAFS MGRKSGKRLF VTNHERMPFS KVKSLCTELQ GTVAIPRNAE ENKAIQEVAT GIAFLGITDE ATEGQFMVYT GGRLTYSNWK
KDEPNNHGSG EDCVTIIDNG LWNDISCQAS FKAVCEFPA

COLLECTIN-L1 [MUS MUSCULUS]
MNGFRVLLRS NLSMLLLAI LHFQSLGLDV DSREAAEVCA THTISPGPKG DDGERGDTGE EGKDGNVGRQ GPRGVKGELG DMGAQGNLGK SGPLGKKGDK
GERGLLGIPG EKGRAGTICD CGRYRKVVGQ LDISVARLKT SMKFIRAVIA GIRETGERFY YTVQEERNYR ESLTHCRIRG GMLAMPKDEV VNTLIADYVA
KSGFFRVFIG VNDLEREGQY VFTDNTPLQN YSNWKEEPS DPSGHEDCVE MLSSGRWNDT ECHLIMYFYC EPVKKK

HUMAN SURFACTANT PROTEIN A1
MWLCPLALNL ILMAASGAVC EVKDVCVGSP GIPGTPGSHG GLPGRDGRDGL LPGRDGRDGL KGDPGPPGPM GPPGEMPCPP GNRGLPGAPG IPGECGEKGE PGERGPPGLP
AHLDEELQAT LHDFRHQILQ TRGALSLQGS IMTVGEKVFS SNGQSITFDA IQEACARAGG RIAVPRNPEE NEAIASFVRK YNTYAYVGLT EGPSPGDFRY
SDGTPVNYTN WYRGEPAGRG KEQCVENYTD GQWNDRNCLY SRLTI

HUMAN SURFACTANT PROTEIN A2
MWLCPLALTL ILMAASGAAC EVKDVCVGSP GIPGTPGSHG GLPGREGRDGV KGDPGPPGPH KGDPGPPGPH IQEACARAGG RIAVPRNPEE NEAIASFVRK YNTYAYVGLT EGPSPGDFRY
SDGTPVNYTN WYRGEPAGRG KEQCVENYTD GQWNDRNCLY SRLTICEF

Figure 32, cont'd.

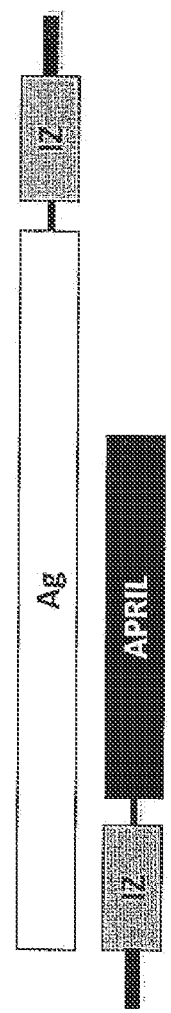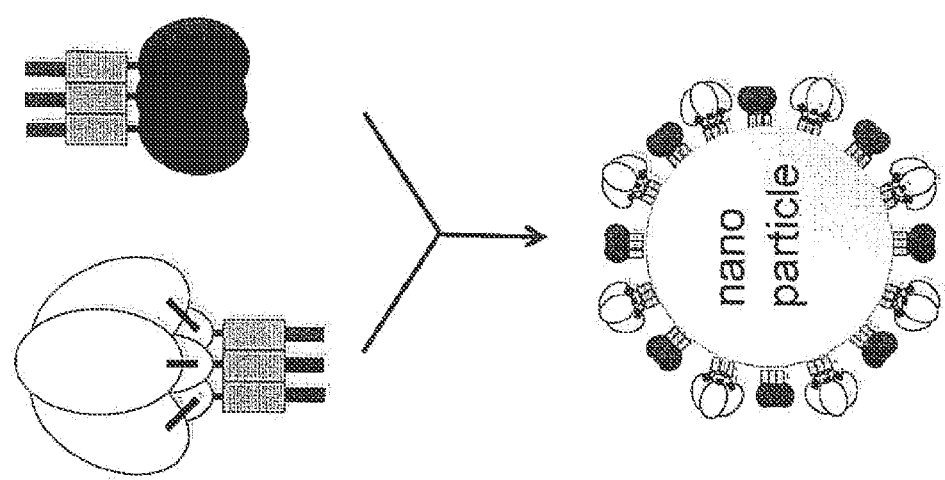
Figure 33

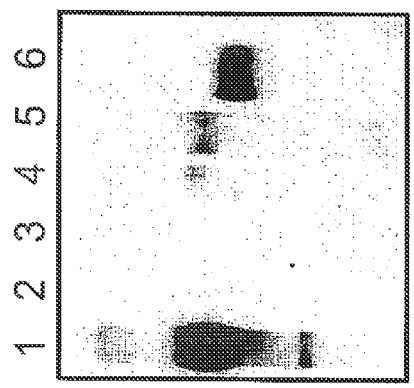

1) Env Beads 15ul (van 30 ul eluate, van 12 ml culture sup)
2) Supernatant Env beads after DNA treatment
3) Supernatant Env beads
4) Medium after Env-bead extraction
5) Medium Env
6) gp120 5 ng/ml Experimental procedure:
Beads were incubated for 2.5 hrs with Env medium (5) at 4 degrees
Env medium after bead extraction was collected (4)
Beads fraction (1) was washed and wash supernatant was collected (3)
Additional bead fraction was treated for DNA restriction
Beads were collected and supernatant was collected (2)

Figure 34

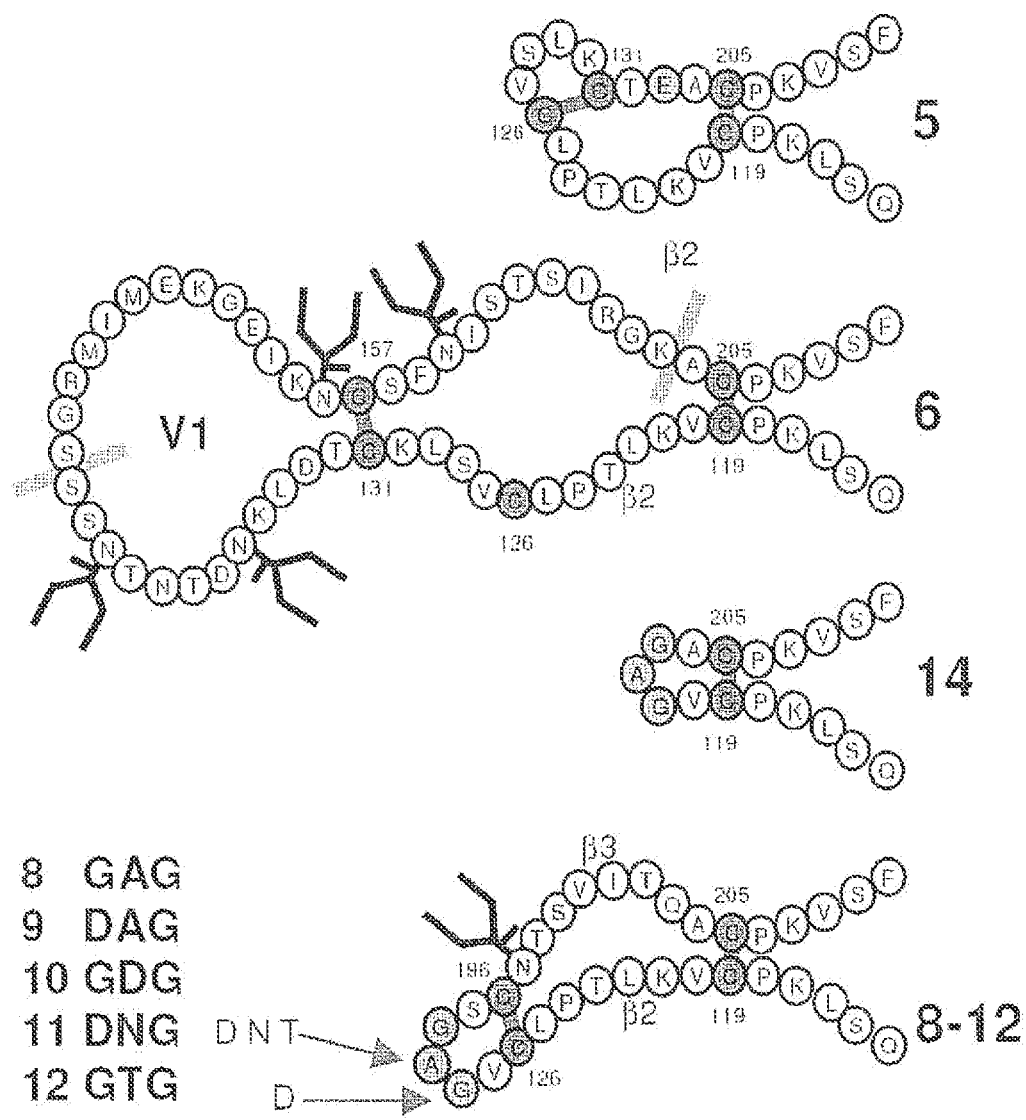
Fig. 39A, contd.

Fig. 39B
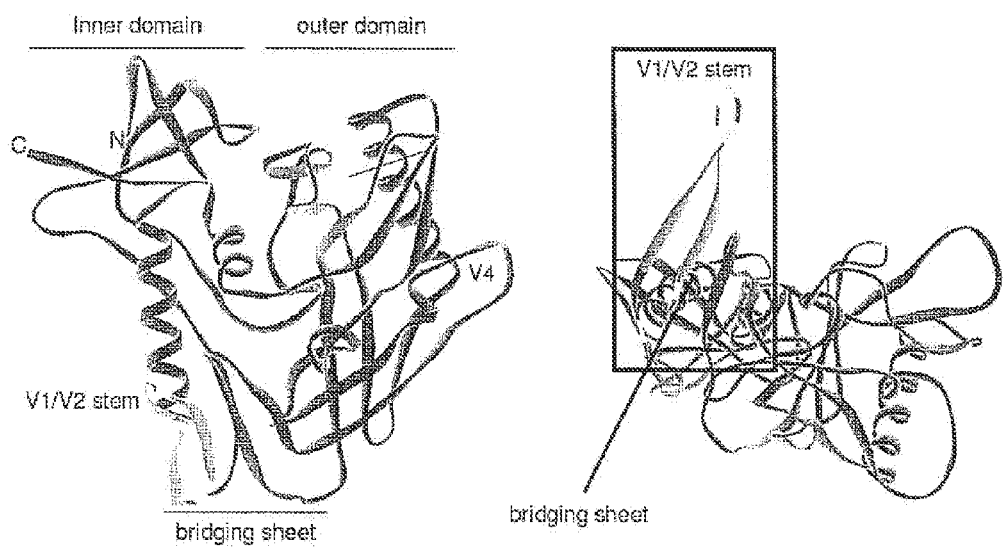
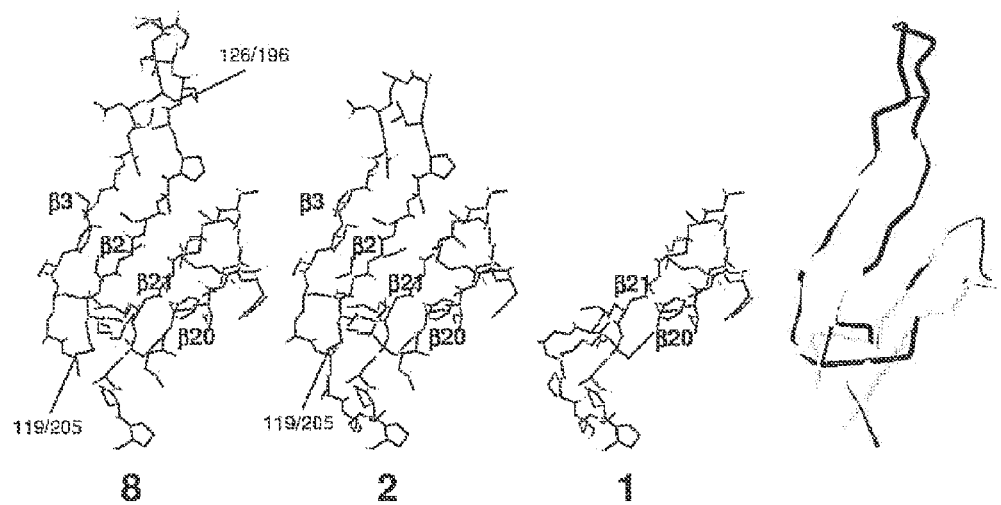

Fig. 39D
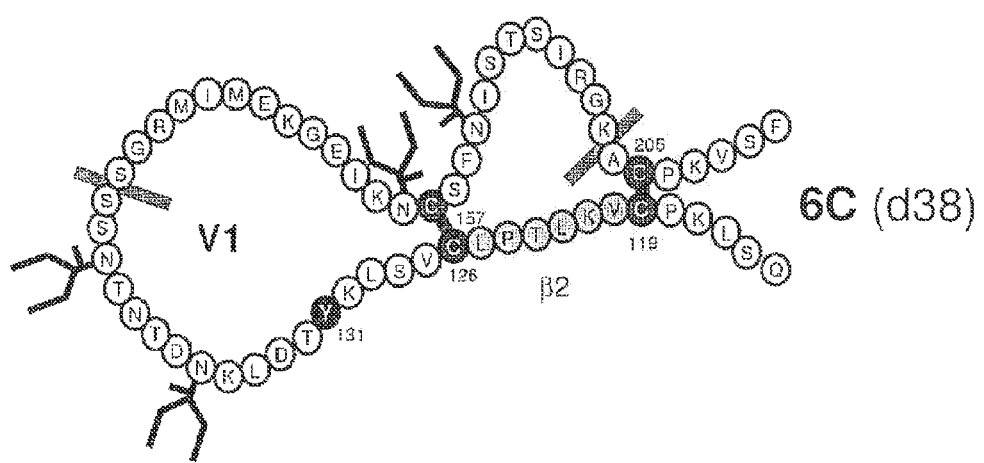
6C (d38)
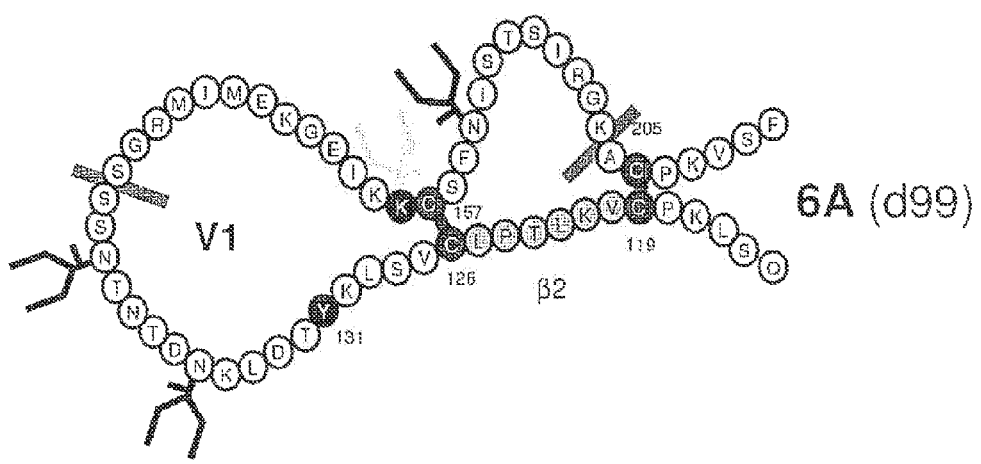
6A (d99)

```
        10         20         30         40         50         60         70
....|....|....|....|....|....|....|....|....|....|....|....|....|....|....|....
MRVKEK~~YQHLWRWGWRWG~~TMLLGMLMICSATEKLWVTVYYGVPVWKEATTTLFCASDAKAYDTEVHNVWATHACV   HXB2
..........K........I............................................              LAI
.DAMKRGLCCV.LLC.AVFVSPSQEIHARFRRGA.V.............................              JRFL
~~~~~~~~~~~~~~~~~~~~~~~~~~~~~~~~~GARNSN..................D.E.......K..K....    KNH1144

80         90        100        110        120        130        140        150
....|....|....|....|....|....|....|....|....|....|....|....|....|....|....|....|....|
PTDPNPQEVVLVNVTENFNMWKNDMVEQMHEDIISLWDQSLKPCVKLTPLCVSLKCTDLKNDTNTNSS~~~SGRMIME      HXB2
........E.......H......N........Q...............T.N.K.VNATNT..D.~~~~~~EGT..        LAI
.......IP.E......E......K.......T........Q...........A....T.N...VT.V.DVSGTRGN~~ITI.KEM  JRFL
                                                                G.A...NTNSS..E.M..   KNH1144

160        170        180        190        200        210        220
....|....|....|....|....|....|....|....|....|....|....|....|....|....|....|
KGEIKNCSFNISTSIRGKVQKEYAFFYKLDIIPIDNDTTS~~~~YKLTSCNTSVITQACPKVSFEPIPIHYCAPAGFA      HXB2
R................T................................T...........                   LAI
.......T...DE......L....VV....NN..~~~~R.I..D.....I.......                         JRFL
E......MA.E..D.K..V.SL..R..VV..NQGNS.SKNSSE.R.I......A.....                        KNH1144

230        240        250        260        270        280        290        300
....|....|....|....|....|....|....|....|....|....|....|....|....|....|....|....|....|
ILKCNNKTFNGTIGPCTNVSTVQCTHGIRPVVSTQLLLNGSLAEEEVVIRSVNFTDNAKTIIVQLNTSVEINCTRPNNNTR    HXB2
.....D.......K.....K........................A............Q......                  LAI
......K........K..........................D..N.........KE...........              JRFL
....RD.E......E.K...................K..K..TE.I.N......VEP.R.S......                KNH1144
```

Fig. 40

```
          310       320       330       340       350       360       370       380
          ....|....|....|....|....|....|....|....|....|....|....|....|....|....|....|....|
          KRIRIQRGPGRAFVTIG-KIGNMRQAHCNISRAKWNNTLKQIASKLREQFGNNKTIIFKQSSGGDPEIVTHSFNCGGEFF   HXB2
          .S..............................................A.............................   LAI
          .S.H..~......Y.T.EI.DI..........D......VT.....E.~...V.NH..............M........   JRFL
          ESV.~....Q..FAT.DI..DI......V..SQ..K..Q.V.EQ...H.K.~....NS..........L.T........   KNH1144

390       400       410       420       430       440       450       460
          ....|....|....|....|....|....|....|....|....|....|....|....|....|....|....|....|
          YCNSTQLFNSTWFNSTWSTEGSNNTEGSDTITLPCRIKQIINMWQKVGKAMYAPPISGQIRCSSNITGLLLTRDGGNSNN   HXB2
          .................................F.....E..................................N..   LAI
          ......N.~~N......~.........N...............E......R...........INE.............   JRFL
          ..TSG.....NT~~.NS..S...TNG......Q........RT.Q.I.....Q.V...E.....EEK............   KNH1144

470       480       490       500       510
          ....|....|....|....|....|....|....|....|....|....|..
          ES~EIFRPGGGDMRDNWRSELYKYKVVKIEPLGVAPTKAKRRVVQREKR     HXB2
          .G..................................................   LAI
          GT-..................................................   JRFL
          STN..........................................R.R....G....   KNH1144
```

```
LOCUS       1029127_mouse_interleukin_4_pMA-T  2781 bp DNA circular
CDS         complement(1793..2653)
            /vntifkey="4"
            /label="AmpR"
rep_origin  complement(978..1645)
            /vntifkey="33"
            /label="ColE1\origin"
CDS         380..798
            /label="mouse_interleukin_4"
ORIGIN
CTAAATTGTAAGCGTTAATATTTTGTTAAAATTCGCGTTAAATTTTGTTAAATCAGCTCATTTTTTAACCAATAGGCCGAAATCGGCAAAATCCCTTATAAATCAAAAGAATAGACCGA
GATAGGGTTGAGTGGCCGCTACAGGGCGCTCCCATTCGCCATTCAGGCTGCGCAACTGTTGGGAAGGGCGTTTCGGTGCGGGCCTCTTCGCTATTACGCCAGCTGGCGAAAGGGGGATCT
GCTCCAAGCGATTAAGTTGGGTAACGCCAGGGTTTTCCCAGTCACGACGTTGTAAAACGACGGCCAGTGAGCGCGCACTGATAGGCGCACTAGCGAGTCACTATAGGGAGACCCGGTCA
AGCGCACGTGCTTGTCCAGTGACTACCAAGCTTCACCTCTCTGTCTGGAGATCTGGGCACCAACCCATTCCGGGCAAATCATCGGCATTCTGAACAAGTGCACTGGCGAGGG
AACACCCTGTACTGAAATGGACGTCCGAATGCTCCTGCACCGAAAAACACAACCGAGAGGAGCCTTTGGAGGTCTGTGTAGAGCCTCAAAACTGCTCAGAATCCTCTACCTGAACACGGCAA
ACCCATGTCTGAAATAAAACTCCTCTGCTCATGGAACTCGGGACTACCCGGAACTGCCTCTTGTAACACTTCGAGCTCTGGAGCACAAGTCGAGCTCAATAGTAGCGATCGGTCAAGCCTCACTGCCT
CAAGGACTTTCTGGAATCCTCGAAATCATCATGGCAGCTGCATTAACATGGTCATAGCTTTCCTTTGGCGTATCGGCGCTCTCCGCTCACGTTGACACCATCGAGGATCTGTCACCTCACT
GCTTTCCAGTGCGGGAAACCTGGTTAATGGGCCAAAAGGCCCCAGGAACCGTAAAGAGGCCAGGATACCGAGAATACCGTGAGCATCACAAAATCAGCT
CAAGTCAGAGGTGGCAAACCTGACAGGTAAGTAGCCGGGTAGGTAGTCGCTAAAGCATACGGAACATGCTGTGCTGCCGCTGCAGGTGCTGAACCGACCGGATCACATACCTGTCCGCCTTC
TCCTTCGGAAGCGTGGCGCTTTCTCATAGCTCACGGCCGGTTATCTCAGTTCGGCTGCACACCTCGTGAAGGCTGGTGTGCACGAACCCCGTTCAGCCCGACCGCTGCG
CCTATCCGGTAACTATCGTCTTGAGTCCAACCCGGTAAGACACGACTTATCGCCACTGGCAGCAGCCACTGGTAACAGGATTAGCAGAGCGAGGTATGTAGGCGGTGCTACAGAGTTCT
TGAAGTGGTGGCCTAACTACGGCTACACTAGAAGAACAGTATTTGGTATCTGCGCTCTGCTGAAGCCAGTTACCTTCGGAAAAAGAGTTGGTAGCTCTTGATCTTTTCTACGGGGTCTGACGCTCAGTGGAACGAAAACTCACGTT
AAGGGATTTTGGTCATGAGATTATCAAAAGGATCTTCACCTAGATCCTTTTAAATTAAAAATGAAGTTTAAATCAATCTAAAGTATATATGAGTAAACTTGGTCTGACAGTTACCAAT
GCTTAATCAGTGAGGCACCTATCTCAGCGATCTGTCTATTTCGTTCATCCATAGTTGCCTGACTCCCCGTCGTGTAGATAACTACGATACGGGAGGGCTTACCATCTGGCCCCAGTGCTG
CAATGATACCGCGAGACCCACGCTCACCGGCTCCAGATTTATCAGCAATAAACCAGCCAGCCGGAAGGGCCGAGCGCAGAAGTGGTCCTGCAACTTTATCCGCCTCCATCCAGTCTATTA
ATTGTTGCCGGGAAGCTAGAGTAAGTAGTTCGCCAGTTAATAGTTTGCGCAACGTTGTTGCCATTGCTACAGGCATCGTGGTGTCACGCTCGTCGTTTGGTATGGCTTCATTCAGCTCCG
GTTCCCAACGATCAAGGCGAGTTACATGATCCCCCATGTTGTGCAAAAAAGCGGTTAGCTCCTTCGGTCCTCCGATCGTTGTCAGAAGTAAGTTGGCCGCAGTGTTATCACTCATGGTTA
TGGCAGCACTGCATAATTCTCTTACTGTCATGCCATCCGTAAGATGCTTTTCTGTGACTGGTGAGTACTCAACCAAGTCATTCTGAGAATAGTGTATGCGGCGACCGAGTTGCTCTTGCC
CGGCGTCAATACGGGATAATACCGCGCCACATAGCAGAACTTTAAAAGTGCTCATCATTGGAAAACGTTCTTCGGGGCGAAAACTCTCAAGGATCTTACCGCTGTTGAGATCCAGTTCGA
TGTAACCCACTCGTGCACCCAACTGATCTTCAGCATCTTTTACTTTCACCAGCGTTTCTGGGTGAGCAAAAACAGGAAGGCAAAATGCCGCAAAAAAGGGAATAAGGGCGACACGGAAAT
GTTGAATACTCATACTCTTCCTTTTTCAATATTATTGAAGCATTTATCAGGGTTATTGTCTCATGAGCGGATACATATTTGAATGTATTTAGAAAAATAAACAAATAGGGGTTCCGCGCA
CATTTCCCCGAAAAGTGCCAC//
```

Figure 48

```
LOCUS    0909560_IL-4_Human_pMA  2810 bp DNA  circular                        
        /label="AmpR"                    /vntifkey="4"
rep_origin  complement(1087..1674)
        /vntifkey="33"                   /label="ColE1\origin"
                                         CDS  complement(378..829)
        /label="IL-4_Human"
ORIGIN
CTAAATTGTAAGCGTTAATATTTGTTAAAATTCGCGTTAAATTTTTGTTAAATCAGCTCATTTTTTAACCAATAGGCCGAAATCGGCAAAATCCCTTATAAATCAAAAGAATAGACCGA
GATAGGGTTGAGTGTTGCCGGTCACGCTGCGCGTAACCACCACCACCCGCCGCGCTTAATGCGCCGCTACAGGGCGCGTCCCATTCGCCATTCAGGCTGCGCAACTGTTGGGAAGGGCGATCGGTGCGGGCCTCT
TCGGCAAGCGCGATTAAGTTGGGTAACGCCAGGGTTTTCCCAGTCACGACGTTGTAAAACGACGGCCAGTGAGCGCGACGTAATACGACTCACTATAGGGCGAATTGGGCCCGACGTCG
CATGCTCCCGGCCGCCATGCGGCCGCGGGAATTCGATTTGACTGTATATTTGAGACGATTTCCCCTCCATAATGTTTCAGCCGTCGAGGAACTGCTGTCATGGAACTGCTGGGCCTGGAGGC
AGGCCTAGGCGCGCCATGAGCTCCGACGTCGCAGAGAGTTCAGGTGGAAGTAGAACTCGGACGTGAGTGCTGCCGCTCAGCCTCTGTACGAAGAGCCAGTCCGCACAGTCCCCACAGGAG
TGGCCTCGTTTCACAGGCAAGCTTCAGGAGTAGAGAACTCGGGACTGTATTTGCAGGAACCGAGCAGTGCCCACAGGAGCTCACAGATGATCCGCATATGTTCTGCCAGAAGGCTCCGGAGCTCTCGATGAT
GGTTGAGATCAACGCCCCTTCATGAAACGCCGTCCGATGAAATGCCGAAGATCGGTCACGGTGGCCGTCACGGTGGCCAGCGATCCAGCGATGCCGCGAGATCGCCGAATCCGAGCTCCTTGATAAC
CTGAGATGTTTTCTCCGCATTCGCTCCACCAGGTATCCACGATCCGGCTCCCCTCCCACAGGCCGCAGGAGATAAGAGTGTGCTGGGCACTAGCCGAGACAGTGCAGGGCACTAGCCGAGAGTGCGTAGATTTAAGATAAC
TGGCCTCATTGCTCCGCTCCGCTCCGCTCAAGCTCCAAGCTCCAAGTCGGAAGCCTCAATGAGCAGAAGCTGCCGAACCCGGCAAAAGGCCAGGGAACCCGGCAAAAGGCCAGGGAACCCGGCAAAAAGGCCAGG
CCTGACGAGCATCACAAAAATCGACCGCGTTTCCCCCTGCAGGGCTCCCTCGTGGGCTCCCTCGTGCGCTCCCTCGTGCGCTCCCTCGTGCGCTCCCTCGTGCGCTCCCTCGTG
CCCTGACGAGCATCACAAAAAATCGACGCTCAAGTCAGAGGTGGCGAAACCCGACAGGACTATAAAGATACCAGGCGTTTCCCCCTGGAAGCTCCCTCGTGCGCTCTCCTGTTCCGACCCT
GCCGCTTACCGGATACCTGTCCGCCTTTCTCCCTTCGGGAAGCGTGGCGCTTTCTCATAGCTCACGCTGTAGGTATCTCAGTTCGGTGTAGGTCGTTCGCTCCAAGCTGGGCTGTGTGCA
CGAACCCCCCGTTCAGCCCGACCGCTGCGCCTTATCCGGTAACTATCGTCTTGAGTCCAACCCGGTAAGACACGACTTATCGCCACTGGCAGCAGCCACTGGTAACAGGATTAGCAGAGC
GAGGTATGTAGGCGGTGCTACAGAGTTCTTGAAGTGGTGGCCTAACTACGGCTACACTAGAAGAACAGTATTTGGTATCTGCGCTCTGCTGAAGCCAGTTACCTTCGGAAAAAGAGTTGG
TAGCTCTTGATCCGGCAAACAAACCACCGCTGGTAGCGGTGGTTTTTTTGTTTGCAAGCAGCAGATTACGCGCAGAAAAAAAGGATCTCAAGAAGATCCTTTGATCTTTTCTACGGGGTC
TGACGCTCAGTGGAACGAAAACTCACGTTAAGGGATTTTGGTCATGAGATTATCAAAAAGGATCTTCACCTAGATCCTTTTAAATTAAAAATGAAGTTTTAAATCAATCTAAAGTATATA
TGAGTAAACTTGGTCTGACAGTTACCAATGCTTAATCAGTGAGGCACCTATCTCAGCGATCTGTCTATTTCGTTCATCCATAGTTGCCTGACTCCCCGTCGTGTAGATAACTACGATACG
GGAGGGCTTACCATCTGGCCCCAGTGCTGCAATGATACCGCGAGACCCACGCTCACCGGCTCCAGATTTATCAGCAATAAACCAGCCAGCCGGAAGGGCCGAGCGCAGAAGTGGTCCTGC
AACTTTATCCGCCTCCATCCAGTCTATTAATTGTTGCCGGGAAGCTAGAGTAAGTAGTTCGCCAGTTAATAGTTTGCGCAACGTTGTTGCCATTGCTACAGGCATCGTGGTGTCACGCTC
GTCGTTTGGTATGGCTTCATTCAGCTCCGGTTCCCAACGATCAAGGCGAGTTACATGATCCCCCATGTTGTGCAAAAAAGCGGTTAGCTCCTTCGGTCCTCCGATCGTTGTCAGAAGTAA
GTTGGCCGCAGTGTTATCACTCATGGTTATGGCAGCACTGCATAATTCTCTTACTGTCATGCCATCCGTAAGATGCTTTTCTGTGACTGGTGAGTACTCAACCAAGTCATTCTGAGAATA
GTGTATGCGGCGACCGAGTTGCTCTTGCCCGGCGTCAATACGGGATAATACCGCGCCACATAGCAGAACTTTAAAAGTGCTCATCATTGGAAAACGTTCTTCGGGGCGAAAACTCTCAAG
GATCTTACCGCTGTTGAGATCCAGTTCGATGTAACCCACTCGTGCACCCAACTGATCTTCAGCATCTTTTACTTTCACCAGCGTTTCTGGGTGAGCAAAAACAGGAAGGCAAAATGCCGC
AAAAAAGGGAATAAGGGCGACACGGAAATGTTGAATACTCATACTCTTCCTTTTTCAATATTATTGAAGCATTTATCAGGGTTATTGTCTCATGAGCGGATACATATTTGAATGTATTTA
GAAAAATAAACAAATAGGGGTTCCGCGCACATTTCCCCGAAAAGTGCCAC//
```

Figure 49

```
LOCUS       1029125_mouse_interleukin_31_pMA-T  2805 bp DNA  circular
CDS         complement(1817..2677)
            /vntifkey="4"
            /label="AmpR"
            rep_origin complement(1002..1669)
            /vntifkey="33"
/label="ColE1\origin"
            /vntifkey="mouse_interleukin_21"
CBS         380..822
ORIGIN
CTAAATTGTAAGCGTTAATATTTGTTAAAATTCGCGTTAAATTTTGTTAAATCAGCTCATTTTTTAACCAATAGGCCGAAATCGGCAAAATCCCTTATAAATCAAAAGAATAGACCGA
GATAGGGTTGAGTGTTGCCGGTCACAGGGCCTCCATTCGCCATTCAGGCTGCGCAACTGTTGGGAAGGGCCGTTTCGGTGCGGGCCTCTTCGCTATTACGCCAGCTGGCGAAAGGGGGATGT
GCTGCAAGGCGATTAAGTTGGGTAACGCCAGGGTTTTCCCAGTCACGACGTTGTAAAACGACGGCCAGTGCCAAGCTTGTTAAACTTAGATGACTCACTATAGGCGAATTGGGCGAAGCGTCA
AGGCCACGTGTCTTGTCCAGGTACCAAGCTTACACCTTCTGTGTGGACTCGGACTGGATCAGGGACCCAGTAGACTGTCTCATTAGACTCCGGCACCTCATCGATATTGTGAACAGCTGAAAAT
CTACGAACGACCTCGACCGTGAACTCCTCTCTCGCCCACAGATGTGAGGGCATTGAAGGCCATTTGCAGATTGTTCTTCCAGAAGGCCAACTGAAACCTGACCTGGCAA
TAACAAAACCTTTATCATCGAACCTGTGCACAGCTCCTAGAGCCCTGCTAGACGAGACTGCCTCTAGACGGGCCGAAAATGACAACACATTCCCCAAATGCCCCCTCCTTGAATCCCTACGAAAAAACG
GACCCCAAAAGAATTTCTCGAACGCCTGAAATGCCTGCTCCACAGAAATCAGCTCAGTCGAATGTTCACCACGACCTGCAGTTCCTTTTGGTATTGGCGTCTCGCCTTCCTTGCTCGTGAC
TCATGGCCTTCCCTCAGCTCCGGCTTTGGGTAAGCCTGGGCTCCTAATGAGCAAACCCGACTGAATGGCAATAGTCTGACGAAAGGGCCAGCAAAGGCCAGACCTAAAAGGCCGTGGCGTTTGCTGGCGTTTTCCATAGGCTCCGCCCCCTG
ACGAGCATCACAAAAATCGACGCTCAAGTCAGAGGTGGCGAAACCCGACAGGACTATAAAGATACCAGGCGTTTCCCCCTGGAAGCTCCCTCGTGCGCTCTCCTGTTCCGACCCTGCCGC
TTACCGGATACCTGTCCGCCTTTCTCCCTTCGGGAAGCGTGGCGCTTTCTCATAGCTCACGCTGTAGGTATCTCAGTTCGGTGTAGGTCGTTCGCTCCAAGCTGGGCTGTGTGCACGAAC
CCCCCGTTCAGCCCGACCGCTGCGCCTTATCCGGTAACTATCGTCTTGAGTCCAACCCGGTAAGACACGACTTATCGCCACTGGCAGCAGCCACTGGTAACAGGATTAGCAGAGCGAGGT
ATGTAGGCGGTGCTACAGAGTTCTTGAAGTGGTGGCCTAACTACGGCTACACTAGAAGAACAGTATTTGGTATCTGCGCTCTGCTGAAGCCAGTTACCTTCGGAAAAAGAGTTGGTAGCT
CTTGATCCGGCAAACAAACCACCGCTGGTAGCGGTGGTTTTTTTGTTTGCAAGCAGCAGATTACGCGCAGAAAAAAGGATCTCAAGAAGATCCTTTGATCTTTTCTACGGGGTCTGACG
CTCAGTGGAACGAAAACTCACGTTAAGGGATTTTGGTCATGAGATTATCAAAAAGGATCTTCACCTAGATCCTTTTAAATTAAAAATGAAGTTTTAAATCAATCTAAAGTATATATGAGT
AAACTTGGTCTGACAGTTACCAATGCTTAATCAGTGAGGCACCTATCTCAGCGATCTGTCTATTTCGTTCATCCATAGTTGCCTGACTCCCCGTCGTGTAGATAACTACGATACGGGAGG
GCTTACCATCTGGCCCCAGTGCTGCAATGATACCGCGAGACCCACGCTCACCGGCTCCAGATTTATCAGCAATAAACCAGCCAGCCGGAAGGGCCGAGCGCAGAAGTGGTCCTGCAACTT
TATCCGCCTCCATCCAGTCTATTAATTGTTGCCGGGAAGCTAGAGTAAGTAGTTCGCCAGTTAATAGTTTGCGCAACGTTGTTGCCATTGCTACAGGCATCGTGGTGTCACGCTCGTCGT
TTGGTATGGCTTCATTCAGCTCCGGTTCCCAACGATCAAGGCGAGTTACATGATCCCCCATGTTGTGCAAAAAAGCGGTTAGCTCCTTCGGTCCTCCGATCGTTGTCAGAAGTAAGTTGG
CCGCAGTGTTATCACTCATGGTTATGGCAGCACTGCATAATTCTCTTACTGTCATGCCATCCGTAAGATGCTTTTCTGTGACTGGTGAGTACTCAACCAAGTCATTCTGAGAATAGTGTA
TGCGGCGACCGAGTTGCTCTTGCCCGGCGTCAATACGGGATAATACCGCGCCACATAGCAGAACTTTAAAAGTGCTCATCATTGGAAAACGTTCTTCGGGGCGAAAACTCTCAAGGATCT
TACCGCTGTTGAGATCCAGTTCGATGTAACCCACTCGTGCACCCAACTGATCTTCAGCATCTTTTACTTTCACCAGCGTTTCTGGGTGAGCAAAAACAGGAAGGCAAAATGCCGCAAAAA
AGGGAATAAGGGCGACACGGAAATGTTGAATACTCATACTCTTCCTTTTTCAATATTATTGAAGCATTTATCAGGGTTATTGTCTCATGAGCGGATACATATTTGAATGTATTTAGAAAAA
ATAAACAATAGGGGTTCCGCGCACATTTCCCCGAAAAGTGCCAC//
```

Figure 50

```
LOCUS       1039124_h_interleukin_21_pMA-T        2808 bp    DNA     circular
CDS             complement(1820..2680)
                /vntifkey="4"
                /label="AmpR"
                rep_origin      complement(1065..1672)
                /vntifkey="33"
CDS             380..825
                /label="ColNE\origin"
                /label="h_Interleukin_21"
ORIGIN
CTAAATGTAAGGTTAATATTTGTTAAATTCCGGTTAAATTTTGTTAAATCAGTCATTTTTAACCAATAGCCGAAATCGGCAAATCCCTATAAATCAAAAGAATAGACCGA
GATAGGGTTGAGTGGCCGCTACAGGGCCTCCATTCGGCATTCAGGCTGCCAACTGTGGGAAGGGCGTTTCGGTGCGGCGCTTCGCTATTACCGCCAGCTGGCGAAAGGGATGT
GCTCAAGCGCATTAAGTTGGGTAACCGCCAGGGTTTTCCCAGTCACGACGTTGTAAAACGACGGCCAGTGAGCGCGACCTAATACCACTCACTATAGGGCGAATTCGGACGCGTCA
AGGCCACGTGTCTTGTCCACGTACCAAGCTGTCCACGTCCCGTCCCAGTTCCTCCCGCTCCGTGTGAGGATGTGGAAACCAACTGTGAGTGAGTTGCTTTTCGTGCTTTCAGAAGGCACAGCTCAAATCCGCAATACCGC
AACTGTGAACGACCTGGTGGCCCGAGTTCCTCCCGTCCCAGCGGGATGTGGAAACCAACTGTGAGTTCGTTTTCAGAAGGCACAGCTCAAATCCGCAATACCGCAAT
CAACAATGAACGGATCATCAACGGTGTCCATCGAACTTCGAACCGTCTCATCCAGAAAACTCAAATCATCACTCAGTCCTGCTGCCCTGTTGCTTGAGAACGTTCTTAACAGCAGTTTCTGCAACTTCTCGAATCACTCTGCCAGATTCATAAACGTTAACAGTGAAGCTGAGCACGAAGACTG
AAAACTCCCCAAGGCCTTCCGCTCACTGCCGGTCGTTCGGCTGCACCCTCGAGCCATCTGTGTCGGAGACACGAGAAGCCAGGGTCATGTTCCTTGCCTATTGGGCGTCTCCCCTTCCTGCCTCACTGTGTCTTGAGAGGTCAGGAATGAGAAGCCAGGTCAATGTCCTTGCCTATTGGGCGTCTCCCCTTCCTGCACT
GCCTATGGGCTGCGGCTGGTCGTTCGGGCGGTGGTCAATCGGACGCTCAAGTCAGACGAGAGGTGGGAAGCTGCGAACCCGGAAGCCGTTTCCCCTGCGGTAGCGTAGGTTATAAGGTGTTGGAAGGCGCAGACCTCAAGCGCAGCAGCCACTGGTAACGCAGTTACCTTCGGAAAAGAGTTGGTA
GACTCCGGATACCGTCGCCCGTTTTCAAACGACGCTCAAGTCAGAGGTGGCGAAACCCGACAGGACTATAAGCTCTCAGTTGCCAGCAGCCACTGGTAACCAGGATATCTGCAGCAGCTGCCAAGACTTACCCGCAGCTCTCAACCGGATATCAAGTTCGCTCTACACCGGTACCCCTGCGGAGACGCCACATGGATCGTGCTGACAGAGA
CCCTGAACCCGCTTCAGCCGATGCTGCTGCCCGTCCTGTGGCACGCAAGACATCTCTTAACGTCAATCCGTCGCAGAGGACGCACCTGCGTCAAGCATATCTGCAGCAGCTCGCCCTTACCCAAACCAACACCCCGACTCTTCTGTTGCAAGCAGCAGATCTTGAATTAAATGAAGTTTAAATCAATCTAAAGTATATATG
GCTCTTGATCCGGCAAACAACCACCGCTGGTAGCGGTGGTTTTTTGTCTGCAAGCAGCAGATTACGCGCAGAAAAAAAGGATCTCAAGAAGATCCTTTGATCTTTTCTACGGGGTCTG
ACGCTCAGTGGAACGAAAACTCACGTTAAGGGATTTTGGTCATGAGATTATCAAAAAGGATCTTCACCTAGATCCTTTTAAATTAAAAATGAAGTTTTAAATCAATCTAAAGTATATATG
AGTAAACTTGGTCTGACAGTTACCAATGCTTAATCAGTGAGGCACCTATCTCAGCGATCTGTCTATTTCGTTCATCCATAGTTGCCTGACTCCCCGTCGTGTAGATAACTACGATACGGG
AGGGCTTACCATCTGGCCCCAGTGCTGCAATGATACCGCGAGACCCACGCTCACCGGCTCCAGATTTATCAGCAATAAACCAGCCAGCCGGAAGGGCCGAGCGCAGAAGTGGTCCTGCAA
CTTTATCCGCCTCCATCCAGTCTATTAATTGTTGCCGGGAAGCTAGAGTAAGTAGTTCGCCAGTTAATAGTTTGCGCAACGTTGTTGCCATTGCTACAGGCATCGTGGTGTCACGCTCGT
CGTTTGGTATGGCTTCATTCAGCTCCGGTTCCCAACGATCAAGGCGAGTTACATGATCCCCCATGTTGTGCAAAAAAGCGGTTAGCTCCTTCGGTCCTCCGATCGTTGTCAGAAGTAAGT
TGGCCGCAGTGTTATCACTCATGGTTATGGCAGCACTGCATAATTCTCTTACTGTCATGCCATCCGTAAGATGCTTTTCTGTGACTGGTGAGTACTCAACCAAGTCATTCTGAGAATAGT
GTATGCGGCGACCGAGTTGCTCTTGCCCGGCGTCAATACGGGATAATACCGCGCCACATAGCAGAACTTTAAAAGTGCTCATCATTGGAAAACGTTCTTCGGGGCGAAAACTCTCAAGGA
TCTTACCGCTGTTGAGATCCAGTTCGATGTAACCCACTCGTGCACCCAATTCTGCGACCGAGTTGCTCTTGCCCGGCGTCATGGTCGCCACCGCGCCAACAACACAAGCTGGAAAATCGCGCAA
AAAAGGGAATAAGGGCGACACGGAAATGTTGAATACTCATACTCTTCCTTTTTCAATATTATTGAAGCATTTATCAGGGTTATTGTCTCATGAGCGGATACATATTTGAATGTATTTAGA
AAAATAAACAAATAGGGGTTCCGCGCACATTTCCCCGAAAAGTGCCAC//
```

Figure 51

SEQUENCE LISTING

<160> NUMBER OF SEQ ID NOS: 94

<210> SEQ ID NO 1
<211> LENGTH: 4
<212> TYPE: PRT
<213> ORGANISM: Artificial
<220> FEATURE:
<223> OTHER INFORMATION: glycine-rich linker
<220> FEATURE:
<221> NAME/KEY: VARIANT
<222> LOCATION: (4)..(4)

```
<223> OTHER INFORMATION: may be T or S

<400> SEQUENCE: 1

Gly Gly Gly Arg
1

<210> SEQ ID NO 2
<211> LENGTH: 7
<212> TYPE: PRT
<213> ORGANISM: Artificial
<220> FEATURE:
<223> OTHER INFORMATION: glycine-rich linker
<220> FEATURE:
<221> NAME/KEY: VARIANT
<222> LOCATION: (4)..(4)
<223> OTHER INFORMATION: may be T or S

<400> SEQUENCE: 2

Gly Gly Gly Arg Gly Gly Gly
1               5

<210> SEQ ID NO 3
<211> LENGTH: 13
<212> TYPE: PRT
<213> ORGANISM: Artificial
<220> FEATURE:
<223> OTHER INFORMATION: glycine-rich linker
<220> FEATURE:
<221> NAME/KEY: VARIANT
<222> LOCATION: (5)..(5)
<223> OTHER INFORMATION: may be T or S
<220> FEATURE:
<221> NAME/KEY: VARIANT
<222> LOCATION: (10)..(10)
<223> OTHER INFORMATION: may be T or S

<400> SEQUENCE: 3

Gly Gly Gly Gly Arg Gly Gly Gly Gly Arg Gly Gly Gly
1               5                   10

<210> SEQ ID NO 4
<211> LENGTH: 18
<212> TYPE: PRT
<213> ORGANISM: Artificial
<220> FEATURE:
<223> OTHER INFORMATION: glycine-rich linker
<220> FEATURE:
<221> NAME/KEY: VARIANT
<222> LOCATION: (5)..(5)
<223> OTHER INFORMATION: may be T or S
<220> FEATURE:
<221> NAME/KEY: VARIANT
<222> LOCATION: (10)..(10)
<223> OTHER INFORMATION: may be T or S
<220> FEATURE:
<221> NAME/KEY: VARIANT
<222> LOCATION: (15)..(15)
<223> OTHER INFORMATION: may be T or S

<400> SEQUENCE: 4

Gly Gly Gly Gly Arg Gly Gly Gly Arg Gly Gly Gly Arg Gly
1               5                   10                  15

Gly Gly

<210> SEQ ID NO 5
<211> LENGTH: 6
<212> TYPE: PRT
<213> ORGANISM: Artificial
<220> FEATURE:
<223> OTHER INFORMATION: glycine-rich linker
```

```
<220> FEATURE:
<221> NAME/KEY: VARIANT
<222> LOCATION: (3)..(3)
<223> OTHER INFORMATION: may be T or S

<400> SEQUENCE: 5

Gly Gly Arg Gly Gly Gly
1               5

<210> SEQ ID NO 6
<211> LENGTH: 11
<212> TYPE: PRT
<213> ORGANISM: Artificial
<220> FEATURE:
<223> OTHER INFORMATION: glycine-rich linker
<220> FEATURE:
<221> NAME/KEY: VARIANT
<222> LOCATION: (5)..(5)
<223> OTHER INFORMATION: may be R or S
<220> FEATURE:
<221> NAME/KEY: VARIANT
<222> LOCATION: (10)..(10)
<223> OTHER INFORMATION: may be R or S

<400> SEQUENCE: 6

Gly Gly Gly Gly Thr Gly Gly Gly Gly Thr Gly
1               5                   10

<210> SEQ ID NO 7
<211> LENGTH: 33
<212> TYPE: PRT
<213> ORGANISM: Artificial
<220> FEATURE:
<223> OTHER INFORMATION: isoleucine zipper motif

<400> SEQUENCE: 7

Arg Met Lys Gln Ile Glu Asp Lys Ile Glu Glu Ile Leu Ser Lys Ile
1               5                   10                  15

Tyr His Ile Glu Asn Glu Ile Ala Arg Ile Lys Lys Leu Ile Gly Glu
            20                  25                  30

Arg

<210> SEQ ID NO 8
<211> LENGTH: 37
<212> TYPE: DNA
<213> ORGANISM: Artificial
<220> FEATURE:
<223> OTHER INFORMATION: primer

<400> SEQUENCE: 8
ctcatactca taggatcctc gatcctcaaa ttgcagc                        37

<210> SEQ ID NO 9
<211> LENGTH: 36
<212> TYPE: DNA
<213> ORGANISM: Artificial
<220> FEATURE:
<223> OTHER INFORMATION: primer

<400> SEQUENCE: 9
ctcatactca tattcgaatt agagtttgag taagcc                         36

<210> SEQ ID NO 10
<211> LENGTH: 49
<212> TYPE: DNA
<213> ORGANISM: Artificial
<220> FEATURE:
```

<223> OTHER INFORMATION: primer

<400> SEQUENCE: 10
ctcatactca taggatcctc ggtggaggta gcgatcctca aattgcagc          49

<210> SEQ ID NO 11
<211> LENGTH: 58
<212> TYPE: DNA
<213> ORGANISM: Artificial
<220> FEATURE:
<223> OTHER INFORMATION: primer

<400> SEQUENCE: 11
ctcatactca taggatcctc ggtggaggta gcggtggagg tgatcctcaa attgcagc    58

<210> SEQ ID NO 12
<211> LENGTH: 50
<212> TYPE: DNA
<213> ORGANISM: Artificial
<220> FEATURE:
<223> OTHER INFORMATION: primer

<400> SEQUENCE: 12
ctcatactca taggatcctc ggcggtggcg gtagcggtgg tggaggtagc          50

<210> SEQ ID NO 13
<211> LENGTH: 47
<212> TYPE: DNA
<213> ORGANISM: Artificial
<220> FEATURE:
<223> OTHER INFORMATION: primer

<400> SEQUENCE: 13
ctcatactca taggatcctc ggtggaggtg gaagcggcgg tggcggt             47

<210> SEQ ID NO 14
<211> LENGTH: 99
<212> TYPE: DNA
<213> ORGANISM: Artificial
<220> FEATURE:
<223> OTHER INFORMATION: lucine zipper
<220> FEATURE:
<221> NAME/KEY: CDS
<222> LOCATION: (1)..(99)

<400> SEQUENCE: 14 aga atg aag cag atc gag gac aag atc gag gag atc ctg agc aag atc    48
Arg Met Lys Gln Ile Glu Asp Lys Ile Glu Glu Ile Leu Ser Lys Ile
1               5                   10                  15 tac cac atc gag aac gag atc gcc aga atc aag aag ctg atc ggc gag    96
Tyr His Ile Glu Asn Glu Ile Ala Arg Ile Lys Lys Leu Ile Gly Glu
                20                  25                  30 aga                                                                99
Arg

<210> SEQ ID NO 15
<211> LENGTH: 33
<212> TYPE: PRT
<213> ORGANISM: Artificial
<220> FEATURE:
<223> OTHER INFORMATION: Synthetic Construct

<400> SEQUENCE: 15

Arg Met Lys Gln Ile Glu Asp Lys Ile Glu Glu Ile Leu Ser Lys Ile
1               5                   10                  15

```
Tyr His Ile Glu Asn Glu Ile Ala Arg Ile Lys Lys Leu Ile Gly Glu
            20                  25                  30

Arg

<210> SEQ ID NO 16
<211> LENGTH: 49
<212> TYPE: DNA
<213> ORGANISM: Artificial
<220> FEATURE:
<223> OTHER INFORMATION: primer

<400> SEQUENCE: 16
ccggtagaat gaagcagatc gaggacaaga tcgaggagat cctgagcaa              49

<210> SEQ ID NO 17
<211> LENGTH: 58
<212> TYPE: DNA
<213> ORGANISM: Artificial
<220> FEATURE:
<223> OTHER INFORMATION: primer

<400> SEQUENCE: 17
gatctaccac atcgagaacg agatcgccag aatcaagaag ctgatcggcg agagaggc    58

<210> SEQ ID NO 18
<211> LENGTH: 49
<212> TYPE: DNA
<213> ORGANISM: Artificial
<220> FEATURE:
<223> OTHER INFORMATION: anti-sense nucleotide

<400> SEQUENCE: 18
gatcttgctc aggatctcct cgatcttgtc ctcgatctgc ttcattcta              49

<210> SEQ ID NO 19
<211> LENGTH: 58
<212> TYPE: DNA
<213> ORGANISM: Artificial
<220> FEATURE:
<223> OTHER INFORMATION: anti-sense nucleotide

<400> SEQUENCE: 19
ggccgcctct ctcgccgatc agcttcttga ttctggcgat ctcgttctcg atgtggta    58

<210> SEQ ID NO 20
<211> LENGTH: 9
<212> TYPE: PRT
<213> ORGANISM: Artificial
<220> FEATURE:
<223> OTHER INFORMATION: histidine tag

<400> SEQUENCE: 20

His His His His His His His His His
1               5

<210> SEQ ID NO 21
<211> LENGTH: 70
<212> TYPE: PRT
<213> ORGANISM: Artificial
<220> FEATURE:
<223> OTHER INFORMATION: VIV2-domain

<400> SEQUENCE: 21

Thr Leu Asn Cys Lys Asp Val Asn Ala Thr Asn Thr Thr Asn Asp Ser
1               5                   10                  15
```

```
Glu Gly Thr Met Glu Arg Gly Glu Ile Lys Asn Cys Ser Phe Asn Ile
            20                  25                  30

Thr Thr Ser Ile Arg Asp Glu Val Gln Lys Glu Tyr Ala Leu Phe Tyr
        35                  40                  45

Lys Leu Asp Val Val Pro Ile Asp Asn Asn Asn Thr Ser Tyr Arg Leu
    50                  55                  60

Ile Ser Cys Asp Thr Ser
65                  70

<210> SEQ ID NO 22
<211> LENGTH: 132
<212> TYPE: PRT
<213> ORGANISM: Artificial
<220> FEATURE:
<223> OTHER INFORMATION: GM-CSF

<400> SEQUENCE: 22

Lys Leu Thr Pro Leu Cys Val Gly Ser Gly Ser Thr Gln Pro Trp Glu
1               5                   10                  15

His Val Asn Ala Ile Gln Glu Ala Arg Arg Leu Leu Asn Leu Ser Arg
            20                  25                  30

Asp Thr Ala Ala Glu Met Asn Glu Thr Val Glu Val Ile Ser Glu Met
        35                  40                  45

Phe Asp Leu Gln Glu Pro Thr Cys Leu Gln Thr Arg Leu Glu Leu Tyr
    50                  55                  60

Lys Gln Gly Leu Arg Gly Ser Leu Thr Lys Leu Lys Gly Pro Leu Thr
65                  70                  75                  80

Met Met Ala Ser His Tyr Lys Gln His Cys Pro Pro Thr Pro Glu Thr
                85                  90                  95

Ser Cys Ala Thr Gln Ile Ile Thr Phe Glu Ser Phe Lys Glu Asn Leu
            100                 105                 110

Lys Asp Phe Leu Leu Val Ile Pro Phe Asp Cys Trp Gly Ser Gly Ser
        115                 120                 125

Cys Asn Thr Ser
    130

<210> SEQ ID NO 23
<211> LENGTH: 129
<212> TYPE: PRT
<213> ORGANISM: Artificial
<220> FEATURE:
<223> OTHER INFORMATION: mouse GM-CSF

<400> SEQUENCE: 23

Lys Leu Thr Pro Leu Cys Val Gly Ser Gly Val Thr Arg Pro Trp Lys
1               5                   10                  15

His Val Glu Ala Ile Lys Glu Ala Leu Asn Leu Leu Asp Asp Met Pro
            20                  25                  30

Val Thr Leu Asn Glu Glu Val Glu Val Val Ser Asn Glu Phe Ser Phe
        35                  40                  45

Lys Lys Leu Thr Cys Val Gln Thr Arg Leu Lys Ile Phe Glu Gln Gly
    50                  55                  60

Leu Arg Gly Asn Phe Thr Lys Leu Lys Gly Ala Leu Asn Met Thr Ala
65                  70                  75                  80

Ser Tyr Tyr Gln Thr Tyr Cys Pro Pro Thr Pro Glu Thr Asp Cys Glu
                85                  90                  95

Thr Gln Val Thr Thr Tyr Ala Asp Phe Ile Asp Ser Leu Lys Thr Phe
            100                 105                 110
```

```
Leu Thr Asp Ile Pro Phe Glu Cys Lys Gly Ser Gly Ser Cys Asn Thr
        115                 120                 125
Ser

<210> SEQ ID NO 24
<211> LENGTH: 261
<212> TYPE: PRT
<213> ORGANISM: Artificial
<220> FEATURE:
<223> OTHER INFORMATION: IgG1-derived protein

<400> SEQUENCE: 24

Gly Gly Arg Ser Pro Gln Pro Gln Pro Lys Pro Gln Pro Lys Pro Glu
1               5                   10                  15

Pro Glu Gly Ser Leu Gln Gly Asp Gln Gly Gly Gly Glu Pro Lys
            20                  25                  30

Ser Cys Asp Lys Thr His Thr Cys Pro Pro Cys Pro Ala Pro Glu Leu
            35                  40                  45

Leu Gly Gly Pro Ser Val Phe Leu Phe Pro Pro Lys Pro Lys Asp Thr
        50                  55                  60

Leu Met Ile Ser Arg Thr Pro Glu Val Thr Cys Val Val Val Asp Val
65                  70                  75                  80

Ser His Glu Asp Pro Glu Val Lys Phe Asn Trp Tyr Val Asp Gly Val
                85                  90                  95

Glu Val His Asn Ala Lys Thr Lys Pro Arg Glu Glu Gln Tyr Asn Ser
            100                 105                 110

Thr Tyr Arg Val Val Ser Val Leu Thr Val Leu His Gln Asp Trp Leu
        115                 120                 125

Asn Gly Lys Glu Tyr Lys Cys Lys Val Ser Asn Lys Ala Leu Pro Ala
    130                 135                 140

Pro Ile Glu Lys Thr Ile Ser Lys Ala Lys Gly Gln Pro Arg Glu Pro
145                 150                 155                 160

Gln Val Tyr Thr Leu Pro Pro Ser Arg Asp Glu Leu Thr Lys Asn Gln
                165                 170                 175

Val Ser Leu Thr Cys Leu Val Lys Gly Phe Tyr Pro Ser Asp Ile Ala
            180                 185                 190

Val Glu Trp Glu Ser Asn Gly Gln Pro Glu Asn Asn Tyr Lys Thr Thr
        195                 200                 205

Pro Pro Val Leu Asp Ser Asp Gly Ser Phe Phe Leu Tyr Ser Lys Leu
    210                 215                 220

Thr Val Asp Lys Ser Arg Trp Gln Gln Gly Asn Val Phe Ser Cys Ser
225                 230                 235                 240

Val Met His Glu Ala Leu His Asn His Tyr Thr Gln Lys Ser Leu Ser
                245                 250                 255

Leu Ser Pro Gly Lys
            260

<210> SEQ ID NO 25
<211> LENGTH: 27
<212> TYPE: DNA
<213> ORGANISM: Artificial
<220> FEATURE:
<223> OTHER INFORMATION: primer

<400> SEQUENCE: 25
atgatagaaa catacagcca accttcc                                      27
```

-continued

<210> SEQ ID NO 26
<211> LENGTH: 23
<212> TYPE: DNA
<213> ORGANISM: Artificial
<220> FEATURE:
<223> OTHER INFORMATION: primer

<400> SEQUENCE: 26
caaacaccga agcatccgct tgc                                              23

<210> SEQ ID NO 27
<211> LENGTH: 6
<212> TYPE: PRT
<213> ORGANISM: Artificial
<220> FEATURE:
<223> OTHER INFORMATION: furin cleavage site

<400> SEQUENCE: 27

Arg Arg Arg Arg Arg Arg
1               5

<210> SEQ ID NO 28
<211> LENGTH: 15
<212> TYPE: PRT
<213> ORGANISM: Artificial
<220> FEATURE:
<223> OTHER INFORMATION: gp140 epitope

<400> SEQUENCE: 28

Ala Pro Thr Lys Ala Lys Arg Arg Val Val Gln Arg Glu Lys Arg
1               5                   10                  15

<210> SEQ ID NO 29
<211> LENGTH: 250
<212> TYPE: PRT
<213> ORGANISM: Homo sapiens

<400> SEQUENCE: 29

Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
    130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

```
Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
            245                 250

<210> SEQ ID NO 30
<211> LENGTH: 241
<212> TYPE: PRT
<213> ORGANISM: Mus musculus

<400> SEQUENCE: 30

Met Pro Ala Ser Ser Pro Gly His Met Gly Gly Ser Val Arg Glu Pro
1               5                   10                  15

Ala Leu Ser Val Ala Leu Trp Leu Ser Trp Gly Ala Val Leu Gly Ala
            20                  25                  30

Val Thr Cys Ala Val Ala Leu Leu Ile Gln Gln Thr Glu Leu Gln Ser
        35                  40                  45

Leu Arg Arg Glu Val Ser Arg Leu Gln Arg Ser Gly Gly Pro Ser Gln
    50                  55                  60

Lys Gln Gly Glu Arg Pro Trp Gln Ser Leu Trp Glu Gln Ser Pro Asp
65                  70                  75                  80

Val Leu Glu Ala Trp Lys Asp Gly Ala Lys Ser Arg Arg Arg Ala
            85                  90                  95

Val Leu Thr Gln Lys His Lys Lys Lys His Ser Val Leu His Leu Val
        100                 105                 110

Pro Val Asn Ile Thr Ser Lys Ala Asp Ser Asp Val Thr Glu Val Met
    115                 120                 125

Trp Gln Pro Val Leu Arg Arg Gly Arg Gly Leu Glu Ala Gln Gly Asp
130                 135                 140

Ile Val Arg Val Trp Asp Thr Gly Ile Tyr Leu Leu Tyr Ser Gln Val
145                 150                 155                 160

Leu Phe His Asp Val Thr Phe Thr Met Gly Gln Val Val Ser Arg Glu
            165                 170                 175

Gly Gln Gly Arg Arg Glu Thr Leu Phe Arg Cys Ile Arg Ser Met Pro
        180                 185                 190

Ser Asp Pro Asp Arg Ala Tyr Asn Ser Cys Tyr Ser Ala Gly Val Phe
    195                 200                 205

His Leu His Gln Gly Asp Ile Ile Thr Val Lys Ile Pro Arg Ala Asn
    210                 215                 220

Ala Lys Leu Ser Leu Ser Pro His Gly Thr Phe Leu Gly Phe Val Lys
225                 230                 235                 240

Leu

<210> SEQ ID NO 31
<211> LENGTH: 250
<212> TYPE: PRT
<213> ORGANISM: Oryctolagus cuniculus

<400> SEQUENCE: 31

Met Pro Ala Ser Ser Pro Phe Leu Leu Ala Pro Lys Gly Pro Gln Gly
```

```
 1               5                  10                 15
Asp Met Gly Gly Pro Val Arg Glu Pro Ala Leu Ser Val Ala Leu Trp
             20                 25                 30

Leu Ser Trp Gly Ala Ala Leu Gly Ala Val Ala Cys Ala Met Ala Leu
             35                 40                 45

Leu Val Gln Gln Thr Glu Leu Gln Ser Leu Arg Lys Glu Val Ser Arg
             50                 55                 60

Leu Gln Arg Ser Gly Gly Pro Ser Gln Lys Gly His Glu Tyr Pro Trp
 65                 70                 75                 80

Gln Ser Leu Trp Glu Gln Ser Pro Asp Ala Leu Glu Ala Trp Val Asn
             85                 90                 95

Gly Glu Arg Pro Arg Arg Arg Ala Leu Pro Thr Gln Lys Gln Lys
            100                105                110

Lys Lys Arg Ser Leu Leu His Leu Val Pro Ile Asn Ile Thr Ser Lys
            115                120                125

Glu Asp Ser Asp Val Thr Glu Val Met Trp Gln Pro Ala Leu Arg Arg
            130                135                140

Gly Arg Gly Leu Glu Ala Gln Gly Tyr Val Val Arg Val Trp Asp Thr
145                150                155                160

Gly Val Tyr Leu Leu Tyr Ser Gln Val Leu Phe His Asp Val Thr Phe
                   165                170                175

Thr Met Gly Gln Val Val Ser Arg Glu Gly Gln Gly Arg Gln Glu Thr
            180                185                190

Leu Phe Arg Cys Val Cys Ser Met Pro Ser Asp Pro Asp Arg Ala Tyr
            195                200                205

Asn Ser Cys Tyr Ser Ala Gly Val Phe His Leu His Gln Gly Asp Ile
            210                215                220

Leu Ser Val Val Ile Pro Arg Ala Arg Ala Lys Phe Ser Leu Ser Pro
225                230                235                240

His Gly Thr Phe Leu Gly Phe Val Lys Leu
                   245                250

<210> SEQ ID NO 32
<211> LENGTH: 247
<212> TYPE: PRT
<213> ORGANISM: Macaca mulatta

<400> SEQUENCE: 32

Met Pro Ala Ser Ser Leu Phe Ser Leu Ala Pro Lys Gly Pro Pro Gly
 1               5                 10                 15

Asn Met Gly Val Pro Val Arg Glu Pro Ala Leu Ser Val Ala Leu Trp
             20                 25                 30

Leu Ser Trp Gly Ala Ala Leu Gly Ala Val Ala Cys Ala Met Ala Leu
             35                 40                 45

Leu Thr Gln Gln Thr Glu Leu Gln Ser Leu Arg Arg Glu Val Ser Arg
             50                 55                 60

Leu Gln Arg Thr Gly Gly Pro Ser Gln Lys Ala Glu Gly Tyr Pro Trp
 65                 70                 75                 80

Gln Ser Leu Pro Glu Gln Ser Ser Asp Ala Pro Glu Ala Trp Glu Asn
             85                 90                 95

Gly Glu Arg Ser Arg Lys Arg Arg Ala Val Leu Thr Gln Lys Gln Lys
            100                105                110

Lys Gln His Ser Val Val His Leu Val Pro Ile Asn Ala Thr Ser Lys
            115                120                125
```

```
Asp Asp Ser Asp Val Thr Glu Val Met Trp Gln Pro Ala Leu Arg Arg
    130                 135                 140

Gly Arg Gly Leu Gln Ala Gln Gly Tyr Gly Val Arg Ile Arg Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Lys Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Leu
                245

<210> SEQ ID NO 33
<211> LENGTH: 285
<212> TYPE: PRT
<213> ORGANISM: Homo sapiens

<400> SEQUENCE: 33

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
    130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
    210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255
```

```
Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
        275                 280                 285

<210> SEQ ID NO 34
<211> LENGTH: 309
<212> TYPE: PRT
<213> ORGANISM: Mus musculus

<400> SEQUENCE: 34

Met Asp Glu Ser Ala Lys Thr Leu Pro Pro Cys Leu Cys Phe Cys
 1               5                  10                  15

Ser Glu Lys Gly Glu Asp Met Lys Val Gly Tyr Asp Pro Ile Thr Pro
                20                  25                  30

Gln Lys Glu Glu Gly Ala Trp Phe Gly Ile Cys Arg Asp Gly Arg Leu
            35                  40                  45

Leu Ala Ala Thr Leu Leu Leu Ala Leu Leu Ser Ser Ser Phe Thr Ala
        50                  55                  60

Met Ser Leu Tyr Gln Leu Ala Ala Leu Gln Ala Asp Leu Met Asn Leu
65                  70                  75                  80

Arg Met Glu Leu Gln Ser Tyr Arg Gly Ser Ala Thr Pro Ala Ala Ala
                85                  90                  95

Gly Ala Pro Glu Leu Thr Ala Gly Val Lys Leu Leu Thr Pro Ala Ala
            100                 105                 110

Pro Arg Pro His Asn Ser Ser Arg Gly His Arg Asn Arg Arg Ala Phe
        115                 120                 125

Gln Gly Pro Glu Glu Thr Glu Gln Asp Val Asp Leu Ser Ala Pro Pro
    130                 135                 140

Ala Pro Cys Leu Pro Gly Cys Arg His Ser Gln His Asp Asp Asn Gly
145                 150                 155                 160

Met Asn Leu Arg Asn Ile Ile Gln Asp Cys Leu Gln Leu Ile Ala Asp
                165                 170                 175

Ser Asp Thr Pro Thr Ile Arg Lys Gly Thr Tyr Thr Phe Val Pro Trp
            180                 185                 190

Leu Leu Ser Phe Lys Arg Gly Asn Ala Leu Glu Glu Lys Glu Asn Lys
        195                 200                 205

Ile Val Val Arg Gln Thr Gly Tyr Phe Phe Ile Tyr Ser Gln Val Leu
    210                 215                 220

Tyr Thr Asp Pro Ile Phe Ala Met Gly His Val Ile Gln Arg Lys Lys
225                 230                 235                 240

Val His Val Phe Gly Asp Glu Leu Ser Leu Val Thr Leu Phe Arg Cys
                245                 250                 255

Ile Gln Asn Met Pro Lys Thr Leu Pro Asn Asn Ser Cys Tyr Ser Ala
            260                 265                 270

Gly Ile Ala Arg Leu Glu Glu Gly Asp Glu Ile Gln Leu Ala Ile Pro
        275                 280                 285

Arg Glu Asn Ala Gln Ile Ser Arg Asn Gly Asp Asp Thr Phe Phe Gly
    290                 295                 300

Ala Leu Lys Leu Leu
305

<210> SEQ ID NO 35
<211> LENGTH: 290
<212> TYPE: PRT
```

<213> ORGANISM: Oryctolagus cuniculus

<400> SEQUENCE: 35

Met Asp Asp Ser Thr Glu Arg Glu Gln Ser Arg Leu Pro Ser Arg Leu
1               5                   10                  15

Lys Gln Gly Glu Glu Met Lys Leu Glu Glu Cys Val Pro Leu Leu Pro
            20                  25                  30

Gln Gln Glu Ser Pro Ser Val Cys Leu Ser Arg Asp Gly Lys Leu Leu
        35                  40                  45

Ala Val Ala Leu Leu Leu Ala Leu Leu Ser Cys Ser Leu Ser Val Val
    50                  55                  60

Ser Leu Tyr Arg Val Ala Ala Leu Gln Ala Asp Leu Leu Ser Pro Arg
65                  70                  75                  80

Ala Ala Val Gln Gly His Gln Ala Glu Gln Leu Pro Glu Leu Pro Gly
                85                  90                  95

Ser Gly Ala Ala Ala Pro Lys Ala Thr Leu Gly Glu Ala Pro Ala Val
            100                 105                 110

Thr Ala Gly Leu Lys Gly Ile Phe Ala Pro Ala Ala Pro Gly Glu Ser
        115                 120                 125

Asn Ser Ser Trp Ser Ser Arg Lys Lys Arg Ala Val Glu Gly Val Glu
    130                 135                 140

Glu Thr Val Ile Gln Asp Cys Leu Gln Leu Ile Ala Asp Ser Asp Thr
145                 150                 155                 160

Pro Ile Ile Arg Lys Gly Ser Tyr Thr Phe Val Pro Trp Leu Leu Ser
                165                 170                 175

Phe Lys Arg Gly Arg Ala Leu Glu Glu Lys Val Asn Lys Ile Val Val
            180                 185                 190

Lys Glu Thr Gly Tyr Phe Phe Ile Tyr Gly Gln Val Leu Tyr Thr Asp
        195                 200                 205

Asn Thr Phe Ala Met Gly His Leu Ile Gln Arg Lys Lys Val His Val
    210                 215                 220

Phe Gly Asp Glu Leu Ser Leu Val Thr Leu Phe Arg Cys Ile Gln Asn
225                 230                 235                 240

Met Pro Glu Thr Leu Pro Asn Asn Ser Cys Tyr Ser Ala Gly Ile Ala
                245                 250                 255

Lys Leu Glu Glu Gly Asp Glu Leu Gln Leu Ala Ile Leu Arg Glu Asn
            260                 265                 270

Ala Gln Ile Ser Arg Asp Gly Asp Gly Thr Phe Phe Gly Ala Leu Lys
        275                 280                 285

Leu Leu
    290

<210> SEQ ID NO 36
<211> LENGTH: 285
<212> TYPE: PRT
<213> ORGANISM: Macaca mulatta

<400> SEQUENCE: 36

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Gln Lys Glu Ser Pro Ser Val Arg Ser Ser Lys Asp Arg Lys Leu Leu
        35                  40                  45

Ala Ala Ala Leu Leu Leu Ala Leu Leu Ser Cys Cys Leu Met Val Val

```
            50                  55                  60
Ser Phe Tyr Gln Val Ala Ala Leu Gln Gly Asp Leu Ala Ser Leu Arg
 65                  70                  75                  80

Ala Glu Leu Gln Ser His His Ala Glu Lys Leu Pro Ala Arg Ala Arg
                     85                  90                  95

Ala Pro Lys Ala Gly Leu Gly Glu Ala Pro Ala Val Thr Ala Gly Leu
                100                 105                 110

Lys Ile Phe Glu Pro Pro Ala Pro Gly Glu Gly Asn Ser Ser Gln Ser
            115                 120                 125

Ser Arg Asn Lys Arg Ala Ile Gln Gly Ala Glu Glu Thr Val Ile Gln
130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
                180                 185                 190

Phe Phe Ile Tyr Gly Gln Val Leu Tyr Thr Asp Lys Thr Tyr Ala Met
            195                 200                 205

Gly His Leu Ile Gln Arg Lys Lys Val His Val Phe Gly Asp Glu Leu
210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
                260                 265                 270

Asp Gly Asp Val Thr Phe Phe Gly Ala Leu Lys Leu Leu
            275                 280                 285

<210> SEQ ID NO 37
<211> LENGTH: 476
<212> TYPE: PRT
<213> ORGANISM: Artificial
<220> FEATURE:
<223> OTHER INFORMATION: gp120

<400> SEQUENCE: 37

Gly Ala Arg Val Glu Lys Leu Trp Val Thr Val Tyr Tyr Gly Val Pro
 1               5                  10                  15

Val Trp Lys Glu Ala Thr Thr Thr Leu Phe Cys Ala Ser Asp Ala Lys
                20                  25                  30

Ala Tyr Asp Thr Glu Val His Asn Val Trp Ala Thr His Ala Cys Val
            35                  40                  45

Pro Thr Asp Pro Asn Pro Gln Glu Val Val Leu Glu Asn Val Thr Glu
        50                  55                  60

His Phe Asn Met Trp Lys Asn Asn Met Val Glu Gln Met Gln Glu Asp
 65                  70                  75                  80

Ile Ile Ser Leu Trp Asp Gln Ser Leu Lys Pro Cys Val Lys Leu Thr
                85                  90                  95

Pro Leu Cys Val Thr Leu Asn Cys Lys Asp Val Asn Ala Thr Asn Thr
                100                 105                 110

Thr Asn Asp Ser Glu Gly Thr Met Glu Arg Gly Glu Ile Lys Asn Cys
            115                 120                 125

Ser Phe Asn Ile Thr Thr Ser Ile Arg Asp Glu Val Gln Lys Glu Tyr
```

```
                130                 135                 140
Ala Leu Phe Tyr Lys Leu Asp Val Val Pro Ile Asp Asn Asn Asn Thr
145                 150                 155                 160

Ser Tyr Arg Leu Ile Ser Cys Asp Thr Ser Val Ile Thr Gln Ala Cys
                165                 170                 175

Pro Lys Ile Ser Phe Glu Pro Ile Pro Ile His Tyr Cys Ala Pro Ala
            180                 185                 190

Gly Phe Ala Ile Leu Lys Cys Asn Asp Lys Thr Phe Asn Gly Lys Gly
        195                 200                 205

Pro Cys Lys Asn Val Ser Thr Val Gln Cys Thr His Gly Ile Arg Pro
    210                 215                 220

Val Val Ser Thr Gln Leu Leu Leu Asn Gly Ser Leu Ala Glu Glu Glu
225                 230                 235                 240

Val Val Ile Arg Ser Asp Asn Phe Thr Asn Asn Ala Lys Thr Ile Ile
                245                 250                 255

Val Gln Leu Lys Glu Ser Val Glu Ile Asn Cys Thr Arg Pro Asn Asn
            260                 265                 270

Asn Thr Arg Lys Ser Ile His Ile Gly Pro Gly Arg Ala Phe Tyr Thr
        275                 280                 285

Thr Gly Glu Ile Ile Gly Asp Ile Arg Gln Ala His Cys Asn Ile Ser
    290                 295                 300

Arg Ala Lys Trp Asn Asp Thr Leu Lys Gln Ile Val Ile Lys Leu Arg
305                 310                 315                 320

Glu Gln Phe Glu Asn Lys Thr Ile Val Phe Asn His Ser Ser Gly Gly
                325                 330                 335

Asp Pro Glu Ile Val Met His Ser Phe Asn Cys Gly Gly Glu Phe Phe
            340                 345                 350

Tyr Cys Asn Ser Thr Gln Leu Phe Asn Ser Thr Trp Asn Asn Asn Thr
        355                 360                 365

Glu Gly Ser Asn Asn Thr Glu Gly Asn Thr Ile Thr Leu Pro Cys Arg
    370                 375                 380

Ile Lys Gln Ile Ile Asn Met Trp Gln Glu Val Gly Lys Ala Met Tyr
385                 390                 395                 400

Ala Pro Pro Ile Arg Gly Gln Ile Arg Cys Ser Ser Asn Ile Thr Gly
                405                 410                 415

Leu Leu Leu Thr Arg Asp Gly Gly Ile Asn Glu Asn Gly Thr Glu Ile
            420                 425                 430

Phe Arg Pro Gly Gly Gly Asp Met Arg Asp Asn Trp Arg Ser Glu Leu
        435                 440                 445

Tyr Lys Tyr Lys Val Val Lys Ile Glu Pro Leu Gly Val Ala Pro Thr
    450                 455                 460

Lys Ala Lys Arg Arg Val Val Gln Arg Glu Lys Arg
465                 470                 475

<210> SEQ ID NO 38
<211> LENGTH: 545
<212> TYPE: PRT
<213> ORGANISM: Artificial
<220> FEATURE:
<223> OTHER INFORMATION: gp120 hIl-2

<400> SEQUENCE: 38

Gly Ala Arg Val

```
            20                  25                  30
Ala Tyr Asp Thr Glu Val His Asn Val Trp Ala Thr His Ala Cys Val
        35                  40                  45
Pro Thr Asp Pro Asn Pro Gln Glu Val Val Leu Glu Asn Val Thr Glu
50                  55                  60
His Phe Asn Met Trp Lys Asn Asn Met Val Glu Gln Met Gln Glu Asp
65                  70                  75                  80
Ile Ile Ser Leu Trp Asp Gln Ser Leu Lys Pro Cys Val Lys Leu Thr
                85                  90                  95
Pro Leu Cys Val Gly Ser Gly Ser Thr Lys Lys Thr Gln Leu Gln Leu
            100                 105                 110
Glu His Leu Leu Leu Asp Leu Gln Met Ile Leu Asn Gly Ile Asn Asn
        115                 120                 125
Tyr Lys Asn Pro Lys Leu Thr Arg Met Leu Thr Phe Lys Phe Tyr Met
    130                 135                 140
Pro Lys Lys Ala Thr Glu Leu Lys His Leu Gln Cys Leu Glu Glu Glu
145                 150                 155                 160
Leu Lys Pro Leu Glu Glu Val Leu Asn Leu Ala Gln Ser Lys Asn Phe
                165                 170                 175
His Leu Arg Pro Arg Asp Leu Ile Ser Asn Ile Asn Val Ile Val Leu
            180                 185                 190
Glu Leu Lys Gly Ser Glu Thr Thr Phe Met Cys Glu Tyr Ala Asp Glu
        195                 200                 205
Thr Ala Thr Ile Val Glu Phe Leu Asn Arg Trp Ile Thr Phe Ala Gln
    210                 215                 220
Ser Ile Ile Ser Thr Leu Thr Gly Ser Gly Ser Cys Asp Thr Ser Val
225                 230                 235                 240
Ile Thr Gln Ala Cys Pro Lys Ile Ser Phe Glu Pro Ile Pro Ile His
                245                 250                 255
Tyr Cys Ala Pro Ala Gly Phe Ala Ile Leu Lys Cys Asn Asp Lys Thr
            260                 265                 270
Phe Asn Gly Lys Gly Pro Cys Lys Asn Val Ser Thr Val Gln Cys Thr
        275                 280                 285
His Gly Ile Arg Pro Val Val Ser Thr Gln Leu Leu Leu Asn Gly Ser
    290                 295                 300
Leu Ala Glu Glu Glu Val Val Ile Arg Ser Asp Asn Phe Thr Asn Asn
305                 310                 315                 320
Ala Lys Thr Ile Ile Val Gln Leu Lys Glu Ser Val Glu Ile Asn Cys
                325                 330                 335
Thr Arg Pro Asn Asn Asn Thr Arg Lys Ser Ile His Ile Gly Pro Gly
            340                 345                 350
Arg Ala Phe Tyr Thr Thr Gly Glu Ile Ile Gly Asp Ile Arg Gln Ala
        355                 360                 365
His Cys Asn Ile Ser Arg Ala Lys Trp Asn Asp Thr Leu Lys Gln Ile
    370                 375                 380
Val Ile Lys Leu Arg Glu Gln Phe Glu Asn Lys Thr Ile Val Phe Asn
385                 390                 395                 400
His Ser Ser Gly Gly Asp Pro Glu Ile Val Met His Ser Phe Asn Cys
                405                 410                 415
Gly Gly Glu Phe Phe Tyr Cys Asn Ser Thr Gln Leu Phe Asn Ser Thr
            420                 425                 430
Trp Asn Asn Asn Thr Glu Gly Ser Asn Asn Thr Glu Gly Asn Thr Ile
        435                 440                 445
```

```
Thr Leu Pro Cys Arg Ile Lys Gln Ile Ile Asn Met Trp Gln Glu Val
    450                 455                 460

Gly Lys Ala Met Tyr Ala Pro Pro Ile Arg Gly Gln Ile Arg Cys Ser
465                 470                 475                 480

Ser Asn Ile Thr Gly Leu Leu Leu Thr Arg Asp Gly Gly Ile Asn Glu
                485                 490                 495

Asn Gly Thr Glu Ile Phe Arg Pro Gly Gly Gly Asp Met Arg Asp Asn
                500                 505                 510

Trp Arg Ser Glu Leu Tyr Lys Tyr Lys Val Val Lys Ile Glu Pro Leu
            515                 520                 525

Gly Val Ala Pro Thr Lys Ala Lys Arg Arg Val Val Gln Arg Glu Lys
        530                 535                 540

Arg
545

<210> SEQ ID NO 39
<211> LENGTH: 546
<212> TYPE: PRT
<213> ORGANISM: Artificial
<220> FEATURE:
<223> OTHER INFORMATION: gp120 hIL-4

<400> SEQUENCE: 39

Gly Ala Arg Val Glu Lys Leu Trp Val Thr Val Tyr Tyr Gly Val Pro
1               5                   10                  15

Val Trp Lys Glu Ala Thr Thr Thr Le

-continued

```
His Tyr Cys Ala Pro Ala Gly Phe Ala Ile Leu Lys Cys Asn Asp Lys
            260                 265                 270

Thr Phe Asn Gly Lys Gly Pro Cys Lys Asn Val Ser Thr Val Gln Cys
        275                 280                 285

Thr His Gly Ile Arg Pro Val Val Ser Thr Gln Leu Leu Leu Asn Gly
    290                 295                 300

Ser Leu Ala Glu Glu Glu Val Val Ile Arg Ser Asp Asn Phe Thr Asn
305                 310                 315                 320

Asn Ala Lys Thr Ile Ile Val Gln Leu Lys Glu Ser Val Glu Ile Asn
                325                 330                 335

Cys Thr Arg Pro Asn Asn Thr Arg Lys Ser Ile His Ile Gly Pro
            340                 345                 350

Gly Arg Ala Phe Tyr Thr Thr Gly Glu Ile Ile Gly Asp Ile Arg Gln
        355                 360                 365

Ala His Cys Asn Ile Ser Arg Ala Lys Trp Asn Asp Thr Leu Lys Gln
    370                 375                 380

Ile Val Ile Lys Leu Arg Glu Gln Phe Glu Asn Lys Thr Ile Val Phe
385                 390                 395                 400

Asn His Ser Ser Gly Gly Asp Pro Glu Ile Val Met His Ser Phe Asn
                405                 410                 415

Cys Gly Gly Glu Phe Phe Tyr Cys Asn Ser Thr Gln Leu Phe Asn Ser
            420                 425                 430

Thr Trp Asn Asn Asn Thr Glu Gly Ser Asn Asn Thr Glu Gly Asn Thr
        435                 440                 445

Ile Thr Leu Pro Cys Arg Ile Lys Gln Ile Ile Asn Met Trp Gln Glu
    450                 455                 460

Val Gly Lys Ala Met Tyr Ala Pro Pro Ile Arg Gly Gln Ile Arg Cys
465                 470                 475                 480

Ser Ser Asn Ile Thr Gly Leu Leu Leu Thr Arg Asp Gly Gly Ile Asn
                485                 490                 495

Glu Asn Gly Thr Glu Ile Phe Arg Pro Gly Gly Gly Asp Met Arg Asp
            500                 505                 510

Asn Trp Arg Ser Glu Leu Tyr Lys Tyr Lys Val Val Lys Ile Glu Pro
        515                 520                 525

Leu Gly Val Ala Pro Thr Lys Ala Lys Arg Arg Val Val Gln Arg Glu
    530                 535                 540

Lys Arg
545

<210> SEQ ID NO 40
<211> LENGTH: 531
<212> TYPE: PRT
<213> ORGANISM: Artificial
<220> FEATURE:
<223> OTHER INFORMATION: gp120 hGM-CSF

<400> SEQUENCE: 40

Gly Ala Arg Val Glu Lys Leu Trp Val Thr Val Tyr Tyr Gly Val

```
His Phe Asn Met Trp Lys Asn Met Val Glu Gln Met Gln Glu Asp
 65                  70                  75                  80

Ile Ile Ser Leu Trp Asp Gln Ser Leu Lys Pro Cys Val Lys Leu Thr
                 85                  90                  95

Pro Leu Cys Val Gly Ser Gly Ser Thr Gln Pro Trp Glu His Val Asn
            100                 105                 110

Ala Ile Gln Glu Ala Arg Arg Leu Leu Asn Leu Ser Arg Asp Thr Ala
            115                 120                 125

Ala Glu Met Asn Glu Thr Val Glu Val Ile Ser Glu Met Phe Asp Leu
        130                 135                 140

Gln Glu Pro Thr Cys Leu Gln Thr Arg Leu Glu Leu Tyr Lys Gln Gly
145                 150                 155                 160

Leu Arg Gly Ser Leu Thr Lys Leu Lys Gly Pro Leu Thr Met Met Ala
                165                 170                 175

Ser His Tyr Lys Gln His Cys Pro Pro Thr Pro Glu Thr Ser Cys Ala
            180                 185                 190

Thr Gln Ile Ile Thr Phe Glu Ser Phe Lys Glu Asn Leu Lys Asp Phe
            195                 200                 205

Leu Leu Val Ile Pro Phe Asp Cys Trp Gly Ser Gly Ser Cys Asp Thr
210                 215                 220

Ser Val Ile Thr Gln Ala Cys Pro Lys Ile Ser Phe Glu Pro Ile Pro
225                 230                 235                 240

Ile His Tyr Cys Ala Pro Ala Gly Phe Ala Ile Leu Lys Cys Asn Asp
            245                 250                 255

Lys Thr Phe Asn Gly Lys Gly Pro Cys Lys Asn Val Ser Thr Val Gln
                260                 265                 270

Cys Thr His Gly Ile Arg Pro Val Val Ser Thr Gln Leu Leu Leu Asn
            275                 280                 285

Gly Ser Leu Ala Glu Glu Val Val Ile Arg Ser Asp Asn Phe Thr
290                 295                 300

Asn Asn Ala Lys Thr Ile Ile Val Gln Leu Lys Glu Ser Val Glu Ile
305                 310                 315                 320

Asn Cys Thr Arg Pro Asn Asn Asn Thr Arg Lys Ser Ile His Ile Gly
                325                 330                 335

Pro Gly Arg Ala Phe Tyr Thr Thr Gly Glu Ile Ile Gly Asp Ile Arg
            340                 345                 350

Gln Ala His Cys Asn Ile Ser Arg Ala Lys Trp Asn Asp Thr Leu Lys
            355                 360                 365

Gln Ile Val Ile Lys Leu Arg Glu Gln Phe Glu Asn Lys Thr Ile Val
        370                 375                 380

Phe Asn His Ser Ser Gly Gly Asp Pro Glu Ile Val Met His Ser Phe
385                 390                 395                 400

Asn Cys Gly Gly Glu Phe Phe Tyr Cys Asn Ser Thr Gln Leu Phe Asn
                405                 410                 415

Ser Thr Trp Asn Asn Asn Thr Glu Gly Ser Asn Asn Thr Glu Gly Asn
            420                 425                 430

Thr Ile Thr Leu Pro Cys Arg Ile Lys Gln Ile Ile Asn Met Trp Gln
            435                 440                 445

Glu Val Gly Lys Ala Met Tyr Ala Pro Pro Ile Arg Gly Gln Ile Arg
        450                 455                 460

Cys Ser Ser Asn Ile Thr Gly Leu Leu Leu Thr Arg Asp Gly Gly Ile
465                 470                 475                 480
```

-continued

Asn Glu Asn Gly Thr Glu Ile Phe Arg Pro Gly Gly Gly Asp Met Arg
                    485                 490                 495

Asp Asn Trp Arg Ser Glu Leu Tyr Lys Tyr Lys Val Val Lys Ile Glu
            500                 505                 510

Pro Leu Gly Val Ala Pro Thr Lys Ala Lys Arg Arg Val Val Gln Arg
        515                 520                 525

Glu Lys Arg
    530

<210> SEQ ID NO 41
<211> LENGTH: 528
<212> TYPE: PRT
<213> ORGANISM: Artificial
<220> FEATURE:
<223> OTHER INFORMATION: gp120-mGM-CSF

<400> SEQUENCE: 41

```
Gly Ala Arg Val Glu Lys Leu Trp Val Thr Val Tyr Tyr Gly Val Pro
1               5                   10                  15

Val Trp Lys Glu Ala Thr Thr Thr Leu Phe Cys Ala Ser Asp Ala Lys
            20                  25                  30

Ala Tyr Asp Thr Glu Val His Asn Val Trp Ala Thr His Ala Cys Val
        35                  40                  45

Pro Thr Asp Pro Asn Pro Gln Glu Val Val Leu Glu Asn Val Thr Glu
    50                  55                  60

His Phe Asn Met Trp Lys Asn Asn Met Val Glu Gln Met Gln Glu Asp
65                  70                  75                  80

Ile Ile Ser Leu Trp Asp Gln Ser Leu Lys Pro Cys Val Lys Leu Thr
                85                  90                  95

Pro Leu Cys Val Gly Ser Gly Val Thr Arg Pro Trp Lys His Val Glu
            100                 105                 110

Ala Ile Lys Glu Ala Leu Asn Leu Leu Asp Asp Met Pro Val Thr Leu
        115                 120                 125

Asn Glu Glu Val Glu Val Val Ser Asn Glu Phe Ser Phe Lys Lys Leu
    130                 135                 140

Thr Cys Val Gln Thr Arg Leu Lys Ile Phe Glu Gln Gly Leu Arg Gly
145                 150                 155                 160

Asn Phe Thr Lys Leu Lys Gly Ala Leu Asn Met Thr Ala Ser Tyr Tyr
                165                 170                 175

Gln Thr Tyr Cys Pro Pro Thr Pro Glu Thr Asp Cys Glu Thr Gln Val
            180                 185                 190

Thr Thr Tyr Ala Asp Phe Ile Asp Ser Leu Lys Thr Phe Leu Thr Asp
        195                 200                 205

Ile Pro Phe Glu Cys Lys Gly Ser Gly Ser Cys Asp Thr Ser Val Ile
    210                 215                 220

Thr Gln Ala Cys Pro Lys Ile Ser Phe Glu Pro Ile Pro Ile His Tyr
225                 230                 235                 240

Cys Ala Pro Ala Gly Phe Ala Ile Leu Lys Cys Asn Asp Lys Thr Phe
                245                 250                 255

Asn Gly Lys Gly Pro Cys Lys Asn Val Ser Thr Val Gln Cys Thr His
            260                 265                 270

Gly Ile Arg Pro Val Val Ser Thr Gln Leu Leu Leu Asn Gly Ser Leu
        275                 280                 285

Ala Glu Glu Glu Val Val Ile Arg Ser Asp Asn Phe Thr Asn Asn Ala
    290                 295                 300
```

```
Lys Thr Ile Ile Val Gln Leu Lys Glu Ser Val Glu Ile Asn Cys Thr
305                 310                 315                 320

Arg Pro Asn Asn Asn Thr Arg Lys Ser Ile His Ile Gly Pro Gly Arg
            325                 330                 335

Ala Phe Tyr Thr Thr Gly Glu Ile Ile Gly Asp Ile Arg Gln Ala His
            340                 345                 350

Cys Asn Ile Ser Arg Ala Lys Trp Asn Asp Thr Leu Lys Gln Ile Val
            355                 360                 365

Ile Lys Leu Arg Glu Gln Phe Glu Asn Lys Thr Ile Val Phe Asn His
            370                 375                 380

Ser Ser Gly Gly Asp Pro Glu Ile Val Met His Ser Phe Asn Cys Gly
385                 390                 395                 400

Gly Glu Phe Phe Tyr Cys Asn Ser Thr Gln Leu Phe Asn Ser Thr Trp
            405                 410                 415

Asn Asn Asn Thr Glu Gly Ser Asn Asn Thr Glu Gly Asn Thr Ile Thr
            420                 425                 430

Leu Pro Cys Arg Ile Lys Gln Ile Ile Asn Met Trp Gln Glu Val Gly
            435                 440                 445

Lys Ala Met Tyr Ala Pro Pro Ile Arg Gly Gln Ile Arg Cys Ser Ser
450                 455                 460

Asn Ile Thr Gly Leu Leu Leu Thr Arg Asp Gly Gly Ile Asn Glu Asn
465                 470                 475                 480

Gly Thr Glu Ile Phe Arg Pro Gly Gly Gly Asp Met Arg Asp Asn Trp
            485                 490                 495

Arg Ser Glu Leu Tyr Lys Tyr Lys Val Val Lys Ile Glu Pro Leu Gly
            500                 505                 510

Val Ala Pro Thr Lys Ala Lys Arg Arg Val Val Gln Arg Glu Lys Arg
            515                 520                 525

<210> SEQ ID NO 42
<211> LENGTH: 513
<212> TYPE: PRT
<213> ORGANISM: Artificial
<220> FEATURE:
<223> OTHER INFORMATION: gp120 hGM-CSF 1

<400> SEQUENCE: 42

Gly Ala Arg Val Glu Lys Leu Trp Val Thr Val Tyr Tyr Gly Val Pro
1               5                   10                  15

```
Glu Leu Tyr Lys Gln Gly Leu Arg Gly Ser Leu Thr Lys Leu Lys Gly
145                 150                 155                 160

Pro Leu Thr Met Met Ala Ser His Tyr Lys Gln His Cys Pro Pro Thr
                165                 170                 175

Pro Glu Thr Ser Cys Ala Thr Gln Ile Ile Thr Phe Glu Ser Phe Lys
            180                 185                 190

Glu Asn Leu Lys Asp Phe Leu Gly Ser Gly Ser Cys Asp Thr Ser Val
        195                 200                 205

Ile Thr Gln Ala Cys Pro Lys Ile Ser Phe Glu Pro Ile Pro Ile His
    210                 215                 220

Tyr Cys Ala Pro Ala Gly Phe Ala Ile Leu Lys Cys Asn Asp Lys Thr
225                 230                 235                 240

Phe Asn Gly Lys Gly Pro Cys Lys Asn Val Ser Thr Val Gln Cys Thr
                245                 250                 255

His Gly Ile Arg Pro Val Val Ser Thr Gln Leu Leu Leu Asn Gly Ser
                260                 265                 270

Leu Ala Glu Glu Glu Val Val Ile Arg Ser Asp Asn Phe Thr Asn Asn
            275                 280                 285

Ala Lys Thr Ile Ile Val Gln Leu Lys Glu Ser Val Glu Ile Asn Cys
        290                 295                 300

Thr Arg Pro Asn Asn Asn Thr Arg Lys Ser Ile His Ile Gly Pro Gly
305                 310                 315                 320

Arg Ala Phe Tyr Thr Thr Gly Glu Ile Ile Gly Asp Ile Arg Gln Ala
                325                 330                 335

His Cys Asn Ile Ser Arg Ala Lys Trp Asn Asp Thr Leu Lys Gln Ile
                340                 345                 350

Val Ile Lys Leu Arg Glu Gln Phe Glu Asn Lys Thr Ile Val Phe Asn
        355                 360                 365

His Ser Ser Gly Gly Asp Pro Glu Ile Val Met His Ser Phe Asn Cys
    370                 375                 380

Gly Gly Glu Phe Phe Tyr Cys Asn Ser Thr Gln Leu Phe Asn Ser Thr
385                 390                 395                 400

Trp Asn Asn Asn Thr Glu Gly Ser Asn Asn Thr Glu Gly Asn Thr Ile
                405                 410                 415

Thr Leu Pro Cys Arg Ile Lys Gln Ile Ile Asn Met Trp Gln Glu Val
                420                 425                 430

Gly Lys Ala Met Tyr Ala Pro Pro Ile Arg Gly Gln Ile Arg Cys Ser
            435                 440                 445

Ser Asn Ile Thr Gly Leu Leu Leu Thr Arg Asp Gly Gly Ile Asn Glu
        450                 455                 460

Asn Gly Thr Glu Ile Phe Arg Pro Gly Gly Gly Asp Met Arg Asp Asn
465                 470                 475                 480

Trp Arg Ser Glu Leu Tyr Lys Tyr Lys Val Val Lys Ile Glu Pro Leu
                485                 490                 495

Gly Val Ala Pro Thr Lys Ala Lys Arg Arg Val Val Gln Arg Glu Lys
                500                 505                 510

Arg
```

<210> SEQ ID NO 43
<211> LENGTH: 521
<212> TYPE: PRT
<213> ORGANISM: Artificial
<220> FEATURE:
<223> OTHER INFORMATION: gp120 hGM-CSF 2

```
<400> SEQUENCE: 43

Gly Ala Arg Val Glu Lys Leu Trp Val Thr Val Tyr Tyr Gly Val Pro
1               5                   10                  15

Val Trp Lys Glu Ala Thr Thr Thr Leu Phe Cys Ala Ser Asp Ala Lys
            20                  25                  30

Ala Tyr Asp Thr Glu Val His Asn Val Trp Ala Thr His Ala Cys Val
        35                  40                  45

Pro Thr Asp Pro Asn Pro Gln Glu Val Leu Glu Asn Val Thr Glu
    50                  55                  60

His Phe Asn Met Trp Lys Asn Asn Met Val Glu Gln Met Gln Glu Asp
65                  70                  75                  80

Ile Ile Ser Leu Trp Asp Gln Ser Leu Lys Pro Cys Val Lys Leu Thr
                85                  90                  95

Pro Leu Cys Val Gly Ser Gly Trp Glu His Val Asn Ala Ile Gln Glu
            100                 105                 110

Ala Arg Arg Leu Leu Asn Leu Ser Arg Asp Thr Ala Ala Glu Met Asn
        115                 120                 125

Glu Thr Val Glu Val Ile Ser Glu Met Phe Asp Leu Gln Glu Pro Thr
    130                 135                 140

Cys Leu Gln Thr Arg Leu Glu Leu Tyr Lys Gln Gly Leu Arg Gly Ser
145                 150                 155                 160

Leu Thr Lys Leu Lys Gly Pro Leu Thr Met Met Ala Ser His Tyr Lys
                165                 170                 175

Gln His Cys Pro Pro Thr Pro Glu Thr Ser Cys Ala Thr Gln Ile Ile
            180                 185                 190

Thr Phe Glu Ser Phe Lys Glu Asn Leu Lys Asp Phe Leu Leu Val Gly
        195                 200                 205

Ser Gly Ser Cys Asp Thr Ser Val Ile Thr Gln Ala Cys Pro Lys Ile
    210                 215                 220

Ser Phe Glu Pro Ile Pro Ile His Tyr Cys Ala Pro Ala Gly Phe Ala
225                 230                 235                 240

Ile Leu Lys Cys Asn Asp Lys Thr Phe Asn Gly Lys Gly Pro Cys Lys
                245                 250                 255

Asn Val Ser Thr Val Gln Cys Thr His Gly Ile Arg Pro Val Val Ser
            260                 265                 270

Thr Gln Leu Leu Leu Asn Gly Ser Leu Ala Glu Glu Val Val Ile
        275                 280                 285

Arg Ser Asp Asn Phe Thr Asn Asn Ala Lys Thr Ile Ile Val Gln Leu
290                 295                 300

Lys Glu Ser Val Glu Ile Asn Cys Thr Arg Pro Asn Asn Asn Thr Arg
305                 310                 315                 320

Lys Ser Ile His Ile Gly Pro Gly Arg Ala Phe Tyr Thr Thr Gly Glu
                325                 330                 335

Ile Ile Gly Asp Ile Arg Gln Ala His Cys Asn Ile Ser Arg Ala Lys
            340                 345                 350

Trp Asn Asp Thr Leu Lys Gln Ile Val Ile Lys Leu Arg Glu Gln Phe
        355                 360                 365

Glu Asn Lys Thr Ile Val Phe Asn His Ser Ser Gly Gly Asp Pro Glu
    370                 375                 380

Ile Val Met His Ser Phe Asn Cys Gly Gly Glu Phe Phe Tyr Cys Asn
385                 390                 395                 400

Ser Thr Gln Leu Phe Asn Ser Thr Trp Asn Asn Thr Glu Gly Ser
                405                 410                 415
```

```
Asn Asn Thr Glu Gly Asn Thr Ile Thr Leu Pro Cys Arg Ile Lys Gln
                420                 425                 430

Ile Ile Asn Met Trp Gln Glu Val Gly Lys Ala Met Tyr Ala Pro Pro
            435                 440                 445

Ile Arg Gly Gln Ile Arg Cys Ser Ser Asn Ile Thr Gly Leu Leu Leu
        450                 455                 460

Thr Arg Asp Gly Gly Ile Asn Glu Asn Gly Thr Glu Ile Phe Arg Pro
465                 470                 475                 480

Gly Gly Gly Asp Met Arg Asp Asn Trp Arg Ser Glu Leu Tyr Lys Tyr
                485                 490                 495

Lys Val Val Lys Ile Glu Pro Leu Gly Val Ala Pro Thr Lys Ala Lys
                500                 505                 510

Arg Arg Val Val Gln Arg Glu Lys Arg
            515                 520

<210> SEQ ID NO 44
<211> LENGTH: 487
<212> TYPE: PRT
<213> ORGANISM: Artificial
<220> FEATURE:
<223> OTHER INFORMATION: gp120 hGM-CSF 3

<400> SEQUENCE: 44

Gly Ala Arg Val Glu Lys Leu Trp Val Th

```
Asp Asn Phe Thr Asn Asn Ala Lys Thr Ile Ile Val Gln Leu Lys Glu
            260                 265                 270

Ser Val Glu Ile Asn Cys Thr Arg Pro Asn Asn Asn Thr Arg Lys Ser
        275                 280                 285

Ile His Ile Gly Pro Gly Arg Ala Phe Tyr Thr Thr Gly Glu Ile Ile
    290                 295                 300

Gly Asp Ile Arg Gln Ala His Cys Asn Ile Ser Arg Ala Lys Trp Asn
305                 310                 315                 320

Asp Thr Leu Lys Gln Ile Val Ile Lys Leu Arg Glu Gln Phe Glu Asn
            325                 330                 335

Lys Thr Ile Val Phe Asn His Ser Ser Gly Gly Asp Pro Glu Ile Val
        340                 345                 350

Met His Ser Phe Asn Cys Gly Gly Glu Phe Phe Tyr Cys Asn Ser Thr
    355                 360                 365

Gln Leu Phe Asn Ser Thr Trp Asn Asn Asn Thr Glu Gly Ser Asn Asn
370                 375                 380

Thr Glu Gly Asn Thr Ile Thr Leu Pro Cys Arg Ile Lys Gln Ile Ile
385                 390                 395                 400

Asn Met Trp Gln Glu Val Gly Lys Ala Met Tyr Ala Pro Pro Ile Arg
            405                 410                 415

Gly Gln Ile Arg Cys Ser Ser Asn Ile Thr Gly Leu Leu Leu Thr Arg
        420                 425                 430

Asp Gly Gly Ile Asn Glu Asn Gly Thr Glu Ile Phe Arg Pro Gly Gly
    435                 440                 445

Gly Asp Met Arg Asp Asn Trp Arg Ser Glu Leu Tyr Lys Tyr Lys Val
450                 455                 460

Val Lys Ile Glu Pro Leu Gly Val Ala Pro Thr Lys Ala Lys Arg Arg
465                 470                 475                 480

Val Val Gln Arg Glu Lys Arg
            485

<210> SEQ ID NO 45
<211> LENGTH: 248
<212> TYPE: PRT
<213> ORGANISM: Mus musculus

<400> SEQUENCE: 45

Met Ser Leu Gly Ser Leu Ala Phe Thr Leu Phe Leu Thr Val Val Ala
1               5                   10                  15

Gly Ile Lys Cys Asn Gly Thr Glu Val Cys Ala Gly Ser Pro Gly Ile
            20                  25                  30

Pro Gly Thr Pro Gly Asn His Gly Leu Pro Gly Arg Asp Gly Arg Asp
        35                  40                  45

Gly Ile Lys Gly Asp Pro Gly Pro Pro Gly Pro Met Gly Pro Pro Gly
    50                  55                  60

Gly Met Pro Gly Leu Pro Gly Arg Asp Gly Leu Pro Gly Ala Pro Gly
65                  70                  75                  80

Ala Pro Gly Glu His Gly Asp Lys Gly Glu Pro Gly Glu Arg Gly Leu
            85                  90                  95

Pro Gly Phe Pro Ala Tyr Leu Asp Glu Glu Leu Gln Thr Ala Ser Tyr
        100                 105                 110

Glu Ile Lys His Gln Ile Leu Gln Thr Met Gly Val Leu Ser Leu Gln
    115                 120                 125

Gly Ser Met Leu Ser Val Gly Asp Lys Val Phe Ser Thr Asn Gly Gln
```

```
            130                 135                 140
Ser Val Asn Phe Asp Thr Ile Arg Glu Met Cys Thr Arg Ala Gly Gly
145                 150                 155                 160

His Ile Ala Ala Pro Arg Asn Pro Glu Glu Asn Glu Ala Ile Ala Ser
                165                 170                 175

Ile Thr Lys Lys Tyr Asn Thr Tyr Pro Tyr Leu Gly Val Ile Glu Gly
                180                 185                 190

Gln Thr Pro Gly Asp Phe His Tyr Leu Asp Gly Ala Ser Val Asn Tyr
            195                 200                 205

Thr Asn Trp Tyr Pro Gly Glu Pro Arg Gly Arg Gly Lys Glu Lys Cys
        210                 215                 220

Val Glu Met Tyr Thr Asp Gly Lys Trp Asn Asp Lys Gly Cys Leu Gln
225                 230                 235                 240

Tyr Arg Leu Ala Ile Cys Glu Phe
                245

<210> SEQ ID NO 46
<211> LENGTH: 245
<212> TYPE: PRT
<213> ORGANISM: Homo sapiens

<400> SEQUENCE: 46

Met Trp Leu Cys Pro Leu Ala Leu Asn Leu Ile Leu Met Ala Ala Ser
1               5                   10                  15

Gly Ala Val Cys Glu Val Lys Asp Val Cys Val Gly Ser Pro Gly Ile
                20                  25                  30

Pro Gly Thr Pro Gly Ser His Gly Leu Pro Gly Arg Asp Gly Arg Asp
            35                  40                  45

Gly Leu Lys Gly Asp Pro Gly Pro Pro Gly Pro Met Gly Pro Pro Gly
        50                  55                  60

Glu Met Pro Cys Pro Pro Gly Asn Asp Gly Leu Pro Gly Ala Pro Gly
65                  70                  75                  80

Ile Pro Gly Glu Cys Gly Glu Lys Gly Glu Pro Gly Glu Arg Gly Pro
                85                  90                  95

Pro Gly Leu Pro Ala His Leu Asp Glu Glu Leu Gln Ala Thr Leu His
            100                 105                 110

Asp Phe Arg His Gln Ile Leu Gln Thr Arg Gly Ala Leu Ser Leu Gln
        115                 120                 125

Gly Ser Ile Met Thr Val Gly Glu Lys Val Phe Ser Ser Asn Gly Gln
130                 135                 140

Ser Ile Thr Phe Asp Ala Ile Gln Glu Ala Cys Ala Arg Ala Gly Gly
145                 150                 155                 160

Arg Ile Ala Val Pro Arg Asn Pro Glu Glu Asn Glu Ala Ile Ala Ser
                165                 170                 175

Phe Val Lys Lys Tyr Asn Thr Tyr Ala Tyr Val Gly Leu Thr Glu Gly
                180                 185                 190

Pro Ser Pro Gly Asp Phe Arg Tyr Ser Asp Gly Thr Pro Val Asn Tyr
            195                 200                 205

Thr Asn Trp Tyr Arg Gly Glu Pro Ala Gly Arg Gly Lys Glu Gln Cys
        210                 215                 220

Val Glu Met Tyr Thr Asp Gly Gln Trp Asn Asp Arg Asn Cys Leu Tyr
225                 230                 235                 240

Ser Arg Leu Thr Ile
                245
```

```
<210> SEQ ID NO 47
<211> LENGTH: 248
<212> TYPE: PRT
<213> ORGANISM: Homo sapiens

<400> SEQUENCE: 47

Met Trp Leu Cys Pro Leu Ala Leu Thr Leu Ile Leu Met Ala Ala Ser
1               5                   10                  15

Gly Ala Ala Cys Glu Val Lys Asp Val Cys Val Gly Ser Pro Gly Ile
            20                  25                  30

Pro Gly Thr Pro Gly Ser His Gly Leu Pro Gly Arg Asp Gly Arg Asp
        35                  40                  45

Gly Val Lys Gly Asp Pro Gly Pro Pro Gly Pro Met Gly Pro Pro Gly
    50                  55                  60

Glu Thr Pro Cys Pro Pro Gly Asn Asn Gly Leu Pro Gly Ala Pro Gly
65                  70                  75                  80

Val Pro Gly Glu Arg Gly Glu Lys Gly Glu Ala Gly Glu Arg Gly Pro
                85                  90                  95

Pro Gly Leu Pro Ala His Leu Asp Glu Glu Leu Gln Ala Thr Leu His
            100                 105                 110

Asp Phe Arg His Gln Ile Leu Gln Thr Arg Gly Ala Leu Ser Leu Gln
        115                 120                 125

Gly Ser Ile Met Thr Val Gly Glu Lys Val Phe Ser Ser Asn Gly Gln
    130                 135                 140

Ser Ile Thr Phe Asp Ala Ile Gln Glu Ala Cys Ala Arg Ala Gly Gly
145                 150                 155                 160

Arg Ile Ala Val Pro Arg Asn Pro Glu Glu Asn Glu Ala Ile Ala Ser
                165                 170                 175

Phe Val Lys Lys Tyr Asn Thr Tyr Ala Tyr Val Gly Leu Thr Glu Gly
            180                 185                 190

Pro Ser Pro Gly Asp Phe Arg Tyr Ser Asp Gly Thr Pro Val Asn Tyr
        195                 200                 205

Thr Asn Trp Tyr Arg Gly Glu Pro Ala Gly Arg Gly Lys Glu Gln Cys
    210                 215                 220

Val Glu Met Tyr Thr Asp Gly Gln Trp Asn Asp Arg Asn Cys Leu Tyr
225                 230                 235                 240

Ser Arg Leu Thr Ile Cys Glu Phe
                245

<210> SEQ ID NO 48
<211> LENGTH: 958
<212> TYPE: PRT
<213> ORGANISM: Artificial
<220> FEATURE:
<223> OTHER INFORMATION: JR-FL SOSIP.R6-mSPA-CD40L-H9 fusion protein

<400> SEQUENCE: 48

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Ala Val Glu Lys Leu Trp Val Thr Val Tyr Tyr Gly Val Pro
        35                  40                  45

Val Trp Lys Glu Ala Thr Thr Thr Leu Phe Cys Ala Ser Asp Ala Lys
    50                  55                  60

Ala Tyr Asp Thr Glu Val His Asn Val Trp Ala Thr His Ala Cys Val
```

-continued

```
             65                  70                  75                  80
Pro Thr Asp Pro Asn Pro Gln Glu Val Val Leu Glu Asn Val Thr Glu
                     85                  90                  95

His Phe Asn Met Trp Lys Asn Asn Met Val Glu Gln Met Gln Glu Asp
                    100                 105                 110

Ile Ile Ser Leu Trp Asp Gln Ser Leu Lys Pro Cys Val Lys Leu Thr
                115                 120                 125

Pro Leu Cys Val Thr Leu Asn Cys Lys Asp Val Asn Ala Thr Asn Thr
            130                 135                 140

Thr Asn Asp Ser Glu Gly Thr Met Glu Arg Gly Glu Ile Lys Asn Cys
145                 150                 155                 160

Ser Phe Asn Ile Thr Thr Ser Ile Arg Asp Glu Val Gln Lys Glu Tyr
                    165                 170                 175

Ala Leu Phe Tyr Lys Leu Asp Val Val Pro Ile Asp Asn Asn Asn Thr
                180                 185                 190

Ser Tyr Arg Leu Ile Ser Cys Asp Thr Ser Val Ile Thr Gln Ala Cys
                195                 200                 205

Pro Lys Ile Ser Phe Glu Pro Ile Pro Ile His Tyr Cys Ala Pro Ala
            210                 215                 220

Gly Phe Ala Ile Leu Lys Cys Asn Asp Lys Thr Phe Asn Gly Lys Gly
225                 230                 235                 240

Pro Cys Lys Asn Val Ser Thr Val Gln Cys Thr His Gly Ile Arg Pro
                    245                 250                 255

Val Val Ser Thr Gln Leu Leu Leu Asn Gly Ser Leu Ala Glu Glu Glu
                260                 265                 270

Val Val Ile Arg Ser Asp Asn Phe Thr Asn Asn Ala Lys Thr Ile Ile
                275                 280                 285

Val Gln Leu Lys Glu Ser Val Glu Ile Asn Cys Thr Arg Pro Asn Asn
            290                 295                 300

Asn Thr Arg Lys Ser Ile His Ile Gly Pro Gly Arg Ala Phe Tyr Thr
305                 310                 315                 320

Thr Gly Glu Ile Ile Gly Asp Ile Arg Gln Ala His Cys Asn Ile Ser
                    325                 330                 335

Arg Ala Lys Trp Asn Asp Thr Leu Lys Gln Ile Val Ile Lys Leu Arg
                340                 345                 350

Glu Gln Phe Glu Asn Lys Thr Ile Val Phe Asn His Ser Ser Gly Gly
                355                 360                 365

Asp Pro Glu Ile Val Met His Ser Phe Asn Cys Gly Gly Glu Phe Phe
            370                 375                 380

Tyr Cys Asn Ser Thr Gln Leu Phe Asn Ser Thr Trp Asn Asn Asn Thr
385                 390                 395                 400

Glu Gly Ser Asn Asn Thr Glu Gly Asn Thr Ile Thr Leu Pro Cys Arg
                    405                 410                 415

Ile Lys Gln Ile Ile Asn Met Trp Gln Glu Val Gly Lys Ala Met Tyr
                420                 425                 430

Ala Pro Pro Ile Arg Gly Gln Ile Arg Cys Ser Ser Asn Ile Thr Gly
            435                 440                 445

Leu Leu Leu Thr Arg Asp Gly Gly Ile Asn Glu Asn Gly Thr Glu Ile
            450                 455                 460

Phe Arg Pro Gly Gly Gly Asp Met Arg Asp Asn Trp Arg Ser Glu Leu
465                 470                 475                 480

Tyr Lys Tyr Lys Val Val Lys Ile Glu Pro Leu Gly Val Ala Pro Thr
                    485                 490                 495
```

```
Lys Cys Lys Arg Arg Val Val Gln Arg Arg Arg Arg Ala Val
            500                 505             510

Gly Ile Gly Ala Val Phe Leu Gly Phe Leu Gly Ala Ala Gly Ser Thr
        515                 520                 525

Met Gly Ala Ala Ser Met Thr Leu Thr Val Gln Ala Arg Leu Leu Leu
    530                 535                 540

Ser Gly Ile Val Gln Gln Gln Asn Asn Leu Leu Arg Ala Pro Glu Ala
545                 550                 555                 560

Gln Gln Arg Met Leu Gln Leu Thr Val Trp Gly Ile Lys Gln Leu Gln
                565                 570                 575

Ala Arg Val Leu Ala Val Glu Arg Tyr Leu Gly Asp Gln Gln Leu Leu
            580                 585                 590

Gly Ile Trp Gly Cys Ser Gly Lys Leu Ile Cys Cys Thr Ala Val Pro
        595                 600                 605

Trp Asn Ala Ser Trp Ser Asn Lys Ser Leu Asp Arg Ile Trp Asn Asn
    610                 615                 620

Met Thr Trp Met Glu Trp Glu Arg Glu Ile Asp Asn Tyr Thr Ser Glu
625                 630                 635                 640

Ile Tyr Thr Leu Ile Glu Glu Ser Gln Asn Gln Gln Glu Lys Asn Glu
                645                 650                 655

Gln Glu Leu Leu Glu Leu Asp Lys Trp Ala Ser Leu Trp Asn Trp Phe
            660                 665                 670

Asp Ile Thr Lys Trp Leu Trp Ile Leu Gly Gly Gly Thr Gly Gly
        675                 680                 685

Gly Gly Thr Gly Asn Gly Thr Glu Val Cys Ala Gly Ser Pro Gly Ile
    690                 695                 700

Pro Gly Thr Pro Gly Asn His Gly Leu Pro Gly Arg Asp Gly Arg Asp
705                 710                 715                 720

Gly Ile Lys Gly Asp Pro Gly Pro Gly Pro Met Gly Pro Pro Gly
                725                 730                 735

Gly Met Pro Gly Leu Pro Gly Arg Asp Gly Leu Pro Gly Ala Pro Gly
            740                 745                 750

Ala Pro Gly Glu His Gly Asp Lys Gly Glu Pro Gly Glu Arg Gly Leu
        755                 760                 765

Pro Gly Phe Pro Ala Tyr Leu Asp Glu Glu Leu Gln Thr Ala Leu Tyr
    770                 775                 780

Glu Ile Lys His Gln Ile Leu Gln Thr Met Gly Val Leu Ser Leu Gln
785                 790                 795                 800

Gly Gly Arg Gly Gly Asp Pro Gln Ile Ala Ala His Val Val Ser
                805                 810                 815

Glu Ala Asn Ser Asn Ala Ala Ser Val Leu Gln Trp Ala Lys Lys Gly
            820                 825                 830

Tyr Tyr Thr Met Lys Ser Asn Leu Val Met Leu Glu Asn Gly Lys Gln
        835                 840                 845

Leu Thr Val Lys Arg Glu Gly Leu Tyr Tyr Val Tyr Thr Gln Val Thr
    850                 855                 860

Phe Cys Ser Asn Arg Glu Pro Ser Ser Gln Arg Pro Phe Ile Val Gly
865                 870                 875                 880

Leu Trp Leu Lys Pro Ser Ser Gly Ser Glu Arg Ile Leu Leu Lys Ala
                885                 890                 895

Ala Asn Thr His Ser Ser Ser Gln Leu Cys Glu Gln Gln Ser Val His
            900                 905                 910
```

```
Leu Gly Gly Val Phe Glu Leu Gln Ala Gly Ala Ser Val Phe Val Asn
            915                 920                 925

Val Thr Glu Ala Ser Gln Val Ile His Arg Val Gly Phe Ser Ser Phe
        930                 935                 940

Gly Leu Leu Lys Leu His His His His His His His His
945                 950                 955

<210> SEQ ID NO 49
<211> LENGTH: 73
<212> TYPE: PRT
<213> ORGANISM: Artificial
<220> FEATURE:
<223> OTHER INFORMATION: Env SP-A junctyion variant TEMP

<400> SEQUENCE: 49

Asp Ile Thr Lys Trp Leu Trp Ile Leu Gly Gly Gly Thr Gly Gly
1               5                   10                  15

Gly Gly Thr Gly Asn Gly Thr Glu Val Cys Ala Gly Ser Pro Gly Ile
            20                  25                  30

Pro Gly Thr Pro Gly Asn His Gly Leu Pro Gly Arg Asp Gly Arg Asp
        35                  40                  45

Gly Ile Lys Gly Asp Pro Gly Pro Gly Pro Met Gly Pro Pro Gly
    50                  55                  60

Gly Met Pro Gly Leu Pro Gly Arg Asp
65                  70

<210> SEQ ID NO 50
<211> LENGTH: 68
<212> TYPE: PRT
<213> ORGANISM: Artificial
<220> FEATURE:
<223> OTHER INFORMATION: Env SP-A junction variant DWIWY

<400> SEQUENCE: 50

Asp Ile Thr Lys Gly Gly Gly Thr Gly Gly Gly Gly Thr Gly Asn
1               5                   10                  15

Gly Thr Glu Val Cys Ala Gly Ser Pro Gly Ile Pro Gly Thr Pro Gly
            20                  25                  30

Asn His Gly Leu Pro Gly Arg Asp Gly Arg Asp Gly Ile Lys Gly Asp
        35                  40                  45

Pro Gly Pro Pro Gly Pro Met Gly Pro Pro Gly Gly Met Pro Gly Leu
    50                  55                  60

Pro Gly Arg Asp
65

<210> SEQ ID NO 51
<211> LENGTH: 68
<212> TYPE: PRT
<213> ORGANISM: Artificial
<220> FEATURE:
<223> OTHER INFORMATION: Env SP-A junction variant 1

<400> SEQUENCE: 51

Asp Ile Thr Lys Gly Gly Gly Thr Gly Gly Gly Gly Thr Gly Asn
1               5                   10                  15

Gly Thr Glu Val Cys Ala Gly Ser Pro Gly Ile Pro Gly Thr Pro Gly
            20                  25                  30

Asn His Gly Leu Pro Gly Arg Asp Gly Arg Asp Gly Ile Lys Gly Asp
        35                  40                  45

Pro Gly Pro Pro Gly Pro Met Gly Pro Pro Gly Gly Met Pro Gly Leu
```

Pro Gly Arg Asp
65

<210> SEQ ID NO 52
<211> LENGTH: 70
<212> TYPE: PRT
<213> ORGANISM: Artificial
<220> FEATURE:
<223> OTHER INFORMATION: Env SP-A junction variant 1A

<400> SEQUENCE: 52

Asp Ile Thr Lys Gly Gly Gly Gly Thr Gly Gly Gly Gly Thr Gly Lys
1               5                   10                  15

Cys Asn Gly Thr Glu Val Cys Ala Gly Ser Pro Gly Ile Pro Gly Thr
                20                  25                  30

Pro Gly Asn His Gly Leu Pro Gly Arg Asp Gly Arg Asp Gly Ile Lys
            35                  40                  45

Gly Asp Pro Gly Pro Gly Pro Met Gly Pro Pro Gly Gly Met Pro
        50                  55                  60

Gly Leu Pro Gly Arg Asp
65                  70

<210> SEQ ID NO 53
<211> LENGTH: 71
<212> TYPE: PRT
<213> ORGANISM: Artificial
<220> FEATURE:
<223> OTHER INFORMATION: Env SP-A junction variant 1B

<400> SEQUENCE: 53

Asp Ile Thr Lys Gly Gly Gly Gly Thr Gly Gly Gly Gly Thr Gly Ile
1               5                   10                  15

Lys Cys Asn Gly Thr Glu Val Cys Ala Gly Ser Pro Gly Ile Pro Gly
                20                  25                  30

Thr Pro Gly Asn His Gly Leu Pro Gly Arg Asp Gly Arg Asp Gly Ile
            35                  40                  45

Lys Gly Asp Pro Gly Pro Pro Gly Pro Met Gly Pro Pro Gly Gly Met
        50                  55                  60

Pro Gly Leu Pro Gly Arg Asp
65                  70

<210> SEQ ID NO 54
<211> LENGTH: 68
<212> TYPE: PRT
<213> ORGANISM: Artificial
<220> FEATURE:
<223> OTHER INFORMATION: Env SP-A junction variant 2

<400> SEQUENCE: 54

Asp Ile Thr Lys Gly Gly Gly Gly Thr Gly Gly Gly Gly Thr Gly Glu
1               5                   10                  15

Val Lys Asp Val Cys Val Gly Ser Pro Gly Ile Pro Gly Thr Pro Gly
                20                  25                  30

Asn His Gly Leu Pro Gly Arg Asp Gly Arg Asp Gly Ile Lys Gly Asp
            35                  40                  45

Pro Gly Pro Pro Gly Pro Met Gly Pro Pro Gly Gly Met Pro Gly Leu
        50                  55                  60

Pro Gly Arg Asp
65

<210> SEQ ID NO 55
<211> LENGTH: 70
<212> TYPE: PRT
<213> ORGANISM: Artificial
<220> FEATURE:
<223> OTHER INFORMATION: Env SP-A junction variant 2A

<400> SEQUENCE: 55

Asp Ile Thr Lys Gly Gly Gly Gly Thr Gly Gly Gly Gly Thr Gly Val
1               5                   10                  15

Cys Glu Val Lys Asp Val Cys Val Gly Ser Pro Gly Ile Pro Gly Thr
            20                  25                  30

Pro Gly Asn His Gly Leu Pro Gly Arg Asp Gly Arg Asp Gly Ile Lys
        35                  40                  45

Gly Asp Pro Gly Pro Pro Gly Pro Met Gly Pro Pro Gly Gly Met Pro
    50                  55                  60

Gly Leu Pro Gly Arg Asp
65                  70

<210> SEQ ID NO 56
<211> LENGTH: 71
<212> TYPE: PRT
<213> ORGANISM: Artificial
<220> FEATURE:
<223> OTHER INFORMATION: Env SP-A junction variant 2B

<400> SEQUENCE: 56

Asp Ile Thr Lys Gly Gly Gly Gly Thr Gly Gly Gly Gly Thr Gly Ala
1               5                   10                  15

Val Cys Glu Val Lys Asp Val Cys Val Gly Ser Pro Gly Ile Pro Gly
            20                  25                  30

Thr Pro Gly Asn His Gly Leu Pro Gly Arg Asp Gly Arg Asp Gly Ile
        35                  40                  45

Lys Gly Asp Pro Gly Pro Pro Gly Pro Met Gly Pro Pro Gly Gly Met
    50                  55                  60

Pro Gly Leu Pro Gly Arg Asp
65                  70

<210> SEQ ID NO 57
<211> LENGTH: 79
<212> TYPE: PRT
<213> ORGANISM: Artificial
<220> FEATURE:
<223> OTHER INFORMATION: Env SP-A junction variant 3

<400> SEQUENCE: 57

Asp Ile Thr Lys Gly Gly Gly Gly Thr Gly Gly Gly Gly Thr Gly Ser
1               5                   10                  15

Gly Ser Gln Thr Cys Glu Asp Thr Leu Lys Thr Cys Ser Val Ile Ala
            20                  25                  30

Cys Gly Ser Pro Gly Ile Pro Gly Thr Pro Gly Asn His Gly Leu Pro
        35                  40                  45

Gly Arg Asp Gly Arg Asp Gly Ile Lys Gly Asp Pro Gly Pro Pro Gly
    50                  55                  60

Pro Met Gly Pro Pro Gly Gly Met Pro Gly Leu Pro Gly Arg Asp
65                  70                  75

<210> SEQ ID NO 58
<211> LENGTH: 68

```
<212> TYPE: PRT
<213> ORGANISM: Artificial
<220> FEATURE:
<223> OTHER INFORMATION: Env SP-A junction variant 4

<400> SEQUENCE: 58
```

Asp Ile Thr Lys Gly Gly Gly Gly Thr Gly Gly Gly Thr Gly Asn
1               5                   10                  15

Gly Thr Glu Val Cys Ala Gly Ser Pro Gly Ile Pro Gly Thr Pro Gly
            20                  25                  30

Asn His Gly Leu Pro Gly Arg Asp Gly Arg Asp Gly Ile Lys Gly Asp
        35                  40                  45

Pro Gly Pro Pro Gly Pro Met Gly Pro Pro Gly Glu Met Pro Cys Leu
    50                  55                  60

Pro Gly Arg Asp
65

```
<210> SEQ ID NO 59
<211> LENGTH: 77
<212> TYPE: PRT
<213> ORGANISM: Artificial
<220> FEATURE:
<223> OTHER INFORMATION: Env Sp-A junction variant 5

<400> SEQUENCE: 59
```

Asp Ile Thr Lys Gly Gly Gly Gly Thr Gly Gly Gly Thr Gly Asn
1               5                   10                  15

Gly Thr Glu Val Cys Ala Gly Ser Pro Gly Ile Pro Gly Arg Asp Gly
            20                  25                  30

Arg Asp Gly Pro Lys Gly Thr Pro Gly Asn His Gly Leu Pro Gly Arg
        35                  40                  45

Asp Gly Arg Asp Gly Ile Lys Gly Asp Pro Gly Pro Pro Gly Pro Met
    50                  55                  60

Gly Pro Pro Gly Gly Met Pro Gly Leu Pro Gly Arg Asp
65                  70                  75

```
<210> SEQ ID NO 60
<211> LENGTH: 248
<212> TYPE: PRT
<213> ORGANISM: Mus musculus

<400> SEQUENCE: 60
```

Met Ser Leu Gly Ser Leu Ala Phe Thr Leu Phe Leu Thr Val Val Ala
1               5                   10                  15

Gly Ile Lys Cys Asn Gly Thr Glu Val Cys Ala Gly Ser Pro Gly Ile
            20                  25                  30

Pro Gly Thr Pro Gly Asn His Gly Leu Pro Gly Arg Asp Gly Arg Asp
        35                  40                  45

Gly Ile Lys Gly Asp Pro Gly Pro Pro Gly Pro Met Gly Pro Pro Gly
    50                  55                  60

Gly Met Pro Gly Leu Pro Gly Arg Asp Gly Leu Pro Gly Ala Pro Gly
65                  70                  75                  80

Ala Pro Gly Glu His Gly Asp Lys Gly Glu Pro Gly Glu Arg Gly Leu
            85                  90                  95

Pro Gly Phe Pro Ala Tyr Leu Asp Glu Glu Leu Gln Thr Ala Ser Tyr
        100                 105                 110

Glu Ile Lys His Gln Ile Leu Gln Thr Met Gly Val Leu Ser Leu Gln
        115                 120                 125

```
Gly Ser Met Leu Ser Val Gly Asp Lys Val Phe Ser Thr Asn Gly Gln
    130                 135                 140

Ser Val Asn Phe Asp Thr Ile Arg Glu Met Cys Thr Arg Ala Gly Gly
145                 150                 155                 160

His Ile Ala Ala Pro Arg Asn Pro Glu Asn Glu Ala Ile Ala Ser
                165                 170                 175

Ile Thr Lys Lys Tyr Asn Thr Tyr Pro Tyr Leu Gly Val Ile Glu Gly
                180                 185                 190

Gln Thr Pro Gly Asp Phe His Tyr Leu Asp Gly Ala Ser Val Asn Tyr
                195                 200                 205

Thr Asn Trp Tyr Pro Gly Glu Pro Arg Gly Arg Gly Lys Glu Lys Cys
    210                 215                 220

Val Glu Met Tyr Thr Asp Gly Lys Trp Asn Asp Lys Gly Cys Leu Gln
225                 230                 235                 240

Tyr Arg Leu Ala Ile Cys Glu Phe
                245
```

```
<210> SEQ ID NO 61
<211> LENGTH: 247
<212> TYPE: PRT
<213> ORGANISM: Mus musculus

<400> SEQUENCE: 61

Met Leu Leu Leu Gln Ala Leu Leu Phe Leu Leu Ile Leu Pro Ser His
1               5                   10                  15

Ala Glu Asp Asp Val Thr Thr Thr Glu Glu Leu Ala Pro Ala Leu Val
                20                  25                  30

Pro Pro Pro Lys Gly Thr Cys Ala Gly Trp Met Ala Gly Ile Pro Gly
            35                  40                  45

His Pro Gly His Asn Gly Thr Pro Gly Arg Asp Gly Arg Asp Gly Thr
        50                  55                  60

Pro Gly Glu Lys Gly Glu Lys Gly Asp Ala Gly Leu Leu Gly Pro Lys
65                  70                  75                  80

Gly Glu Thr Gly Asp Val Gly Met Thr Gly Ala Glu Gly Pro Arg Gly
                85                  90                  95

Phe Pro Gly Thr Pro Gly Arg Lys Gly Glu Pro Gly Glu Ala Ala Tyr
            100                 105                 110

Val Tyr Arg Ser Ala Phe Ser Val Gly Leu Glu Thr Arg Val Thr Val
        115                 120                 125

Pro Asn Val Pro Ile Arg Phe Thr Lys Ile Phe Tyr Asn Gln Gln Asn
130                 135                 140

His Tyr Asp Gly Ser Thr Gly Lys Phe Tyr Cys Asn Ile Pro Gly Leu
145                 150                 155                 160

Tyr Tyr Phe Ser Tyr His Ile Thr Val Tyr Met Lys Asp Val Lys Val
                165                 170                 175

Ser Leu Phe Lys Lys Asp Lys Ala Val Leu Phe Thr Tyr Asp Gln Tyr
                180                 185                 190

Gln Glu Lys Asn Val Asp Gln Ala Ser Gly Ser Val Leu Leu His Leu
            195                 200                 205

Glu Val Gly Asp Gln Val Trp Leu Gln Val Tyr Gly Asp Gly Asp His
        210                 215                 220

Asn Gly Leu Tyr Ala Asp Asn Val Asn Asp Ser Thr Phe Thr Gly Phe
225                 230                 235                 240

Leu Leu Tyr His Asp Thr Asn
                245
```

<210> SEQ ID NO 62
<211> LENGTH: 245
<212> TYPE: PRT
<213> ORGANISM: Mus musculus

<400> SEQUENCE: 62

Met Glu Thr Ser Gln Gly Trp Leu Val Ala Cys Val Leu Thr Met Thr
1               5                   10                  15

Leu Val Trp Thr Val Ala Glu Asp Val Cys Arg Ala Pro Asn Gly Lys
                20                  25                  30

Asp Gly Ala Pro Gly Asn Pro Gly Arg Pro Gly Arg Pro Gly Leu Lys
            35                  40                  45

Gly Glu Arg Gly Glu Pro Gly Ala Ala Gly Ile Arg Thr Gly Ile Arg
        50                  55                  60

Gly Phe Lys Gly Asp Pro Gly Glu Ser Gly Pro Pro Gly Lys Pro Gly
65                  70                  75                  80

Asn Val Gly Leu Pro Gly Pro Ser Gly Pro Leu Gly Asp Ser Gly Pro
                85                  90                  95

Gln Gly Leu Lys Gly Val Lys Gly Asn Pro Gly Asn Ile Arg Asp Gln
            100                 105                 110

Pro Arg Pro Ala Phe Ser Ala Ile Arg Gln Asn Pro Met Thr Leu Gly
        115                 120                 125

Asn Val Val Ile Phe Asp Lys Val Leu Thr Asn Gln Glu Ser Pro Tyr
130                 135                 140

Gln Asn His Thr Gly Arg Phe Ile Cys Ala Val Pro Gly Phe Tyr Tyr
145                 150                 155                 160

Phe Asn Phe Gln Val Ile Ser Lys Trp Asp Leu Cys Leu Phe Ile Lys
                165                 170                 175

Ser Ser Ser Gly Gly Gln Pro Arg Asp Ser Leu Ser Phe Ser Asn Thr
            180                 185                 190

Asn Asn Lys Gly Leu Phe Gln Val Leu Ala Gly Gly Thr Val Leu Gln
        195                 200                 205

Leu Arg Arg Gly Asp Glu Val Trp Ile Glu Lys Asp Pro Ala Lys Gly
    210                 215                 220

Arg Ile Tyr Gln Gly Thr Glu Ala Asp Ser Ile Phe Ser Gly Phe Leu
225                 230                 235                 240

Ile Phe Pro Ser Ala
                245

<210> SEQ ID NO 63
<211> LENGTH: 253
<212> TYPE: PRT
<213> ORGANISM: Mus musculus

<400> SEQUENCE: 63

Met Lys Thr Gln Trp Gly Glu Val Trp Thr His Leu Leu Leu Leu Leu
1               5                   10                  15

Leu Gly Phe Leu His Val Ser Trp Ala Gln Ser Ser Cys Thr Gly Pro
                20                  25                  30

Pro Gly Ile Pro Gly Ile Pro Gly Val Pro Gly Val Pro Gly Ser Asp
            35                  40                  45

Gly Gln Pro Gly Thr Pro Gly Ile Lys Gly Glu Lys Gly Leu Pro Gly
        50                  55                  60

Leu Ala Gly Asp Leu Gly Glu Phe Gly Glu Lys Gly Asp Pro Gly Ile
65                  70                  75                  80

```
Pro Gly Thr Pro Gly Lys Val Gly Pro Lys Gly Pro Val Gly Pro Lys
                85                  90                  95

Gly Thr Pro Gly Pro Ser Gly Pro Arg Gly Pro Lys Gly Asp Ser Gly
            100                 105                 110

Asp Tyr Gly Ala Thr Gln Lys Val Ala Phe Ser Ala Leu Arg Thr Ile
        115                 120                 125

Asn Ser Pro Leu Arg Pro Asn Gln Val Ile Arg Phe Glu Lys Val Ile
130                 135                 140

Thr Asn Ala Asn Glu Asn Tyr Glu Pro Arg Asn Gly Lys Phe Thr Cys
145                 150                 155                 160

Lys Val Pro Gly Leu Tyr Tyr Phe Thr Tyr His Ala Ser Ser Arg Gly
                165                 170                 175

Asn Leu Cys Val Asn Leu Val Arg Gly Arg Asp Arg Asp Ser Met Gln
            180                 185                 190

Lys Val Val Thr Phe Cys Asp Tyr Ala Gln Asn Thr Phe Gln Val Thr
        195                 200                 205

Thr Gly Gly Val Val Leu Lys Leu Glu Gln Glu Glu Val Val His Leu
210                 215                 220

Gln Ala Thr Asp Lys Asn Ser Leu Leu Gly Ile Glu Gly Ala Asn Ser
225                 230                 235                 240

Ile Phe Thr Gly Phe Leu Leu Phe Pro Asp Met Asp Ala
                245                 250

<210> SEQ ID NO 64
<211> LENGTH: 246
<212> TYPE: PRT
<213> ORGANISM: Mus musculus

<400> SEQUENCE: 64

Met Val Val Gly Pro Ser Cys Gln Pro Gln Cys Gly Leu Cys Leu Leu
1               5                   10                  15

Leu Leu Phe Leu Leu Ala Leu Pro Leu Arg Ser Gln Ala Ser Ala Gly
                20                  25                  30

Cys Tyr Gly Ile Pro Gly Met Pro Gly Met Pro Gly Ala Pro Gly Lys
            35                  40                  45

Asp Gly His Asp Gly Leu Gln Gly Pro Lys Gly Glu Pro Gly Ile Pro
        50                  55                  60

Ala Val Pro Gly Thr Gln Gly Pro Lys Gly Gln Lys Gly Glu Pro Gly
65                  70                  75                  80

Met Pro Gly His Arg Gly Lys Asn Gly Pro Arg Gly Thr Ser Gly Leu
                85                  90                  95

Pro Gly Asp Pro Gly Pro Arg Gly Pro Pro Gly Glu Pro Gly Val Glu
            100                 105                 110

Gly Arg Tyr Lys Gln Lys His Gln Ser Val Phe Thr Val Thr Arg Gln
        115                 120                 125

Thr Thr Gln Tyr Pro Glu Ala Asn Ala Leu Val Arg Phe Asn Ser Val
130                 135                 140

Val Thr Asn Pro Gln Gly His Tyr Asn Pro Ser Thr Gly Lys Phe Thr
145                 150                 155                 160

Cys Glu Val Pro Gly Leu Tyr Tyr Phe Val Tyr Tyr Thr Ser His Thr
                165                 170                 175

Ala Asn Leu Cys Val His Leu Asn Leu Asn Leu Ala Arg Val Ala Ser
            180                 185                 190

Phe Cys Asp His Met Phe Asn Ser Lys Gln Val Ser Ser Gly Gly Ala
```

```
                    195                 200                 205
Leu Leu Arg Leu Gln Arg Gly Asp Glu Val Trp Leu Ser Val Asn Asp
    210                 215                 220

Tyr Asn Gly Met Val Gly Ile Glu Gly Ser Asn Ser Val Phe Ser Gly
225                 230                 235                 240

Phe Leu Leu Phe Pro Asp
                245

<210> SEQ ID NO 65
<211> LENGTH: 244
<212> TYPE: PRT
<213> ORGANISM: Mus musculus

<400> SEQUENCE: 65

Met Ser Ile Phe Thr Ser Phe Leu Leu Cys Val Val Thr Val Val
1               5                   10                  15

Tyr Ala Glu Thr Leu Thr Glu Gly Val Gln Asn Ser Cys Pro Val Val
            20                  25                  30

Thr Cys Ser Ser Pro Gly Leu Asn Gly Phe Pro Gly Lys Asp Gly Arg
        35                  40                  45

Asp Gly Ala Lys Gly Glu Lys Gly Glu Pro Gly Gln Gly Leu Arg Gly
50                  55                  60

Leu Gln Gly Pro Pro Gly Lys Val Gly Pro Thr Gly Pro Pro Gly Asn
65                  70                  75                  80

Pro Gly Leu Lys Gly Ala Val Gly Pro Lys Gly Asp Arg Gly Asp Arg
                85                  90                  95

Ala Glu Phe Asp Thr Ser Glu Ile Asp Ser Glu Ile Ala Ala Leu Arg
            100                 105                 110

Ser Glu Leu Arg Ala Leu Arg Asn Trp Val Leu Phe Ser Leu Ser Glu
        115                 120                 125

Lys Val Gly Lys Lys Tyr Phe Val Ser Ser Val Lys Lys Met Ser Leu
    130                 135                 140

Asp Arg Val Lys Ala Leu Cys Ser Glu Phe Gln Gly Ser Val Ala Thr
145                 150                 155                 160

Pro Arg Asn Ala Glu Glu Asn Ser Ala Ile Gln Lys Val Ala Lys Asp
                165                 170                 175

Ile Ala Tyr Leu Gly Ile Thr Asp Val Arg Val Glu Gly Ser Phe Glu
            180                 185                 190

Asp Leu Thr Gly Asn Arg Val Arg Tyr Thr Asn Trp Asn Asp Gly Glu
        195                 200                 205

Pro Asn Asn Thr Gly Asp Gly Glu Asp Cys Val Val Ile Leu Gly Asn
    210                 215                 220

Gly Lys Trp Asn Asp Val Pro Cys Ser Asp Ser Phe Leu Ala Ile Cys
225                 230                 235                 240

Glu Phe Ser Asp

<210> SEQ ID NO 66
<211> LENGTH: 239
<212> TYPE: PRT
<213> ORGANISM: Mus musculus

<400> SEQUENCE: 66

Met Leu Leu Leu Pro Leu Leu Pro Val Leu Leu Cys Val Val Ser Val
1               5                   10                  15

Ser Ser Ser Gly Ser Gln Thr Cys Glu Asp Thr Leu Lys Thr Cys Ser
            20                  25                  30
```

Val Ile Ala Cys Gly Arg Asp Gly Arg Asp Gly Pro Lys Gly Glu Lys
             35                  40                  45

Gly Glu Pro Gly Gln Gly Leu Arg Gly Leu Gln Gly Pro Pro Gly Lys
 50                  55                  60

Leu Gly Pro Pro Gly Ser Val Gly Ser Pro Ser Pro Gly Pro Lys
 65                  70                  75                  80

Gly Gln Lys Gly Asp His Gly Asp Asn Arg Ala Ile Glu Glu Lys Leu
             85                  90                  95

Ala Asn Met Glu Ala Glu Ile Arg Ile Leu Lys Ser Lys Leu Gln Leu
            100                 105                 110

Thr Asn Lys Leu His Ala Phe Ser Met Gly Lys Lys Ser Gly Lys Lys
            115                 120                 125

Leu Phe Val Thr Asn His Glu Lys Met Pro Phe Ser Lys Val Lys Ser
130                 135                 140

Leu Cys Thr Glu Leu Gln Gly Thr Val Ala Ile Pro Arg Asn Ala Glu
145                 150                 155                 160

Glu Asn Lys Ala Ile Gln Glu Val Ala Thr Gly Ile Ala Phe Leu Gly
            165                 170                 175

Ile Thr Asp Glu Ala Thr Glu Gly Gln Phe Met Tyr Val Thr Gly Gly
            180                 185                 190

Arg Leu Thr Tyr Ser Asn Trp Lys Lys Asp Glu Pro Asn Asn His Gly
            195                 200                 205

Ser Gly Glu Asp Cys Val Ile Ile Leu Asp Asn Gly Leu Trp Asn Asp
            210                 215                 220

Ile Ser Cys Gln Ala Ser Phe Lys Ala Val Cys Glu Phe Pro Ala
225                 230                 235

<210> SEQ ID NO 67
<211> LENGTH: 277
<212> TYPE: PRT
<213> ORGANISM: Mus musculus

<400> SEQUENCE: 67

Met Asn Gly Phe Arg Val Leu Leu Arg Ser Asn Leu Ser Met Leu Leu
 1               5                  10                  15

Leu Leu Ala Leu Leu His Phe Gln Ser Leu Gly Leu Asp Val Asp Ser
             20                  25                  30

Arg Ser Ala Ala Glu Val Cys Ala Thr His Thr Ile Ser Pro Gly Pro
             35                  40                  45

Lys Gly Asp Asp Gly Glu Arg Gly Asp Thr Gly Glu Glu Gly Lys Asp
 50                  55                  60

Gly Lys Val Gly Arg Gln Gly Pro Lys Gly Val Lys Gly Glu Leu Gly
 65                  70                  75                  80

Asp Met Gly Ala Gln Gly Asn Ile Gly Lys Ser Gly Pro Ile Gly Lys
             85                  90                  95

Lys Gly Asp Lys Gly Glu Lys Gly Leu Leu Gly Ile Pro Gly Glu Lys
            100                 105                 110

Gly Lys Ala Gly Thr Ile Cys Asp Cys Gly Arg Tyr Arg Lys Val Val
            115                 120                 125

Gly Gln Leu Asp Ile Ser Val Ala Arg Leu Lys Thr Ser Met Lys Phe
130                 135                 140

Ile Lys Asn Val Ile Ala Gly Ile Arg Glu Thr Glu Glu Lys Phe Tyr
145                 150                 155                 160

Tyr Ile Val Gln Glu Glu Lys Asn Tyr Arg Glu Ser Leu Thr His Cys

```
                   165                 170                 175

Arg Ile Arg Gly Gly Met Leu Ala Met Pro Lys Asp Glu Val Val Asn
            180                 185                 190

Thr Leu Ile Ala Asp Tyr Val Ala Lys Ser Gly Phe Phe Arg Val Phe
                195                 200                 205

Ile Gly Val Asn Asp Leu Glu Arg Glu Gly Gln Tyr Val Phe Thr Asp
            210                 215                 220

Asn Thr Pro Leu Gln Asn Tyr Ser Asn Trp Lys Glu Glu Pro Ser
225                 230                 235                 240

Asp Pro Ser Gly His Glu Asp Cys Val Glu Met Leu Ser Ser Gly Arg
                245                 250                 255

Trp Asn Asp Thr Glu Cys His Leu Thr Met Tyr Phe Val Cys Glu Phe
                260                 265                 270

Val Lys Lys Lys Lys
            275

<210> SEQ ID NO 68
<211> LENGTH: 245
<212> TYPE: PRT
<213> ORGANISM: Homo sapiens

<400> SEQUENCE: 68

Met Trp Leu Cys Pro Leu Ala Leu Asn Leu Ile Leu Met Ala Ala Ser
1               5                   10                  15

Gly Ala Val Cys Glu Val Lys Asp Val Cys Val Gly Ser Pro Gly Ile
                20                  25                  30

Pro Gly Thr Pro Gly Ser His Gly Leu Pro Gly Arg Asp Gly Arg Asp
            35                  40                  45

Gly Leu Lys Gly Asp Pro Gly Pro Gly Pro Met Gly Pro Pro Gly
50                  55                  60

Glu Met Pro Cys Pro Pro Gly Asn Asp Gly Leu Pro Gly Ala Pro Gly
65                  70                  75                  80

Ile Pro Gly Glu Cys Gly Glu Lys Gly Glu Pro Gly Glu Arg Gly Pro
                85                  90                  95

Pro Gly Leu Pro Ala His Leu Asp Glu Glu Leu Gln Ala Thr Leu His
            100                 105                 110

Asp Phe Arg His Gln Ile Leu Gln Thr Arg Gly Ala Leu Ser Leu Gln
        115                 120                 125

Gly Ser Ile Met Thr Val Gly Glu Lys Val Phe Ser Ser Asn Gly Gln
130                 135                 140

Ser Ile Thr Phe Asp Ala Ile Gln Glu Ala Cys Ala Arg Ala Gly Gly
145                 150                 155                 160

Arg Ile Ala Val Pro Arg Asn Pro Glu Glu Asn Glu Ala Ile Ala Ser
                165                 170                 175

Phe Val Lys Lys Tyr Asn Thr Tyr Ala Tyr Val Gly Leu Thr Glu Gly
            180                 185                 190

Pro Ser Pro Gly Asp Phe Arg Tyr Ser Asp Gly Thr Pro Val Asn Tyr
        195                 200                 205

Thr Asn Trp Tyr Arg Gly Glu Pro Ala Gly Arg Gly Lys Glu Gln Cys
    210                 215                 220

Val Glu Met Tyr Thr Asp Gly Gln Trp Asn Asp Arg Asn Cys Leu Tyr
225                 230                 235                 240

Ser Arg Leu Thr Ile
            245
```

```
<210> SEQ ID NO 69
<211> LENGTH: 248
<212> TYPE: PRT
<213> ORGANISM: Homo sapiens

<400> SEQUENCE: 69

Met Trp Leu Cys Pro Leu Ala Leu Thr Leu Ile Leu Met Ala Ala Ser
1               5                   10                  15

Gly Ala Ala Cys Glu Val Lys Asp Val Cys Val Gly Ser Pro Gly Ile
            20                  25                  30

Pro Gly Thr Pro Gly Ser His Gly Leu Pro Gly Arg Asp Gly Arg Asp
        35                  40                  45

Gly Val Lys Gly Asp Pro Gly Pro Pro Gly Pro Met Gly Pro Pro Gly
    50                  55                  60

Glu Thr Pro Cys Pro Pro Gly Asn Asn Gly Leu Pro Gly Ala Pro Gly
65                  70                  75                  80

Val Pro Gly Glu Arg Gly Glu Lys Gly Glu Ala Gly Glu Arg Gly Pro
                85                  90                  95

Pro Gly Leu Pro Ala His Leu Asp Glu Glu Leu Gln Ala Thr Leu His
            100                 105                 110

Asp Phe Arg His Gln Ile Leu Gln Thr Arg Gly Ala Leu Ser Leu Gln
            115                 120                 125

Gly Ser Ile Met Thr Val Gly Glu Lys Val Phe Ser Ser Asn Gly Gln
130                 135                 140

Ser Ile Thr Phe Asp Ala Ile Gln Glu Ala Cys Ala Arg Ala Gly Gly
145                 150                 155                 160

Arg Ile Ala Val Pro Arg Asn Pro Glu Glu Asn Glu Ala Ile Ala Ser
                165                 170                 175

Phe Val Lys Lys Tyr Asn Thr Tyr Ala Tyr Val Gly Leu Thr Glu Gly
            180                 185                 190

Pro Ser Pro Gly Asp Phe Arg Tyr Ser Asp Gly Thr Pro Val Asn Tyr
        195                 200                 205

Thr Asn Trp Tyr Arg Gly Glu Pro Ala Gly Arg Gly Lys Glu Gln Cys
    210                 215                 220

Val Glu Met Tyr Thr Asp Gly Gln Trp Asn Asp Arg Asn Cys Leu Tyr
225                 230                 235                 240

Ser Arg Leu Thr Ile Cys Glu Phe
                245

<210> SEQ ID NO 70
<211> LENGTH: 12
<212> TYPE: PRT
<213> ORGANISM: Artificial
<220> FEATURE:
<223> OTHER INFORMATION: V1/V2 deletion variant 1

<400> SEQUENCE: 70

Gln Ser Leu Lys Pro Ala Ala Pro Lys Val Ser Phe
1               5                   10

<210> SEQ ID NO 71
<211> LENGTH: 28
<212> TYPE: PRT
<213> ORGANISM: Artificial
<220> FEATURE:
<223> OTHER INFORMATION: V1/V2 deletion variant 2

<400> SEQUENCE: 71
```

```
Gln Ser Leu Lys Pro Cys Val Lys Leu Thr Pro Leu Ala Ala Asn Thr
1               5                   10                  15

Ser Val Ile Thr Gln Ala Cys Pro Lys Val Ser Phe
            20                  25
```

<210> SEQ ID NO 72
<211> LENGTH: 31
<212> TYPE: PRT
<213> ORGANISM: Artificial
<220> FEATURE:
<223> OTHER INFORMATION: Vi/V2 deletion variant 4

<400> SEQUENCE: 72

```
Gln Ser Leu Lys Pro Cys Val Lys Leu Thr Pro Leu Cys Gly Ala Gly
1               5                   10                  15

Cys Asp Thr Ser Val Ile Thr Gln Ala Cys Pro Lys Val Ser Phe
            20                  25                  30
```

<210> SEQ ID NO 73
<211> LENGTH: 44
<212> TYPE: PRT
<213> ORGANISM: Artificial
<220> FEATURE:
<223> OTHER INFORMATION: V1/V2 deletion variant 3

<400> SEQUENCE: 73

```
Gln Ser Leu Lys Pro Cys Val Lys Leu Thr Pro Leu Cys Val Thr Leu
1               5                   10                  15

Asn Cys Lys Gly Ala Gly Asn Cys Ser Gly Ala Gly Ser Cys Asp Thr
            20                  25                  30

Ser Val Ile Thr Gln Ala Cys Pro Lys Val Ser Phe
        35                  40
```

<210> SEQ ID NO 74
<211> LENGTH: 102
<212> TYPE: PRT
<213> ORGANISM: Artificial
<220> FEATURE:
<223> OTHER INFORMATION: V1/V2 wild type

<400> SEQUENCE: 74

```
Gln Ser Leu Lys Pro Cys Val Lys Leu Thr Pro Leu Cys Val Ser Leu
1               5                   10                  15

Lys Cys Thr Asp Leu Gly Asn Ala Thr Asn Thr Asn Ser Ser Asn Thr
            20                  25                  30

Asn Ser Ser Ser Gly Glu Met Met Met Glu Lys Gly Glu Ile Lys Asn
        35                  40                  45

Cys Ser Phe Asn Ile Ser Thr Ser Ile Arg Gly Lys Val Gln Lys Glu
50                  55                  60

Tyr Ala Phe Phe Tyr Lys Leu Asp Ile Ile Pro Ile Asp Asn Asp Thr
65                  70                  75                  80

Thr Ser Tyr Thr Leu Thr Ser Cys Asn Thr Ser Val Ile Thr Gln Ala
            85                  90                  95

Cys Pro Lys Val Ser Phe
                100
```

<210> SEQ ID NO 75
<211> LENGTH: 62
<212> TYPE: PRT
<213> ORGANISM: Artificial
<220> FEATURE:
<223> OTHER INFORMATION: V1/V2 deletion mutant 6

<400> SEQUENCE: 75

Gln Ser Leu Lys Pro Cys Val Lys Leu Thr Pro Leu Cys Val Ser Leu
1               5                   10                  15

Lys Cys Thr Asp Leu Lys Asn Asp Thr Asn Thr Asn Ser Ser Ser Gly
            20                  25                  30

Arg Met Ile Met Glu Lys Gly Glu Ile Lys Asn Cys Ser Phe Asn Ile
        35                  40                  45

Ser Thr Ser Ile Arg Gly Lys Ala Cys Pro Lys Val Ser Phe
    50                  55                  60

<210> SEQ ID NO 76
<211> LENGTH: 27
<212> TYPE: PRT
<213> ORGANISM: Artificial
<220> FEATURE:
<223> OTHER INFORMATION: V1/V2 deletion variant 5

<400> SEQUENCE: 76

Gln Ser Leu Lys Pro Cys Val Lys Leu Thr Pro Leu Cys Val Ser Leu
1               5                   10                  15

Lys Cys Thr Glu Ala Cys Pro Lys Val Ser Phe
            20                  25

<210> SEQ ID NO 77
<211> LENGTH: 33
<212> TYPE: PRT
<213> ORGANISM: Artificial
<220> FEATURE:
<223> OTHER INFORMATION: V1/V2 deletion variant 8-12

<400> SEQUENCE: 77

Gln Ser Leu Lys Pro Cys Val Lys Leu Thr Pro Leu Cys Val Gly Ala
1               5                   10                  15

Gly Ser Cys Asn Thr Ser Val Ile Thr Gln Ala Cys Pro Lys Val Ser
            20                  25                  30

Phe

<210> SEQ ID NO 78
<211> LENGTH: 17
<212> TYPE: PRT
<213> ORGANISM: Artificial
<220> FEATURE:
<223> OTHER INFORMATION: V1/V2 deletion variant 14

<400> SEQUENCE: 78

Gln Ser Leu Lys Pro Cys Val Gly Ala Gly Ala Cys Pro Lys Val Ser
1               5                   10                  15

Phe

<210> SEQ ID NO 79
<211> LENGTH: 62
<212> TYPE: PRT
<213> ORGANISM: Artificial
<220> FEATURE:
<223> OTHER INFORMATION: V1/V2 deletion variant 6C

<400> SEQUENCE: 79

Gln Ser Leu Lys Pro Cys Val Lys Leu Thr Pro Leu Cys Val Ser Leu
1               5                   10                  15

Lys Tyr Thr Asp Leu Lys Asn Asp Thr Asn Thr Asn Ser Ser Ser Gly
            20                  25                  30

```
Arg Met Ile Met Glu Lys Gly Glu Ile Lys Asn Cys Ser Phe Asn Ile
         35                  40                  45

Ser Thr Ser Ile Arg Gly Lys Ala Cys Pro Lys Val Ser Phe
     50                  55                  60

<210> SEQ ID NO 80
<211> LENGTH: 62
<212> TYPE: PRT
<213> ORGANISM: Artificial
<220> FEATURE:
<223> OTHER INFORMATION: V1/V2 deletion variant 6C

<400> SEQUENCE: 80

Gln Ser Leu Lys Pro Cys Val Lys Leu Thr Pro Leu Cys Val Ser Leu
1               5                   10                  15

Lys Tyr Thr Asp Leu Lys Asn Asp Thr Asn Thr Asn Ser Ser Ser Gly
            20                  25                  30

Arg Met Ile Met Glu Lys Gly Glu Ile Lys Lys Cys Ser Phe Asn Ile
         35                  40                  45

Ser Thr Ser Ile Arg Gly Lys Ala Cys Pro Lys Val Ser Phe
     50                  55                  60

<210> SEQ ID NO 81
<211> LENGTH: 26
<212> TYPE: PRT
<213> ORGANISM: Artificial
<220> FEATURE:
<223> OTHER INFORMATION: V3 deletion variant 17

<400> SEQUENCE: 81

Glu Ile Asn Cys Thr Arg Pro Asn Asn Asn Thr Arg Gly Pro Gly Arg
1               5                   10                  15

Ala Phe Val Thr Ala His Cys Asn Ile Ser
            20                  25

<210> SEQ ID NO 82
<211> LENGTH: 33
<212> TYPE: PRT
<213> ORGANISM: Artificial
<220> FEATURE:
<223> OTHER INFORMATION: V3 deletion variant 16

<400> SEQUENCE: 82

Glu Ile Asn Cys Thr Arg Pro Asn Asn Asn Thr Arg Lys Ser Ile Arg
1               5                   10                  15

Ile Gln Arg Gly Pro Gly Arg Ala Phe Val Thr Ala His Cys Asn Ile
            20                  25                  30

Ser

<210> SEQ ID NO 83
<211> LENGTH: 35
<212> TYPE: PRT
<213> ORGANISM: Artificial
<220> FEATURE:
<223> OTHER INFORMATION: V3 deletion variant 15

<400> SEQUENCE: 83

Glu Ile Asn Cys Thr Arg Pro Asn Asn Asn Thr Arg Gly Pro Gly Arg
1               5                   10                  15

Ala Phe Val Thr Ile Gly Lys Ile Gly Asn Met Arg Gln Ala His Cys
            20                  25                  30
```

```
Asn Ile Ser
        35

<210> SEQ ID NO 84
<211> LENGTH: 42
<212> TYPE: PRT
<213> ORGANISM: Artificial
<220> FEATURE:
<223> OTHER INFORMATION: V3 wild type

<400> SEQUENCE: 84

Glu Ile Asn Cys Thr Arg Pro Asn Asn Asn Thr Arg Lys Ser Ile Arg
1               5                   10                  15

Ile Gln Arg Gly Pro Gly Arg Ala Phe Val Thr Ile Gly Lys Ile Gly
            20                  25                  30

Asn Met Arg Gln Ala His Cys Asn Ile Ser
        35                  40

<210> SEQ ID NO 85
<211> LENGTH: 511
<212> TYPE: PRT
<213> ORGANISM: Human immunodeficiency virus type 1

<400> SEQUENCE: 85

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Glu Val Val Ile
```

```
                260                 265                 270
Arg Ser Val Asn Phe Thr Asp Asn Ala Lys Thr Ile Ile Val Gln Leu
        275                 280                 285

Asn Thr Ser Val Glu Ile Asn Cys Thr Arg Pro Asn Asn Asn Thr Arg
        290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
        340                 345                 350

Phe Gly Asn Asn Lys Thr Ile Ile Phe Lys Gln Ser Ser Gly Gly Asp
        355                 360                 365

Pro Glu Ile Val Thr His Ser Phe Asn Cys Gly Gly Glu Phe Phe Tyr
        370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
        420                 425                 430

Ala Met Tyr Ala Pro Pro Ile Ser Gly Gln Ile Arg Cys Ser Ser Asn
        435                 440                 445

Ile Thr Gly Leu Leu Leu Thr Arg Asp Gly Gly Asn Ser Asn Asn Glu
        450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg
        500                 505                 510

<210> SEQ ID NO 86
<211> LENGTH: 516
<212> TYPE: PRT
<213> ORGANISM: Human immunodeficiency virus type 1

<400> SEQUENCE: 86

Met Arg Val Lys Glu Lys Tyr Gln His Leu Trp Arg Trp Gly Trp Lys
1               5                   10                  15

Trp Gly Thr Met Leu Leu Gly Ile Leu Met Ile Cys Ser Ala Thr Glu
                20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125
```

```
Leu Lys Cys Thr Asp Leu Gly Asn Ala Thr Asn Thr Asn Ser Ser Asn
    130                 135                 140
Thr Asn Ser Ser Ser Gly Glu Met Met Met Glu Lys Gly Glu Ile Lys
145                 150                 155                 160
Asn Cys Ser Phe Asn Ile Ser Thr Ser Ile Arg Gly Lys Val Gln Lys
                165                 170                 175
Glu Tyr Ala Phe Phe Tyr Lys Leu Asp Ile Ile Pro Ile Asp Asn Asp
            180                 185                 190
Thr Thr Ser Tyr Thr Leu Thr Ser Cys Asn Thr Ser Val Ile Thr Gln
        195                 200                 205
Ala Cys Pro Lys Val Ser Phe Glu Pro Ile Pro Ile His Tyr Cys Ala
    210                 215                 220
Pro Ala Gly Phe Ala Ile Leu Lys Cys Asn Asn Lys Thr Phe Asn Gly
225                 230                 235                 240
Thr Gly Pro Cys Thr Asn Val Ser Thr Val Gln Cys Thr His Gly Ile
                245                 250                 255
Arg Pro Val Val Ser Thr Gln Leu Leu Leu Asn Gly Ser Leu Ala Glu
            260                 265                 270
Glu Glu Val Val Ile Arg Ser Ala Asn Phe Thr Asp Asn Ala Lys Thr
        275                 280                 285
Ile Ile Val Gln Leu Asn Gln Ser Val Glu Ile Asn Cys Thr Arg Pro
    290                 295                 300
Asn Asn Asn Thr Arg Lys Ser Ile Arg Ile Gln Arg Gly Pro Gly Arg
305                 310                 315                 320
Ala Phe Val Thr Ile Gly Lys Ile Gly Asn Met Arg Gln Ala His Cys
                325                 330                 335
Asn Ile Ser Arg Ala Lys Trp Asn Ala Thr Leu Lys Gln Ile Ala Ser
            340                 345                 350
Lys Leu Arg Glu Gln Phe Gly Asn Asn Lys Thr Ile Ile Phe Lys Gln
        355                 360                 365
Ser Ser Gly Gly Asp Pro Glu Ile Val Thr His Ser Phe Asn Cys Gly
    370                 375                 380
Gly Glu Phe Phe Tyr Cys Asn Ser Thr Gln Leu Phe Asn Ser Thr Trp
385                 390                 395                 400
Phe Asn Ser Thr Trp Ser Thr Glu Gly Ser Asn Asn Thr Glu Gly Ser
                405                 410                 415
Asp Thr Ile Thr Leu Pro Cys Arg Ile Lys Gln Phe Ile Asn Met Trp
            420                 425                 430
Gln Glu Val Gly Lys Ala Met Tyr Ala Pro Pro Ile Ser Gly Gln Ile
        435                 440                 445
Arg Cys Ser Ser Asn Ile Thr Gly Leu Leu Leu Thr Arg Asp Gly Gly
    450                 455                 460
Asn Asn Asn Asn Gly Ser Glu Ile Phe Arg Pro Gly Gly Gly Asp Met
465                 470                 475                 480
Arg Asp Asn Trp Arg Ser Glu Leu Tyr Lys Tyr Lys Val Val Lys Ile
                485                 490                 495
Glu Pro Leu Gly Val Ala Pro Thr Lys Ala Lys Arg Arg Val Val Gln
            500                 505                 510
Arg Glu Lys Arg
        515

<210> SEQ ID NO 87
<211> LENGTH: 508
<212> TYPE: PRT
```

<213> ORGANISM: Human immunodeficiency virus type 1

<400> SEQUENCE: 87

```
Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Ala Val Glu Lys Leu Trp Val Thr Val Tyr Tyr Gly Val Pro
        35                  40                  45

Val Trp Lys Glu Ala Thr Thr Thr Leu Phe Cys Ala Ser Asp Ala Lys
50                  55                  60

Ala Tyr Asp Thr Glu Val His Asn Val Trp Ala Thr His Ala Cys Val
65                  70                  75                  80

Pro Thr Asp Pro Asn Pro Gln Glu Val Val Leu Glu Asn Val Thr Glu
                85                  90                  95

His Phe Asn Met Trp Lys Asn Asn Met Val Glu Gln Met Gln Glu Asp
            100                 105                 110

Ile Ile Ser Leu Trp Asp Gln Ser Leu Lys Pro Cys Val Lys Leu Thr
        115                 120                 125

Pro Leu Cys Val Thr Leu Asn Cys Lys Asp Val Asn Ala Thr Asn Thr
130                 135                 140

Thr Asn Asp Ser Glu Gly Thr Met Glu Arg Gly Glu Ile Lys Asn Cys
145                 150                 155                 160

Ser Phe Asn Ile Thr Thr Ser Ile Arg Asp Glu Val Gln Lys Glu Tyr
                165                 170                 175

Ala Leu Phe Tyr Lys Leu Asp Val Val Pro Ile Asp Asn Asn Asn Thr
            180                 185                 190

Ser Tyr Arg Leu Ile Ser Cys Asp Thr Ser Val Ile Thr Gln Ala Cys
        195                 200                 205

Pro Lys Ile Ser Phe Glu Pro Ile Pro Ile His Tyr Cys Ala Pro Ala
210                 215                 220

Gly Phe Ala Ile Leu Lys Cys Asn Asp Lys Thr Phe Asn Gly Lys Gly
225                 230                 235                 240

Pro Cys Lys Asn Val Ser Thr Val Gln Cys Thr His Gly Ile Arg Pro
                245                 250                 255

Val Val Ser Thr Gln Leu Leu Leu Asn Gly Ser Leu Ala Glu Glu Glu
            260                 265                 270

Val Val Ile Arg Ser Asp Asn Phe Thr Asn Asn Ala Lys Thr Ile Ile
        275                 280                 285

Val Gln Leu Lys Glu Ser Val Glu Ile Asn Cys Thr Arg Pro Asn Asn
290                 295                 300

Asn Thr Arg Lys Ser Ile His Ile Gly Pro Gly Arg Ala Phe Tyr Thr
305                 310                 315                 320

Thr Gly Glu Ile Ile Gly Asp Ile Arg Gln Ala His Cys Asn Ile Ser
                325                 330                 335

Arg Ala Lys Trp Asn Asp Thr Leu Lys Gln Ile Val Ile Lys Leu Arg
            340                 345                 350

Glu Gln Phe Glu Asn Lys Thr Ile Val Phe Asn His Ser Ser Gly Gly
        355                 360                 365

Asp Pro Glu Ile Val Met His Ser Phe Asn Cys Gly Gly Glu Phe Phe
370                 375                 380

Tyr Cys Asn Ser Thr Gln Leu Phe Asn Ser Thr Trp Asn Asn Asn Thr
385                 390                 395                 400
```

```
Glu Gly Ser Asn Asn Thr Glu Gly Asn Thr Ile Thr Leu Pro Cys Arg
                405                 410                 415

Ile Lys Gln Ile Ile Asn Met Trp Gln Glu Val Gly Lys Ala Met Tyr
            420                 425                 430

Ala Pro Pro Ile Arg Gly Gln Ile Arg Cys Ser Ser Asn Ile Thr Gly
            435                 440                 445

Leu Leu Leu Thr Arg Asp Gly Gly Ile Asn Glu Asn Gly Thr Glu Ile
        450                 455                 460

Phe Arg Pro Gly Gly Gly Asp Met Arg Asp Asn Trp Arg Ser Glu Leu
465                 470                 475                 480

Tyr Lys Tyr Lys Val Val Lys Ile Glu Pro Leu Gly Val Ala Pro Thr
                485                 490                 495

Lys Ala Lys Arg Arg Val Val Gln Arg Glu Lys Arg
            500                 505

<210> SEQ ID NO 88
<211> LENGTH: 489
<212> TYPE: PRT
<213> ORGANISM: Human immunodeficiency virus type 1

<400> SEQUENCE: 88

Gly Ala Arg Asn Ser Asn Leu Trp Val Thr Val Tyr Tyr Gly Val Pro
1               5                   10                  15

Val Trp Lys Asp Ala Glu Thr Thr Leu Phe Cys Ala Ser Asp Ala Lys
            20                  25                  30

Ala Tyr Lys Thr Glu Lys His Asn Val Trp Ala Thr His Ala Cys Val
            35                  40                  45

Pro Thr Asp Pro Asn Pro Gln Glu Ile Pro Leu Glu Asn Val Thr Glu
        50                  55                  60

Glu Phe Asn Met Trp Lys Asn Lys Met Val Glu Gln Met His Thr Asp
65                  70                  75                  80

Ile Ile Ser Leu Trp Asp Gln Ser Leu Gln Pro Cys Val Lys Leu Ala
                85                  90                  95

Pro Leu Cys Val Thr Leu Asn Cys Thr Asp Val Thr Asn Val Thr Asp
            100                 105                 110

Val Ser Gly Thr Arg Gly Asn Ile Thr Ile Met Lys Glu Met Glu Gly
            115                 120                 125

Glu Ile Lys Asn Cys Ser Phe Asn Met Ala Thr Glu Ile Arg Asp Lys
        130                 135                 140

Lys Gln Lys Val Tyr Ser Leu Phe Tyr Arg Leu Asp Val Val Pro Ile
145                 150                 155                 160

Asn Gln Gly Asn Ser Ser Ser Lys Asn Ser Ser Glu Tyr Arg Leu Ile
                165                 170                 175

Ser Cys Asn Thr Ser Ala Ile Thr Gln Ala Cys Pro Lys Val Ser Phe
            180                 185                 190

Glu Pro Ile Pro Ile His Tyr Cys Ala Pro Ala Gly Phe Ala Ile Leu
            195                 200                 205

Lys Cys Arg Asp Lys Glu Phe Asn Gly Thr Gly Glu Cys Lys Asn Val
        210                 215                 220

Ser Thr Val Gln Cys Thr His Gly Ile Lys Pro Val Ser Thr Gln
225                 230                 235                 240

Leu Leu Leu Asn Gly Ser Leu Ala Glu Glu Lys Val Lys Ile Arg Thr
                245                 250                 255

Glu Asn Ile Thr Asn Asn Ala Lys Thr Ile Ile Val Gln Leu Val Glu
            260                 265                 270
```

```
Pro Val Arg Ile Ser Cys Thr Arg Pro Asn Asn Asn Thr Arg Glu Ser
            275                 280                 285

Val Arg Ile Gly Pro Gly Gln Ala Phe Phe Ala Thr Gly Asp Ile Ile
        290                 295                 300

Gly Asp Ile Arg Gln Ala His Cys Asn Val Ser Arg Ser Gln Trp Asn
305                 310                 315                 320

Lys Thr Leu Gln Gln Val Ala Glu Gln Leu Arg Glu His Phe Lys Asn
            325                 330                 335

Lys Thr Ile Ile Phe Asn Ser Ser Gly Gly Asp Leu Glu Ile Thr
            340                 345                 350

Thr His Ser Phe Asn Cys Gly Gly Glu Phe Phe Tyr Cys Asn Thr Ser
            355                 360                 365

Gly Leu Phe Asn Ser Thr Trp Asn Thr Ser Met Ser Gly Ser Ser Asn
        370                 375                 380

Thr Glu Thr Asn Gly Thr Ile Thr Leu Gln Cys Arg Ile Lys Gln Ile
385                 390                 395                 400

Ile Asn Met Trp Gln Arg Thr Gly Gln Ala Ile Tyr Ala Pro Pro Ile
            405                 410                 415

Gln Gly Val Ile Arg Cys Glu Ser Asn Ile Thr Gly Leu Leu Leu Thr
        420                 425                 430

Arg Asp Gly Gly Glu Glu Lys Asn Ser Thr Asn Glu Ile Phe Arg Pro
            435                 440                 445

Gly Gly Gly Asp Met Arg Asp Asn Trp Arg Ser Glu Leu Tyr Lys Tyr
        450                 455                 460

Lys Val Val Lys Ile Glu Pro Leu Gly Val Ala Pro Thr Arg Ala Arg
465                 470                 475                 480

Arg Arg Val Val Gly Arg Glu Lys Arg
            485
```

<210> SEQ ID NO 89
<211> LENGTH: 4136
<212> TYPE: DNA
<213> ORGANISM: Artificial
<220> FEATURE:
<223> OTHER INFORMATION: Sequence vector encoding GP antigen of Ebola
      virus

<400> SEQUENCE: 89

| | | |
|---|---|---|
| ctaaattgta agcgttaata ttttgttaaa attcgcgtta aattttgtt aaatcagctc | 60 |
| attttttaac caataggccg aaatcggcaa atcccttat aaatcaaaag aatagaccga | 120 |
| gatagggttg agtggccgct acagggcgct cccattcgcc attcaggctg cgcaactgtt | 180 |
| gggaagggcg tttcggtgcg ggcctcttcg ctattacgcc agctggcgaa aggggggatgt | 240 |
| gctgcaaggc gattaagttg ggtaacgcca gggttttccc agtcacgacg ttgtaaaacg | 300 |
| acggccagtg agcgcgacgt aatacgactc actatagggc gaattgaagg aaggccgtca | 360 |
| aggcctaggc gcgccaagct tatccctctg ggcgtgatcc acaattctac actccaggtg | 420 |
| tccgatgtcg acaaactggt ctgtagggac aaactctcct ccaccaatca gctgagatct | 480 |
| gtgggactga atctggaggg caatggcgtg gctaccgatg tgccttctgc tactaaacga | 540 |
| tggggctttc gatccggcgt ccccctaaa gtggtgaatt acgaggctgg cgaatgggcc | 600 |
| gagaactgtt acaacctcga atcaaaaaa cccgacggct ctgaatgtct gcctgctgct | 660 |
| cccgacggaa tccggggctt ccctcgatgc cgatacgtcc acaaagtgtc tggaactggc | 720 |
| ccttgtgctg gggattttgc ctttcacaaa gagggcgctt tcttcctgta cgatcgcctg | 780 |

```
gcttcaactg tgatctaccg gggaaccaca tttgctgagg gcgtggtcgc ttttctcatt    840
ctgccacagg ctaaaaagga cttcttctct tctcacccac tccgggaacc cgtgaatgct    900
actgaggacc cttcttccgg ctactactct accaccatcc gataccaggc tactggattt    960
ggcacaaacg aaaccgagta cctgtttgaa gtggataacc tcacctacgt ccagctcgaa    1020
tctcgcttta cacccagtt tctgctccag ctgaacgaga caatctacac ctccggaaaa    1080
cggtccaaca caaccggcaa actcatctgg aaagtgaacc ccgagatcga cactacaatt    1140
ggcgaatggg cattctggga gacaaagaaa atctcacac ggaaaattcg gagcgaggag    1200
ctgtcttta ctgtcgtgtc caacggagcc aaaaacatct ctggccagag tcctgctaga    1260
acatcctccg atcctgggac caataccaca actgaggacc acaaaatcat ggctagcgag    1320
aactctagtg ctatggtcca ggtccactct cagggacgag aggccgccgt gtcacatctc    1380
actacactgg ctacaatctc cacctccccc cagtctctca acaaaaacc cggacccgat    1440
aatagtacac acaacacccc cgtctacaaa ctcgatatta gcgaggccac acaggtcgaa    1500
cagcaccata ggagaaccga caacgattca accgcttccg acacaccttc tgccacaact    1560
gctgctgggc cccctaaggc tgaaaacacc aatactagca aatcaaccga tttcctggac    1620
cctgccacta ccacttcacc tcagaaccac tctgaaaccg ctggcaacaa caatacccac    1680
catcaggata ctggcgagga atctgcctct tctggcaaac tcggactcat caccaacact    1740
atcgctggcg tcgccgggct cattaccggc ggacggcgaa cacggcgaga ggctatcgtg    1800
aacgcccagc ccaaatgtaa tcccaacctc cactactgga caacacagga tgagggagcc    1860
gctattggac tggcatggat tccctacttt ggccccgctg ccgagggcat ctacattgag    1920
ggcctcatgc acaatcagga tggactcatc tgtggactcc gacagctggc caatgaaacc    1980
actcaggcac tccagctgtt tctccgggct acaactgaac tgagaacctt ctcaatcctg    2040
aaccggaagg ctatcgactt tctcctccag cgctggggcg aacatgtca tattctggga    2100
cccgattgct gtatcgagcc tcacgattgg accaaaaaca ttaccgacaa aatcgatcag    2160
atcatccacg acttcgtcga caaaacactg cccgatggga tcctcggtgg aggtggtacc    2220
ttaattaact ggcctcatgg gccttccttt cactgcccgc tttccagtcg ggaaacctgt    2280
cgtgccagct gcattaacat ggtcatagct gtttccttgc gtattgggcg ctctccgctt    2340
cctcgctcac tgactcgctg cgctcggtcg ttcgggtaaa gctgggtg cctaatgagc    2400
aaaaggccag caaaaggcca ggaaccgtaa aaaggccgcg ttgctggcgt ttttccatag    2460
gctccgcccc cctgacgagc atcacaaaaa tcgacgctca agtcagaggt ggcgaaaccc    2520
gacaggacta taaagatacc aggcgtttcc ccctggaagc tccctcgtgc gctctcctgt    2580
tccgaccctg ccgcttaccg gatacctgtc cgcctttctc ccttcgggaa gcgtggcgct    2640
ttctcatagc tcacgctgta ggtatctcag ttcggtgtag gtcgttcgct ccaagctggg    2700
ctgtgtgcac gaacccccg ttcagcccga ccgctgcgcc ttatccggta actatcgtct    2760
tgagtccaac ccggtaagac acgacttatc gccactggca gcagccactg gtaacaggat    2820
tagcagagcg aggtatgtag gcggtgctac agagttcttg aagtggtggc ctaactacgg    2880
ctacactaga agaacagtat ttggtatctg cgctctgctg aagccagtta ccttcggaaa    2940
aagagttggt agctcttgat ccggcaaaca aaccaccgct ggtagcggtg ttttttttgt    3000
ttgcaagcag cagattacgc gcagaaaaaa aggatctcaa gaagatcctt tgatcttttc    3060
tacggggtct gacgctcagt ggaacgaaaa ctcacgttaa gggattttgg tcatgagatt    3120
```

-continued

```
atcaaaaagg atcttcacct agatcctttt aaattaaaaa tgaagtttta aatcaatcta   3180
aagtatatat gagtaaactt ggtctgacag ttattagaaa aattcatcca gcagacgata   3240
aaacgcaata cgctggctat ccggtgccgc aatgccatac agcaccagaa aacgatccgc   3300
ccattcgccg cccagttctt ccgcaatatc acgggtggcc agcgcaatat cctgataacg   3360
atccgccacg cccagacggc cgcaatcaat aaagccgcta aaacggccat tttccaccat   3420
aatgttcggc aggcacgcat caccatgggt caccaccaga tcttcgccat ccggcatgct   3480
cgctttcaga cgcgcaaaca gctctgccgg tgccaggccc tgatgttctt catccagatc   3540
atcctgatcc accaggcccg cttccatacg ggtacgcgca cgttcaatac gatgtttcgc   3600
ctgatgatca aacggacagg tcgccgggtc cagggtatgc agacgacgca tggcatccgc   3660
cataatgctc actttttctg ccggcgccag atggctagac agcagatcct gacccggcac   3720
ttcgcccagc agcagccaat cacggcccgc ttcggtcacc acatccagca ccgccgcaca   3780
cggaacaccg gtggtggcca gccagctcag acgcgccgct tcatcctgca gctcgttcag   3840
cgcaccgctc agatcggttt tcacaaacag caccggacga ccctgcgcgc tcagacgaaa   3900
caccgccgca tcagagcagc caatggtctg ctgcgcccaa tcatagccaa acagacgttc   3960
cacccacgct gccgggctac ccgcatgcag gccatcctgt tcaatcatac tcttcctttt   4020
tcaatattat tgaagcattt atcagggtta ttgtctcatg agcggataca tatttgaatg   4080
tatttagaaa aataaacaaa taggggttcc gcgcacattt ccccgaaaag tgccac       4136
```

<210> SEQ ID NO 90
<211> LENGTH: 3833
<212> TYPE: DNA
<213> ORGANISM: Artificial
<220> FEATURE:
<223> OTHER INFORMATION: sequence vector encoding HA antigen of influenza virus

<400> SEQUENCE: 90

```
ctaaattgta agcgttaata ttttgttaaa attcgcgtta aatttttgtt aaatcagctc     60 atttttaac caataggccg aaatcggcaa aatcccttat aaatcaaaag aatagaccga     120
gatagggttg agtggccgct acagggcgct cccattcgcc attcaggctg cgcaactgtt    180
gggaagggcg tttcggtgcg ggcctcttcg ctattacgcc agctggcgaa agggggatgt    240
gctgcaaggc gattaagttg ggtaacgcca gggttttccc agtcacgacg ttgtaaaacg    300
acggccagtg agcgcgacgt aatacgactc actatagggc gaattgaagg aaggccgtca    360
aggcctaggc gcgccaagct tgaccagatt tgtatcggct accacgccaa caatagcact    420
gaacaggtgg acaccatcat ggagaaaaat gtcaccgtca cacacgctca ggatattctg    480
gaacggaccc acaacggcaa actctgtgat ctgaatggag tgaaacccct catcctccgg    540
gattgctccg tggctggatg gctgctggga aatccaatgt gtgatgagtt catcaacgtg    600
cctgagtggt cttacattgt cgagaaggcc tcacctgcca atgacctgtg ttaccctggc    660
aacttcaacg attacgagga gctgaaacat ctgctgtctc ggatcaacca ttttgaaaaa    720
atccagatca tccccaaatc ctcttggtcc aaccatgacg cctctagcgg cgtgtctagt    780
gcttgtcctt acctcggccg gtcctcattc ttccggaacg tcgtctggct catcaaaaaa    840
aactccgcct accccacaat caaacggtcc tacaataata ccaaccagga ggacctgctg    900
gtcctctggg gcgtccatca tccaaatgat gccgccgaac agacaaaact ctaccagaac    960
cccaccacat acatctctgt cggaacctct accctgaatc agcgactggt gcctgaaatc   1020
```

-continued

```
gctactaggc ccaaagtgaa tgggcagagc gggcgaatgg agttcttctg gactatcctc    1080
aaacccaacg acgctatcaa ttttgagtca aatgggaatt tcattgcccc cgaatacgcc    1140
tacaaaatcg tgaaaagggc gactctact atcatgaaat ccgagctgga gtacggcaac    1200
tgtaatacaa aatgccagac ccctatgggc gctatcaact cttctatgcc tttccataac    1260
attcatcctc tcaccatcgg cgaatgccca aaatacgtca aatcaaatcg ctggtgctg    1320 gctactggac tgagaaacac cccacagcgg aacggcgac ggaaaaaacg gggactcttt    1380
ggcgctatcg ctggctttat tgagggcgga tggcagggaa tggtggatgg atggtacgga    1440
taccaccata gtaacgagca gggctccgga tacgctgccg acaaggagtc tacacagaag    1500
gcaatcgacg gagtcaccaa caaagtcaat tctatcatca acaaaatgaa cacccagttc    1560
gaggctgtcg ggcgagagtt caacaatctg gagaggcgga tcgaaaacct gaacaaaaaa    1620
atggaggacg gcttcctgga tgtgtggaca tacaatgctg aactgctggt gctcatggag    1680
aacgagagaa ccctggactt ccacgactcc aacgtgaaaa acctgtacga caaagtccgg    1740
ctccagctga gagacaatgc caaggaactc ggcaacggct gtttcgagtt ctaccacaaa    1800
tgtgacaacg agtgtatgga gagcgtcaaa aacggcacct acgactaccc acagtactct    1860
gaggaggcta ggctgaatcg ggaggagatc tctgggatcc tcggtggagg tggtaccta    1920 attaactggc tcatgggcc ttcctttcac tgcccgcttt ccagtcggga aacctgtcgt    1980
gccagctgca ttaacatggt catagctgtt tccttgcgta ttgggcgctc tccgcttcct    2040
cgctcactga ctcgctgcgc tcggtcgttc gggtaaagcc tggggtgcct aatgagcaaa    2100
aggccagcaa aaggccagga accgtaaaaa ggccgcgttg ctggcgtttt tccataggct    2160
ccgcccccct gacgagcatc acaaaaatcg acgctcaagt cagaggtggc gaaacccgac    2220
aggactataa agataccagg cgtttccccc tggaagctcc ctcgtgcgct ctcctgttcc    2280
gaccctgccg cttaccggat acctgtccgc ctttctccct tcgggaagcg tggcgctttc    2340
tcatagctca cgctgtaggt atctcagttc ggtgtaggtc gttcgctcca agctgggctg    2400
tgtgcacgaa ccccccgttc agcccgaccg ctgcgcctta ccggtaact atcgtcttga    2460 gtccaacccg gtaagacacg acttatcgcc actggcagca gccactggta acaggattag    2520
cagagcgagg tatgtaggcg gtgctacaga gttcttgaag tggtggccta actacggcta    2580
cactagaaga acagtatttg gtatctgcgc tctgctgaag ccagttacct tcggaaaaag    2640
agttggtagc tcttgatccg gcaaacaaac caccgctggt agcggtggtt ttttgtttg    2700 caagcagcag attacgcgca gaaaaaaagg atcctcaagaa gatcctttga tcttttctac    2760
ggggtctgac gctcagtgga acgaaaactc acgttaaggg attttggtca tgagattatc    2820 aaaaggatc ttcacctaga tccttttaaa ttaaaaatga agttttaaat caatctaaag    2880
tatatatgag taaacttggt ctgacagtta ttagaaaaat tcatccagca gacgataaaa    2940
cgcaatacgc tggctatccg gtgccgcaat gccatacagc accagaaaac gatccgccca    3000
ttcgccgccc agttcttccg caatatcacg ggtggccagc gcaatatcct gataacgatc    3060
cgccacgccc agacggccgc aatcaataaa gccgctaaaa cggccatttt ccaccataat    3120
gttcggcagg cacgcatcac catgggtcac caccagatct tcgccatccg gcatgctcgc    3180
tttcagacgc gcaaacagct ctgccggtgc caggccctga tgttcttcat ccagatcatc    3240
ctgatccacc aggcccgctt ccatacgggt acgcgcacgt tcaatacgat gtttcgcctg    3300
atgatcaaac ggacaggtcg ccgggtccag ggtatgcaga cgacgcatgg catccgccat    3360
aatgctcact ttttctgccg gcgccagatg gctagacagc agatcctgac ccggcacttc    3420
```

-continued

```
gcccagcagc agccaatcac ggcccgcttc ggtcaccaca tccagcaccg ccgcacacgg    3480
aacaccggtg gtggccagcc agctcagacg cgccgcttca tcctgcagct cgttcagcgc    3540
accgctcaga tcggttttca caaacagcac cggacgaccc tgcgcgctca gacgaaacac    3600
cgccgcatca gagcagccaa tggtctgctg cgcccaatca tagccaaaca gacgttccac    3660
ccacgctgcc gggctacccg catgcaggcc atcctgttca atcatactct tccttttca     3720 atattattga agcatttatc agggttattg tctcatgagc ggatacatat ttgaatgtat    3780
ttagaaaaat aaacaaatag gggttccgcg cacatttccc cgaaaagtgc cac           3833
```

<210> SEQ ID NO 91
<211> LENGTH: 2781
<212> TYPE: DNA
<213> ORGANISM: Artificial
<220> FEATURE:
<223> OTHER INFORMATION: sequence vector encoding mouse IL-4

<400> SEQUENCE: 91

```
ctaaattgta agcgttaata ttttgttaaa attcgcgtta aattttgtt aaatcagctc      60 attttttaac caataggccg aaatcggcaa atcccttat aaatcaaaag aatagaccga    120
gatagggttg agtggccgct acagggcgct cccattcgcc attcaggctg cgcaactgtt    180
gggaagggcg tttcggtgcg ggcctcttcg ctattacgcc agctggcgaa aggggggatgt   240 gctgcaaggc gattaagttg ggtaacgcca gggttttccc agtcacgacg ttgtaaaacg    300
acggccagtg agcgcgacgt aatacgactc actatagggc gaattggcgg aaggccgtca    360
aggccacgtg tcttgtccag gtaccaagct tacacctctc tgtgtgggat ctgggcacgg    420
atgtgacaaa aaccatctcc gggaaatcat cggcattctg aacgaagtga ctggcgaggg    480
aacaccctgt actgaaatgg acgtccccaa tgtgctcact gccaccaaaa acacaaccga    540
gagcgaactg gtgtgtagag cctcaaaagt gctgagaatc ttctacctga acacggcaa     600 aaccccatgt ctgaaaaaaa actcctctgt cctcatggaa ctccagcgac tgtttagggc    660
ctttcggtgt ctggatagta gcatctcttg tacaatgaat gagtccaaat ccacctcact    720
caaggacttt ctggaatctc tcaaatcaat catgcagatg gactactccg gatctggctc    780
ttgtaacacg tcgagctctg gagcacaaga ctggcctcat gggccttccg ctcactgccc    840
gctttccagt cgggaaacct gtcgtgccag ctgcattaac atggtcatag ctgtttcctt    900
gcgtattggg cgctctccgc ttcctcgctc actgactcgc tgcgctcggt cgttcgggta    960
aagcctgggg tgcctaatga gcaaaaggcc agcaaaggcc aggaaccgt aaaaaggccg    1020 cgttgctggc gtttttccat aggctccgcc ccctgacga gcatcacaaa aatcgacgct    1080
caagtcagag gtggcgaaac ccgacaggac tataaagata ccaggcgttt ccccctggaa    1140
gctccctcgt gcgctctcct gttccgaccc tgccgcttac cggatacctg tccgcctttc    1200
tcccttcggg aagcgtggcg ctttctcata gctcacgctg taggtatctc agttcggtgt    1260
aggtcgttcg ctccaagctg ggctgtgtgc acgaaccccc cgttcagccc gaccgctgcg    1320
ccttatccgg taactatcgt cttgagtcca acccggtaag acacgactta tcgccactgg    1380
cagcagccac tggtaacagg attagcagag cgaggtatgt aggcggtgct acagagttct    1440
tgaagtggtg gcctaactac ggctacacta agaacagt atttggtatc tgcgctctgc     1500
tgaagccagt taccttcgga aaaagagttg gtagctcttg atccggcaaa caaaccaccg    1560
ctggtagcgg tggttttttt gtttgcaagc agcagattac gcgcagaaaa aaaggatctc    1620
```

```
aagaagatcc tttgatcttt tctacggggt ctgacgctca gtggaacgaa aactcacgtt      1680
aagggatttt ggtcatgaga ttatcaaaaa ggatcttcac ctagatcctt ttaaattaaa      1740
aatgaagttt taaatcaatc taaagtatat atgagtaaac ttggtctgac agttaccaat      1800
gcttaatcag tgaggcacct atctcagcga tctgtctatt tcgttcatcc atagttgcct      1860
gactccccgt cgtgtagata actacgatac gggagggctt accatctggc cccagtgctg      1920
caatgatacc gcgagaacca cgctcaccgg ctccagattt atcagcaata accagccag       1980 ccggaagggc cgagcgcaga agtggtcctg caactttatc cgcctccatc cagtctatta      2040
attgttgccg ggaagctaga gtaagtagtt cgccagttaa tagtttgcgc aacgttgttg      2100
ccattgctac aggcatcgtg gtgtcacgct cgtcgtttgg tatggcttca ttcagctccg      2160
gttcccaacg atcaaggcga gttacatgat cccccatgtt gtgcaaaaaa gcggttagct      2220
ccttcggtcc tccgatcgtt gtcagaagta agttggccgc agtgttatca ctcatggtta      2280
tggcagcact gcataattct cttactgtca tgccatccgt aagatgcttt tctgtgactg      2340
gtgagtactc aaccaagtca ttctgagaat agtgtatgcg gcgaccgagt tgctcttgcc      2400
cggcgtcaat acgggataat accgcgccac atagcagaac tttaaaagtg ctcatcattg      2460
gaaaacgttc ttcggggcga aaactctcaa ggatcttacc gctgttgaga tccagttcga      2520
tgtaacccac tcgtgcaccc aactgatctt cagcatcttt tactttcacc agcgtttctg      2580
ggtgagcaaa aacaggaagg caaaatgccg caaaaaaggg aataagggcg acacggaaat      2640
gttgaatact catactcttc ctttttcaat attattgaag catttatcag ggttattgtc      2700
tcatgagcgg atacatattt gaatgtattt agaaaaataa acaaataggg gttccgcgca      2760
catttccccg aaaagtgcca c                                                2781
```

<210> SEQ ID NO 92
<211> LENGTH: 2810
<212> TYPE: DNA
<213> ORGANISM: Artificial
<220> FEATURE:
<223> OTHER INFORMATION: sequence vector encoding human IL-4

<400> SEQUENCE: 92

```
ctaaattgta agcgttaata ttttgttaaa attcgcgtta aattttttgtt aaatcagctc      60 attttttaac caataggccg aaatcggcaa aatcccttat aaatcaaaag aatagaccga      120
gatagggttg agtggccgct acagggcgct cccattcgcc attcaggctg cgcaactgtt      180
gggaagggcg tttcggtgcg ggcctcttcg ctattacgcc agctggcgaa aggggggatgt     240 gctgcaaggc gattaagttg ggtaacgcca gggttttccc agtcacgacg ttgtaaaacg      300
acggccagtg agcgcgacgt aatacgactc actatagggc gaattggcgg aaggccgtca      360
aggcctaggc gcgccatgag ctcgacgtgt acaagagcc agatccgcta gagcattttg       420 agtattttc cctcataatg gttttcagcc gttcgagaaa attctccagt gtagactgat       480
tggcctcttt cacagggcaa gagttcaggc cagcgagtcc ccacaggttt ctatccagtc      540
gtttgaggaa ccggatgagc tgtttgtgtc tatgaaactg ctgggcggtg gctccgaggc      600
atcgggtgtc cttctcatga tgggagtaga actgtctcag cacagtagcg gctcgacaga      660
atgtttcctt ttcggtggtg ttttttggaag cggcgaagat gtcggtcacg gtgagttcgg    720
tacagagtgt tttctgctca gtgagtgagt tcagggtttt gataatctcc tggagtgtga      780
tgtcacattt gtgcccagat cccacacaga gaggtgtaag cttggtacct cttaattaac      840
tggcctcatg ggccttccgc tcactgcccg ctttccagtc gggaaacctg tcgtgccagc      900
```

```
tgcattaaca tggtcatagc tgtttccttg cgtattgggc gctctccgct tcctcgctca    960
ctgactcgct gcgctcggtc gttcgggtaa agcctgggt gcctaatgag caaaaggcca   1020 gcaaaggcc aggaaccgta aaaaggccgc gttgctggcg ttttccata ggctccgccc    1080 ccctgacgag catcacaaaa atcgacgctc aagtcagagg tggcgaaacc cgacaggact   1140
ataaagatac caggcgtttc ccctggaag ctccctcgtg cgctctcctg ttccgaccct    1200
gccgcttacc ggatacctgt ccgcctttct cccttcggga agcgtggcgc tttctcatag   1260
ctcacgctgt aggtatctca gttcggtgta ggtcgttcgc tccaagctgg ctgtgtgca    1320 cgaaccccc gttcagcccg accgctgcgc cttatccggt aactatcgtc ttgagtccaa   1380
cccggtaaga cacgacttat cgccactggc agcagccact ggtaacagga ttagcagagc   1440
gaggtatgta ggcggtgcta cagagttctt gaagtggtgg cctaactacg gctacactag   1500
aagaacagta tttggtatct gcgctctgct gaagccagtt accttcggaa aaagagttgg   1560
tagctcttga tccggcaaac aaaccaccgc tggtagcggt ggttttttg tttgcaagca   1620 gcagattacg cgcagaaaaa aaggatctca agaagatcct ttgatctttt ctacggggtc   1680
tgacgctcag tggaacgaaa actcacgtta agggattttg gtcatgagat tatcaaaaag   1740
gatcttcacc tagatccttt taaattaaaa atgaagtttt aaatcaatct aaagtatata   1800
tgagtaaact tggtctgaca gttaccaatg cttaatcagt gaggcaccta tctcagcgat   1860
ctgtctattt cgttcatcca tagttgcctg actccccgtc gtgtagataa ctacgatacg   1920
ggagggctta ccatctggcc ccagtgctgc aatgataccg cgagaaccac gctcaccggc   1980
tccagattta tcagcaataa accagccagc cggaagggcc gagcgcagaa gtggtcctgc   2040
aactttatcc gcctccatcc agtctattaa ttgttgccgg gaagctagag taagtagttc   2100
gccagttaat agtttgcgca acgttgttgc cattgctaca ggcatcgtgg tgtcacgctc   2160
gtcgtttggt atggcttcat tcagctccgg ttcccaacga tcaaggcgag ttacatgatc   2220
ccccatgttg tgcaaaaaag cggttagctc cttcggtcct ccgatcgttg tcagaagtaa   2280
gttggccgca gtgttatcac tcatggttat ggcagcactg cataattctc ttactgtcat   2340
gccatccgta agatgctttt ctgtgactgg tgagtactca accaagtcat tctgagaata   2400
gtgtatgcgg cgaccgagtt gctcttgccc ggcgtcaata cgggataata ccgcgccaca   2460
tagcagaact ttaaaagtgc tcatcattgg aaaacgttct cggggcgaa aactctcaag    2520 gatcttaccg ctgttgagat ccagttcgat gtaacccact cgtgcaccca actgatcttc   2580
agcatctttt actttcacca gcgtttctgg gtgagcaaaa acaggaaggc aaaatgccgc   2640
aaaaaaggga ataagggcga cacggaaatg ttgaatactc atactcttcc ttttcaata    2700 ttattgaagc atttatcagg gttattgtct catgagcgga tacatatttg aatgtattta   2760
gaaaaataaa caaatagggg ttccgcgcac atttccccga aagtgccac              2810
```

<210> SEQ ID NO 93
<211> LENGTH: 2805
<212> TYPE: DNA
<213> ORGANISM: Artificial
<220> FEATURE:
<223> OTHER INFORMATION: sequence vector encoding mouse IL-21

<400> SEQUENCE: 93

```
ctaaattgta agcgttaata ttttgttaaa attcgcgtta aattttgtt aaatcagctc      60 atttttaac caataggccg aaatcggcaa atcccttat aaatcaaaag aatagaccga     120
```

```
gatagggttg agtggccgct acagggcgct cccattcgcc attcaggctg cgcaactgtt        180
gggaagggcg tttcggtgcg ggcctcttcg ctattacgcc agctggcgaa aggggggatgt      240 gctgcaaggc gattaagttg ggtaacgcca gggttttccc agtcacgacg ttgtaaaacg       300
acggccagtg agcgcgacgt aatacgactc actatagggc gaattggcgg aaggccgtca       360
aggccacgtg tcttgtccag gtaccaagct tacacctctc tgtgtgggat ctggcatggg       420
acccgataga ctgctcatta gactccggca cctcatcgat attgtggaac agctgaaaat       480
ctacgagaac gacctcgacc ctgaactcct gtctgcccca caggatgtga agggccattg       540
tgaacacgcc gctttcgctt gtttccagaa ggccaaactg aaaccctcca acccctggcaa     600 taacaaaacc tttatcatcg acctggtggc acagctccga cggagactgc ctgctagacg       660
gggcggaaaa aaacagaaac acattgccaa atgcccctct tgtgactcct acgaaaaacg       720
gaccccaaaa gaatttctcg aacgcctgaa atggctgctc cagaaaatga ttcaccagca       780
cctgagttct agggggagcg atcatgtaa cacgtcgagc tctggagcac aagactggcc        840
tcatgggcct tccgctcact gcccgctttc cagtcgggaa acctgtcgtg ccagctgcat       900
taacatggtc atagctgttt ccttgcgtat tgggcgctct ccgcttcctc gctcactgac       960
tcgctgcgct cggtcgttcg ggtaaagcct ggggtgccta atgagcaaaa ggccagcaaa      1020
aggccaggaa ccgtaaaaag gccgcgttgc tggcgttttt ccataggctc cgccccctg      1080 acgagcatca caaaaatcga cgctcaagtc agaggtggcg aaacccgaca ggactataaa     1140
gataccaggc gtttccccct ggaagctccc tcgtgcgctc tcctgttccg accctgccgc      1200
ttaccggata cctgtccgcc tttctccctt cgggaagcgt ggcgctttct catagctcac      1260
gctgtaggta tctcagttcg gtgtaggtcg ttcgctccaa gctgggctgt gtgcacgaac      1320
cccccgttca gcccgaccgc tgcgccttat ccggtaacta tcgtcttgag tccaacccgg      1380
taagacacga cttatcgcca ctggcagcag ccactggtaa caggattagc agagcgaggt      1440
atgtaggcgg tgctacagag ttcttgaagt ggtggcctaa ctacggctac actagaagaa      1500
cagtatttgg tatctgcgct ctgctgaagc cagttacctt cggaaaaaga gttggtagct      1560
cttgatccgg caaacaaacc accgctggta gcggtggttt ttttgtttgc aagcagcaga      1620
ttacgcgcag aaaaaaagga tctcaagaag atcctttgat ctttttctacg ggtctgacg      1680 ctcagtggaa cgaaaactca cgttaaggga ttttggtcat gagattatca aaaaggatct      1740
tcacctagat ccttttaaat taaaaatgaa gttttaaatc aatctaaagt atatatgagt      1800
aaacttggtc tgacagttac caatgcttaa tcagtgaggc acctatctca gcgatctgtc      1860
tatttcgttc atccatagtt gcctgactcc ccgtcgtgta gataactacg atacgggagg     1920
gcttaccatc tggccccagt gctgcaatga taccgcgaga accacgctca ccggctccag      1980
atttatcagc aataaaccag ccagccggaa gggccgagcg cagaagtggt cctgcaactt      2040
tatccgcctc catccagtct attaattgtt gccgggaagc tagagtaagt agttcgccag      2100
ttaatagttt gcgcaacgtt gttgccattg ctacaggcat cgtggtgtca cgctcgtcgt      2160
ttggtatggc ttcattcagc tccggttccc aacgatcaag gcgagttaca tgatcccccca     2220 tgttgtgcaa aaaagcggtt agctccttcg gtcctccgat cgttgtcaga gtaagttgg      2280 ccgcagtgtt atcactcatg gttatggcag cactgcataa ttctcttact gtcatgccat      2340
ccgtaagatg cttttctgtg actggtgagt actcaaccaa gtcattctga gaatagtgta      2400
tgcggcgacc gagttgctct tgcccggcgt caatacggga taataccgcg ccacatagca      2460
gaactttaaa agtgctcatc attggaaaac gttcttcggg gcgaaaactc tcaaggatct      2520
```

```
taccgctgtt gagatccagt tcgatgtaac ccactcgtgc acccaactga tcttcagcat    2580
cttttacttt caccagcgtt tctgggtgag caaaaacagg aaggcaaaat gccgcaaaaa    2640
agggaataag ggcgacacgg aaatgttgaa tactcatact cttcctttttt caatattatt    2700 gaagcattta tcagggttat tgtctcatga gcggatacat atttgaatgt atttagaaaa    2760
ataaacaaat aggggttccg cgcacatttc cccgaaaagt gccac                    2805
```

<210> SEQ ID NO 94
<211> LENGTH: 2808
<212> TYPE: DNA
<213> ORGANISM: Artificial
<220> FEATURE:
<223> OTHER INFORMATION: sequence vector encoding human IL-21

<400> SEQUENCE: 94

```
ctaaattgta agcgttaata ttttgttaaa attcgcgtta aatttttgtt aaatcagctc     60
attttttaac caataggccg aaatcggcaa aatcccttat aaatcaaaag aatagaccga    120
gatagggttg agtggccgct acagggcgct cccattcgcc attcaggctg cgcaactgtt    180
gggaagggcg tttcggtgcg ggcctcttcg ctattacgcc agctggcgaa agggggatgt    240
gctgcaaggc gattaagttg ggtaacgcca gggttttccc agtcacgacg ttgtaaaacg    300
acggccagtg agcgcgacgt aatacgactc actatagggc gaattggcgg aaggccgtca    360
aggccacgtg tcttgtccag gtaccaagct tacacctctc tgtgtgggat ctggcatgca    420
gggacaggat aggcatatga ttcggatgag acagctcatc gacatcgtgg atcagctcaa    480
aaactacgtg aacgacctgg tgcccgagtt cctccccgct cctgaggatg tggaaaccaa    540
ctgtgagtgg agtgcttttt cctgctttca gaaggcacag ctcaaatccg ccaataccgg    600
caacaatgaa cggatcatca cgtgtccat caaaaaactc aaacggaaac cccctctac    660 aaatgctggc cgacggcaga acaccgcct cacttgtcct tcatgtgact cctacgaaaa    720
aaaacctccc aaggagtttc tcgaacgctt caaatcactg ctccagaaaa tgattcatca    780
gcacctgagt agtagggga gcggatcatg taacacgtcg agctctggag cacaagactg    840
gcctcatggg ccttccgctc actgcccgct ttccagtcgg gaaacctgtc gtgccagctg    900
cattaacatg gtcatagctg tttccttgcg tattgggcgc tctccgcttc ctcgctcact    960
gactcgctgc gctcggtcgt tcgggtaaag cctggggtgc ctaatgagca aaaggccagc   1020
aaaaggccag gaaccgtaaa aaggccgcgt tgctggcgtt tttccatagg ctccgccccc   1080
ctgacgagca tcacaaaaat cgacgctcaa gtcagaggtg gcgaaacccg acaggactat   1140
aaagatacca ggcgtttccc cctggaagct ccctcgtgcg ctctcctgtt ccgaccctgc   1200
cgcttaccgg atacctgtcc gcctttctcc cttcgggaag cgtggcgctt tctcatagct   1260
cacgctgtag gtatctcagt tcggtgtagg tcgttcgctc caagctgggc tgtgtgcacg   1320
aaccccccgt tcagcccgac cgctgcgcct tatccggtaa ctatcgtctt gagtccaacc   1380
cggtaagaca cgacttatcg ccactggcag cagccactgg taacaggatt agcagagcga   1440
ggtatgtagg cggtgctaca gagttcttga agtggtggcc taactacggc tacactagaa   1500
gaacagtatt tggtatctgc gctctgctga agccagttac cttcggaaaa agagttggta   1560
gctcttgatc cggcaaacaa accaccgctg gtagcggtgg tttttttgtt tgcaagcagc   1620
agattacgcg cagaaaaaaa ggatctcaag aagatccttt gatcttttct acggggtctg   1680
acgctcagtg gaacgaaaac tcacgttaag ggattttggt catgagatta tcaaaaagga   1740
```

```
tcttcaccta gatccttta aattaaaaat gaagttttaa atcaatctaa agtatatatg    1800
agtaaacttg gtctgacagt taccaatgct taatcagtga ggcacctatc tcagcgatct    1860
gtctatttcg ttcatccata gttgcctgac tccccgtcgt gtagataact acgatacggg    1920
agggcttacc atctggcccc agtgctgcaa tgataccgcg agaaccacgc tcaccggctc    1980
cagatttatc agcaataaac cagccagccg gaagggccga gcgcagaagt ggtcctgcaa    2040
ctttatccgc ctccatccag tctattaatt gttgccggga agctagagta agtagttcgc    2100
cagttaatag tttgcgcaac gttgttgcca ttgctacagg catcgtggtg tcacgctcgt    2160
cgtttggtat ggcttcattc agctccggtt cccaacgatc aaggcgagtt acatgatccc    2220
ccatgttgtg caaaaaagcg gttagctcct tcggtcctcc gatcgttgtc agaagtaagt    2280
tggccgcagt gttatcactc atggttatgt cagcactgca taattctctt actgtcatgc    2340
catccgtaag atgcttttct gtgactggtg agtactcaac caagtcattc tgagaatagt    2400
gtatgcggcg accgagttgc tcttgcccgg cgtcaatacg ggataatacc gcgccacata    2460
gcagaacttt aaaagtgctc atcattggaa aacgttcttc ggggcgaaaa ctctcaagga    2520
tcttaccgct gttgagatcc agttcgatgt aacccactcg tgcacccaac tgatcttcag    2580
catcttttac tttcaccagc gtttctgggt gagcaaaaac aggaaggcaa aatgccgcaa    2640
aaaagggaat aagggcgaca cggaaatgtt gaatactcat actcttcctt tttcaatatt    2700
attgaagcat ttatcagggt tattgtctca tgagcggata catatttgaa tgtatttaga    2760
aaaataaaca aatagggggtt ccgcgcacat ttccccgaaa agtgccac              2808
```

B-CELL STIMULATING FUSION PROTEINS OF AN ANTIGEN WITH BAFF OR APRIL

CROSS REFERENCE TO RELATED APPLICATIONS

This application is a §371 National Stage Application of PCT/NL2011/050159, filed Mar. 7, 2011, which claims priority to European Application No. 10155702.3, filed Mar. 5, 2010.

BACKGROUND OF THE INVENTION

1. Field of the Invention

The invention relates to the fields of molecular biology, medicine, virology and Vaccine development.

2. Description of Related Art

Vaccination is the administration of antigenic material (the vaccine) to produce immunity to a disease. Vaccines can prevent or ameliorate the effects of infection by many pathogens and are generally considered to be the most effective means of preventing infectious diseases. The material administered can for instance be live but weakened forms of pathogens (such as for instance bacteria or viruses), killed or inactivated forms of these pathogens, or purified material such as proteins.

Disadvantages of live, but weakened forms of pathogens are that these pathogens are still able to replicate and can in some cases manifest as a full-blown possibly life-threatening infection, especially in immunocompromised hosts. These forms of pathogens also have the possibility to mutate and become more virulent through such mutations. Killed or inactivated forms, if properly inactivated, do not have these disadvantages, but they have other disadvantages. Since a killed or inactivated pathogen cannot multiply, a large number of pathogens is required to stimulate immunity. Further, periodic boosters must be given to maintain immunity, only humoral immunity can be induced and since the vaccine must be injected (and not for instance orally taken), it is costly to administer.

Subunit vaccines are protein based vaccines that contain purified antigens rather than whole organisms; an example is the Bordetella pertussis antigens included in the acellular DPT vaccine. The acellular DPT vaccine comprises diphtheria and tetanus toxins and selected antigens of the pertussis pathogen. Subunit vaccines are not infectious, so they can safely be given to immunocompromised individuals, and they are less likely to induce unfavorable immune reactions that may cause side effects. Disadvantages of subunit vaccines are that the antigens may not retain their native conformation, so that antibodies produced against the subunit may not recognize the same protein on the pathogen surface. In general it takes at least two inoculations with a protein based vaccine to confer adequate protection. Another disadvantage is that isolated protein does not stimulate the immune system as well as a whole organism vaccine, because various components of live-attenuated and whole-inactivated vaccines provide co stimulatory signals.

In general, the effectiveness of subunit vaccines is increased by giving them in combination with adjuvant. Adjuvant slows antigen release for a more sustained immune stimulation, binds toll-like receptors on macrophages and dendritic cells to stimulate production of inflammatory cytokines, and activates APC to express B7. Alum (aluminum salts) is a common adjuvant used in human vaccines; it aggregates proteins to make them easier for phagocytes to engulf. Pertussis toxin, one of the components of the acellular DPT, acts as an adjuvant in that vaccine. Some bacterial components used as adjuvant in animals but which cause too much inflammation to be safe in humans are whole Mycobacterium tuberculosis, muramyl dipeptide from Mycobacterial cell walls, and bacterial DNA. One drawback of adjuvant used in human subunit vaccines is that such adjuvant induces a broad non-specific immune response rather than a specific immune response restricted to the administered antigen.

Because the different forms of the presently available vaccines all have their specific drawbacks, there is a need for alternative vaccine strategies.

SUMMARY

The current invention provides means and methods for such alternative vaccine strategies.

In a first embodiment, the invention provides a fusion protein comprising an antigen and a ligand capable of inducing, enhancing or sustaining a B cell immune response, wherein said ligand is selected from the group consisting of a compound comprising at least the extracellular domain of a proliferation inducing ligand (APRIL), a compound comprising at least the extracellular domain of a B-cell activating factor (BAFF), a compound comprising an amino acid sequence having at least 80% sequence identity with at least the extracellular domain of APRIL, and a compound comprising an amino acid sequence having at least 80% sequence identity with at least the extracellular domain of BAFF (Cerutti 2008, Kimberley 2009, Mackay 2009)(FIGS. 1 and 38). In a more preferred embodiment said sequence identity is at least 85%, preferably at least 90%, more preferably at least 95%, more preferably at least 98%, most preferably 100%. In a preferred embodiment, said ligand is selected from the group consisting of a compound comprising at least the extracellular domain of a proliferation inducing ligand (APRIL), a compound comprising an amino acid sequence having at least 80% sequence identity with at least the extracellular domain of APRIL. In a more preferred embodiment said sequence identity is at least 85%, preferably at least 90%, more preferably at least 95%, more preferably at least 98%, most preferably 100%

DETAILED DESCRIPTION OF A PREFERRED EMBODIMENT

Figure 1:
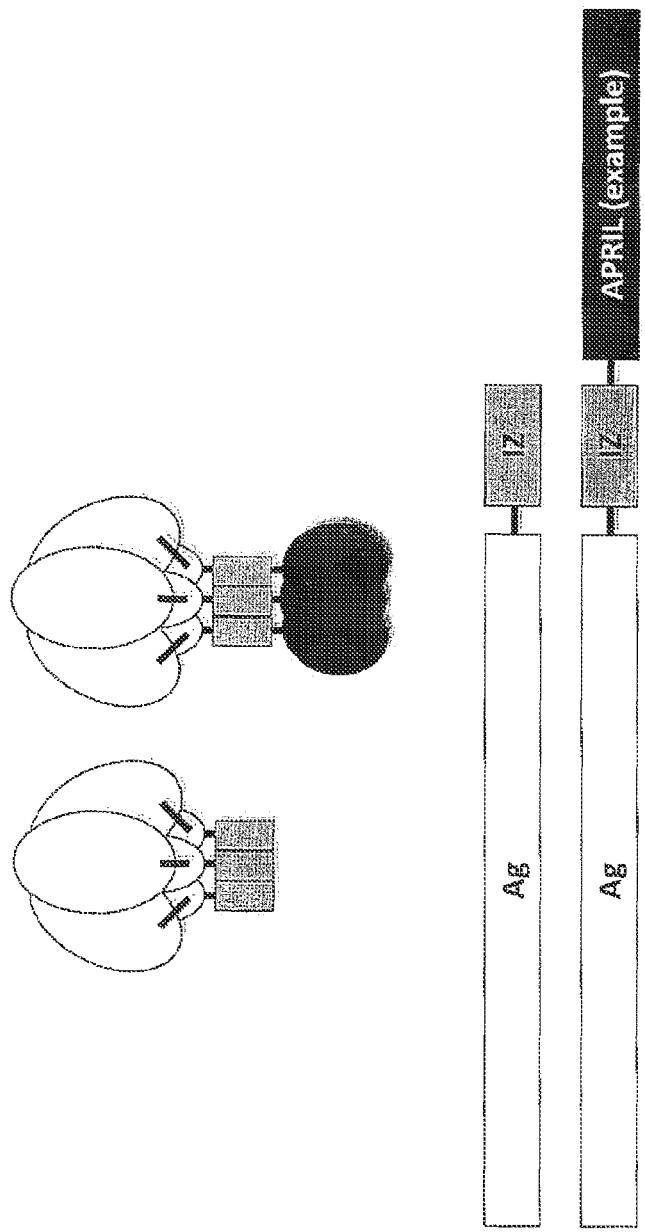
FIGS. 1-57 depict embodiments of the present invention as described herein.

As used herein, a compound comprising at least the extracellular domain of a proliferation inducing ligand (APRIL) or comprising an amino acid sequence having at least 80% sequence identity with the extracellular domain of APRIL will be referred to as "APRIL" or an "APRIL-like compound or protein". Consequently, a compound comprising at least the extracellular domain of a B-cell activating factor (BAFF) or comprising an amino acid sequence having at least 80% sequence identity with at least the extracellular domain of BAFF will be referred to as "BAFF" or a "BAFF-like compound or protein". Also within this definition of an APRIL-like and a BAFF-like compound said sequence identity is preferably at least 85%, more preferably at least 90%, more preferably at least 95%, more preferably at least 98%, most preferably 100%. De terms "APRIL" and "BAFF" are used whenever said amino acid sequence has 100% sequence identity with at least the extracellular domain of APRIL and BAFF, respectively. As used herein, de terms APRIL and BAFF include any orthologue thereof. The terms "APRIL" and "BAFF" thus includes sequences with 100% sequence identity with at least the extracellular domain of APRIL or BAFF of any species, preferably with at least the extracellular domain of human APRIL or human BAFF. The antigen can be any antigen known in the art, such as proteins or peptides, DNA, RNA, or chemicals, such as a hapten. It is preferred, however, that the antigen is an immunogenic part of a microorganism, preferably of a pathogenic microorganism, such as a bacterium, fungus, yeast, parasite or virus. It is preferred that the antigen resembles its native conformation when present in a fusion protein of the invention in order to closely mimic the antigen as present on the microorganism.

The term "% sequence identity" is defined herein as the percentage of nucleotides in a nucleic acid sequence that is identical with the nucleotides in a nucleic aid sequence of interest, after aligning the sequences and optionally introducing gaps, if necessary, to achieve the maximum percent sequence identity. Methods and computer programs for alignments are well known in the art. As used herein, the terms "nucleic acid sequence" and "nucleotides" also encompass non-natural molecules based on and/or derived from nucleic acid sequences, such as for instance artificially modified nucleic acid sequences, peptide nucleic acids, as well as nucleic acid sequences comprising at least one modified nucleotide and/or non-natural nucleotide such as for instance inosine, LNA, Morpholino, and 2'-O-methyl RNA.

The TNF family ligands BAFF (also called BLyS) and APRIL regulate lymphocyte survival and activation (Cerutti 2008, Kimberley 2009, Mackay 2009). BAFF can bind to three receptors, BAFF-R, TACI and BCMA, whereas APRIL can interact with TACI, BCMA and proteoglycans. BAFF and APRIL contribute amongst other to B-cell and plasma-cell survival, CD154 (CD40L)-independent antibody isotype switching, germinal center maintenance, T cell-dependent and T cell-independent antibody responses, and T cell co-stimulation. Human BAFF is a 285-amino acid long peptide glycoprotein which undergoes glycosylation at residue 124. It is expressed as transmembrane protein on various cell types including monocytes, dendritic cells and bone marrow stromal cells.

Human APRIL is a 250-amino acid long peptide glycoprotein. It is expressed as transmembrane protein on various cell types including B cells, dendritic cells, monocytes, macrophages, epithelial cells, T cells and osteoclasts. Importantly, both BAFF and APRIL are expressed as membrane forms as well as secreted forms.

A fusion protein of the present invention comprises APRIL or BAFF or an APRIL-like or a BAFF-like compound as defined above. A fusion protein of the present invention thus comprises at least the extracellular domain of APRIL or BAFF or comprises an amino acid sequence having at least 80% sequence identity with said extracellular domain. The extracellular domain of human BAFF consists of the amino acids 183-323, wherein the numbers correspond to the numbers used in FIG. 12. For human APRIL, the extracellular domain consists of the amino acids 115-250, wherein the numbers correspond to the numbers used in FIG. 12. A skilled person is capable of determining the corresponding domain in APRIL or BAFF of other species. A fusion protein comprising APRIL or BAFF or an APRIL-like or BAFF-like compound is superior in eliciting an immune reaction to an antigen than fusion proteins comprising no co-stimulatory molecule or some other co-stimulatory molecule, for instance CD40L. In a preferred embodiment, a fusion protein according to the invention is provided, wherein said antigen comprises a protein derived from a pathogen, preferably a virus protein, or an immunogenic part thereof.

Normally BAFF and APRIL act on their receptor counterpart in the form of a trimer. This can be either a heterotrimer or a homotrimer. Heterotrimers comprise for instance 1 APRIL protein and 2 BAFF proteins or for instance 2 APRIL proteins and 1 BAFF protein.

In another preferred embodiment, therefore, a fusion protein according to the invention is provided, further comprising a multimerizing polypeptide, preferably a trimerizing polypeptide. A trimerizing polypeptide, for instance an isoleucine zipper peptide, enables the formation of trimeric complexes comprising preferably three fusion proteins according to the invention.

As already mentioned, a fusion protein of the invention preferably comprises a virus protein or an immunogenic part thereof. One example of a virus for which vaccine development is hampered because of many of the problems discussed previously is human immunodeficiency virus (HIV). The classical vaccination approaches that have been successful in the control of various viral diseases by priming the adaptive immunity to recognize viral envelope proteins have failed for instance in the case of HIV. Reasons for the failure may be that the epitopes of the HIV viral envelope glycoprotein complex (Env) are too variable (due to HIV's high mutation rate) and that the functionally important epitopes of the HIV Env are masked by glycosylation, trimerisation and receptor-induced conformational changes, making it difficult to induce neutralizing antibodies to the virus.

Protein-based vaccines to HIV have failed to elicit protective immune responses. We improved the immunogenicity of HIV envelope glycoprotein (Env) based protein vaccines by fusion of an Env antigen to APRIL(-like) or BAFF(-like) proteins which are co-stimulatory molecules that target the Env antigen directly to B cells and at the same time activate these cells. The present invention provides the surprising insight that APRIL and BAFF are superior to CD40L. Unexpectedly, CD40L is less efficient in inducing an immune response than APRIL and BAFF. This is a surprising finding, because one would expect CD40L to be efficient in inducing an immune response, as CD40L is known to target dendritic cells. Dendritic cells are very efficient antigen presenting cells and one would thus expect that CD40L would be very efficient in inducing an immune response. Use of CD40L as an adjuvant is therefore frequently suggested in the literature, for instance in virus vaccines or for tumor therapy. The present invention shows, however, that direct targeting of antigens to B cells via APRIL(-like) and BAFF(-like) proteins, is superior for subunit vaccines for HIV and other microbial diseases. The invention furthermore provides the insight that especially APRIL(-like) proteins are superior for subunit vaccines for several viruses, because APRIL preferably induces an IgA response, which is beneficial for protection against viruses that enter via the mucosal route, such as HIV, Ebola and Influenza. As IgA is an immunoglobulin present on mucosa, it is especially useful to induce an IgA response for strengthening the first line of defense against a virus that uses the mucosa for entry. Non-limiting examples of such viruses are HIV, Ebola and Influenza virus.

Although live-attenuated SIV/HIV vaccines have consistently elicited protective immune responses in monkey models and are thus also superior to subunit or protein-based vaccines, the use of live-attenuated HIV vaccines is considered to be unsafe for human use (Reynolds 2008). Recombinant viral vectors such as adenovirus that express HIV-1 proteins continue to be evaluated despite recent setbacks, but they have so far not elicited neutralizing antibody (NAb)

responses efficiently (Liu 2009). Mucosal immunity against HIV-1 has also proven hard to elicit by any vaccine approach, a substantial problem considering that the virus is sexually transmitted (Shattock 2008).

Inducing high titers of broadly active NAbs is a major goal of many HIV vaccine approaches that has not yet been achieved. The most common approaches are based around protein subunit immunogens that mimic the native viral envelope glycoprotein complex (Env), which is the only target for NAbs. Unfortunately, most anti-Env antibodies are unable to neutralize primary HIV-1 isolates. Vaccines based on monomeric gp120 proteins failed to confer protection in efficacy trials (Flynn 2005, Pitisuttithum 2006). The difficulty in inducing NAbs is in part rooted in the structure of the Env complex, which has evolved multiple defenses that limit the induction and binding of such antibodies. Thus, various structural devices shield otherwise vulnerable conserved neutralization epitopes such as the receptor binding sites (Burton 2004, Eggink 2007, Kwong 2009), and highly immunogenic but non-neutralizing epitopes exposed on non-functional forms of Env serve as immune decoys (Parren 1997).

As already said above, one limitation to subunit protein vaccines in general (or DNA plasmid vaccines that encode such proteins) is their poor immunogenicity compared to live-attenuated or inactivated viral vaccines. Moreover, the HIV-1 Env proteins are particularly poor immunogens. Thus, the anti-Env titers in current studies with vaccinated individuals are relatively low compared to those raised against other protein antigens, and the anti-Env antibodies have an unusually short half-life of 30-60 days (Gilbert 2005). Other factors such as the magnitude and duration of the antibody response, affinity maturation and the induction of B cell memory are also relevant to the design of an effective B-cell vaccine against HIV-1. The poor performance of Env-based vaccines in these areas is rooted in the structure of the Env complex and how the latter interacts with the immune system. By providing additional stimulatory signals to B cells it is possible not only to increase the extent and duration of antibody production, but also improve their quality, probably because the increase in B cell stimulation promotes antibody affinity maturation (Delgado 2009). A few attempts to conjugate HIV-1 Env immunogens to co-stimulatory molecules to improve antibody responses have been made, but with limited success (Bower 2004, Koch 2005). Another approach to the problem, using model antigens, showed that antigen targeting to dendritic cells (DC) via lectins such as DC-SIGN, DEC205, DCIR2 or Clec 12A can augment antigen-specific immune responses (Bonifaz 2004, Dudziak 2007, Yang 2008, Lahoud 2009).

DC are thought to be critical in orchestrating efficient antibody and T cell responses and targeting vaccines to DC is thought to be the most efficient way to enhance the immunogenicity of vaccines (Steinman&Banchereau 2007). This is a reason why others have used CD40L as an adjuvant in vaccine development. In contrast to these approaches that aim at targeting vaccines to DC, the present invention uses APRIL (-like) and BAFF(-like) compounds which do not target dendritic cells. Instead, an antigen is directly targeted to B cells. Although dendritic cells, which play a central role in immunity are not targeted, antigenic constructs according to the invention appear to provide better immune responses as compared to currently known vaccines.

The invention shows for the first time that a fusion protein according to the invention is preferred for the development of an immunogenic composition for HIV. Of course, fusion proteins according to the invention are also useful for the development of an immunogenic composition for other pathogens, such as for instance Ebola virus and influenza virus.

In a preferred embodiment, therefore, a fusion protein according to the invention is provided, wherein said antigen has at least 80% sequence identity with a virus protein of HIV, influenza virus, or Ebola virus, or with an immunogenic part of a protein of any of these viruses. In a more preferred embodiment said sequence identity is at least 85%, preferably at least 90%, more preferably at least 95%, more preferably least 98%, most preferably 100%.

In a more preferred embodiment, the invention provides a fusion protein according to the invention, wherein said virus protein is a gp120 protein or a gp160 protein of HIV, a hemagglutinin protein of influenza or a glycoprotein of Ebola.

An immunogenic part of a protein is defined herein as a part of a protein which is capable of eliciting an immune response in a human individual and/or a non-human animal. Preferably said immunogenic part is capable of eliciting the same immune response in kind, albeit not necessarily in amount, as said protein. The immune response elicited by said immunogenic part is preferably directed to the native (whole) protein as it is present in vivo, for instance on the surface of a pathogen. An immunogenic part of a protein preferably comprises one or more epitopes of said protein. An epitope of a protein is defined as a part of said protein, at least about 5 amino acids in length, capable of eliciting a specific antibody and/or immune cell capable of specifically binding said epitope. Two different kinds of epitopes exist: linear epitopes and conformational epitopes. A linear epitope comprises a stretch of consecutive amino acids. A conformational epitope is formed by several stretches of consecutive amino acids that are folded in position and together form an epitope in a properly folded protein. An immunogenic part of the invention is capable of comprising either one, or both, of said kinds of epitopes. An immunogenic part of a protein comprises at least 5 amino acid residues. Preferably said immunogenic part comprises at least 10, more preferably at least 15, more preferably at least 25 and most preferably at least 30 amino acids. Said immunogenic part preferably comprises at most about 500 amino acid residues, more preferably at most 250 amino acid residues, depending on the kind of protein from which said immunogenic part is derived.

The invention preferably makes use of APRIL or BAFF or BAFF-like or APRIL-like compounds because the invention shows that a fusion protein according to the invention comprising a BAFF(-like) protein or an APRIL(-like) protein is superior in inducing an immune response to an antigen as compared to a fusion protein comprising CD40L. APRIL and BAFF are important in inducing IgA secretion from mucosal B cells (Cerutti 2008, Xu 2008) and are therefore also superior in improving mucosal immunity to an antigen as compared to CD40L. Examples of pathogens that are preferably targeted at mucosal sites are HIV, hepatitis virus, influenza virus, and salmonella bacteria.

In a preferred embodiment, a fusion protein according to the invention is provided, wherein said inducing, enhancing or sustaining a B cell immune response involves immunoglobulin class switching, preferably a class switch to an immunoglobulin of class A (IgA). In more preferred embodiment, a fusion protein according to the invention is provided, wherein said ligand is an APRIL or APRIL-like protein.

In a working example, the invention shows that soluble trimeric gp140-APRIL/BAFF/CD40L fusion proteins can be expressed and trimerize efficiently, and bind CD4 and anti-Env Nabs demonstrating that the proteins are well folded. In another working example the invention shows that Env-APRIL and Env-BAFF induce higher titers of Env-specific antibodies in rabbits than Env alone or than Env fused to CD40L. Importantly, the virus neutralizing antibody responses were also improved, in particular with Env-APRIL. The invention further shows that rabbits primed with Env-APRIL induced an enhanced memory response upon recall with Env protein (without co-stimulatory molecule) and an Env-specific T cell response was enhanced when mice were immunized with Env-APRIL or Env-BAFF as compared to Env alone or Env-CD40L. Further, the examples show that Env-CD40L was less effective than the APRIL or BAFF containing fusion proteins in eliciting B- or T-cell responses.

Although an antigen can be directly linked to an APRIL (-like) protein or a BAFF(-like) protein of the invention, it is preferred that the antigen is linked via a linker. Such linker for instance enables the correct folding of the BAFF(-like) or APRIL(-like) protein and of the antigen, independently from one another. The linker preferably supplies enough freedom for the two protein domains to not interact with each other and to not disturb the correct folding of the domains. Said linker preferably comprises an amino acid stretch with a preferred length of between 1 and 20 amino acids, preferably between 4 and 13 amino acids, most preferred with a length of 11 amino acids.

Preferably, said linker is a glycine-rich linker, preferably comprising an amino acid sequence selected from the group consisting of GGGX (SEQ ID NO:1), GGGXGGG (SEQ ID NO:2), GGGGXGGGGXGGG (SEQ ID NO:3), GGGGXGGGGXGGGGXGGG (SEQ ID NO:4), GGXGGG (SEQ ID NO:5), and GGGGXGGGGXG (SEQ ID NO:6), wherein X is an amino acid selected from the group consisting of Arginine (R), Threonine (T) and Serine (S).

In a preferred embodiment, therefore, a fusion protein according to the invention is provided, wherein said antigen is indirectly linked to said APRIL(like) or BAFF(-like) protein via a linker comprising an amino acid sequence with a length of between 1 and 20 amino acids, preferably between 4 and 13 amino acids, most preferably 11 amino acids. In a preferred embodiment, said linker is a glycine-rich linker, preferably comprising an amino acid sequence selected from the group consisting of GGGX (SEQ ID NO:1), GGGXGGG (SEQ ID NO:2), GGGGXGGGGXGGG (SEQ ID NO:3), GGGGXGGGGXGGGGXGGG (SEQ ID NO:4), GGXGGG (SEQ ID NO:5), and GGGGXGGGGXG (SEQ ID NO:6), wherein X is an amino acid selected from the group consisting of Arginine (R), Threonine (T) and Serine (S).

A fusion protein comprising an APRIL-like compound or a BAFF-like compound of the invention linked directly or indirectly via a linker, to an antigen in one embodiment results in a monomer.

However, a multimer is preferred, because, as said before, APRIL and BAFF exert their function as a trimer. Also, for instance the Env protein of HIV forms trimeric complexes on the surface of a HIV particle. In order to produce a trimeric complex of fusion proteins according to the invention, a multimerizing polypeptide is preferably introduced in said fusion proteins. Said multimerizing polypeptide is preferably inserted in a fusion protein according to the invention between a BAFF(-like) or APRIL(-like) protein and an antigen. Multimerization of multiple fusion proteins according to the invention, however, can result in suboptimal conformation of the BAFF(-like) or APRIL(-like) protein or the antigen when the polypeptide is coupled directly to the compound or the antigen. It is therefore preferred that a linker is introduced between the BAFF(-like) or APRIL(-like) protein and the multimerizing polypeptide. It is also preferred to introduce a linker between the multimerizing polypeptide and the antigen.

Such linker enables the different parts forming a trimeric complex to adapt a conformation that is not restricted by the multimerizing polypeptide. As shown schematically in figure YYY, a complex according to the invention preferably enables the parts that for instance form a BAFF-like or APRIL-like trimer to have some degrees of freedom in order to form a conformation resembling a native conformation. As said above, said linker also enables the correct folding of the BAFF(-like) or APRIL(-like) protein and of the antigen, independently from one another within each monomeric fusion protein. In one preferred embodiment, a fusion protein according to the invention thus comprises an antigen, linked via a first linker to a multimerizing peptide, said multimerizing peptide being linked via a second linker to an APRIL-like or BAFF-like compound. Preferably said first and said second linker have, independently from one another, a length of between 1 and 20 amino acids, preferably between 4 and 13 amino acids, more preferred with a length of 6 or 11 amino acids. It is most preferred that said first linker has a length of 6 amino acids and said second linker has a length of 11 amino acids. Preferably, said first and/or said second linker is a glycine-rich linker comprising an amino acid sequence selected from the group consisting of GGGX (SEQ ID NO:1), GGGXGGG (SEQ ID NO:2), GGGGXGGGGXGGG (SEQ ID NO:3), GGGGXGGGGXGGGGXGGG (SEQ ID NO:4), GGXGGG (SEQ ID NO:5), and GGGGXGGGGXG (SEQ ID NO:6), wherein X is an amino acid selected from the group consisting of Arginine (R), Threonine (T) and Serine (S).

Preferably said first linker comprises an amino acid sequence consisting of GGRGGG (SEQ ID NO:5) and said second linker comprises an amino acid sequence consisting of GGGGTGGGGTG (SEQ ID NO:6). The combination of these two linkers in a fusion protein according to invention enables both, the correct folding of the BAFF(-like) or APRIL (-like) protein and of the antigen, independently from one another within each monomeric fusion protein, and the trimeric complex adapting a conformation that is not restricted by the multimerizing polypeptide.

As the invention provides a fusion protein useful for vaccine development, the invention also provides a nucleic acid molecule encoding a fusion protein according to the invention. Such a nucleic acid molecule can for instance be inserted into a vector or a virus and be used for expressing said fusion protein using a suitable expression system.

As already said above, BAFF and APRIL generally act as trimeric complexes. A trimeric complex of a fusion protein according to the invention is thus preferably used. The invention thus provides an oligomeric complex comprising at least 1, preferably at least 2, more preferably at least 3 fusion protein(s) according to the invention.

In a preferred embodiment, an oligomeric complex according to the invention is provided, comprising a multitude of trimeric fusion proteins according to the invention. Such polytrimeric constructs form, as the name implies, a multitude of trimers.

Although BAFF and APRIL function when they are trimeric, optimal activation is achieved when they are multimeric (i.e. a multitude of trimers). Multimeric fusion constructs are therefore preferably created. As an additional advantage increased multimerization also contributes to enhanced Env-BCR cross-linking and enhanced B cell activation. Thus, when HIV-Env is used as an antigen, a multimer is preferably used.

Of course, other proteins or for instance particles can be used to form polytrimeric constructs. The inventors show in working examples that this concept works for instance with fusion proteins of the invention immobilized on nanoparticles when the C-terminal trimerization domain is fused to a C-terminal Histidine tag that enables immobilization on a Ni-NTA coated nanoparticle. In addition it is shown that fusion proteins of the invention can be immobilized on nanoparticles when the C-terminal trimerization domain is fused to the Fc part of immunoglobulin G, resulting in hexameric molecules, via binding of the Fc domain to protein A/G on nanoparticles.

Methods for producing a fusion protein according to the invention are also provided. This is for instance done by expressing a nucleic acid sequence encoding a fusion protein according to the invention.

The invention therefore further provides a method for producing a fusion protein according to the invention, said method comprising generating/providing a nucleic acid molecule encoding a fusion protein according to the invention and expressing said nucleic acid molecule in a suitable expression system. This is for instance done by generating a nucleic acid molecule comprising a first nucleic acid sequence encoding an antigen and a second nucleic acid sequence encoding an amino acid sequence with at least 80% sequence identity with at least the extracellular domain of APRIL and/or BAFF. In a preferred embodiment, said nucleic acid molecule further comprises, between said first and said second nucleic acid sequence, a nucleic sequence encoding a polypeptide, which is a linker. In another preferred embodiment said sequence identity is at least 85%, preferably at least 90%, more preferably at least 95%, more preferably least 98%, most preferably 100%.

As already said before, a complex of multiple fusion proteins according to the invention is preferred. Therefore, in another preferred embodiment, said nucleic acid molecule further comprises a third nucleic acid sequence encoding a multimerizing polypeptide. In a more preferred embodiment, said nucleic acid molecule further comprises, between said first and said second nucleic acid sequence another nucleic acid sequence encoding a polypeptide, which is a first linker, and between said second and said third nucleotide sequence yet another nucleotide sequence encoding yet another polypeptide, which is a second linker. Said first and said second linker can have different lengths and/or different amino acid sequences, but they can also be identical. In a more preferred embodiment, said first and said second linker comprise an amino acid sequence having, independently from one another, a preferred length of between 1 and 20 amino acids, preferably between 4 and 13 amino acids, more preferred with a length of 6 or 11 amino acids. It is most preferred that said first linker has a length of 6 amino acids and said second linker has a length of 11 amino acids. As already outlined above, such linker is preferred because it enables the correct folding of the BAFF(-like) or APRIL(-like) protein and of the antigen, independently from one another, and it enables the different parts forming a trimeric complex to adapt a conformation that is not restricted by the multimerizing polypeptide. In a more preferred embodiment said first and/or said second linker comprise amino acid sequence selected from the group consisting of GGGX (SEQ ID NO:1), GGGXGGG (SEQ ID NO:2), GGGGXGGGGXGGG (SEQ ID NO:3), GGGGXGGGGXGGGGXGGG (SEQ ID NO:4), GGXGGG (SEQ ID NO:5), and GGGGXGGGGXG (SEQ ID NO:6), wherein X is an amino acid selected from the group consisting of Arginine (R), Threonine (T) and Serine (S).

In a most preferred embodiment, said first linker comprises a polypeptide having the amino acid sequence GGRGGG (SEQ ID NO:5) and said second linker comprises a polypeptide having the amino acid sequence GGGGTGGGGTG (SEQ ID NO:6).

In a preferred embodiment, said allowing expression of said fusion protein from said nucleic acid molecule comprises expression of said fusion protein from said nucleic acid molecule in a virus.

Now that the invention provides fusion proteins, methods, complexes and nucleic acid molecules according to the invention, in yet another embodiment, the invention provides a virus comprising a fusion protein according to the invention or obtainable by a method according to the invention. A virus comprising a complex and/or a nucleic acid sequence according to the invention is also provided. Such a virus is especially useful for preparing an immunogenic composition as such a virus is still capable of reproduction. An advantage of a reproducing virus is that less virions are needed for one vaccine dose, as the virus is able to replicate further in the host. Furthermore, such a virus comprises an APRIL(-like) or BAFF(-like) protein which are very efficient in inducing, sustaining or improving an immune response. In a preferred embodiment, a virus comprising an APRIL(-like) protein is provided, which is very efficient in inducing, sustaining or improving an IgA response. For an immunogenic composition of the invention, a fusion protein, a complex, and/or a nucleic acid according to the invention can also be used. In yet another embodiment therefore, the invention provides an immunogenic composition comprising a fusion protein according to the invention or a fusion protein obtainable by a method according to the invention, and/or comprising a complex, a nucleic acid, and/or a virus according to the invention. An immunogenic composition according to the invention is especially useful for developing a vaccine for use in preventing, treating and/or diminishing an infection with a pathogen. In a preferred embodiment therefore, an immunogenic composition according to the invention comprises a vaccine. Said vaccine preferably comprises a suitable adjuvant such as for instance Specol or a double oil emulsion.

In one embodiment, an immunogenic composition is provided which comprises at least one fusion protein according to the invention. Preferably, said composition comprises a complex of at least three fusion proteins according to the invention. In another preferred embodiment, however, an immunogenic composition is provided which comprises a virus, which virus comprises at least one fusion protein according to the invention. As stated above, an immunogenic composition comprising a virus according to the invention is especially useful because such virus is preferably capable of replicating to some extent in the host. Said fusion protein is preferably at least in part present on the surface of said virus, so that said fusion protein is exposed to an immune response of an animal and/or human. Said virus preferably comprises an attenuated virus, so that the virus's capability of spreading upon administration to a subject is diminished as compared to a wild-type virus. It is useful to have some spreading in the host in order to increase antigen exposure, but a virus according to the invention preferably does not manifest itself as a full-blown infection. In one embodiment, said virus is an attenuated HIV virus which is especially useful for an AIDS vaccine. Use of a live attenuated HIV vaccine has however generally been avoided by vaccine developers, because of the fear that the attenuated vaccine strain could revert over time to a virulent and pathogenic phenotype, raising serious safety concerns. It is therefore that preferably another kind of viral vector is used, for instance a viral vector based on a virus such as, but not limited to, Sindis virus, Semliki (like) Forest virus, canarypox virus, chicken pox virus, or Vaccina virus.

An immunogenic composition according to the invention is especially useful for developing a vaccine for use in at least in part preventing, treating and/or diminishing a virus infection, especially an HIV infection. In a preferred embodiment therefore, an immunogenic composition according to the invention comprises a vaccine. An immunogenic composition according to the invention for use in at least in part preventing, treating and/or diminishing an infection, preferably a virus infection, more preferably an infection selected from the group consisting of HIV infection, influenza virus infection and Ebola virus infection is also provided. Also provided is a fusion protein according to the invention or obtainable by a method according to the invention, and/or a complex, a nucleic acid molecule, a virus, and/or an immunogenic composition according to the invention, for use as a medicament and/or prophylactic agent. An immunogenic composition according to the invention is preferably used for inducing or enhancing an immune response specific for a virus, preferably HIV, influenza virus or Ebola virus. A fusion protein of the invention, or a nucleic acid molecule encoding said fusion protein, or a complex or a virus comprising said fusion protein is especially useful for the purpose of inducing or enhancing an immune response specific for a virus, preferably HIV, influenza virus or Ebola virus. Fusion proteins according to the invention allow an immune system of an animal and/or human to recognize at least one part, called epitope, of a virus protein, such as for instance of the HIV envelope glycoprotein or of a hemagglutinin protein of influenza or of a glycoprotein of Ebola, that is shielded in a wild-type virus without the modifications of the invention. A fusion protein of the invention is especially useful for this purpose, because it comprises an antigen and a BAFF(-like) compound or an APRIL(-like) compound, which are very efficient in inducing, sustaining and/or improving an immune response to said antigen. Many viruses enter the human body via the mucosa. It is known that especially IgA plays an important role in mucosal immunological first line of defense. In a preferred embodiment, the invention thus provides a fusion protein for use in inducing an immune response to an antigen, wherein said immune response comprises an IgA respons. In a more preferred embodiment, said antigen is a virus antigen. The immune response thus generated by a fusion protein of the invention allows for the induction of antibodies, preferably IgA antibodies, directed against said epitope. In one embodiment, said epitope comprises at least part of a conserved epitope of the gp120 protein and/or at least part of a conserved epitope of the gp160 protein and/or at least part of a conserved epitope of the hemagglutinin protein of influenza and/or at least part of a conserved epitope of the glycoprotein of Ebola. Preferably said epitope comprises the receptor binding site of the gp120 protein or of the hemagglutinin protein of influenza or of the glycoprotein of Ebola. Antibodies directed against at least part of a conserved epitope will, since the epitope is conserved, bind several strains of a pathogen. If said epitope is for instance present on a receptor binding-site, an antibody directed towards said epitope will at least partially inhibit a function of the protein, for instance binding of the receptor binding-site of an Env protein to the CD4 receptor on T-cells, thereby for instance inhibiting entry of the virus into said T cell.

In another preferred embodiment, however, said epitope comprises another epitope such as for instance a conformational mannose epitope in gp120, or a membrane proximal region in gp41. Antibodies that are capable of inhibiting function of a pathogen are called neutralizing antibodies, because they are able to neutralize the function of a protein from said pathogen such that the pathogen is deficient in its capability of performing at least one function. For instance the Env protein enables a HIV virus to enter a T cell and spread infection. A neutralizing antibody binding an Env protein will thus prevent a HIV virus entering a T cell, or at least slow down the process of entering a T cell. With deficient is meant herein that the pathogen has a diminished capability of performing at least one of its functions, for example a HIV virus is slowed down in entering a T cell or the virus is completely unable to enter the T cell. It is especially useful if said pathogen is deficient in such a way that the host is able to combat said pathogen and spread of infection is prevented, halted or slowed down.

In a preferred embodiment therefore, the invention provides a fusion protein according to the invention or a fusion protein obtainable by a method according to the invention, and/or a complex, a nucleic acid molecule, a virus, and/or an immunogenic composition according to the invention for use in inducing, enhancing and/or sustaining an immune response specific for a virus, preferably HIV, influenza virus or Ebola virus. In a more preferred embodiment, said immune response comprises production of an antibody, preferably a neutralizing antibody.

In an even more preferred embodiment, said antibody is specific for HIV, influenza virus or Ebola virus. As said before, it is preferred that an antibody is specific for a conserved amino acid sequence of the envelope glycoprotein complex (Env) of HIV, or specific for a conserved amino acid sequence of the hemagglutinin protein of influenza virus, or specific for a conserved amino acid sequence of a glycoprotein of Ebola virus because an antibody to a conserved epitope is capable of binding several strains. More preferred, said antibody is specific for a CD4 receptor binding-site of HIV.

As a fusion protein, complex, nucleic acid molecule, virus or composition according to the invention is especially useful for inducing, enhancing, and/or improving an immune response against a virus, in yet another embodiment, the invention provides the use of a fusion protein according to the invention or obtainable by a method according to the invention, and/or use of a complex, a nucleic acid molecule, a virus, and/or an immunogenic composition according to the invention for the preparation of a medicament or prophylactic agent for inducing or enhancing an immune response specific for a virus, preferably a human immunodeficiency virus (HIV), influenza virus or Ebola virus.

The invention thus provides means and methods for inducing an antibody response to an antigen, preferably a virus protein, more preferably a virus protein of HIV, influenza virus or Ebola virus. The means and methods according to the invention are especially useful for inducing an improved antibody response because APRIL(-like) or BAFF(-like) proteins are used in said means and methods. Preferably APRIL(-like) proteins are used in said means and methods. The present invention shows that APRIL(-like) or BAFF(-like) proteins are superior in improving an antibody response when compared to the antigen alone or even when compared to the antigen coupled to another co-stimulatory molecule, for instance CD40L. The use of antibodies to an antigen is thought to be especially useful in at least in part preventing or treating infection when a subject is thought to be very recently infected or if an individual is at risk of getting infected. Use of antibodies for such a purpose is known under the term "passive vaccination". Passive vaccination is used under certain circumstances, sometimes in combination with active vaccination. The passive component of such a combination quickly counteracts the pathogen which has or may have entered the body, whereas the active vaccine counteracts subsequent infections. This concept is also especially useful in the present invention. For instance, a person involved in a so called "prick or puncture accident" in a hospital setting may be first administered a passive vaccine, containing antibodies obtained using a fusion protein according to the invention specific for the pathogen. Preferably said antibodies are neutralizing antibodies. Optionally, such an individual may thereafter be actively immunized with a fusion protein, a complex, a nucleic acid, a virus, and/or an immunogenic composition according to the invention, for instance if said individual still suffers or is at risk of suffering from an infection with the pathogen. In such a case, the passive immunization will counteract penetrated pathogens, for instance virus particles, thereby counteracting spread of infection within the host, whereas a subsequent active immunization will induce antibodies that counteract pathogens that were not neutralized by the passive vaccine, but also any future infections with the same or a similar pathogen. In another situation, it may be preferred to only use passive immunization, for instance if the host is immunocompromised and active immunization is either impossible or dangerous to the host. In another situation, only active immunization may be preferred, for instance if it is unclear if and when an infection may occur and when it is useful to induce (protective) immunity in the host as a preventive measure. By employing forced virus evolution to select for improved Env deletion variants the inventors previously obtained functionally improved Env variants lacking at least part of the V1/V2 domain. Functionally improved variants were obtained wherein for instance at least part of the V1/V2 domain of HIV-Env was deleted and/or wherein amino acids within the V1/V2 domain of HIV-Env had been exchanged. This is described in more detail in PCT/NL2009/050609, which is incorporated herein by reference. Compensatory changes in gp120, but also in gp41 were identified that improve folding and secretion of stable loop-deleted Env trimers and that benefit the generation of recombinant Env trimers for vaccine and structural studies. The present invention thus also encompasses a fusion protein according to the invention, wherein at least part of the V1/V2 domain of HIV-Env is deleted and/or wherein amino acids within the V1/V2 domain of HIV-Env have been exchanged. Such fusion protein has at least two advantages. First, the deletions and/or amino acid exchanges within the V1 and/or V2 loop improve the folding and secretion of the Env trimers. Second, because of the inclusion of at least one APRIL(-like) or BAFF(-like) compound, such fusion protein is very well capable of inducing, sustaining and/or improving an immune response to said improved folded Env trimer. For the amino acid numbering reference is made to the alignment of gp120 of different strains as depicted in FIG. 40, whereas the variant numbers refer to the structural variants as depicted in FIG. 39.

In respect of the above, the invention thus provides in a preferred embodiment, a fusion protein and/or a method and/or a complex according to the invention, wherein said fusion protein comprises a polypeptide with a length of at least 300 amino acids with at least 80% sequence identity to a gp120 protein or gp160 protein of HIV with a deletion of at least 5 amino acids, preferably at least 10, more preferably at least 20, more preferably at least 40, most preferably at least 60 amino acids in the region corresponding to amino acid positions 120-204 of HXB2, wherein the amino acid positions are indicated in FIG. 40. For other isolates, the corresponding gp120 region is determined by conventional alignment with at least one sequence of FIG. 40. Preferably, said deletion comprises at least 10, more preferably at least 20, even more preferably at least 40, most preferably at least 60 amino acids in the region comprising, or corresponding to said amino acid positions 120-204. In a more preferred embodiment said sequence identity is at least 85%, preferably at least 90%, more preferably at least 95%, more preferably least 98%, most preferably 100%. In another preferred embodiment, said polypeptide has a length of at least 350, more preferred at least 375, more preferred at least 400, more preferred at least 425, more preferred at least 450, most preferred at least 475 amino acids. As already stated above, such deletions improve the secretion and/or folding of Env timers. Furthermore, it is possible, as the inventors have shown in a working example, to insert other amino acid sequences at the site of deletion.

There are advantages to inserting an amino acid sequence at the site of deletion in a gp120 or gp160 protein of HIV. In a working example, the inventors have shown for instance that by deleting part of the V1 and V2 loop and replacing the deleted part by an amino acid sequence encoding a GMCSF protein, an Env-specific immune response is induced that is superior to that elicited by a protein without the GMCSF inserted. The invention thus provides proof of principle that replacing at least part of the V1 and/or V2 loop and replacing the deleted part by an amino acid sequence coding for a co-stimulatory molecule, such as a cytokine, improves an immune response towards the Env protein of HIV.

In one embodiment, therefore, the invention provides a fusion protein comprising an antigen and a polypeptide comprising an amino acid sequence having at least 80% sequence identity with a cytokine capable of inducing or sustaining a B cell immune response. In a preferred embodiment, said sequence identities are, independently from one another at least 85%, preferably at least 90%, more preferably at least 95%, more preferably at least 98%, most preferably 100%.

The polypeptide comprising an amino acid sequence having at least 80%, preferably at least 85%, preferably at least 90%, more preferably at least 95%, more preferably at least 98%, most preferably 100% sequence identity with a cytokine are preferably linked to the antigen directly at the C-terminal or N-terminal end of the antigen sequence. It is also possible to use linkers or spacers for coupling the cytokine sequence to the antigen sequence.

In a preferred embodiment, the polypeptide is not coupled to the C-terminal or N-terminal amino acid, but instead inserted in the antigen sequence, such that it is flanked by two amino acid sequences of the antigenic sequence. It is preferred that a part of the antigen sequence is deleted and that the cytokine sequence is inserted at this deletion site. In a preferred embodiment, the antigen is a HIV antigen. In a most preferred embodiment, the invention provides a fusion protein according to the invention, wherein said antigen comprises an amino acid sequence with a length of at least 300 amino acids with at least 80% sequence identity to a gp120 protein and/or a gp160 protein of HIV envelope glycoprotein complex (Env), wherein at least 5 amino acids of the V1 loop and/or at least 5 amino acids of the V2 loop of said gp120 molecule are absent, and wherein at the deletion site in V1 and/or at the deletion site in V2, said polypeptide is inserted. In a preferred embodiment, said sequence identity is at least 85%, preferably at least 90%, more preferably at least 95%, more preferably at least 98%, most preferably 100%.

In a preferred embodiment, a fusion protein according to the invention is provided, wherein said cytokine is GMCSF or IL-21.

In one embodiment, the invention thus provides a fusion protein comprising an amino acid sequence with a length of at least 300 amino acids with at least 80% sequence identity to a gp120 protein or a gp160 protein of HIV envelope glycoprotein complex (Env), wherein at least 5 amino acids of the V1 loop and/or at least 5 amino acids of the V2 loop of said gp120 molecule are absent, and wherein at the deletion site in V1 and/or at the deletion site in V2, a polypeptide is inserted with at least 80% sequence identity with a co-stimulatory molecule. Said co-stimulatory molecule is preferably selected from the group consisting of GMCSF, IL2, IL4, IL-5, IL-10, IFN$_\gamma$, IL12, IL17, IL-21, IL-23 and TSLP. In a particularly preferred embodiment, said co-stimulatory molecule is a cytokine selected from GMCSF and IL-21. In another preferred embodiment said sequence identities are, independently from one another at least 85%, preferably at least 90%, more preferably at least 95%, more preferably at least 98%, most preferably 100%. In another preferred embodiment, said polypeptide has a length of at least 350, more preferred at least 375, more preferred at least 400, more preferred at least 425, more preferred at least 450, most preferred at least 475 amino acids.

In a preferred embodiment, said fusion protein also comprises an APRIL(-like) or BAFF(-like) protein, preferably an APRIL(-like) protein. This is, however, not necessary since the present inventors have demonstrated that the introduction of a co-stimulatory molecule into the V1 loop and/or V2 loop also results in an improved immune response in the absence of APRIL or BAFF. A method for production of a fusion protein according the invention is also provided, said method comprising a) generating or providing a nucleic acid molecule comprising a nucleotide sequence encoding:

an amino acid sequence with a length of at least 300 amino acids with at least 80% sequence identity to a gp120 protein or a gp160 protein of HIV envelope glycoprotein complex (Env), wherein at least 5 amino acids of the V1 loop and/or at least 5 amino acids of the V2 loop are deleted, and wherein an amino acid sequence with at least 80% sequence identity with a co-stimulatory molecule is inserted at the site of deletion in V1 and/or V2; and b) allowing expression of said amino acid sequence from said nucleic acid in a suitable expression system.

In a more preferred embodiment said sequence identities are, independently from one another at least 85%, preferably at least 90%, more preferably at least 95%, more preferably at least 98%, most preferably 100%. Said co-stimulatory molecule is preferably selected from the group consisting of GMCSF, IL2, IL4, IL-5, IL-10, IFN$_\gamma$, IL12, IL17, IL-21, IL-23 and TSLP. In a particularly preferred embodiment, said co-stimulatory molecule is GMCSF. In another more preferred embodiment, said polypeptide has a length of at least 350, more preferred at least 375, more preferred at least 400, more preferred at least 425, more preferred at least 450, most preferred at least 475 amino acids. A fusion protein of the invention is useful for inducing, enhancing and/or improving an immune reaction to a gp120 and/or gp160 protein of HIV, especially when a fusion protein according to the invention is used that comprises both an APRIL(-like) protein and/or a BAFF(-like) protein, and a co-stimulatory molecule at a site of deletion in the V1 and/or V2 loop of the Env protein. Such a fusion protein enhances an immune response to the Env protein both through the APRIL(-like) or (BAFF-like) protein and through the co-stimulatory molecule present within the Env protein sequence. Combinations are preferred that activate immune cells, in particular B cells, synergistically.

In a preferred embodiment, the invention thus provides a fusion protein comprising an amino acid sequence with a length of at least 300 amino acids with at least 80% sequence identity to a gp120 protein or a gp160 protein of HIV envelope glycoprotein complex (Env), wherein at least 5 amino acids of the V1 loop and at least 5 amino acids of the V2 loop of said gp120 molecule are absent, and wherein at the deletion site in V1 or at the deletion site in V2, a polypeptide is inserted with at least 80% sequence identity with a co-stimulatory molecule, preferably selected from the group consisting of GMCSF, IL2, IL4, IL-5, IL-10, IFN$_\gamma$, IL12, IL17, IL-21, IL-23 and TSLP, wherein said fusion protein further comprises a compound selected from the group consisting of a compound comprising at least the extracellular domain of APRIL, and/or BAFF, and compounds having at least 80% sequence identity with at least the extracellular domain of APRIL and/or BAFF. In a more preferred embodiment said sequence identities are, independently from one another at least 85%, preferably at least 90%, more preferably at least 95%, more preferably least 98%, most preferably 100%. In another more preferred embodiment, said polypeptide has a length of at least 350, more preferred at least 375, more preferred at least 400, more preferred at least 425, more preferred at least 450, most preferred at least 475 amino acids. Such fusion proteins induce a vigorous immune response against the Env protein because, as said before, it comprises multiple features that improve said immune response.

Using forced virus evolution experiments the inventors frequently observed deletions in the region corresponding to amino acid positions 127-195 of HXB2, which led to functionally improved Env variants.

In another preferred embodiment, therefore, the invention provides a fusion protein and/or a method and/or a complex according to the invention, wherein said fusion protein comprises a polypeptide with a length of at least 300 amino acids with 80% sequence identity to a gp120 protein of HIV with a deletion of at least 5 amino acids, preferably at least 10, more preferably at least 20, more preferably at least 40, more preferably at least 60, even more preferably at least 67, most preferably 69 amino acids in the region corresponding to amino acid positions 127-195 of HIV-virus reference strain HXB2, wherein the amino acid positions are indicated in FIG. 40. In a more preferred embodiment said sequence identity is at least 85%, preferably at least 90%, more preferably at least 95%, more preferably least 98%, most preferably 100%. In another more preferred embodiment, said polypeptide has a length of at least 350, more preferred at least 375, more preferred at least 400, more preferred at least 425, more preferred at least 450, most preferred at least 475 amino acids. As said above, HXB2 is the HIV-virus reference strain to which amino acid numbering is generally adhered to. This by no means implies that the invention is limited to HXB2. It is for instance preferred to use an amino acid sequence of subtype C of HIV in a fusion protein according to the invention for use in Africa and subtype B of HIV in a fusion protein according to the invention for use in the United States and Europe, as these are predominant strains in the respective areas.

Even more frequently, the inventors observed functionally improved Env variants in their forced virus evolution experiments that had deletions in the region corresponding to amino acid positions 142 to 148 and/or deletions in the region corresponding to amino acid positions 168 to 203 of HXB2. In yet another preferred embodiment, therefore, a fusion protein and/or a method and/or a complex according to the invention is provided, wherein said fusion protein comprises a polypeptide with a length of at least 300 amino acids with at least 80% sequence identity to a gp120 protein of HIV with a deletion of at least 5 amino acids in the region corresponding to amino acid positions 142 to 148 of HXB2 and/or a deletion of at least 5 amino acids, preferably at least 10, more preferably at least 20, more preferably at least 30, most preferably 36 amino acids in the region corresponding to amino acid positions 168 to 203 of HXB2, wherein the amino acid positions are indicated in FIG. 40. In a more preferred embodiment said sequence identity is at least 85%, preferably at least 90%, more preferably at least 95%, more preferably least 98%, most preferably 100%. In another more preferred embodiment, said polypeptide has a length of at least 350, more preferred at least 375, more preferred at least 400, more preferred at least 425, more preferred at least 450, most preferred at least 475 amino acids.

Most frequently, the inventors observed deletions in the region corresponding to amino acid positions 133-155 of HXB2 and deletions in the region corresponding to amino acid positions 159-194 of HXB2. In an even more preferred embodiment, the invention therefore provides a fusion protein and/or a method and/or a complex according to the invention, wherein said fusion protein comprises a polypeptide with a length of at least 300 amino acids with at least 80% sequence identity to a gp120 protein of HIV with a deletion of at least 5 amino acids, preferably at least 10, more preferably at least 20, more preferably 23, in the region corresponding to amino acid positions 133-155 of HXB2 and/or a deletion of at least 5 amino acids, preferably at least 10, more preferably at least 20, even more preferably at least 30, most preferably 36, in the region corresponding to amino acid positions 159-194 of HXB2, wherein the amino acid positions are indicated in FIG. 40. In a more preferred embodiment said sequence identity is at least 85%, preferably at least 90%, more preferably at least 95%, more preferably least 98%, most preferably 100%. In another more preferred embodiment, said polypeptide has a length of at least 350, more preferred at least 375, more preferred at least 400, more preferred at least 425, more preferred at least 450, most preferred at least 475 amino acids.

The inventors have found that it is especially useful to delete one or more of the disulfide bonds in the gp120 molecule involved in protein folding. Especially deletion of the disulfide bridges formed between cysteines at positions corresponding to position 126 and 196 and between cysteines at positions corresponding to position 131 and position 157 of HXB2 result in improved folding and/or secretion of a fusion protein according to the invention. In one preferred embodiment therefore, the invention provides a fusion protein and/or a method and/or a complex according to the invention, wherein said fusion protein comprises a polypeptide with a length of at least 300 amino acids with at least 80% sequence identity to a gp120 protein of HIV and wherein at least one cysteine at a position corresponding to position 126 and/or position 196 and/or position 131 and/or position 157 of HXB2 is exchanged for another amino acid, preferably for another non-hydrophobic amino acid(s), more preferably for alanine, wherein the amino acid positions are indicated in FIG. 40. In a more preferred embodiment said sequence identity is at least 85%, preferably at least 90%, more preferably at least 95%, more preferably least 98%, most preferably 100%. In another more preferred embodiment, said polypeptide has a length of at least 350, more preferred at least 375, more preferred at least 400, more preferred at least 425, more preferred at least 450, most preferred at least 475 amino acids.

In yet another embodiment, at least two cysteines of gp120 are replaced. A fusion protein useful in the invention is obtained for example by substituting the cysteines at positions 126 and at position 196 of gp120 for another non-hydrophobic amino acid, for instance alanine. Another fusion protein useful in the invention is obtained for example by substituting cysteines at position 131 and 196 for another non-hydrophobic amino acid, for instance alanine. Therefore, in yet another preferred embodiment, a fusion protein and/or a method and/or a complex according to the invention is provided, wherein said fusion protein comprises a polypeptide with a length of at least 300 amino acids with at least 80% sequence identity to a gp120 protein of HIV and wherein at least two cysteines at a position corresponding to position 126 and to position 196, or to position 131 and to position 196 of HXB2 are exchanged into another amino acid, preferably into another non-hydrophobic amino acid, more preferably into alanine, wherein the amino acid positions are indicated in FIG. 40. In a more preferred embodiment said sequence identity is at least 85%, preferably at least 90%, more preferably at least 95%, more preferably least 98%, most preferably 100%. In another more preferred embodiment, said polypeptide has a length of at least 350, more preferred at least 375, more preferred at least 400, more preferred at least 425, more preferred at least 450, most preferred at least 475 amino acids. It is of course also possible to delete or modify at least one cysteine at a position corresponding to position 126 and/or position 196 and/or position 131 and/or position 157 of HXB2 in order to delete at least one disulfide bond in the gp120 molecule.

N-linked carbohydrates are frequently lost upon optimization of a fusion protein useful in the invention, namely at positions corresponding to positions 156, 234, 295, 301, 339 and 625 of HXB2. This implicates that loss of these N-linked carbohydrates improves folding and/or secretion of a fusion protein of the invention.

In a preferred embodiment therefore, a fusion protein and/or a method and/or a complex according to the invention is provided, wherein said fusion protein comprises polypeptide with a length of at least 300 amino acids with at least 80% sequence identity to a gp120 protein of HIV with at least one amino acid exchange comprising loss of a glycosylation site at a position corresponding to amino acid position 156, 234, 295, 301, 339 and/or 625 of HXB2, wherein the amino acid positions are indicated in FIG. 40. In a more preferred embodiment, said at least one amino acid exchange comprises loss of a glycosylation site corresponding to amino acid position 156 of HXB2. As said before, the numbering of the amino acid positions is shown in FIG. 40. For other HIV isolates, the corresponding amino acid positions are determined by alignment with at least one sequence of FIG. 40. As used herein, a reference to an amino acid position therefore also encompasses the corresponding amino acid position in a different HIV strain. In a more preferred embodiment said sequence identity is at least 85%, preferably at least 90%, more preferably at least 95%, more preferably least 98%, most preferably 100%. In another more preferred embodiment, said polypeptide has a length of at least 350, more preferred at least 375, more preferred at least 400, more preferred at least 425, more preferred at least 450, most preferred at least 475 amino acids.

With the term "loss of a glycosylation site" is meant a situation in which said glycosylation site is no longer capable of being glycosylated and/or in which said glycosylation site is no longer present. Inhibiting glycosylation is achieved in various ways. It is for instance possible to delete, substitute and/or insert amino acids near said glycosylation site, such that glycosylation is no longer possible or at least inhibited. A person skilled in the art is aware of the fact that N-glycosylation sites comprise in general a consensus sequence consisting of Asp-Xaa-Ser or Asp-Xaa-Thr, wherein Xaa can be any natural amino acid (except proline) or functional equivalent thereof, for instance a spacer that introduces a similar space between the first aspartate and the third amino acid (serine or threonine) in said above consensus amino acid sequence. Said loss of a glycosylation site can thus be achieved by deleting or exchanging asparagine and/or serine or threonine in said consensus sequence. Further said loss can be achieved by deletion of said natural amino acid or functional equivalent thereof in said consensus sequence, or by insertion of an amino acid and/or functional equivalent thereof in said consensus sequence such, that the new sequence no longer comprises a consensus sequence for glycosylation, and/or exchanging Xaa in said consensus sequence with a proline, leading to inhibition and/or abrogation of glycosylation at said site.

In a preferred embodiment therefore, a fusion protein and/or a method and/or a complex according to the invention is provided, wherein said loss of a glycosylation site comprises a mutation in the N-glycosylation consensus sequence Asp-Xaa-Ser or Asp-Xaa-Thr, wherein Xaa is any natural amino acid except proline, such that the resulting sequence no longer comprises said consensus sequence.

As said before, the loss of a glycosylation site is especially useful in a fusion protein of the invention. On the other hand, a glycosylation site can also be beneficial for improving folding and/or secretion of a fusion protein, a complex, and/or a method according to the invention. This is especially true for the asparagine on position 197. Some of the HIV strains do not possess a glycosylation site at this position, such as strain WT JR-FL, others do. It has been observed that retaining or introducing a glycosylation site on or near position 197 is especially useful, for instance for correct folding of the Env protein. In one preferred embodiment therefore, a fusion protein and/or a method and/or a complex according to the invention is provided, wherein said fusion protein comprises a polypeptide with a length of at least 300 amino acids with at least 80% sequence identity to a gp120 protein of HIV with at least one amino acid exchange comprising retaining or introducing a glycosylation site at a position corresponding to amino acid position 197 of HXB2, preferably retaining or introducing an asparagine at a position corresponding to amino acid position 197 of HXB2 and a serine/threonine at a position corresponding to amino acid position 199 of HXB2, wherein the amino acid positions are indicated in FIG. 40. In a more preferred embodiment said sequence identity is at least 85%, preferably at least 90%, more preferably at least 95%, more preferably least 98%, most preferably 100%. In another more preferred embodiment, said polypeptide has a length of at least 350, more preferred at least 375, more preferred at least 400, more preferred at least 425, more preferred at least 450, most preferred at least 475 amino acids.

All the above mentioned gp120 fusion proteins with deletions and/or mutations in the V1 and/or V2 loop are particularly well capable of eliciting a HIV-specific immune reaction. Furthermore, a virus comprising these gp120 fusion proteins is still capable of infecting host cells, so that production of these viruses is possible.

In yet another embodiment, the invention provides a non-human animal which has been provided with a fusion protein and/or a complex and/or a nucleic acid molecule and/or a virus and/or an immunogenic composition according to the invention. Such a non-human animal preferably mounts a specific antibody response, wherein said antibody is preferably capable of specifically binding and neutralizing a wild-type pathogen, such as for instance HIV. Said antibodies are preferably harvested from said animal. As said before, antibodies that are capable of specifically binding and neutralizing a wild-type pathogen are especially useful for passive immunization. These antibodies are, when given immediately after an infection, capable of instantly binding and neutralizing said pathogen, thereby inhibiting or at least decreasing the amount of spreading within the infected individual or animal.

In another embodiment, therefore, the invention provides an isolated or recombinant antibody and/or functional equivalent thereof, capable of specifically binding to a fusion protein and/or a complex according to the invention. Most preferably, said antibody and/or functional equivalent thereof is capable of specifically binding a pathogen, preferably a virus, more preferably HIV, an influenza virus or an Ebola virus. In a particularly preferred embodiment, said antibody or functional equivalent is capable of neutralizing said pathogen. Preferably said antibody and/or functional equivalent is for use as a medicament. In another preferred embodiment, said antibody and/or functional equivalent is for use in preventing, treating and/or diminishing an infection with a pathogen, preferably a virus infection and/or for the preparation of a medicament for preventing, treating and/or diminishing an infection with a pathogen, preferably a virus infection. In a preferred embodiment, said virus infection is an HIV, influenza virus or Ebola virus infection. In another preferred embodiment, said antibody is a neutralizing antibody.

The invention also provides a method for obtaining an antibody capable of specifically binding a fusion protein and/or a complex and/or a nucleic acid molecule and/or a virus according to the invention, the method comprising
    providing a non-human animal with a fusion protein and/or a complex and/or a nucleic acid molecule and/or a virus and/or an immunogenic composition according to the invention; and
    obtaining an antibody capable of specifically binding said fusion protein, complex, nucleic acid molecule, and/or virus from said non-human animal.

It is not only possible to obtain binding molecules from a non-human animal, but it is also possible to construct and/or select such a binding molecule in vitro. For instance a phage display library is screened. Also provided, therefore is the use of a fusion protein, complex, nucleic acid molecule, and/or virus according to the invention in an ex vivo method for producing an antibody, or a functional equivalent of an antibody, which is capable of specifically binding said fusion protein, complex, nucleic acid molecule, and/or virus. The skilled artisan is aware of the different methods for producing an antibody ex vivo, such as B-cell hybrodima techniques, antibody phage display technologies and the like.

A functional equivalent of an antibody is defined herein as a part which has at least one same property as said antibody in kind, not necessarily in amount. Said functional equivalent is preferably capable of binding the same antigen as said antibody, albeit not necessarily to the same extent. A functional equivalent of an antibody preferably comprises a single domain antibody, a single chain antibody, a Fab fragment or a F(ab')$_2$ fragment. A functional equivalent also comprises an antibody which has been altered such that at least one property—preferably an antigen-binding property—of the resulting compound is essentially the same in kind, not necessarily in amount. A functional equivalent is provided in many ways, for instance through conservative amino acid substitution, whereby an amino acid residue is substituted by another residue with generally similar properties (size, hydrophobicity, etc), such that the overall functioning is likely not to be seriously affected.

The invention also provides a method for inducing an immune response to an antigen in an individual in need thereof, comprising administering an effective amount of: a fusion protein according to the invention and/or fusion protein obtainable by a method according to the invention, and/or a nucleic acid molecule according to the invention, and/or a virus according to the invention, and/or an immunogenic composition according to the invention and/or an antibody obtained by a method according to the invention to said individual. Preferably, said individual is first diagnosed with an infection, preferably a virus infection, more preferably a HIV virus infection, an influenza infection or an Ebola virus infection.

The invention further provides a method for treating, diminishing or preventing an infection, preferably a virus infection, more preferably an HIV, influenza virus or Ebola virus infection in an individual in need thereof, comprising administering an effective amount of a fusion protein according to the invention and/or obtainable by a method according to the invention, and/or a nucleic acid, and/or a virus, and/or an immunogenic composition according to the invention and/or an antibody obtained by a method according to the invention to said individual.

The invention is further illustrated by the following non-limiting examples. The examples do not limit the scope of the invention in any way.

FIG. 1. Concept of trimeric fusion construct of antigen (Ag) and a co-stimulatory molecule such as APRIL. Cartoon (top) and linear (bottom) presentations. White: trimeric antigen; grey: trimerization domain; black: co-stimulatory molecule (example: APRIL) with linkers in between.

Figure 2:
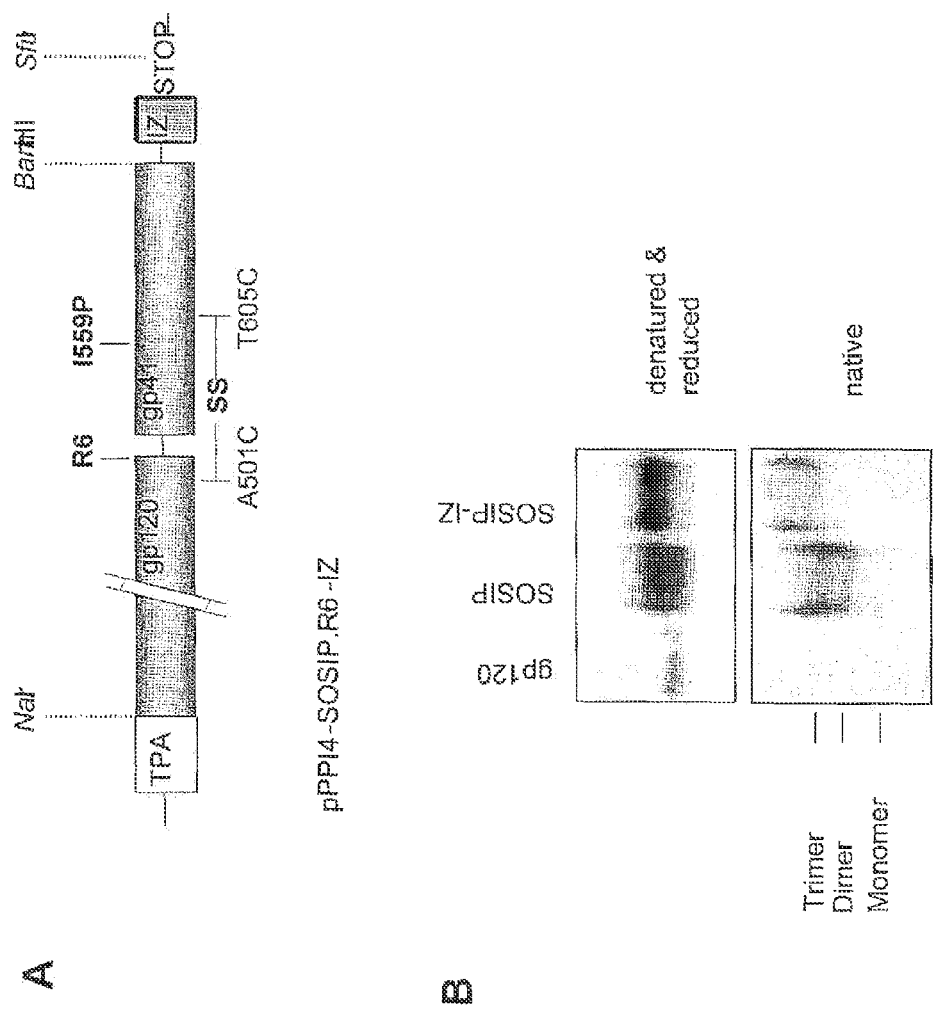

FIG. 2. Design and construction of trimeric gp140-IZ proteins. (A) Schematic of the gp140-IZ design. SOSIP.R6 gp140 (amino acids 31-681 encompassing the gp120 and the gp41 ectodomain) contained several modifications that have been previously described: an intermolecular disulfide bond between gp120 and gp41 (A501C T605C) (Binley 2000); a trimer-stabilizing substitution in gp41 (I559P; Sanders 2002), and a hexa-arginine motif to promote gp140 cleavage (R6; Binley 2002). H8: octa-histidine tag; TPA: signal sequence from tissue plasminogen activator. (B) Reducing SDS-PAGE and BN-PAGE analysis of SOSIP.R6 gp140 and SOSIP.R6-IZ gp140 (gp140-IZ) proteins derived from transiently transfected 293T cells.

Figure 3:
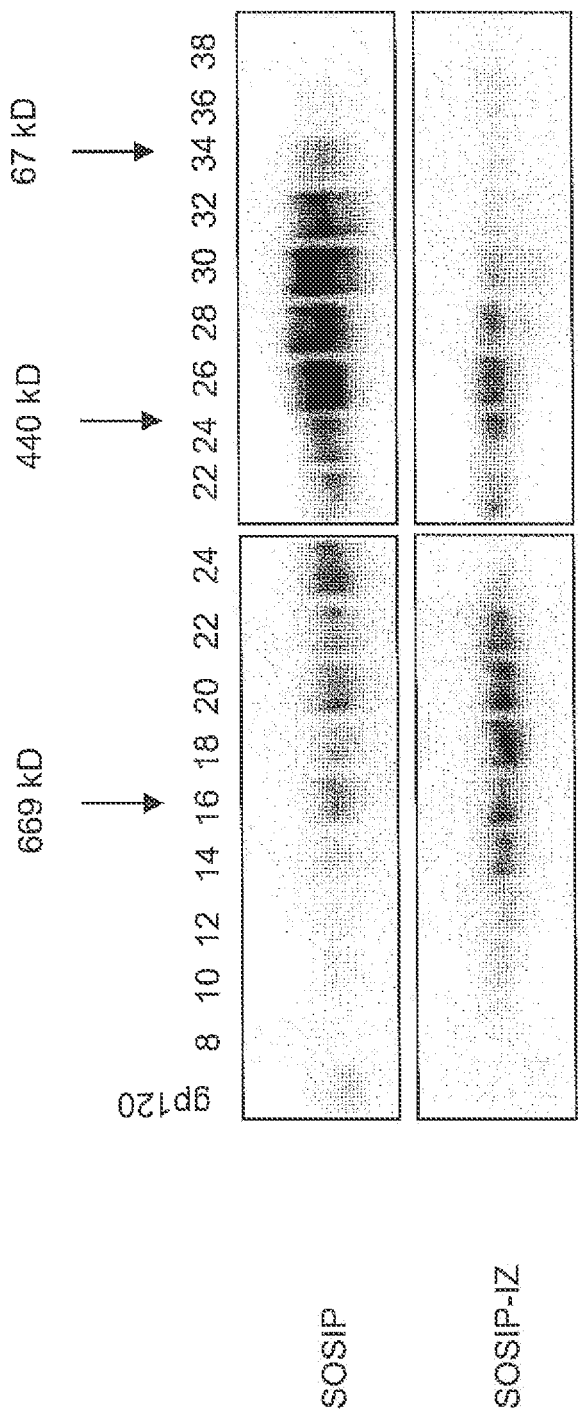

FIG. 3. Gel filtration analysis of gp140 and gp140-IZ proteins. Concentrated culture supernatants, derived from transiently transfected 293T cells, containing the SOSIP.R6 gp140 or SOSIP.R6-IZ proteins were fractionated on a Superose-6 column, followed by analysis by SDS-PAGE and western blot. The elution of standard proteins is indicated.

Figure 4:
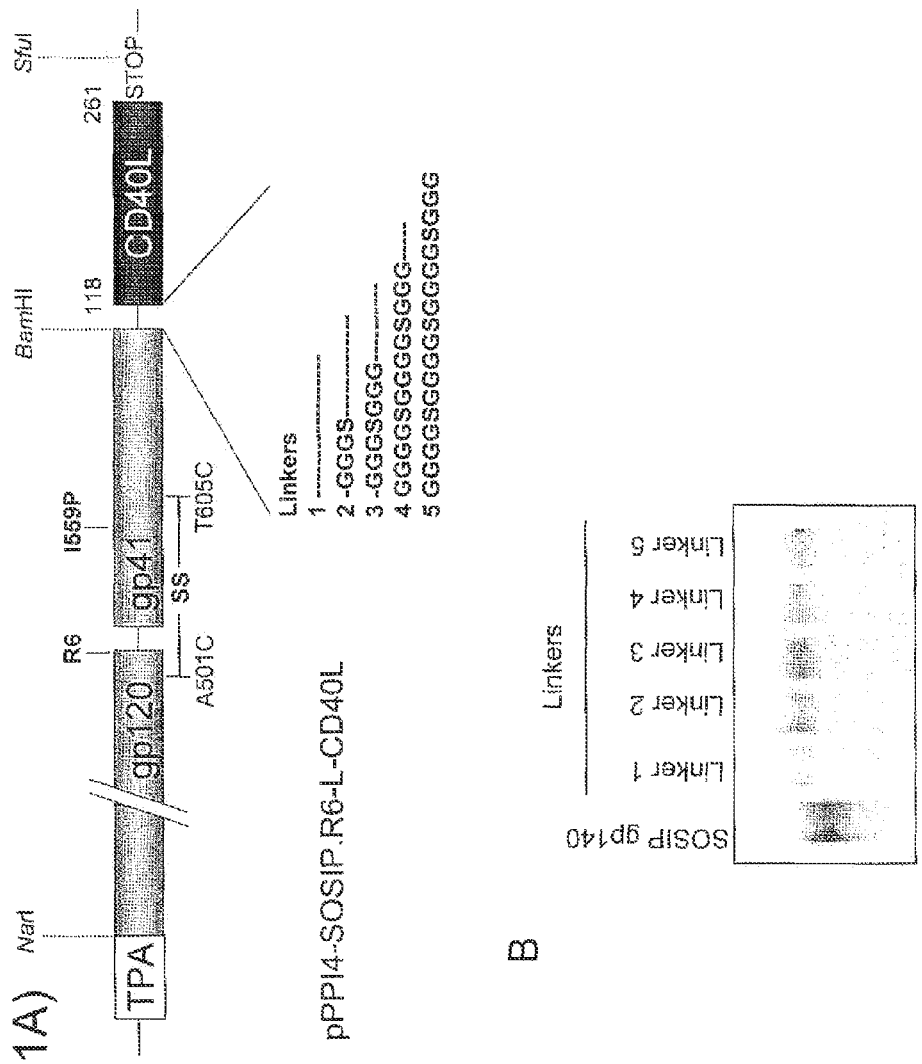

FIG. 4. Design and construction of chimeric gp140-CD40L proteins. (A) Schematic of the gp140-CD40L design. The active domain of murine CD40L (amino acids 118-261) was added to the C-terminus of SOSIP gp140, with flexible linkers of varying length (L1-L5) present as indicated. Reducing SDS-PAGE (B) analysis of gp140 and gp140-CD40L proteins derived from transiently transfected 293T cells.

Figure 5:
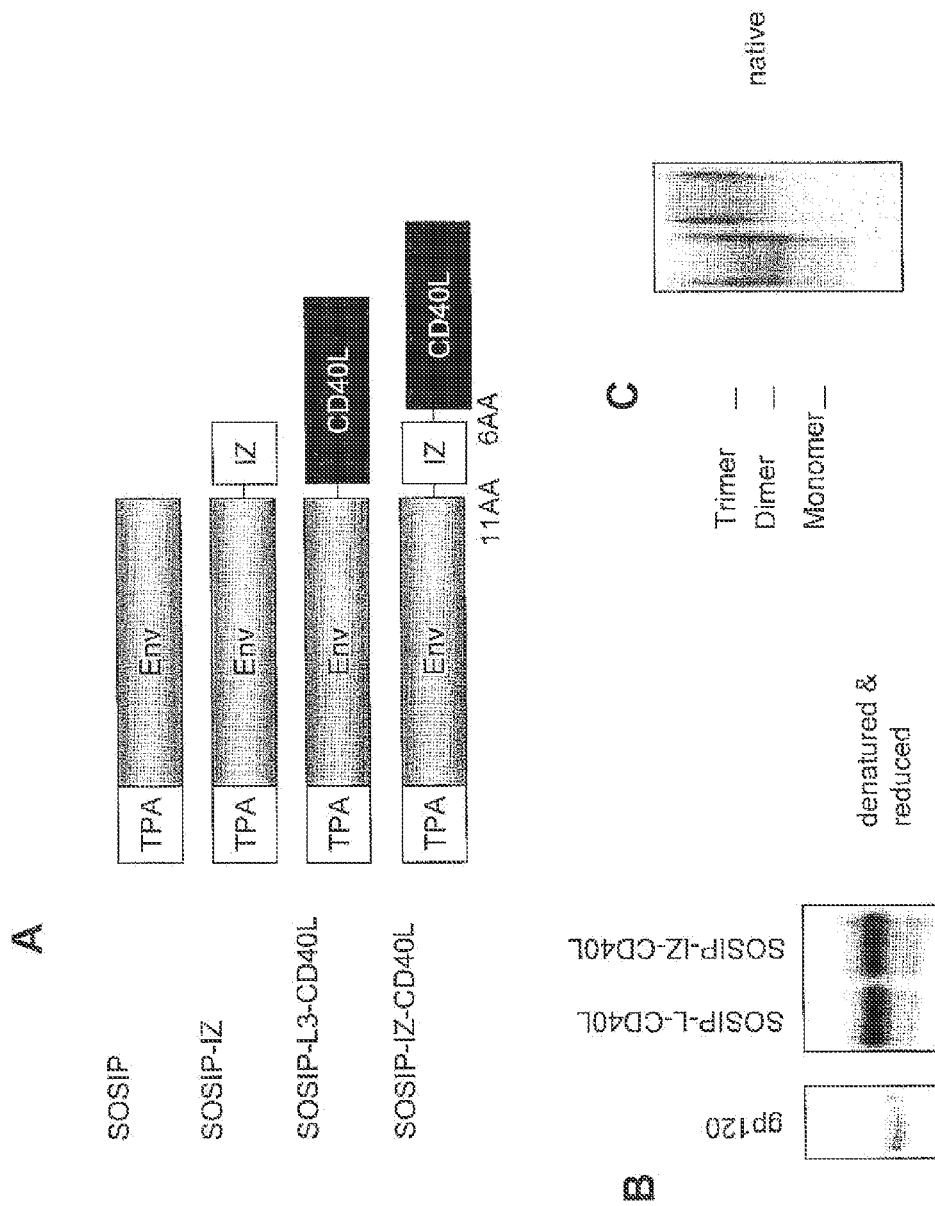

FIG. 5. Design and construction of trimeric gp140-IZ-CD40L proteins. (A) Schematic of the gp140-IZ-CD40L design. A GCN4-based isoleucine zipper motif (IZ; amino acid sequence RMKQIEDKIEEILSKIYHIENE-IARIKKLIGER; Harbury 1994) (SEQ ID NO:7) was inserted between the gp140 and CD40L moieties, with 11 and 6 amino acid linkers between the gp140 and IZ components, and between the IZ and CD40L components, respectively. Reducing SDS-PAGE (B) and BN-PAGE (C) analysis of the gp140-L3-CD40L and gp140-IZ-CD40L proteins derived from transiently transfected 293T cells.

Figure 6:
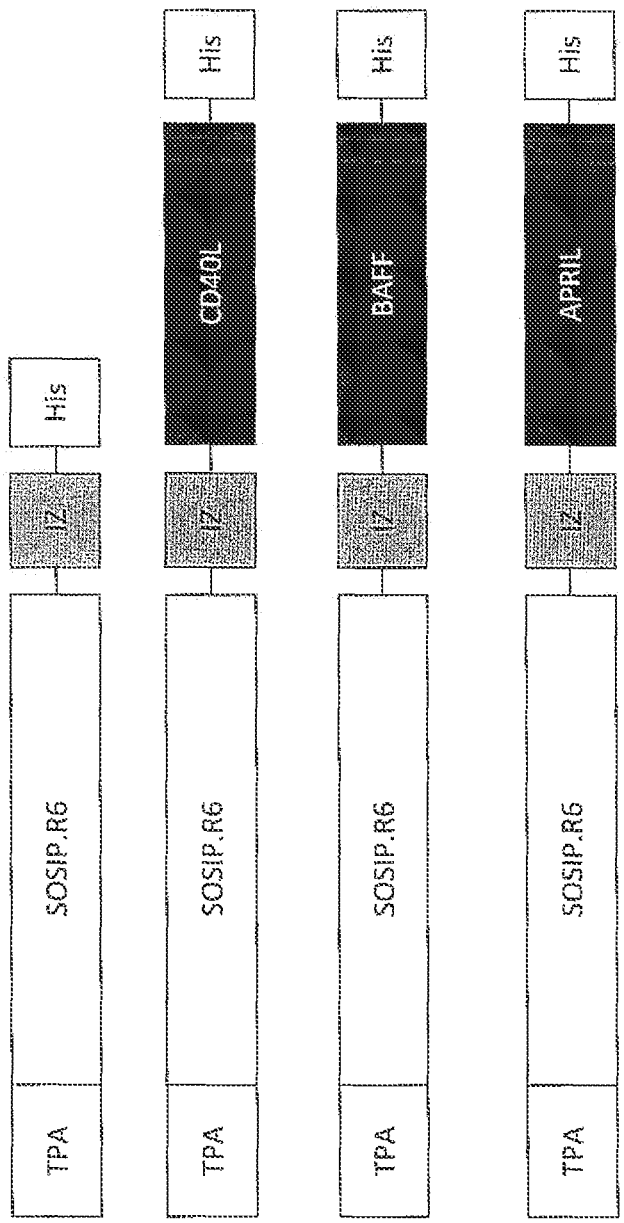

FIG. 6. Linear presentation of trimeric fusion constructs of a stabilized soluble HIV-1 envelope glycoprotein (SOSIP.R6 gp140; in white) with APRIL, BAFF or CD40L (in black) with a trimerization domain (IZ; grey) in between, flanked by flexible linkers. TPA: tissue plasminogen activator derived signal sequence for efficient secretion; His: polyhistidine tag for purification and immobilization. Env from the subtype B JR-FL strain is used throughout this study (although amino acid numbering is based on that of the HXB2 strain).

Figure 7:
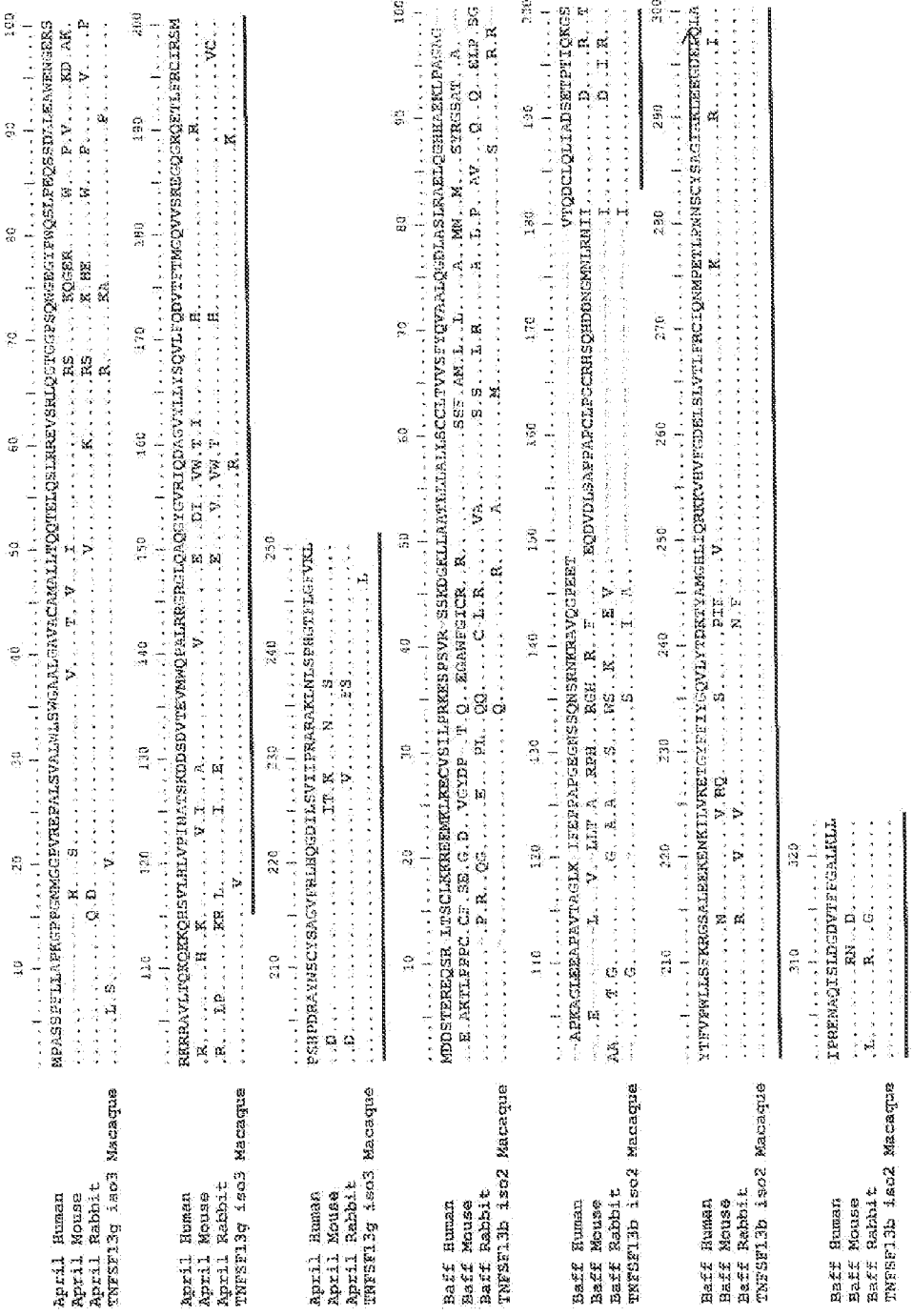

FIG. 7. Sequence alignment of human (SEQ ID NO:29), mouse (SEQ ID NO:30), macaque (SEQ ID NO:32) and rabbit (SEQ ID NO:31) APRIL (top) and human (SEQ ID NO:33), mouse (SEQ ID NO:34), macaque (SEQ ID NO:36) and rabbit(SEQ ID NO:35) BAFF (bottom) proteins. The extracellular domains used in our studies are underlined.

Figure 8:
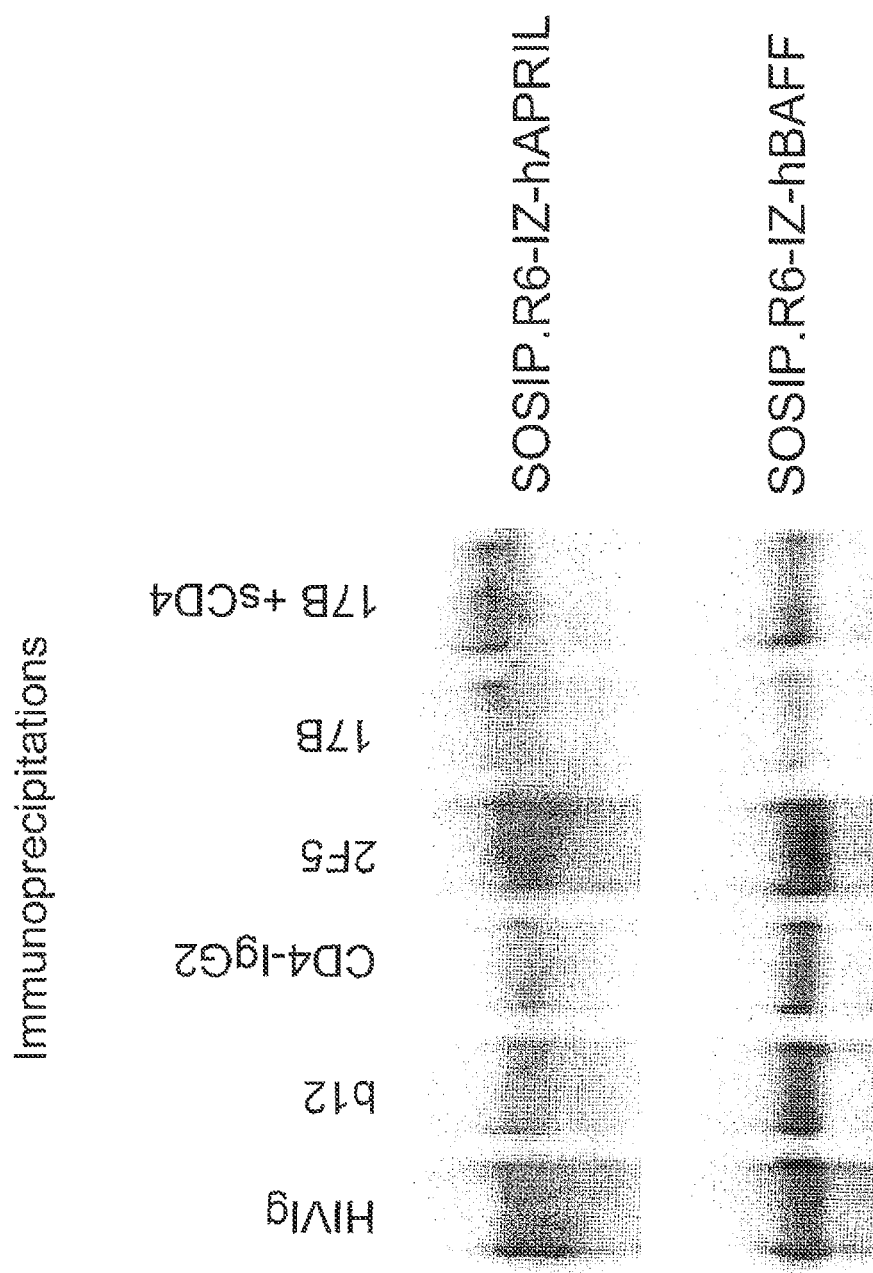

FIG. 8. Conformational probing of SOSIP.R6-IZ-APRIL and SOSIP.R6-IZ-BAFF fusion constructs. 293T expressed fusion proteins were immunoprecipitated by polyclonal Ig from infected individuals (HIVIg), a CD4 mimetic (CD4-IgG2), and various MAbs.

Figure 9:
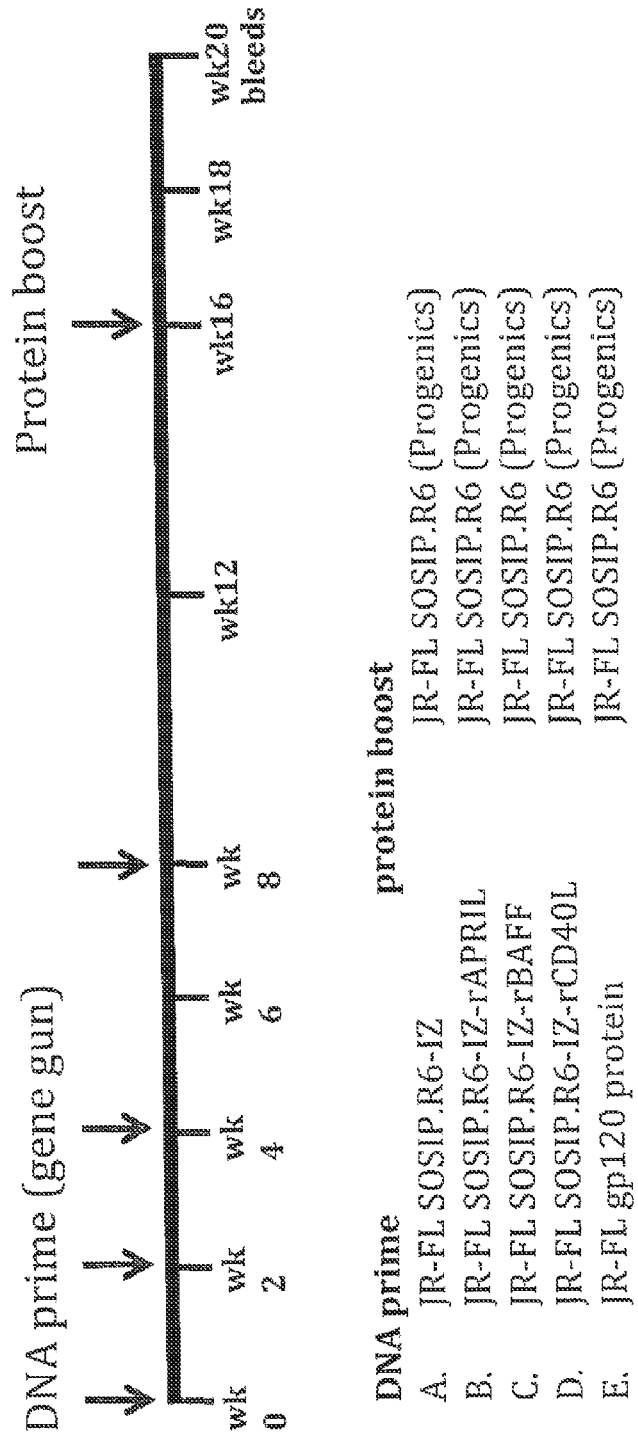

FIG. 9. Rabbit immunization schedule. Rabbits were immunized as described in the material and methods and according to the schedule. Thus, rabbit were primed four times with DNA expressed SOSIP.R6-IZ or SOSIP.R6-IZ-APRIL/BAFF/CD40L fusion constructs, or gp120 protein (wk 0, 2, 4, 8) and all groups were boosted with stabilized Env protein (SOSIP.R6 gp140; wk 16) in the saponin-based Quil A adjuvant.

Figure 10:
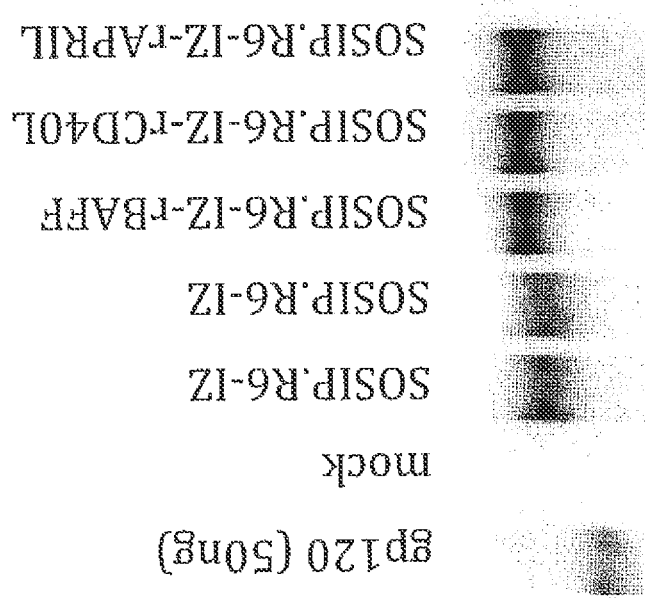

FIG. 10. Expression of Env fusion constructs using rabbit versions of the co-stimulatory molecules. Reducing SDS-PAGE analysis of SOSIP.R6-IZ gp140 and SOSIP.R6-IZ-rAPRIL/rBAFF/rCD40L proteins derived from transiently transfected 293T cells.

Figure 11:
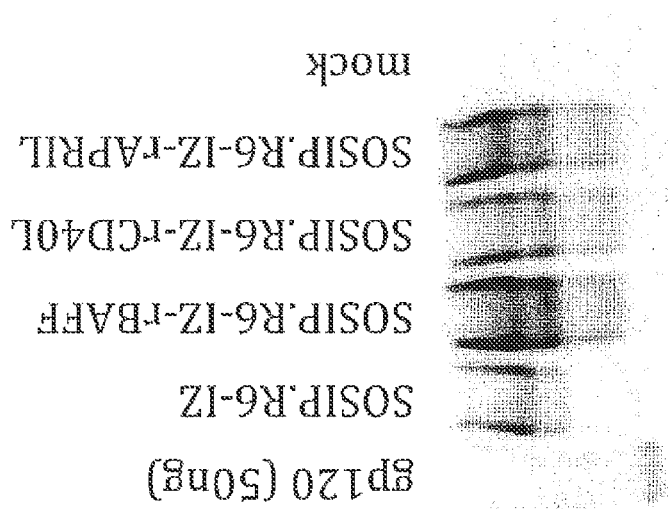

FIG. 11. Oligomerization of Env fusion constructs using rabbit versions of the co-stimulatory molecules. BN-PAGE analysis of SOSIP.R6-IZ gp140 and SOSIP.R6-IZ-rAPRIL/rBAFF/rCD40L proteins derived from transiently transfected 293T cells.

Figure 12:
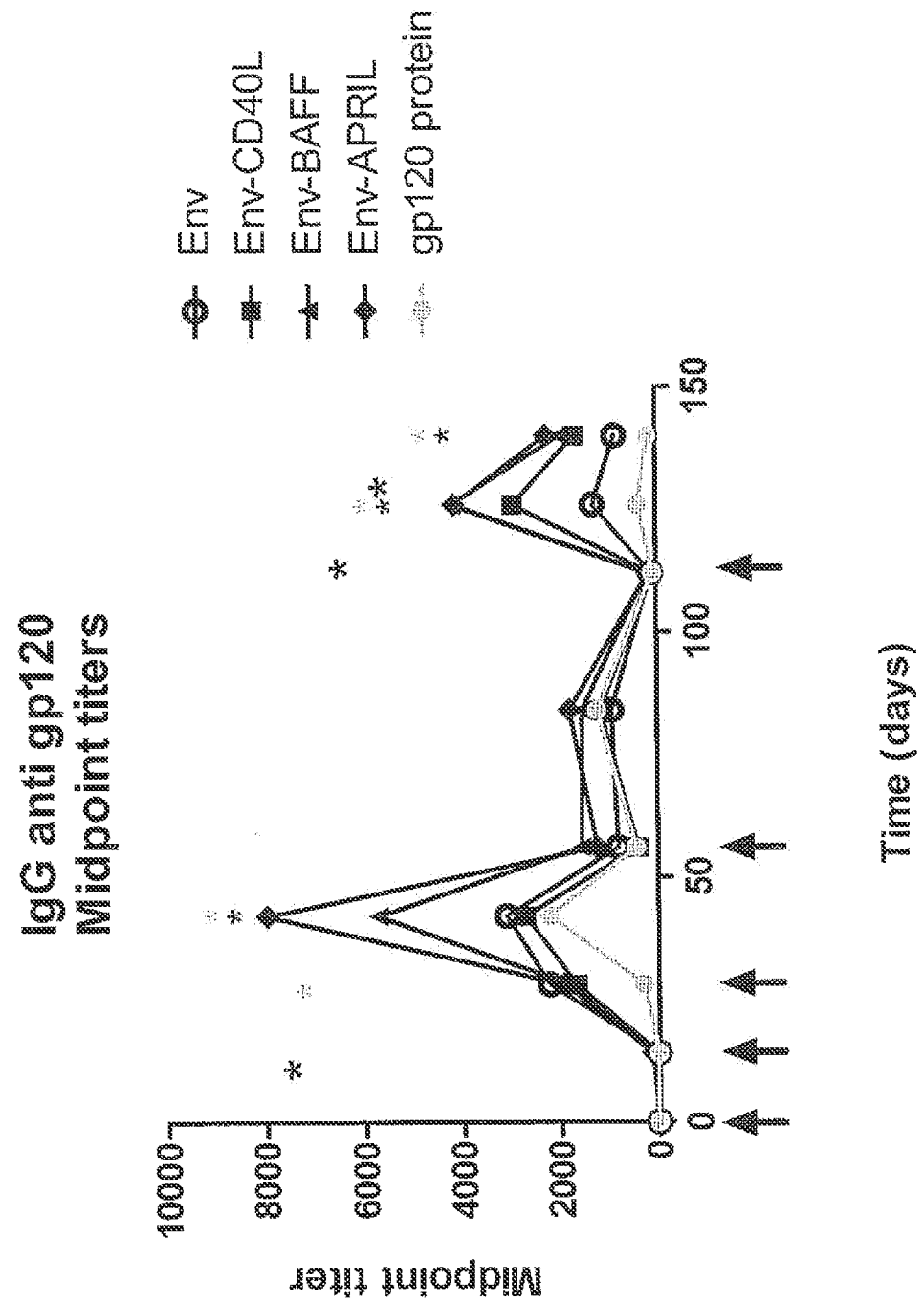

FIG. 12. Induction of enhanced gp120-specific antibody titers by Env APRIL in rabbits. Rabbits were immunized with plasmids encoding Env (SOSIP.R6 gp140) or fusion construct using rabbit versions of APRIL, BAFF or CD40L as described in the materials and methods section. The anti-gp120 titers in rabbit sera were measured by ELISA. * p<0.05.

Figure 13:
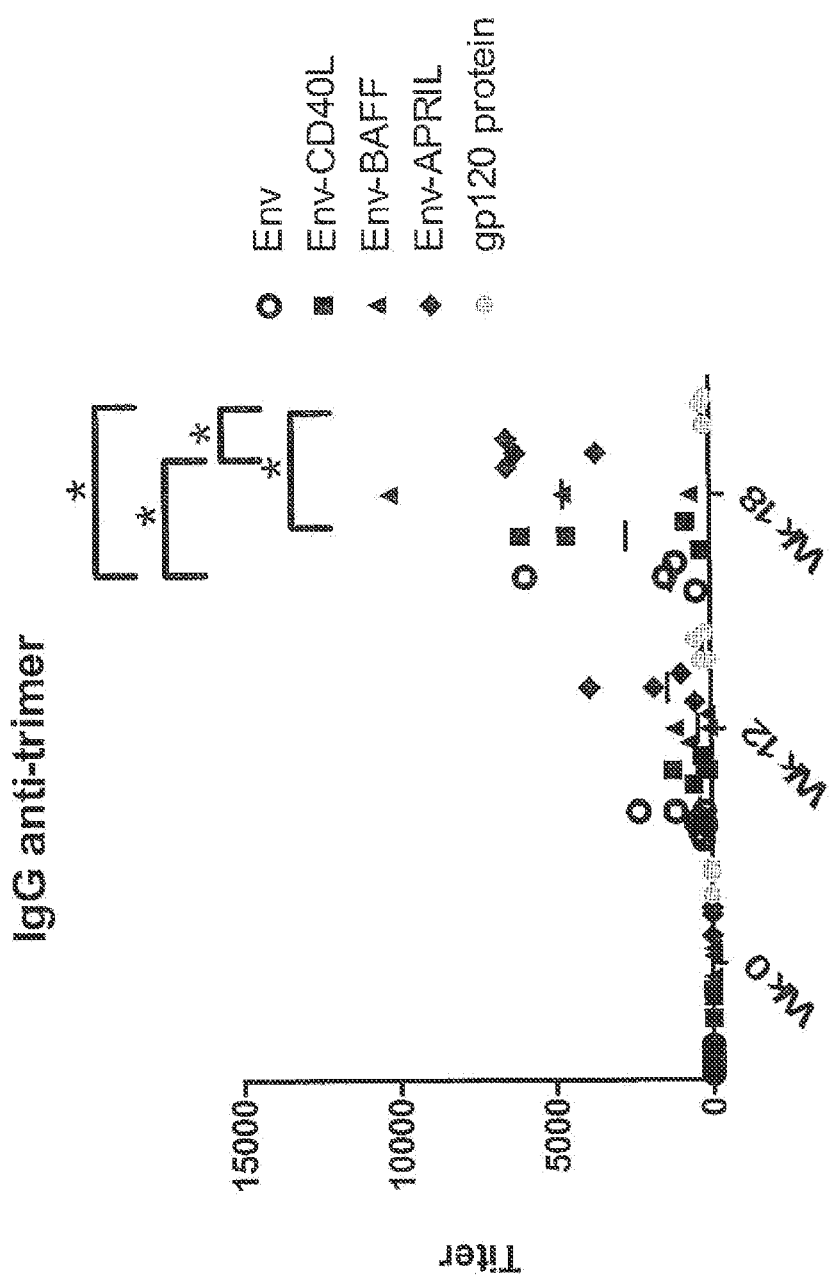

FIG. 13. Induction of enhanced Env trimer-specific antibody titers by Env APRIL in rabbits. The anti-trimer titers in rabbit sera were measured by ELISA similar as done for the anti-gp120 titers. In stead of gp120, Env trimers containing a C-terminal D7324 tag were captured on the ELISA plate. * p<0.05.

Figure 14:
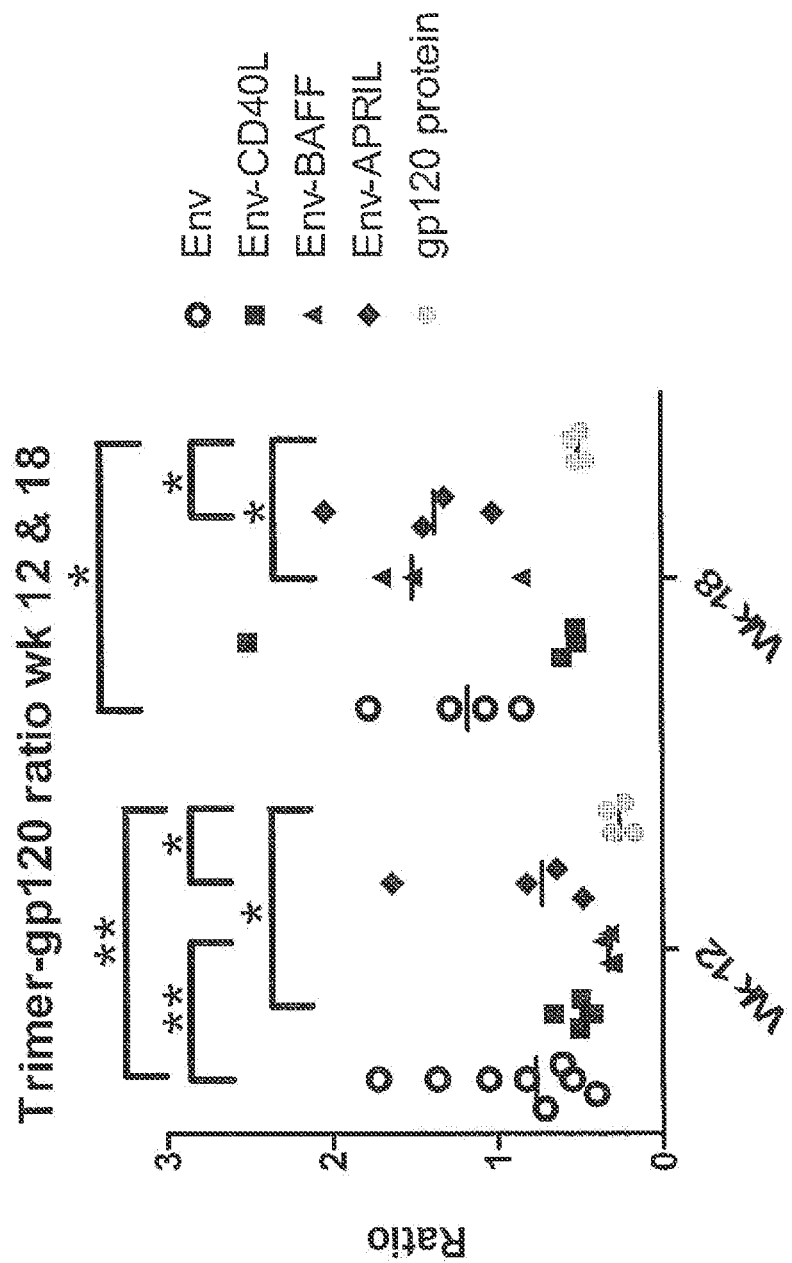

FIG. 14. Ratio of trimer and monomer specific antibodies. The ratio of the anti-trimer and anti-gp120 titers were calculated for each rabbit at wk 12 and wk 18.

FIG. 15. Enhanced virus neutralization induced by Env-APRIL. Rabbit sera of wk 18 were tested in a single cycle neutralization assay against three heterologous viruses (MN, SF162 and BaL). The numbers represent the dilution at which 50% neutralization was achieved. Increased neutralization titers are indicated by increased intensities of grey. The experiments were performed at the NIH reference lab for immune monitoring (David Montefiori, Duke University) and were in accordance with our in-house experiments.

Figure 16:
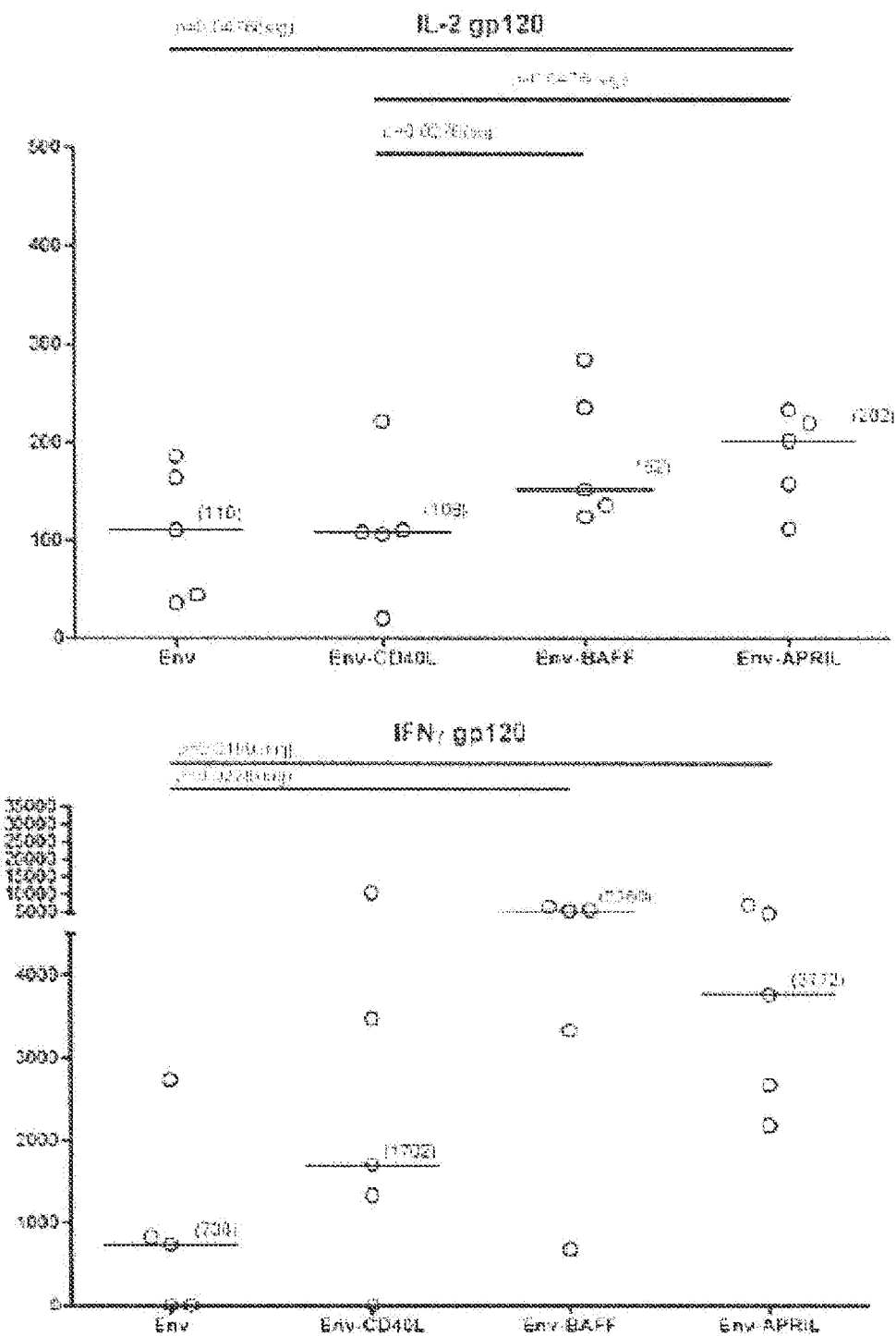

FIG. 16. Enhanced T cell responses induced by Env-APRIL and Env-BAFF (1). Mice were immunized with plasmids encoding Env (SOSIP.R6 gp140) or fusion construct using mouse versions of APRIL, BAFF or CD40L as described in the materials and methods section. At day the T cell responses in the spleen were analyzed using gp120 as recall antigen. The secretion of IL-2 (top) and IFNg (bottom) was measured. Negative (medium) and positive (anti-CD3) controls were also included (not shown).

Figure 17:
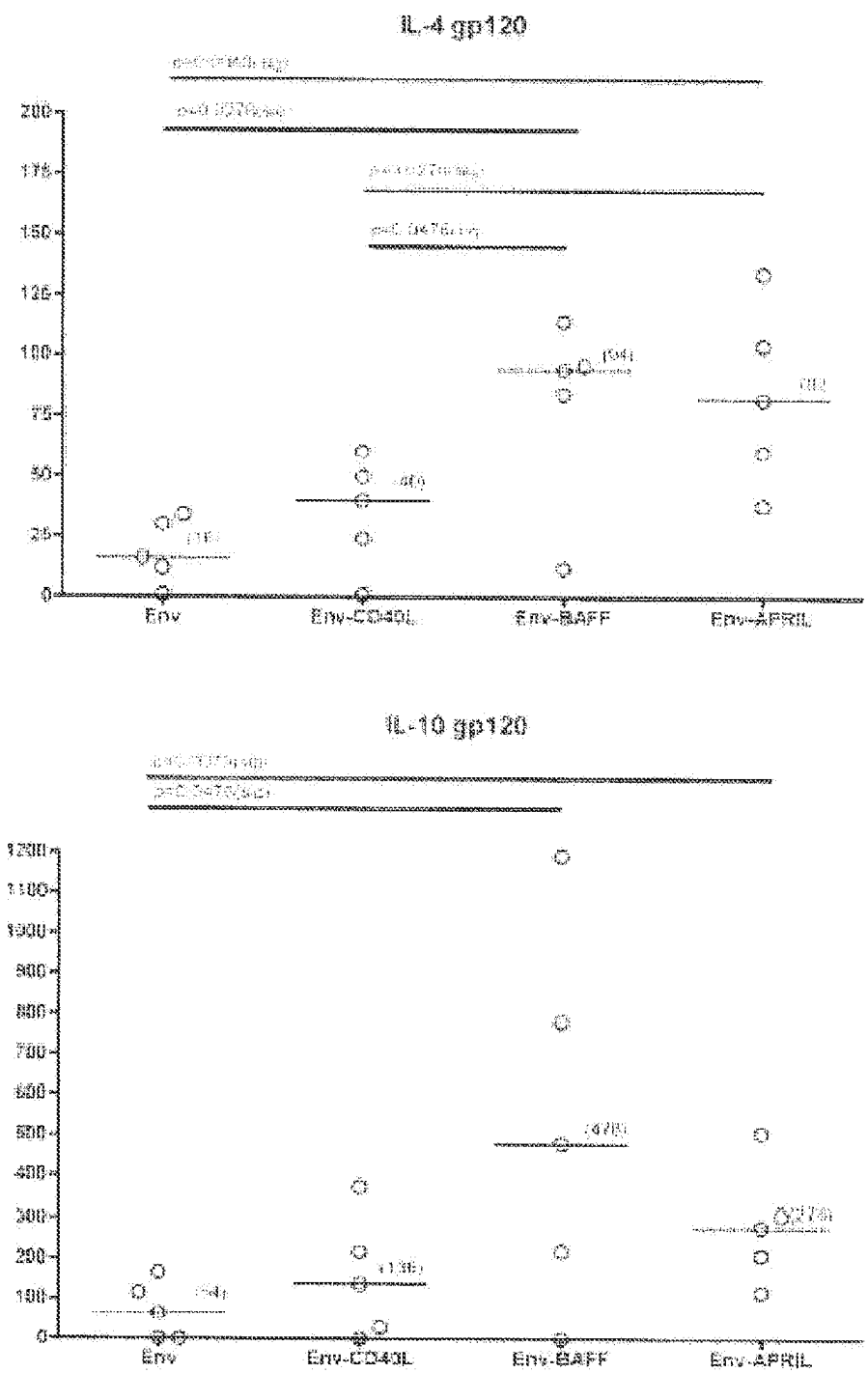

FIG. 17. Enhanced T cell responses induced by Env-APRIL and Env-BAFF (2). Mice were immunized with plasmids encoding Env (SOSIP.R6 gp140) or fusion construct using mouse versions of APRIL, BAFF or CD40L as described in the materials and methods section. At day the T cell responses in the spleen were analyzed using gp120 as recall antigen. The secretion of IL-4 (top) and IL-10 (bottom) was measured. Negative (medium) and positive (anti-CD3) controls were also included (not shown).

Figure 18:
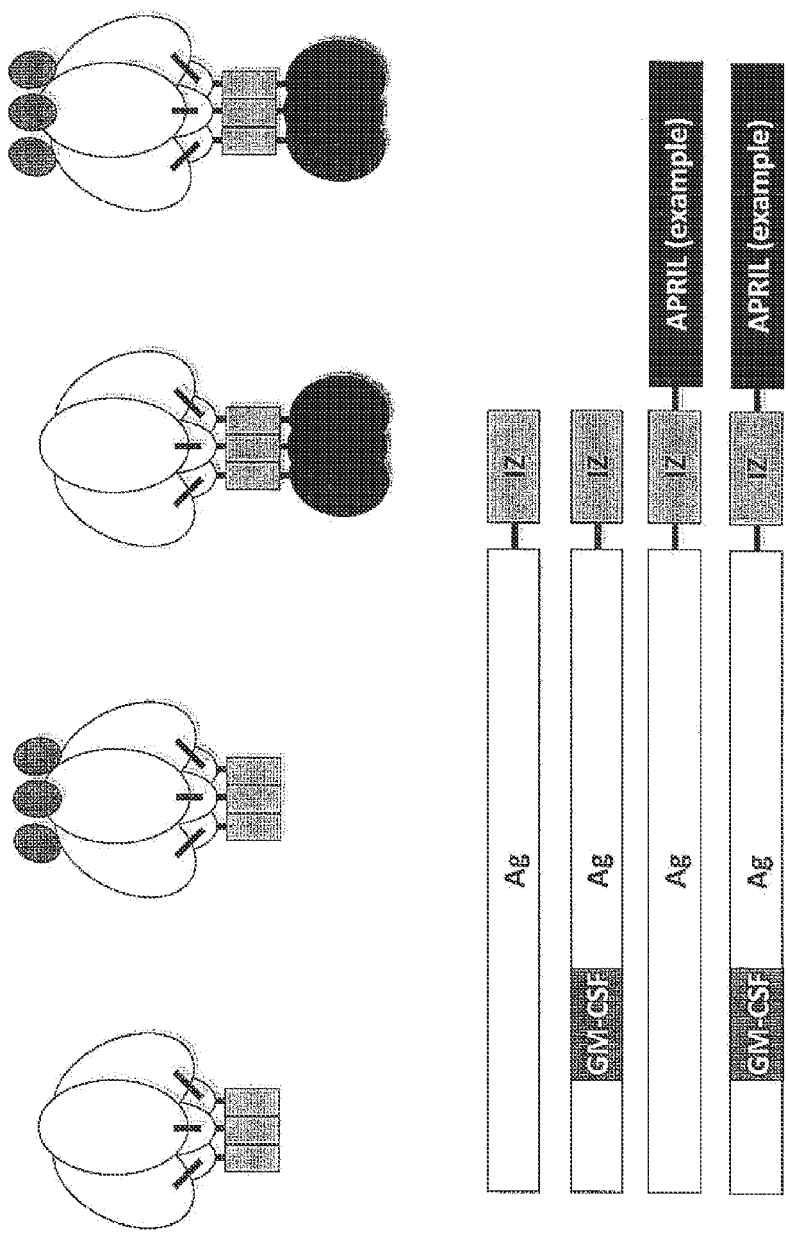

FIG. 18. Concept of trimeric fusion construct of Env and a co-stimulatory molecule such as APRIL at the C-terminus, as well as an co-stimulatory molecule such as GM-CSF replacing the V1V2 domain. Cartoon (top) and linear (bottom) presentations. White: trimeric antigen; grey: trimerization domain; black: co-stimulatory molecule (example: APRIL) with linkers in between; dark grey: co-stimulatory molecule (cytokine such as GM-CSF).

Figure 19:
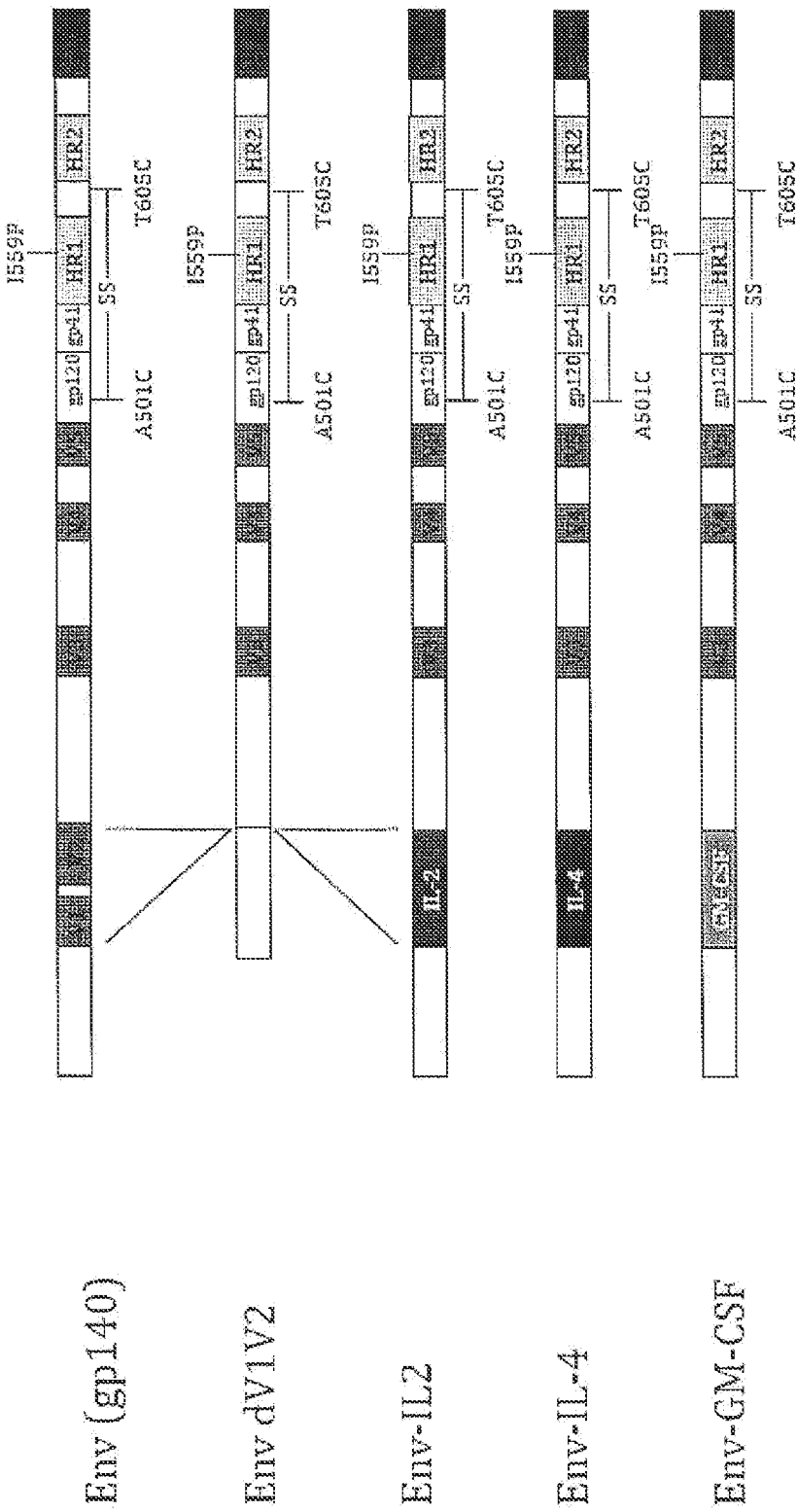

FIG. 19. Linear representation of soluble and stabilized trimeric Env (top), with a V1V2 deletion (second) and with IL-2, IL-4 or GM-CSF sequences replacing the V1V2 (bottom three).

FIG. 20. Sequences of gp120 (SEQ ID NO:37) and gp120 variants in which the V1V2 is replaced by a full length cytokine (h(human)IL-2 (SEQ ID NO:38), hIL-4 (SEQ ID NO:39), hGM-CSF (SEQ ID NO:40), m(mouse)GM-CSF (SEQ ID NO:41) or a truncated cytokine (hGM-CSF 1-3) (SEQ ID NO:42), (SEQ ID NO:43), (SEQ ID NO:44).

Figure 21:
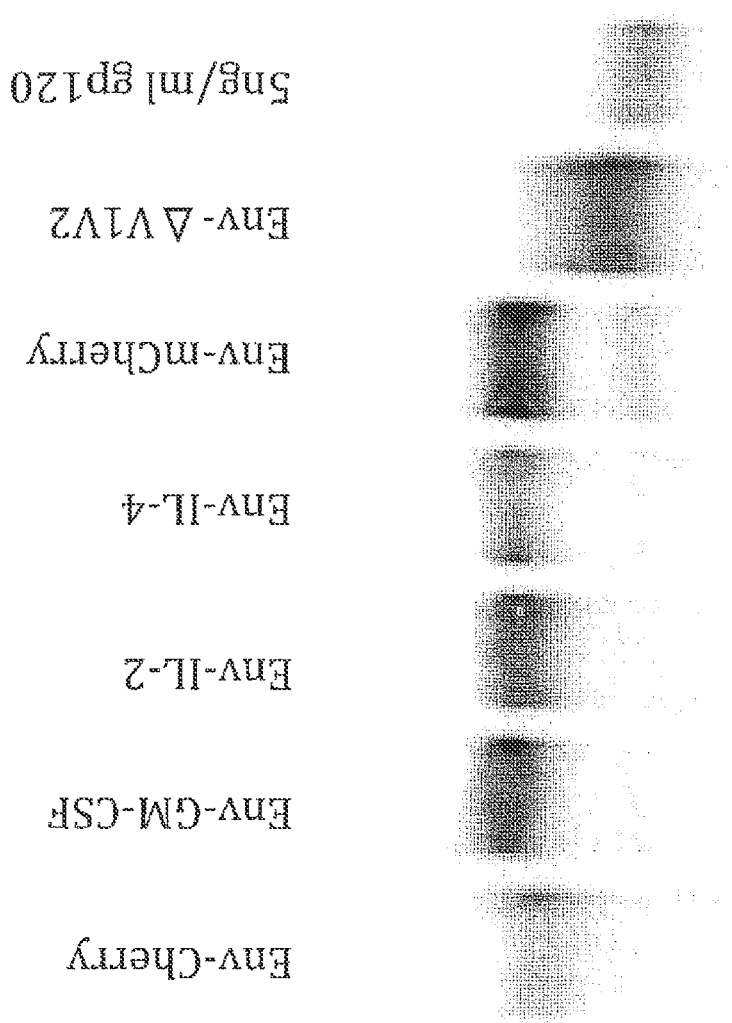

FIG. 21. Expression of Env (SOSIP.R6-IZ gp140) constructs containing co-stimulatory molecules (cytokines: IL-2; IL-4; GM-CSF), or irrelevant molecules (Cherry; mCherry) replacing the V1V2 domain. Reducing SDS-PAGE analysis of proteins derived from transiently transfected 293T cells.

Figure 22:
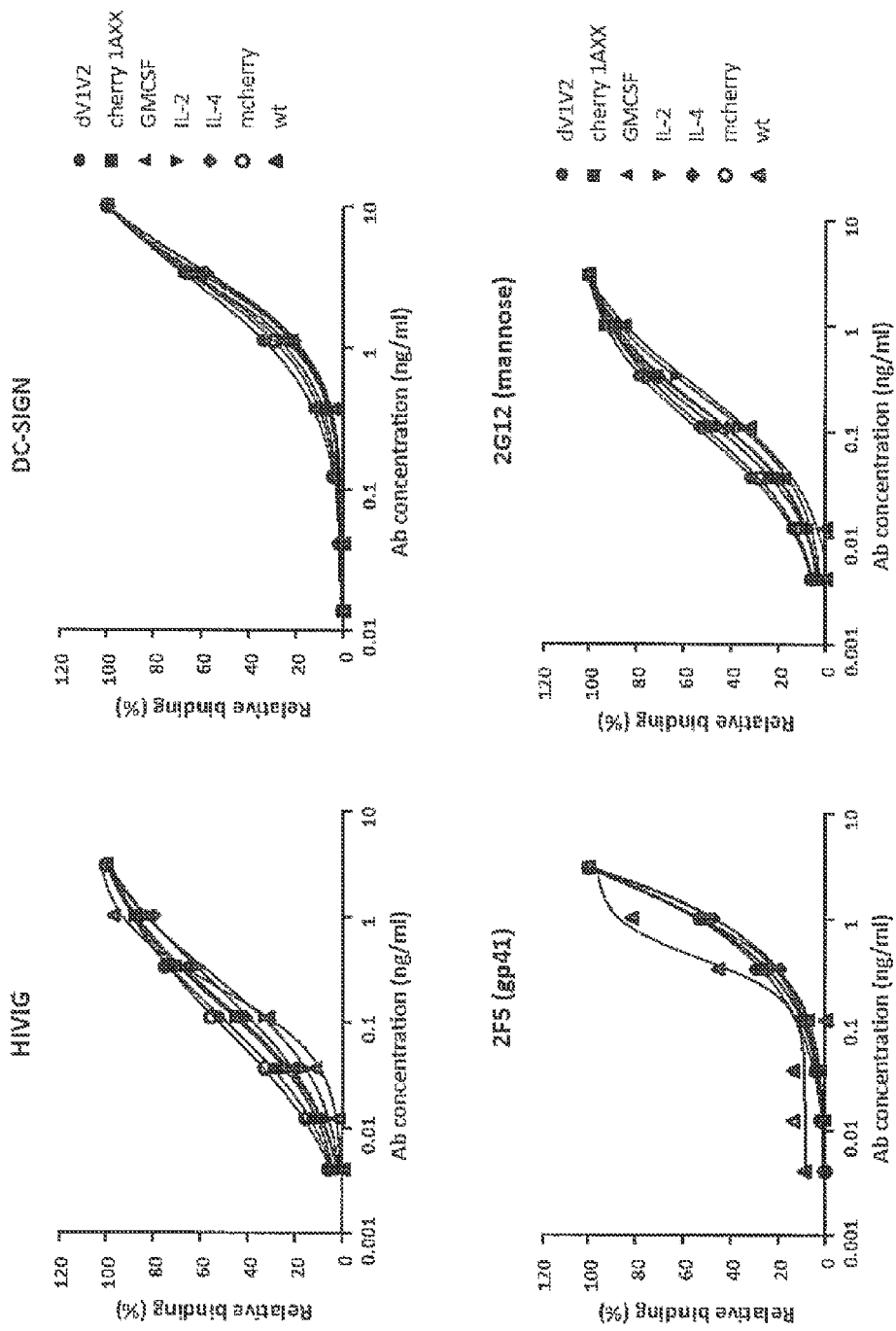

FIG. 22. Conformational probing Expression of Env (SOSIP.R6-IZ gp140) constructs containing co-stimulatory molecules (cytokines: IL-2; IL-4; GM-CSF), or irrelevant molecules (Cherry; mCherry) replacing the V1V2 domain (1). Proteins were captured using a C-terminal polyhistidine tag onto Ni-NTA plates and the binding of polyclonal Ig from infected individuals (HIVIg), DC-SIGN-Fc, and MAbs 2F5 and 2G12 was assessed.

Figure 23:
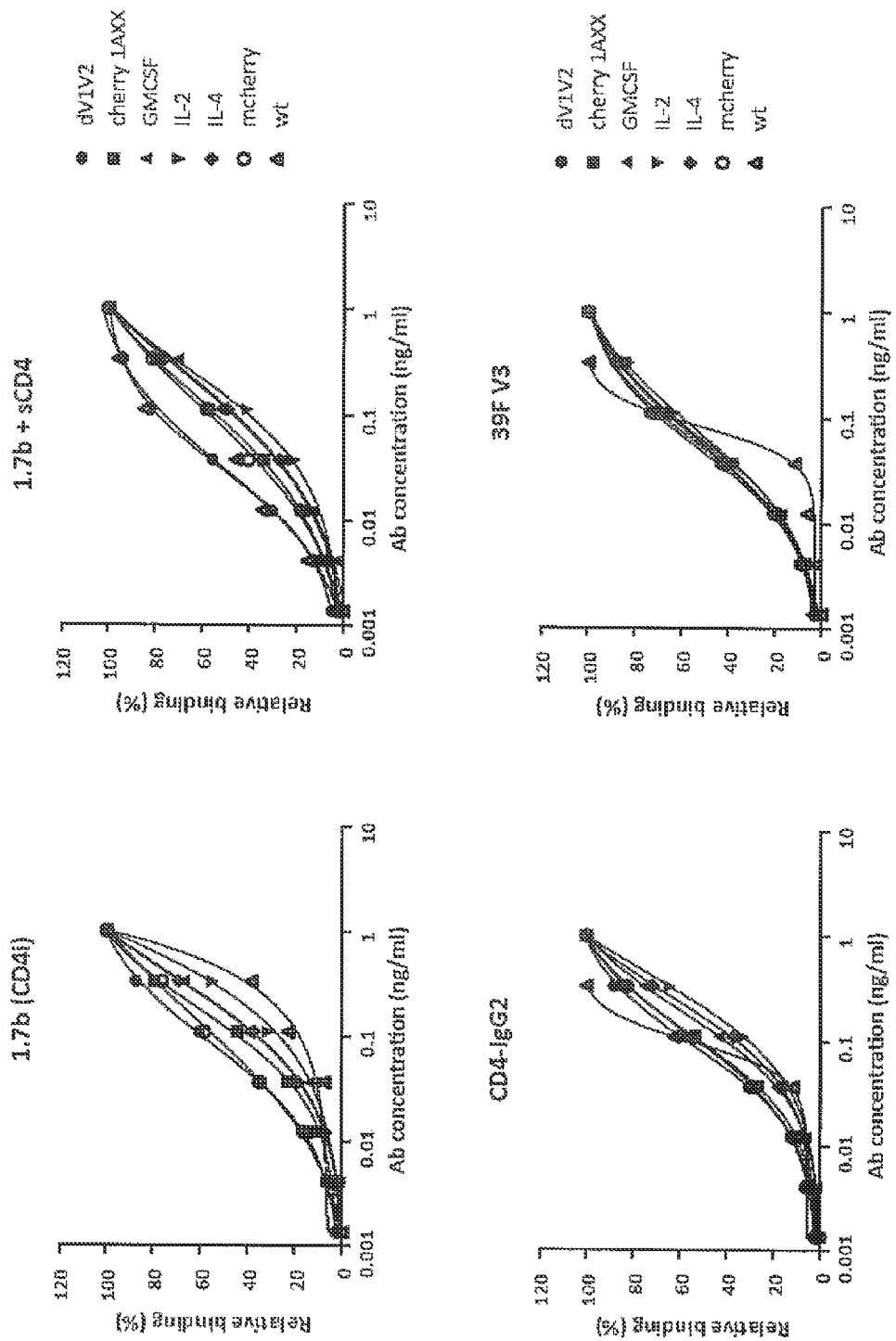

FIG. 23. Conformational probing of Env (SOSIP.R6-IZ gp140) constructs containing co-stimulatory molecules (cytokines: IL-2; IL-4; GM-CSF), or irrelevant molecules (Cherry; mCherry) replacing the V1V2 domain (2). Proteins were captured using a C-terminal polyhistidine tag onto Ni-NTA plates and the binding of CD4-IgG2 and MAbs 39F and 17b was assessed.

Figure 24:
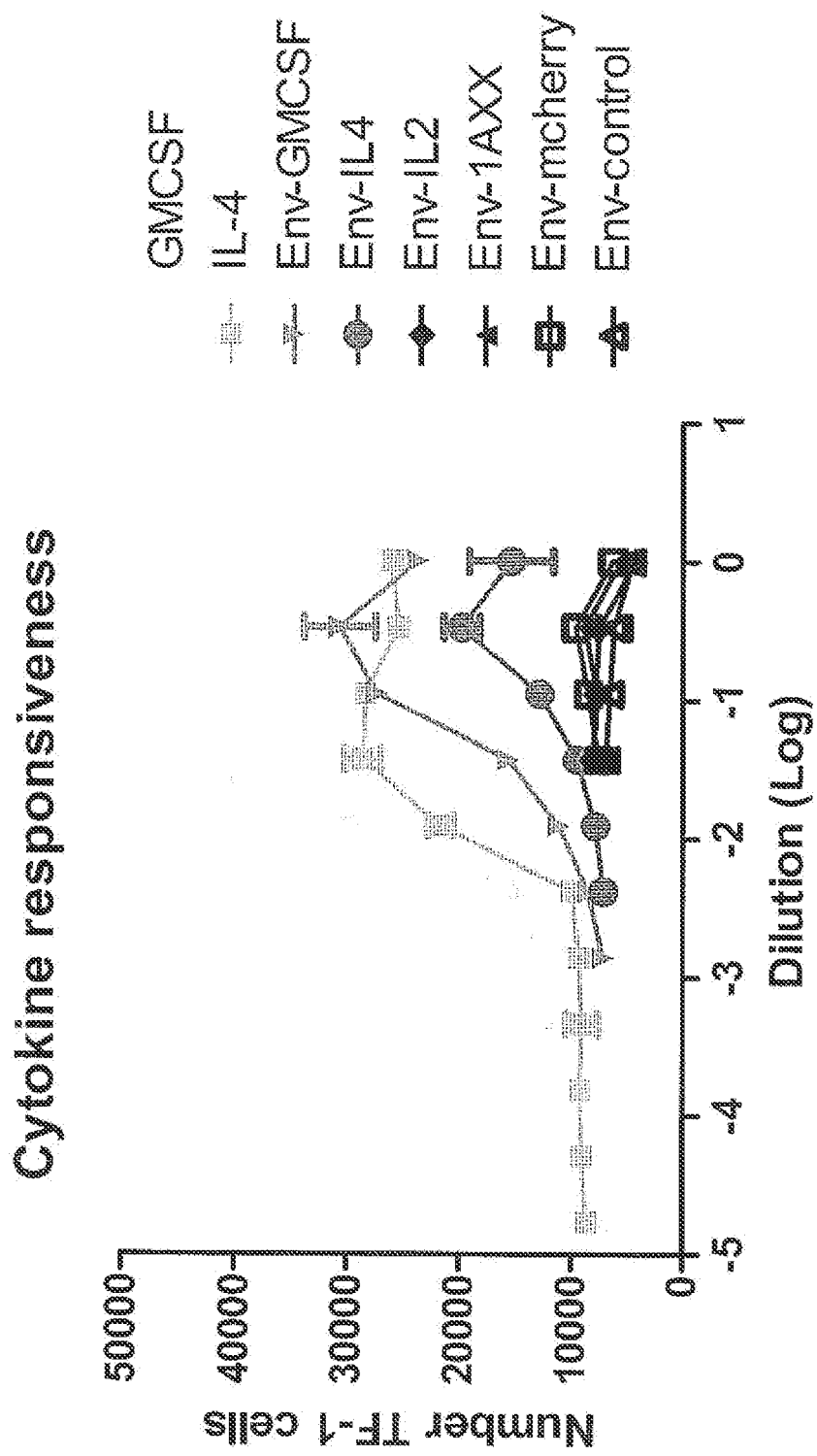

FIG. 24. Bioactivity of Env-GM-CSF and Env-IL-4 proteins. The functionality of Env (SOSIP.R6-IZ gp140) constructs containing co-stimulatory molecules (cytokines: IL-2; IL-4; GM-CSF), or irrelevant molecules (Cherry(1AXX); mCherry) replacing the V1V2 domain was assessed using Tf1 cells. Tf1 cells can only proliferate in the presence of functional GM-CSF or IL-4. Tf1 cells were incubated with recombinant GM-CSF or IL-4 or with transiently expressed Env constructs and proliferation was measured by FACS.

Figure 25:
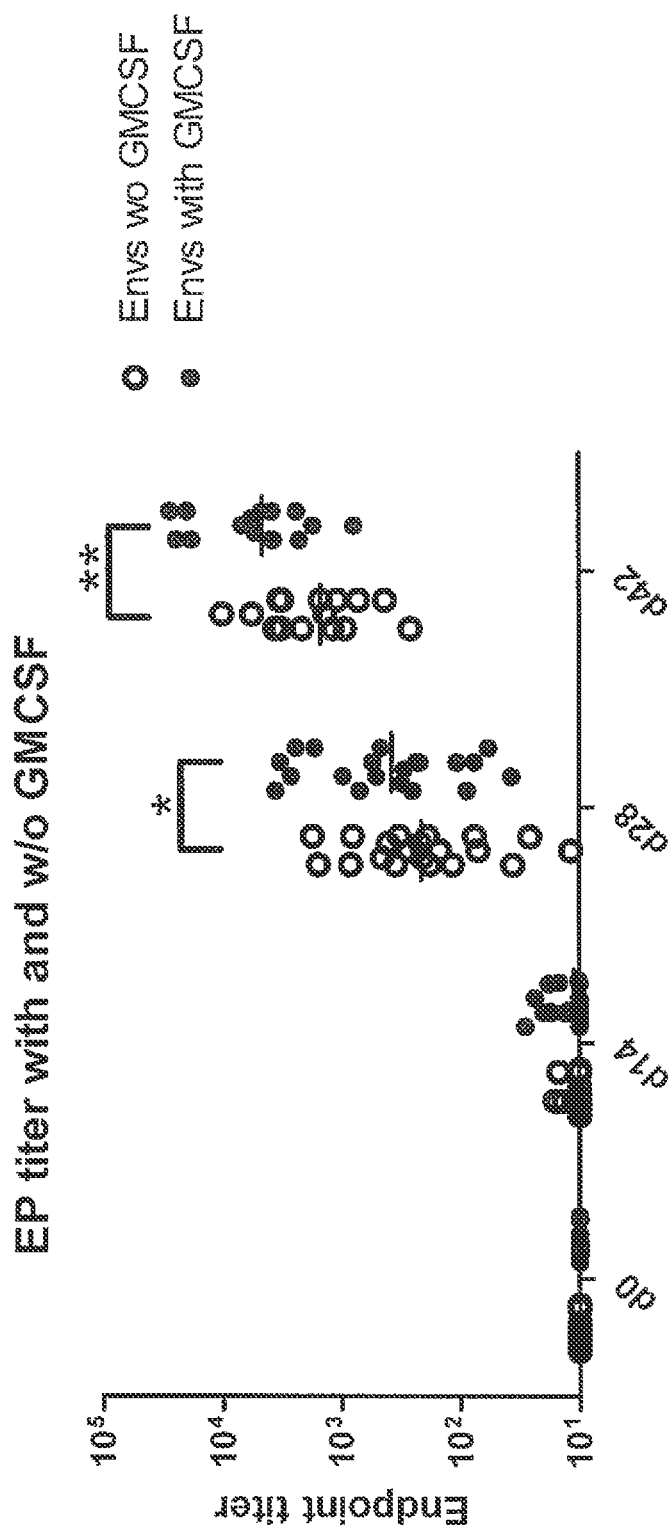

FIG. 25. Enhanced antibody responses induced by Env-GM-CSF. Mice were immunized with plasmids encoding Env (SOSIP.R6 gp140) or fusion construct using mouse versions of APRIL, BAFF or CD40L with or without GM-CSF as described in the materials and methods section. The anti-gp120 responses were monitored by ELISA. The equally matched groups were separated based on the absence or presence of mouse GM-CSF replacing the V1V2 domain.

Figure 26:
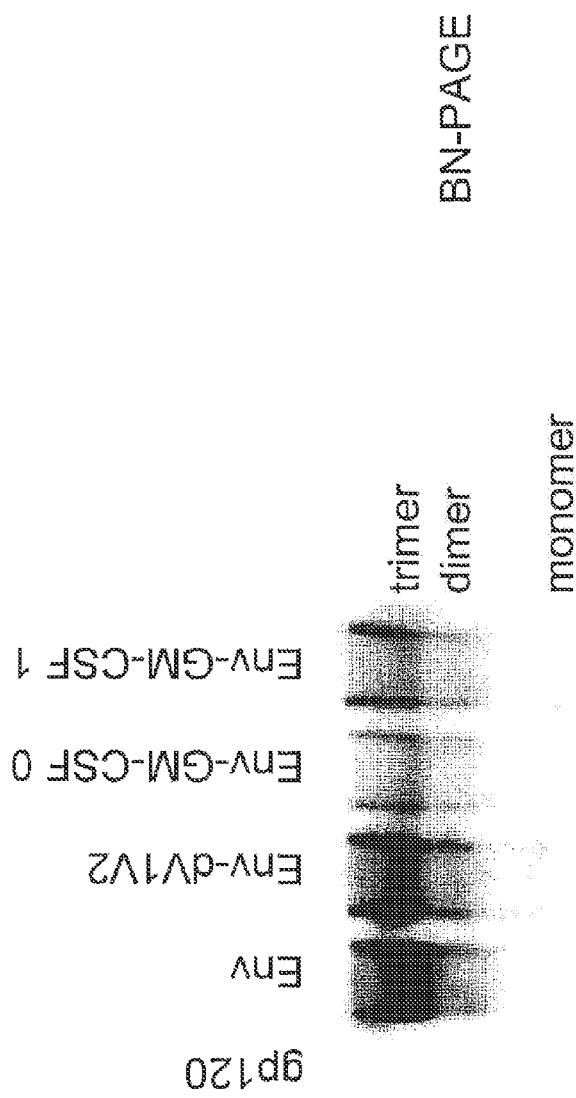

FIG. 26. Expression and oligomerization of Env (SOSIP.R6-IZ gp140) containing a full length GM-CSF (GM-CSF 0) or a truncated GM-CSF (GM-CSF 1) replacing the V1V2 domain. BN-PAGE analysis of proteins derived from transiently transfected 293T cells.

Figure 27:
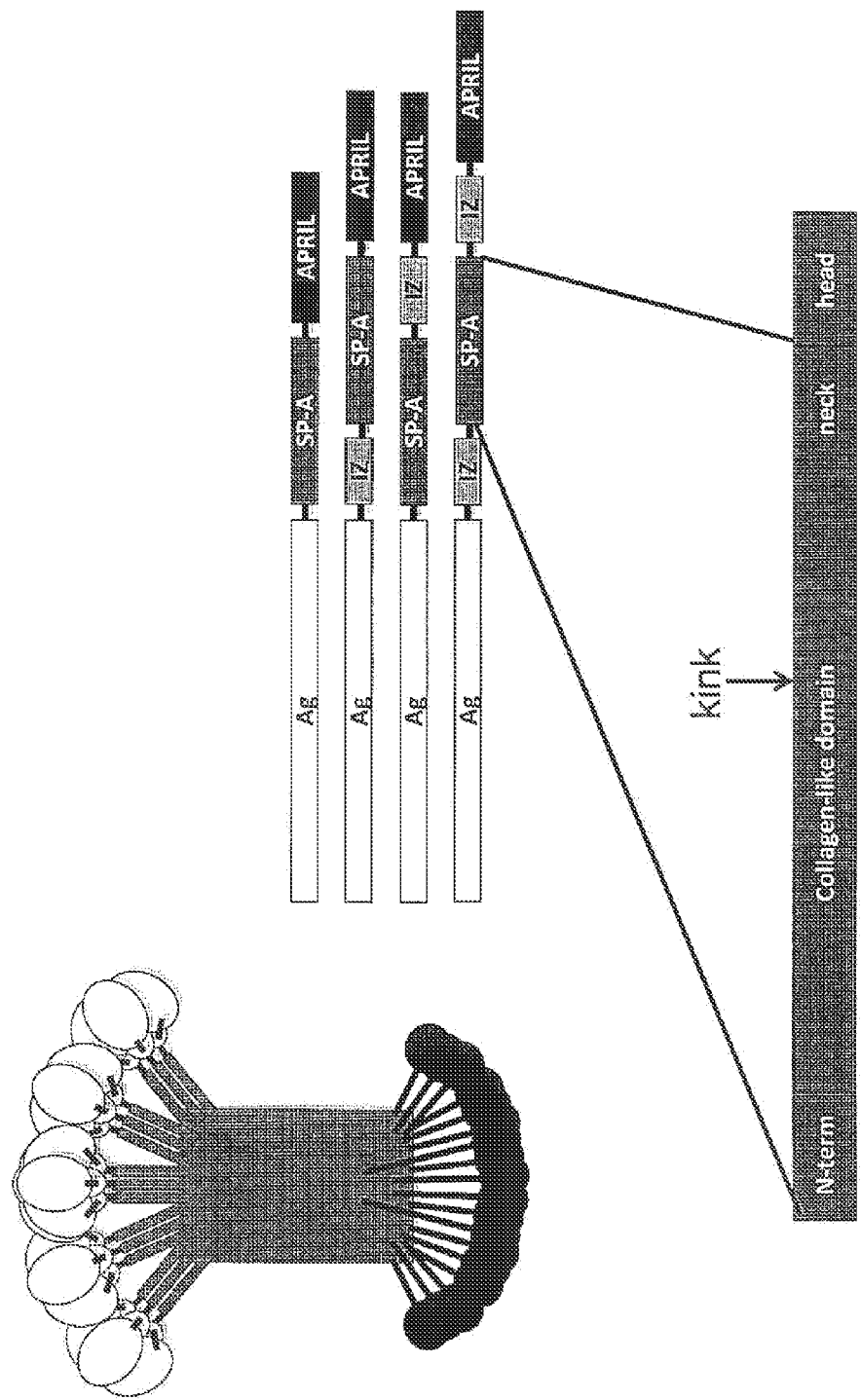

FIG. 27. Concept of polytrimeric fusion constructs of Env and a co-stimulatory molecule such as APRIL with a multimerizing molecule such as surfactant protein A (SP-A) in between. Cartoon (left) and linear (right) presentations. White: trimeric antigen; grey: trimerization domain; black: co-stimulatory molecule (example: APRIL); dark grey: multimerization molecule (example: SP-A).

FIG. 28. Sequence alignment of human (SEQ ID NO:46), (SEQ ID NO:47) and mouse (SEQ ID NO:45) surfactant protein A (top) and sequence of a SOSIP.R6-mSP-A-CD40L fusion construct (SEQ ID NO:48) (bottom).

Figure 29:
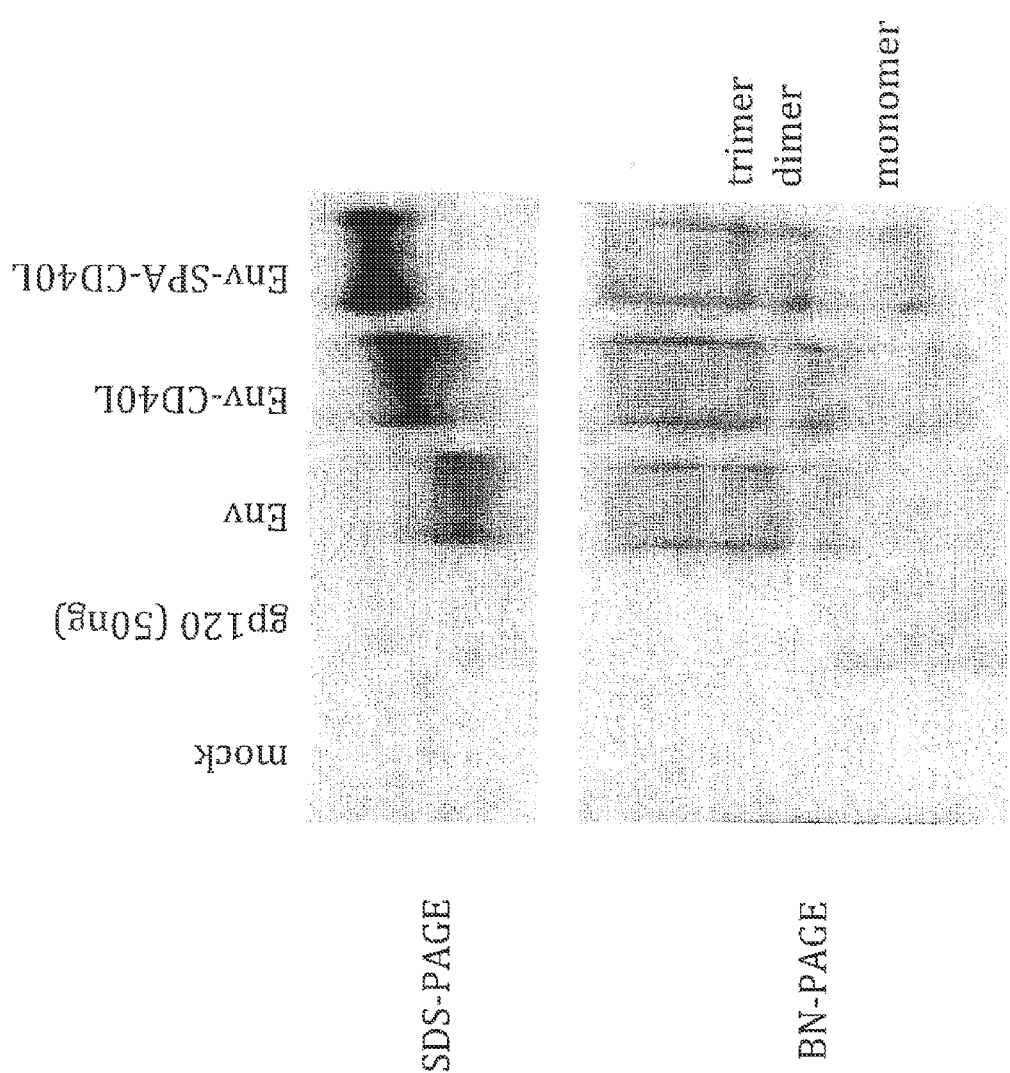

FIG. 29. Expression and oligomerization of Env (SOSIP.R6-IZ gp140) fused to mouse SP-A followed by CD40L. Reducing SDS-PAGE (top) and BN-PAGE (bottom) analysis of proteins derived from transiently transfected 293T cells.

FIG. 30. Sequences (SEQ ID NO:49), (SEQ ID NO:50), (SEQ ID NO:51), (SEQ ID NO:52), (SEQ ID NO:53), (SEQ ID NO:54), (SEQ ID NO:55), (SEQ ID NO:56), (SEQ ID NO:57), (SEQ ID NO:58), (SEQ ID NO:59) of the Env-SP-A junction of variants designed to improve polytrimerization of fusion proteins.

Figure 31:
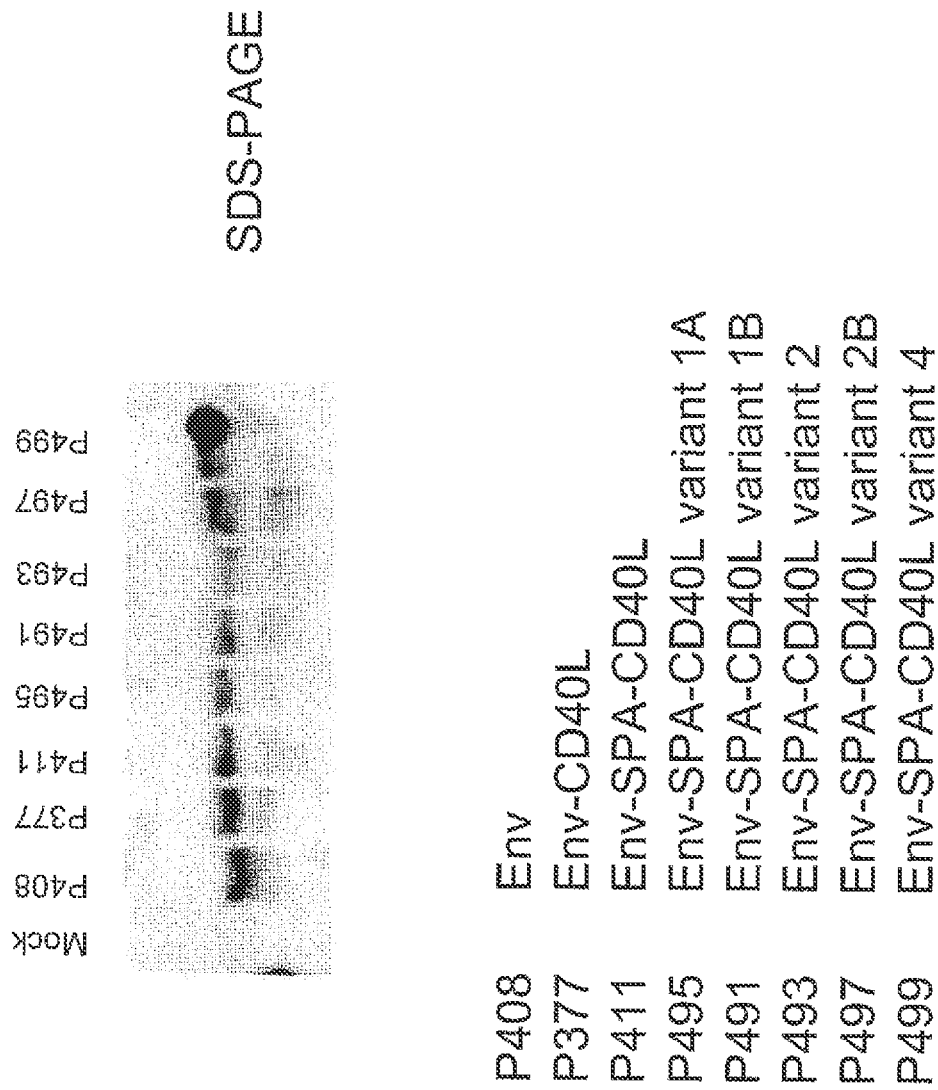

FIG. 31. Expression of Env (SOSIP.R6-IZ gp140) fused to mouse SP-A followed by CD40L with modifications at the Env-SP-A junctions. Reducing SDS-PAGE analysis of proteins derived from transiently transfected 293T cells.

FIG. 32. Sequences mouse surfactant protein A (SEQ ID NO:60), C1q (SEQ ID NO:62), (SEQ ID NO:63), (SEQ ID NO:64), adiponectin (SEQ ID NO:61), collectin (SEQ ID NO:67), MBL (SEQ ID NO:65), (SEQ ID NO:66) and human surfactant protein a (SEQ ID NO:68), (SEQ ID NO:69), all examples of molecules that can be used for polytrimerization of fusion proteins.

FIG. 33. Concept of multimerization of Env and a co-stimulatory molecules such as APRIL on nanoparticles. Cartoon (left) and linear (right) presentations. White: trimeric antigen; grey: trimerization domain; black: co-stimulatory molecule (example: APRIL); dark grey: polyhistidine tag as an example method for immobilization on nanoparticles. Other tags are also possible such as Fc (for interaction with protein A/G; see below).

FIG. 34. Efficient immobilization of Env (SOSIP.R6-IZ gp140) trimers on microparticles. Ni-NTA coated microparticles (Talon beads) were incubated with polyhistidine tagged Env (lane 5) and the immobilized Env was analyzed by SDS-PAGE (lane 1). Washes are devoid of Env (lanes 2&3) and low levels of Env are present in supernatant from which Env was depleted (lane 4).

Figure 35:
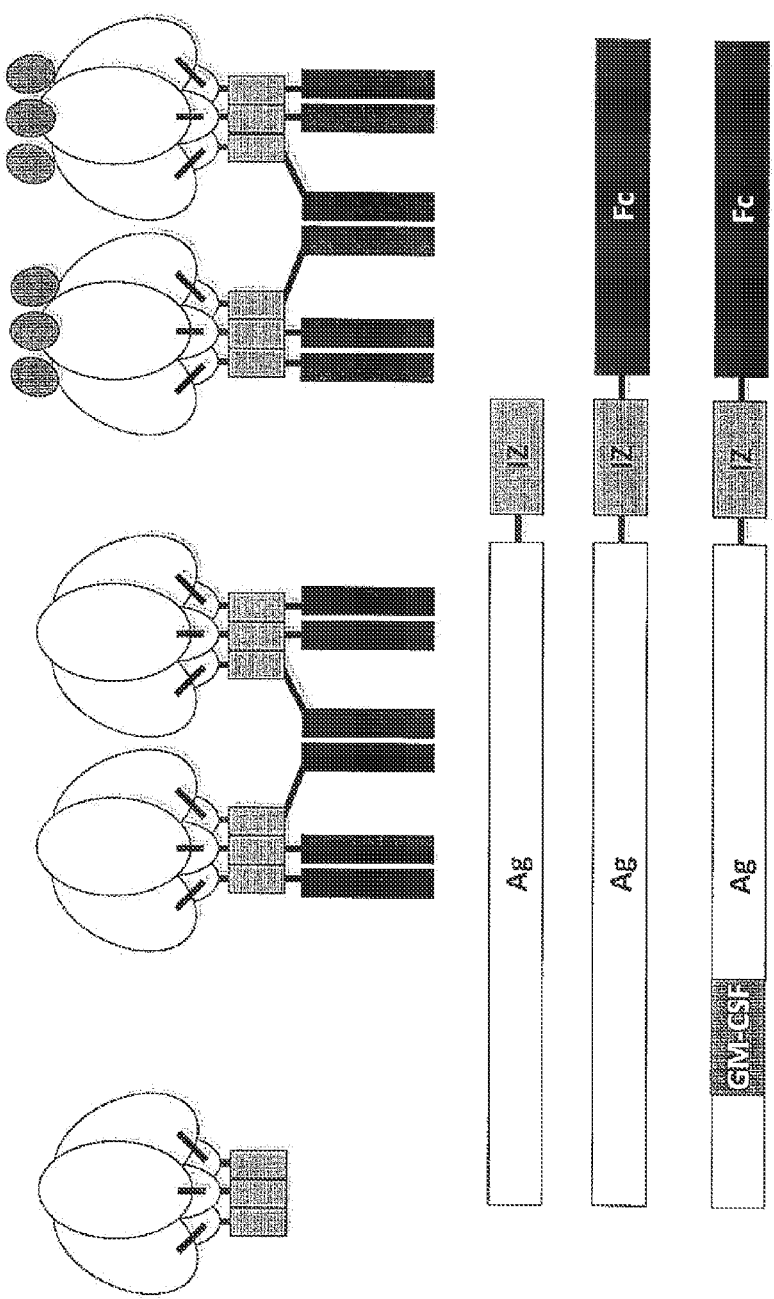

FIG. 35. Concept of hexameric fusion construct of Env and a co-stimulatory molecule such as GM-CSF replacing the V1V2 domain, fused at the C-terminus to the Fc tail of an antibody. Cartoon (top) and linear (bottom) presentations. White: trimeric antigen; grey: trimerization domain; black: Fc tail; dark grey: co-stimulatory molecule (cytokine such as GM-CSF).

Figure 36:
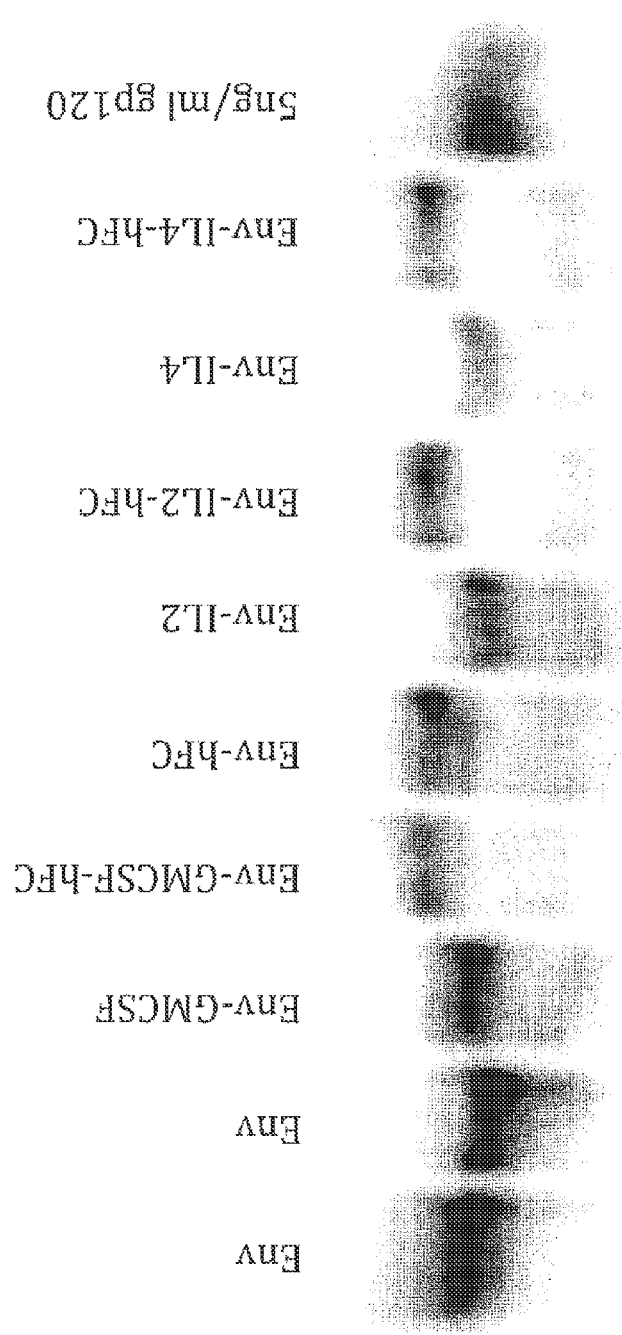

FIG. 36. Expression of Env (SOSIP.R6-IZ gp140) fused to the Fc tail of human IgG1 and containing a cytokine (IL-2, IL-4 or GM-CSF) replacing the V1V2 domain. Reducing SDS-PAGE analysis of proteins derived from transiently transfected 293T cells.

Figure 37:
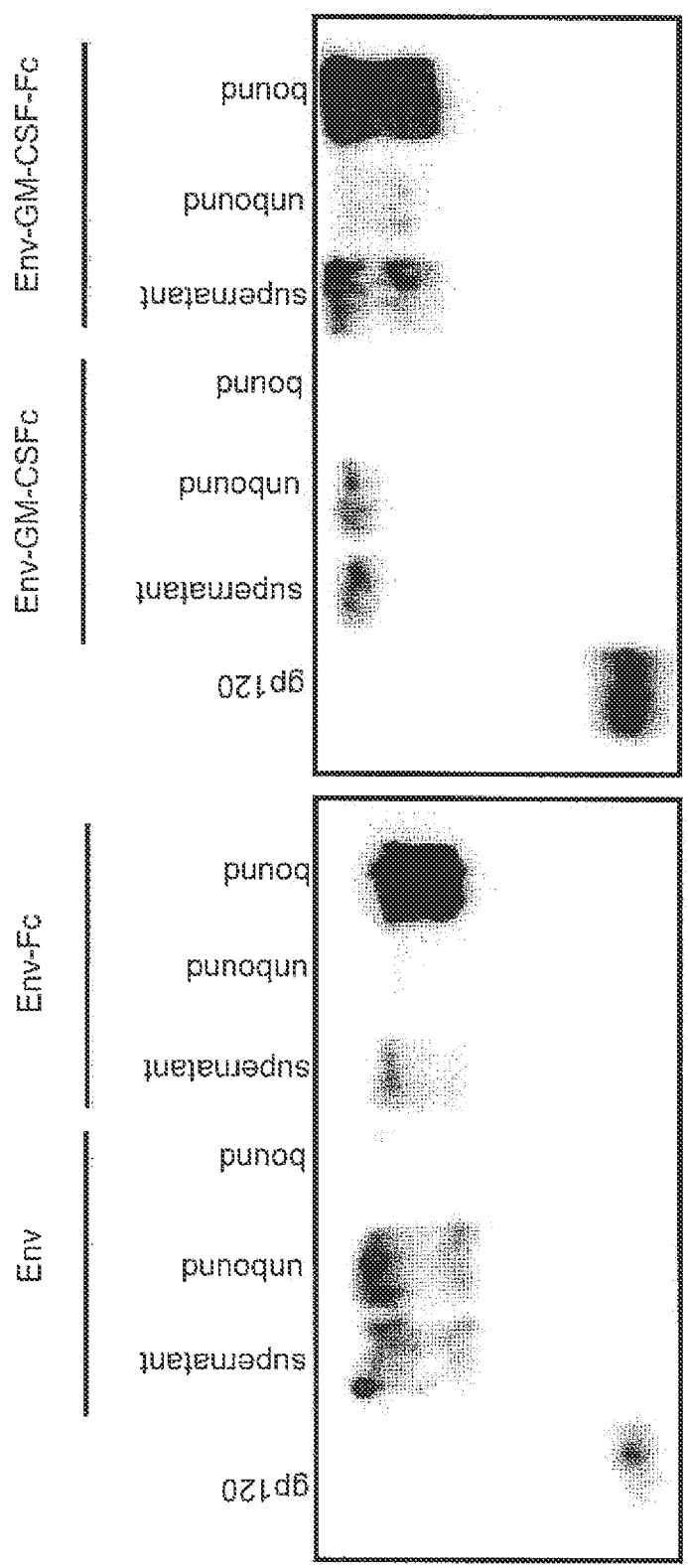

FIG. 37. Efficient immobilization of Env (SOSIP.R6-IZ gp140) trimers fused to the Fc domain of human IgG and containing GM-CSF replacing the V1V2 on microparticles. Fc tagged protein are efficiently captured on protein G coated particles (bound lanes).

Figure 38:
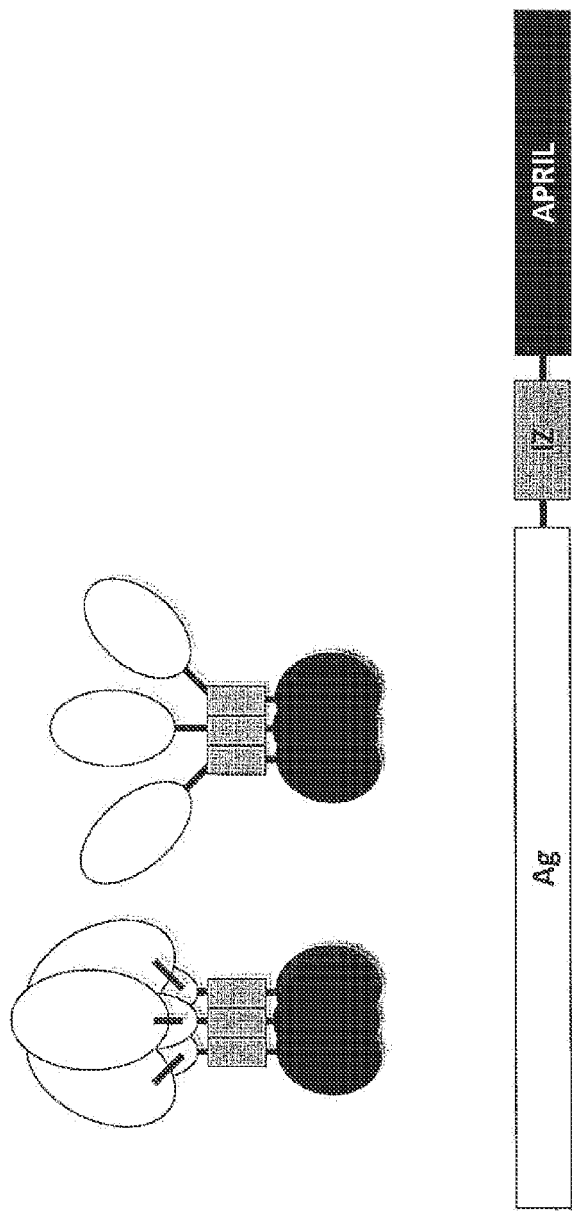

FIG. 38. Concept of trimeric fusion constructs of an otherwise monomeric (right) antigen (Ag) and a co-stimulatory molecule such as APRIL. Cartoon (top) and linear (bottom) presentations. White: antigen; grey: trimerization domain; black: co-stimulatory molecule (example: APRIL) with linkers in between.

Figure 39A:
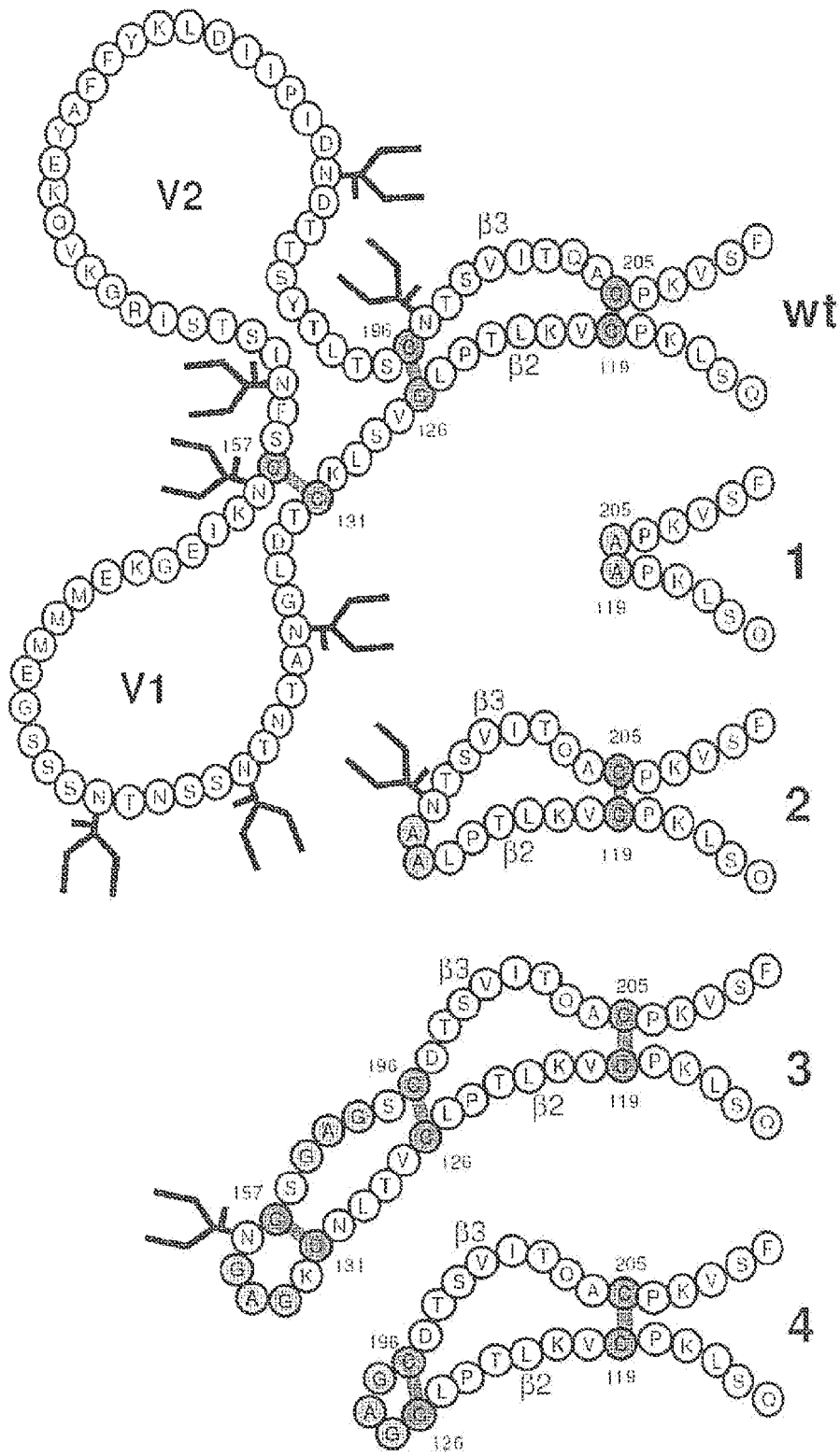
Figure 39C:
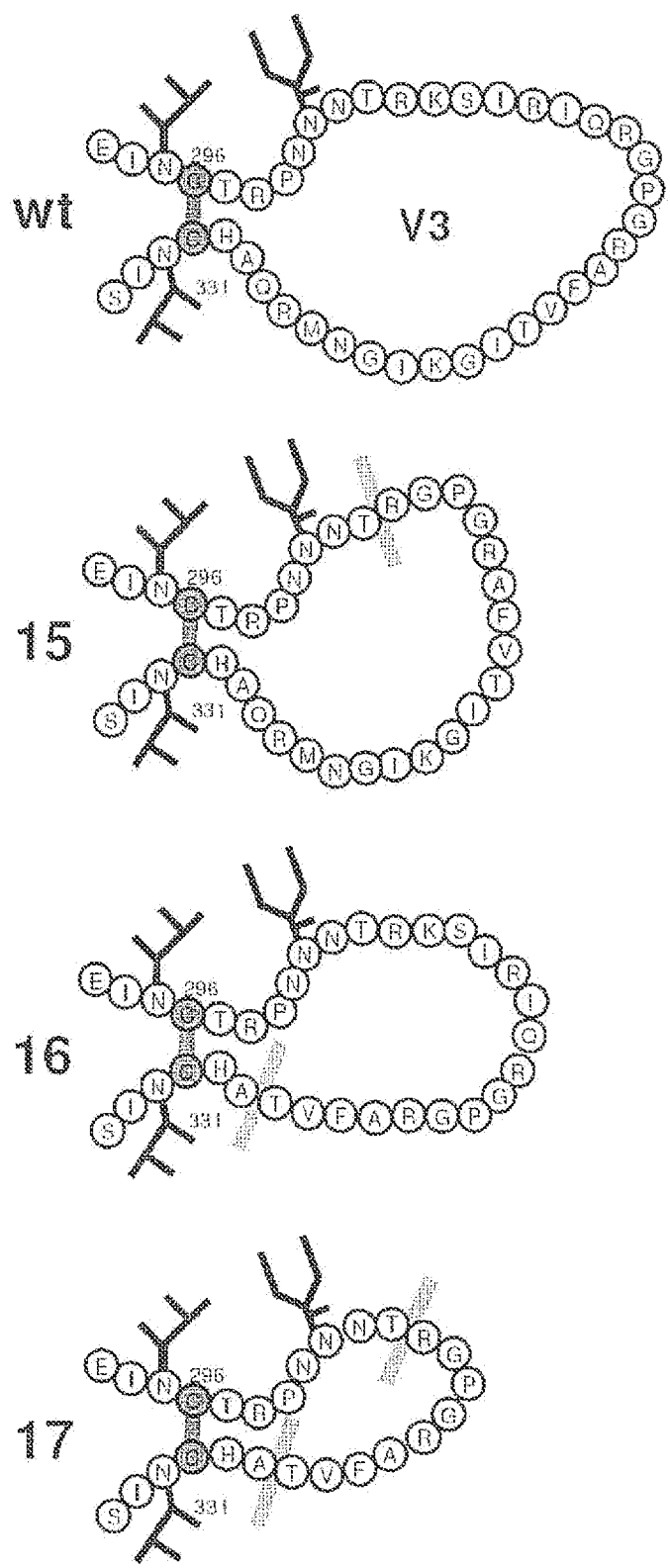

FIG. 39. Design of loop deletion variants. A. Schematic representation of the V1/V2deletion variants (SEQ ID NO:74), (SEQ ID NO:70), (SEQ ID NO:71), (SEQ ID NO:73), (SEQ ID NO:72), (SEQ ID NO:76), (SEQ ID NO:75), (SEQ ID NO:78), (SEQ ID NO:77) used in this study. Note that the designation of disulfide bonds is based on studies with the wild-type protein. We do not know whether the designated disulfide bonds do in fact form in these variants. This is particularly questionable in mutants 5 and 6 where one or two wt cysteine pairs cannot be formed. In variant 5 an alternative and hypothetical disulfide bond between 126 and 131 is drawn. In variant 6 the native C131-C157 bond is drawn and C126 is left unpaired. B. Assumed 3D models of selected ΔV1/V2 variants. The upper panel provides perspectives on gp120 as seen from CD4 (left) and the co-receptor (right; rotated over the y-axis by)90°. The rectangle in the upper right panel encloses the V1/V2-stem and the bridging sheet. The lower panels represent details of this area for the variants 1, 2 and 8 and an overlay of these variants. The four β-strands that compose the bridging sheet and the local disulfide bonds are indicated. The LAI gp120 core and variant cores were modeled by SWISS-MODEL (swissmodel.expasy.org//SWISS-MODEL.html) using the HXB2 core (pdb accession code 1G9M,) and drawn using Viewerlite (Accelrys Inc.). The overlay in the lower right panel was prepared with Deepview/SWISS pdb Viewer (www.expasy.org/spdbv/) and rendered in Viewerlite. C. Schematic representation of the V3 deletion variants. (SEQ ID NO:84), (SEQ ID NO:83), (SEQ ID NO:82), (SEQ ID NO:81), (SEQ ID NO:79), (SEQ ID NO:80) D. Rearrangement of the V1/V2-stem in variant 6. The starting situation is in FIG. 39A. Note that the drawn disulfide bond between residues C131 and C157 is purely speculative. However, in the wt protein these cysteines do form a disulfide bond. Left panel: hypothetical situation after the first substitution (C131Y) with a new non-native disulfide bond between C126 and C157, resulting in restoration of the V1 to its full length and formation of a pseudo-V2. Right panel: removal of N156 after prolonged culturing. Note that we observe the removal of the glycosylation site at N156 in two independent culture in two different substitutions: N156K (as indicated in the Figure) in culture 6A and S158F in culture 6B. The sequences were derived from sequencing clones at day 38 (6C) and day 99 (6A).

FIG. 40. Alignment of the amino acid sequences encoding a gp120 of strains JR-CSF (SEQ ID NO:88), JR-FL (SEQ ID NO:87), LAI (SEQ ID NO:86), and HXB2 (SEQ ID NO:85).

Figure 41:
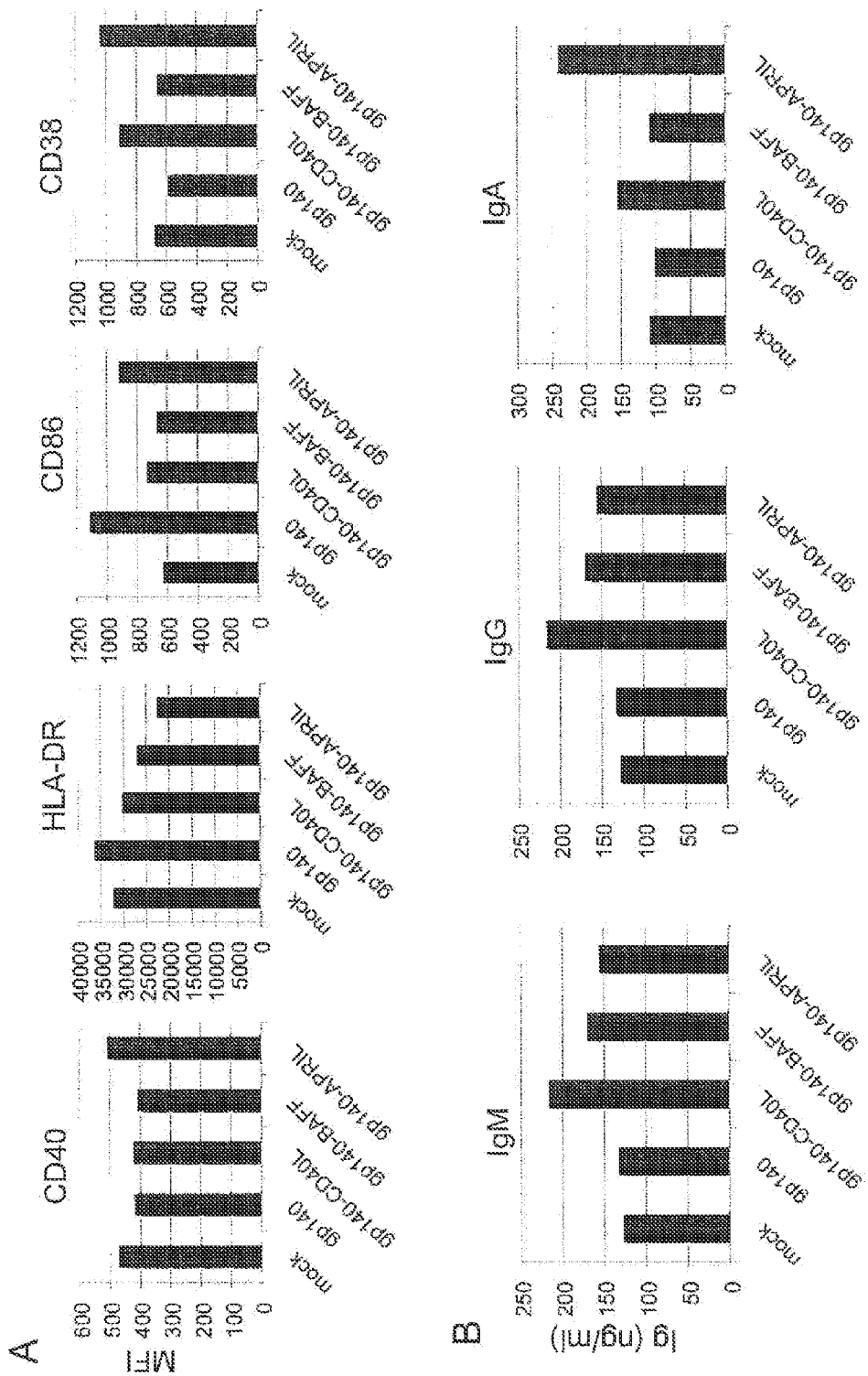

FIG. 41. Env-APRIL activates B cells. Naïve B cells isolated from human blood were activated using IL-4 and IL-10. In addition we supplied CD40L as a control, or Env, Env-APRIL, Env-BAFF or Env-CD40L. A. The expression of the cell surface markers HLA-DR, CD40, CD38 and CD86 was measured at day 5 by FACS and the mean fluorescent intensities are shown. B. At day 14 the secretion of IgM, IgG and IgA was measured by ELISA.

Figure 42:
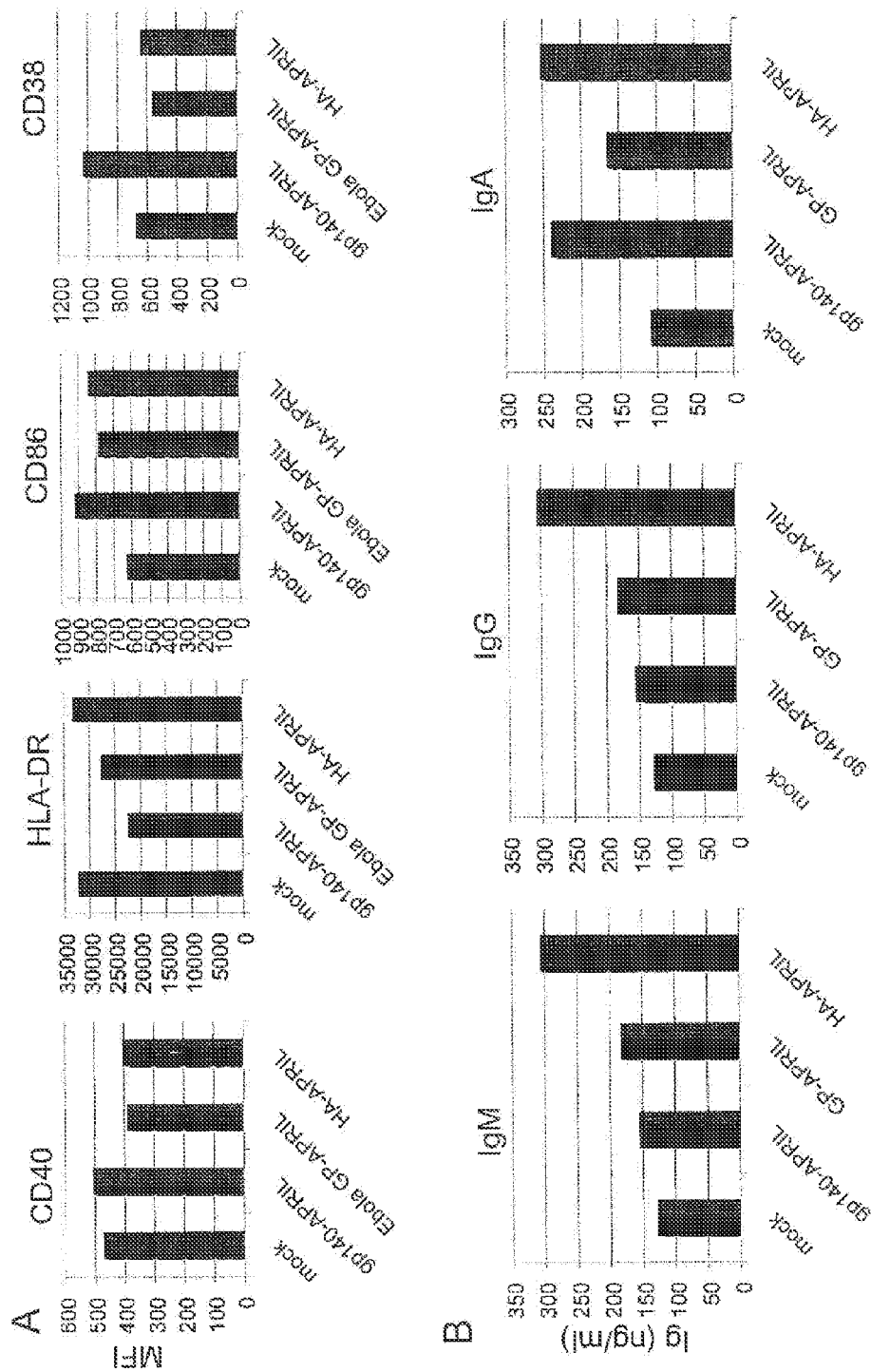

FIG. 42. GP-APRIL and HA-APRIL activate B cells. Naïve B cells isolates from human blood were activated using IL-4 and IL-10. In addition we supplied CD40L as a control, or GP-APRIL, or HA-APRIL. A. The expression of the cell surface markers HLA-DR, CD40, CD38 and CD86 was measured at day 5 by FACS and the mean fluorescent intensities are shown. B. At day 14 the secretion of IgM, IgG and IgA was measured by ELISA.

Figure 43:
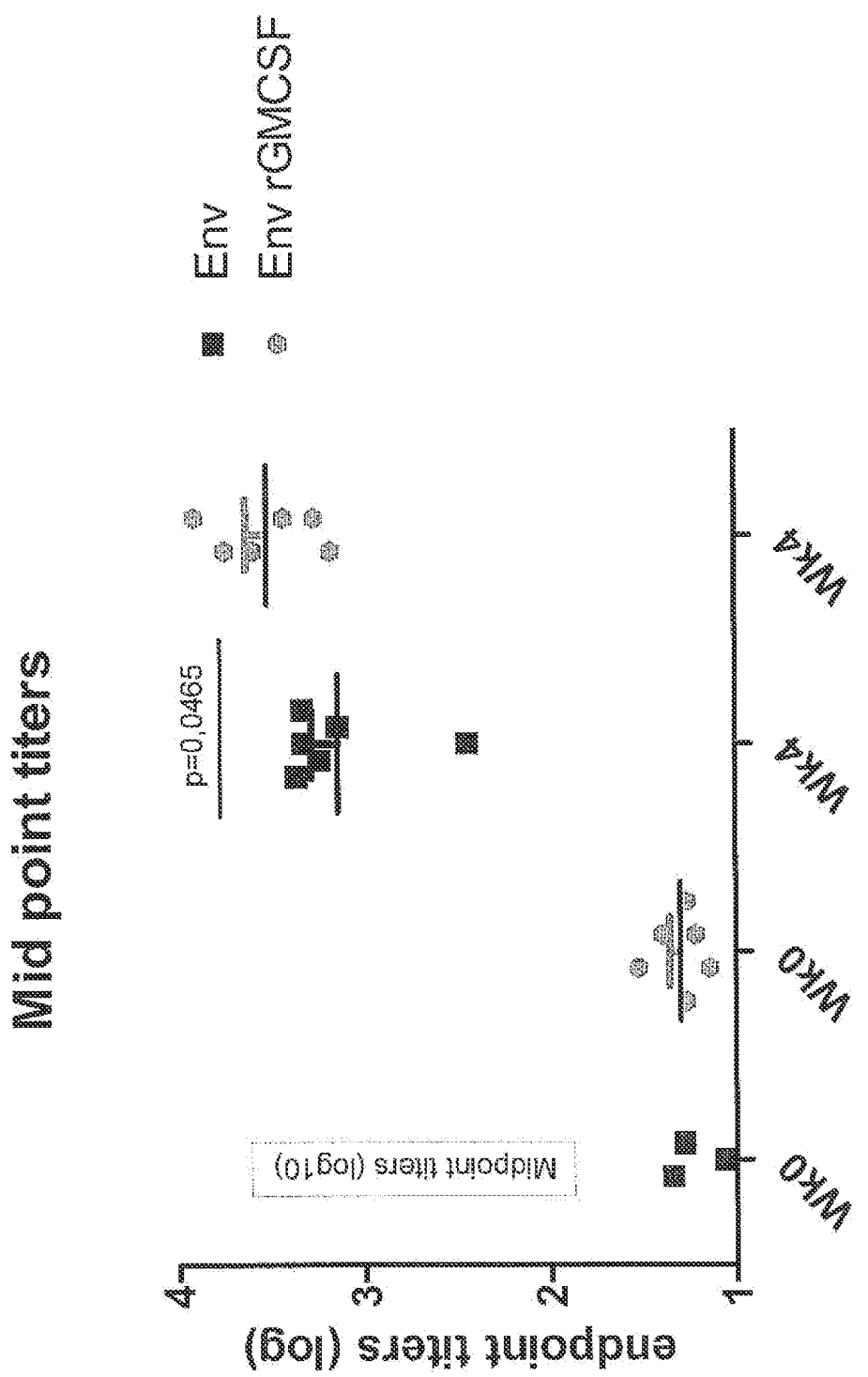

FIG. 43. Env-GMCSF induces enhanced antibody responses in rabbits. Rabbits (6 per group) were immunized at wk 0 and wk 2 with a plasmid encoding Env or Env-GMCSF. The Env-specific antibody titers were measured at wk 4.

Figure 44:
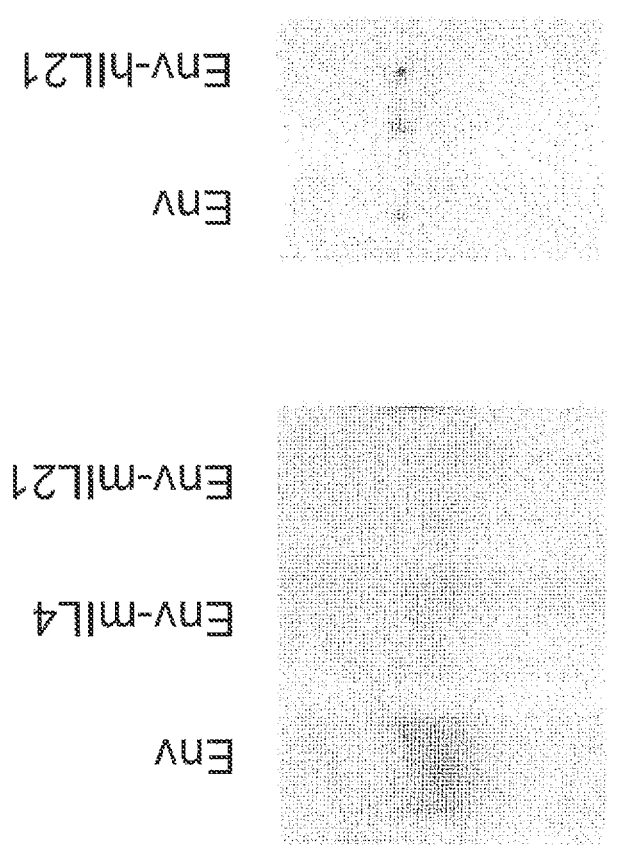

FIG. 44. Chimeric Env-IL21 can be made and expressed. Env-IL21 (human and mouse versions) were expressed in 293T cells and analyzed by SDS-PAGE and western blot analysis.

Figure 45:
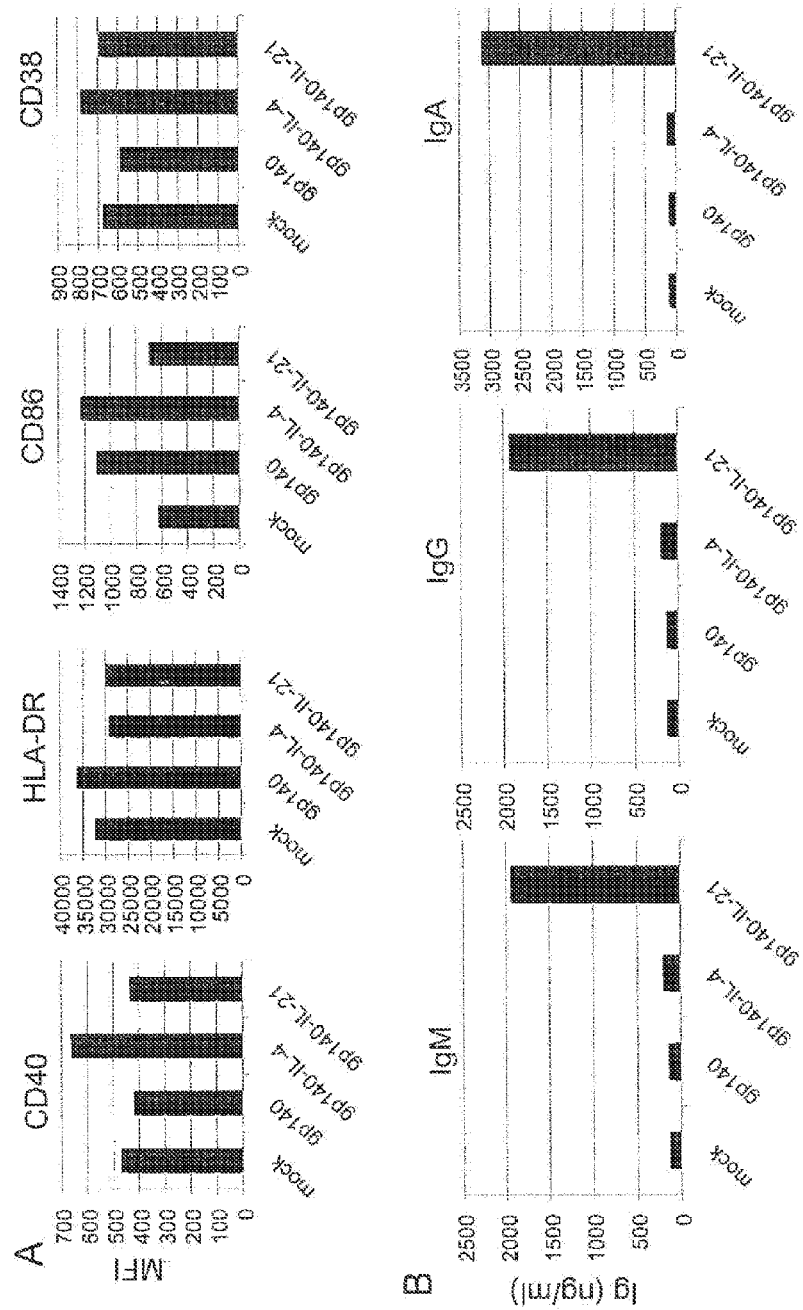

FIG. 45. Env-IL21 activates B cells. Naïve B cells isolates from human blood were activated using CD40L. In addition we supplied IL-4 as a control, or Env, Env-IL4 Env-IL21. A. The expression of the cell surface markers HLA-DR, CD40, CD38 and CD86 was measured at day 5 by FACS and the mean fluorescent intensities are shown. B. At day 14 the secretion of IgM, IgG and IgA was measured by ELISA.

FIG. 46. Sequence encoding GP antigen of Ebola virus (SEQ ID NO:89).

FIG. 47. Sequence encoding HA antigen of Influenza virus (SEQ ID NO:90).

FIG. 48. Sequence encoding murine IL-4 (SEQ ID NO:91).

FIG. 49. Sequence encoding human IL-4 (SEQ ID NO:92).

FIG. 50. Sequence encoding murine IL-21 (SEQ ID NO:93).

FIG. 51. Sequence encoding human IL-21 (SEQ ID NO:94).

Figure 52:
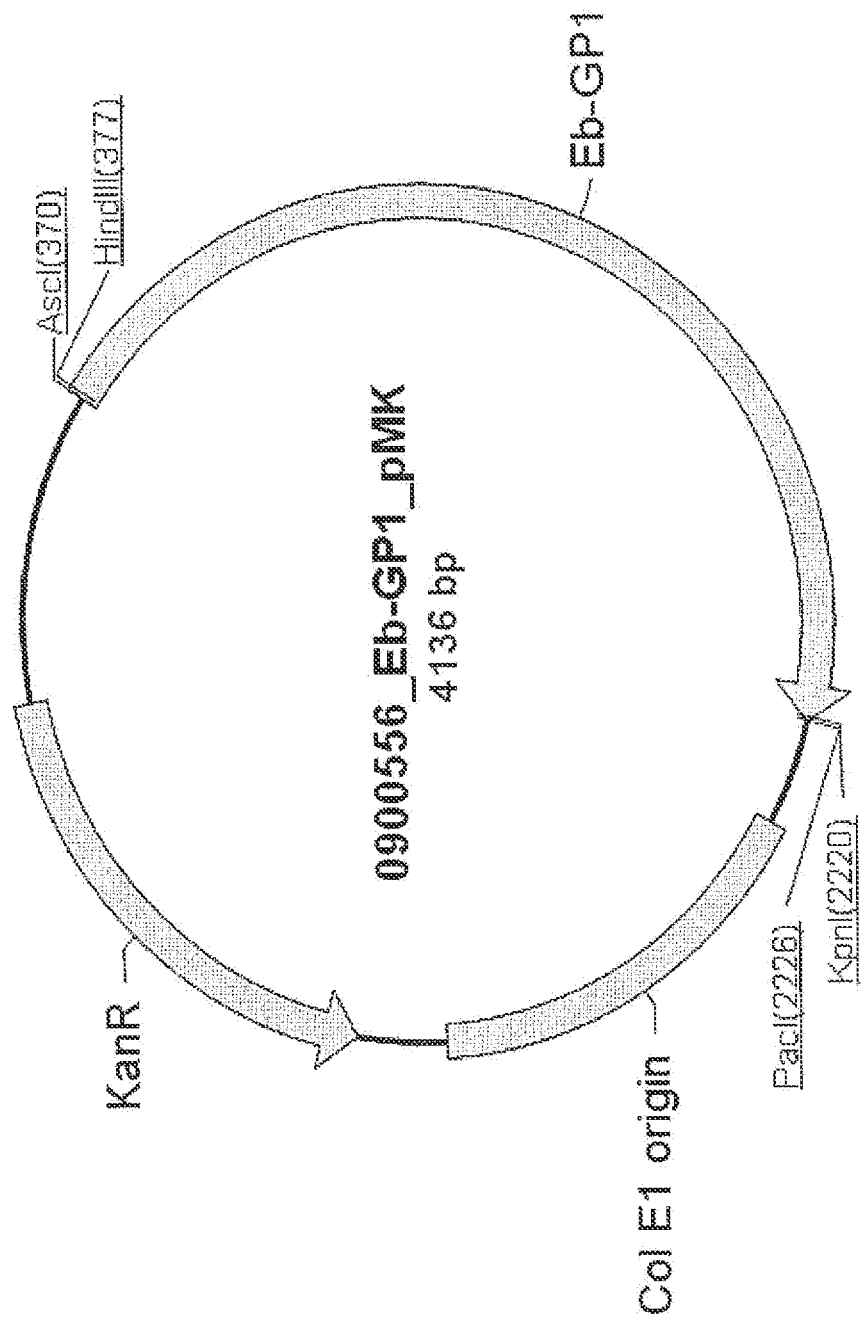
Figure 53:
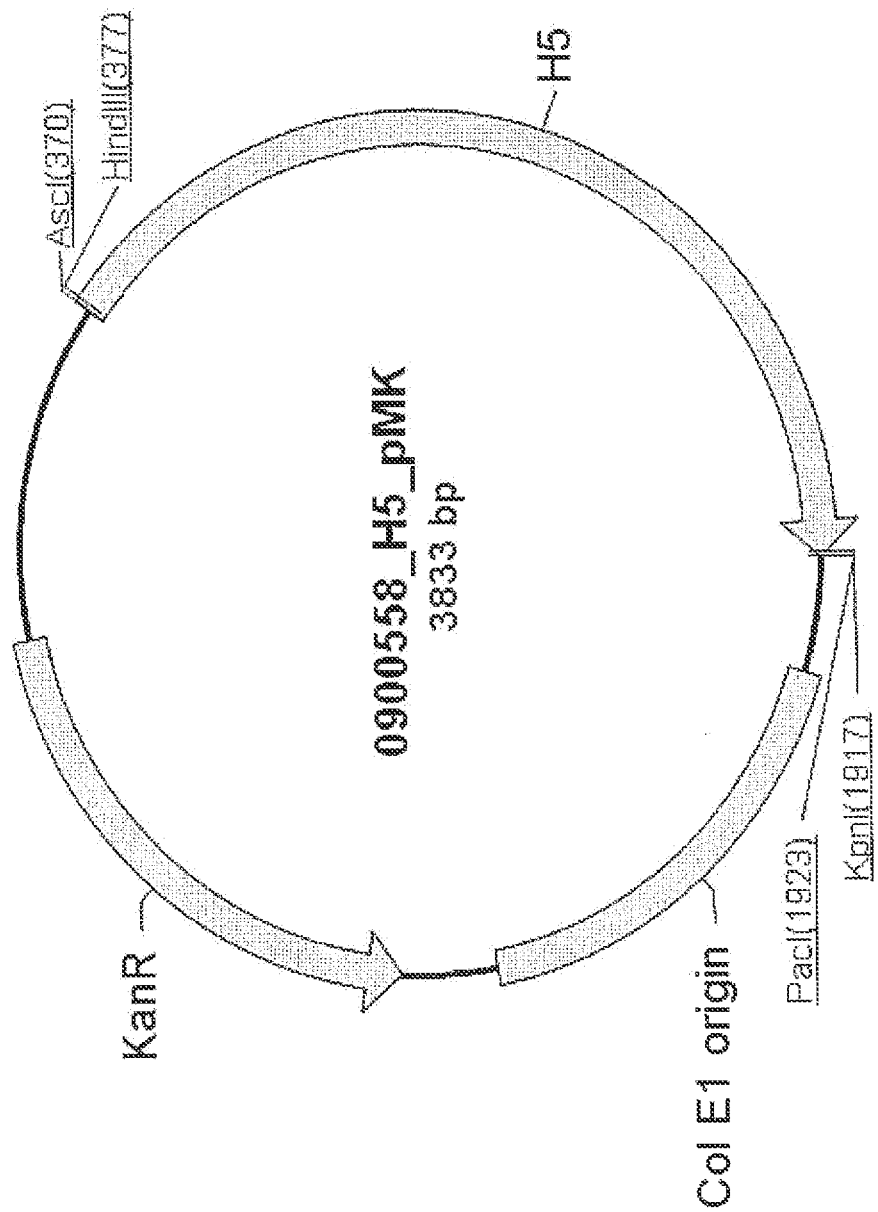
Figure 54:
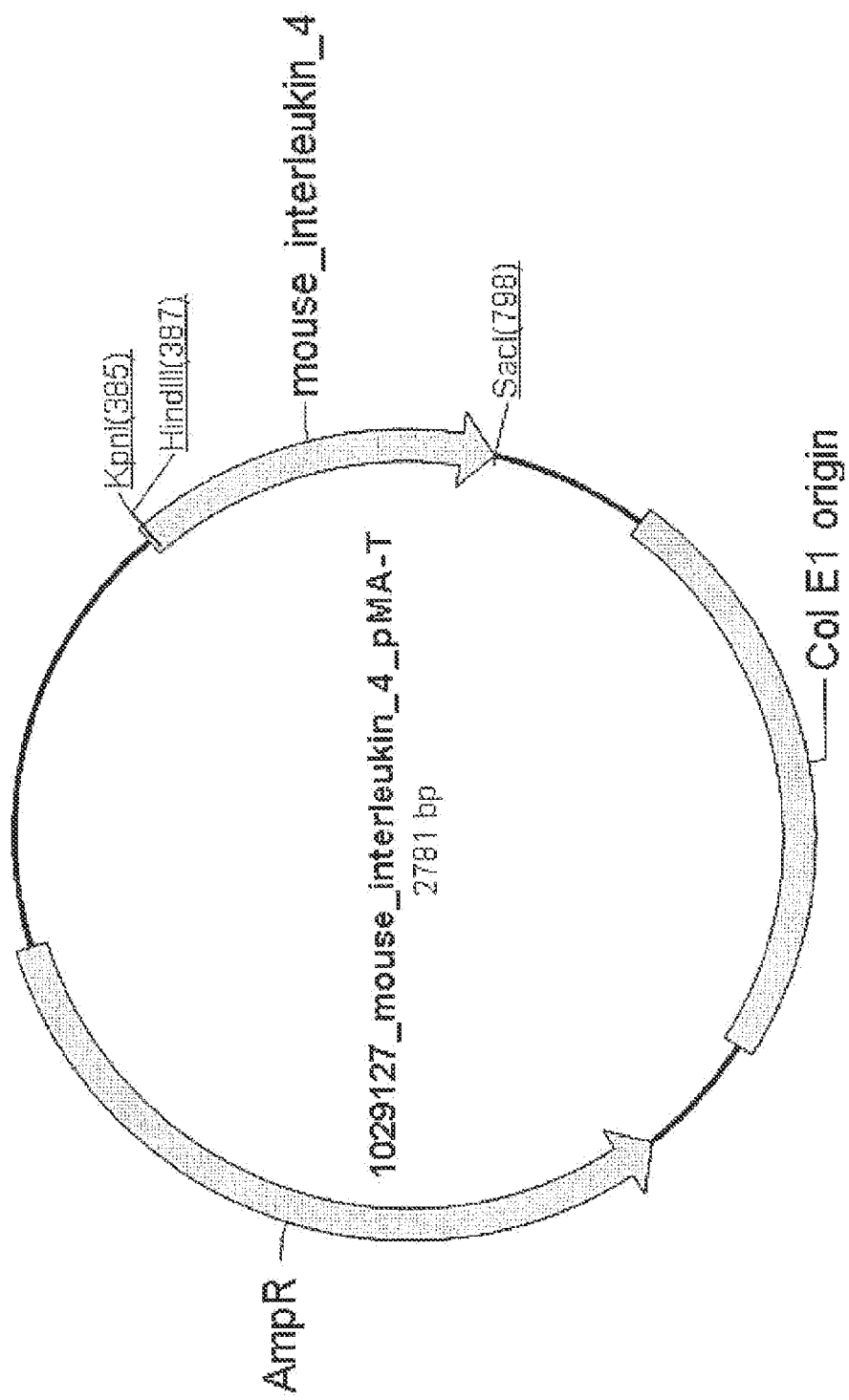
Figure 55:
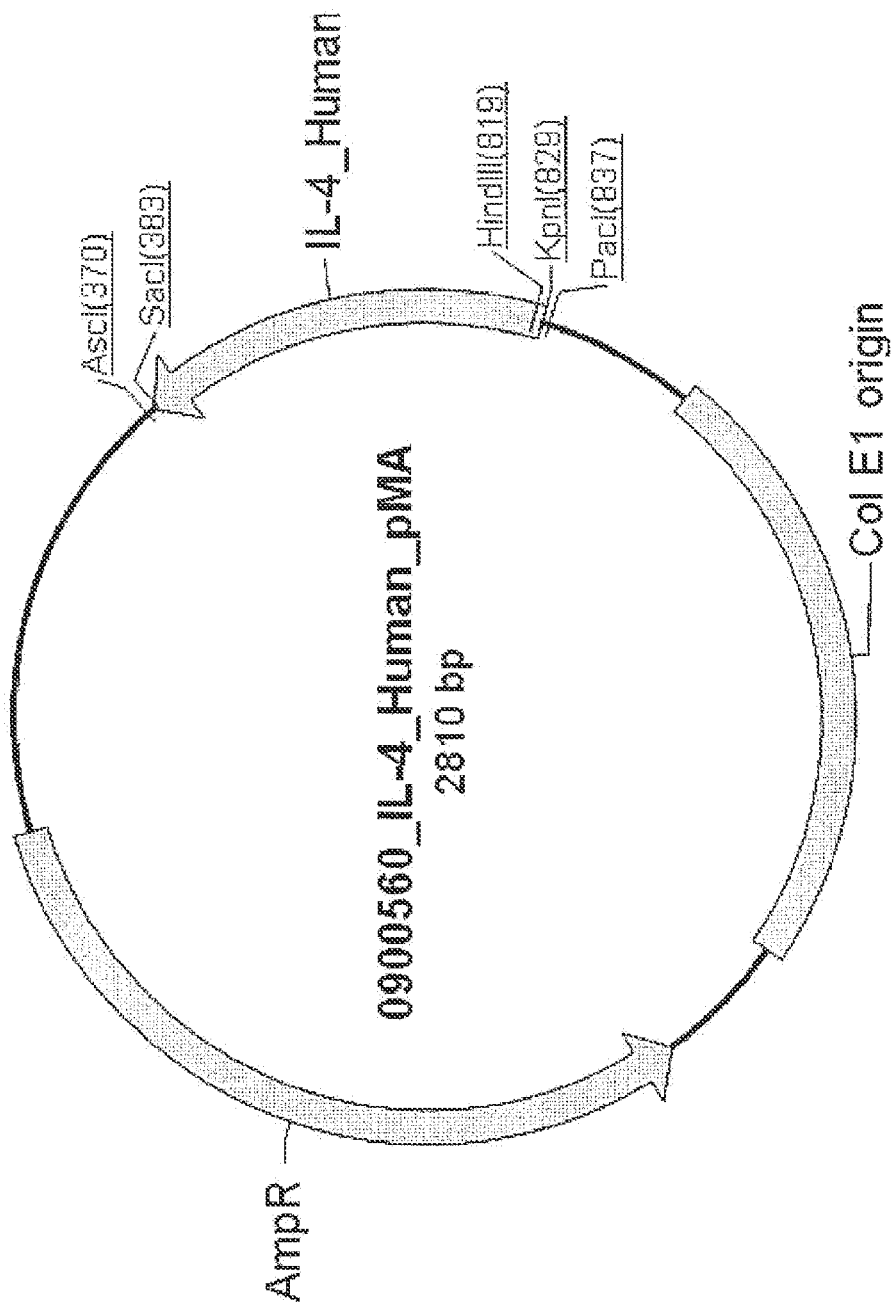
Figure 56:
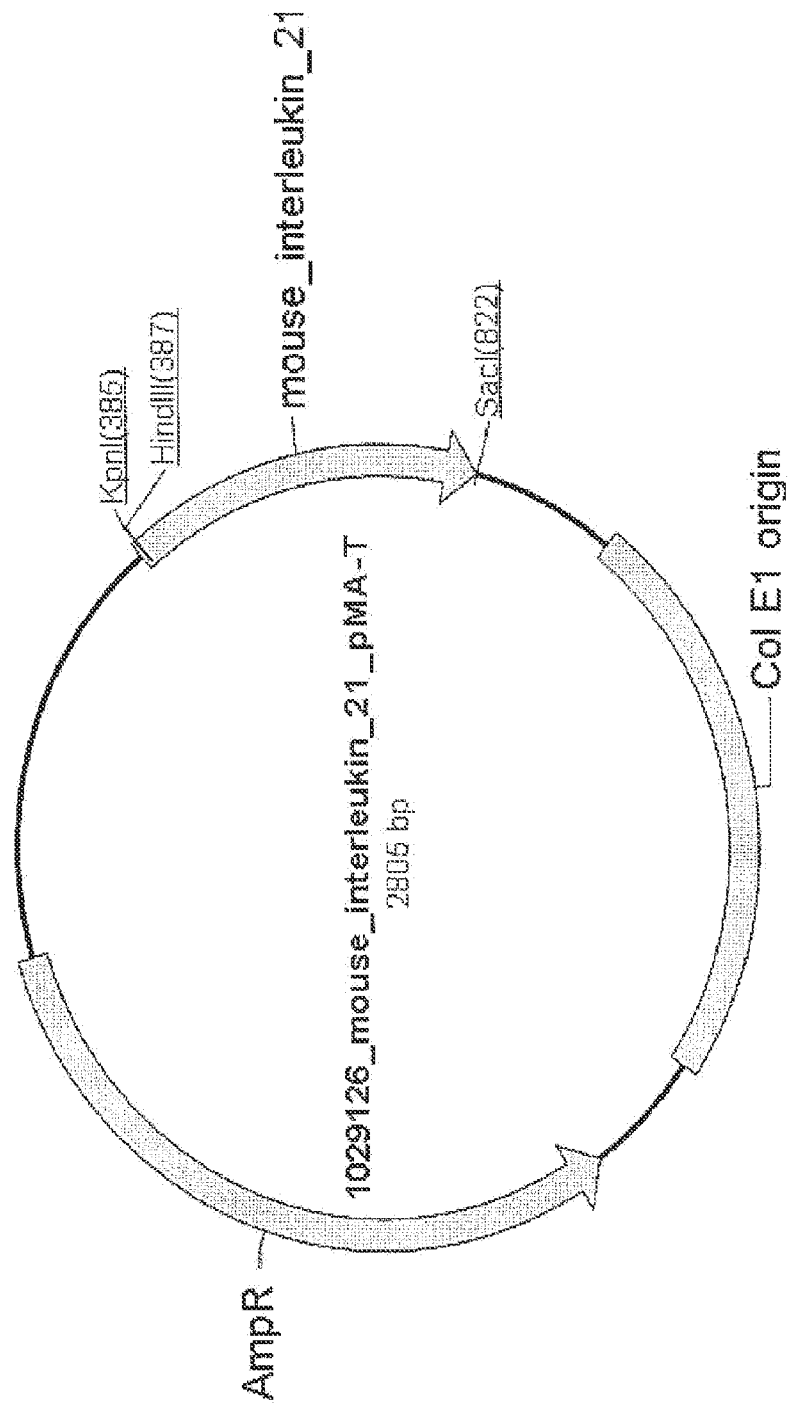
Figure 57:
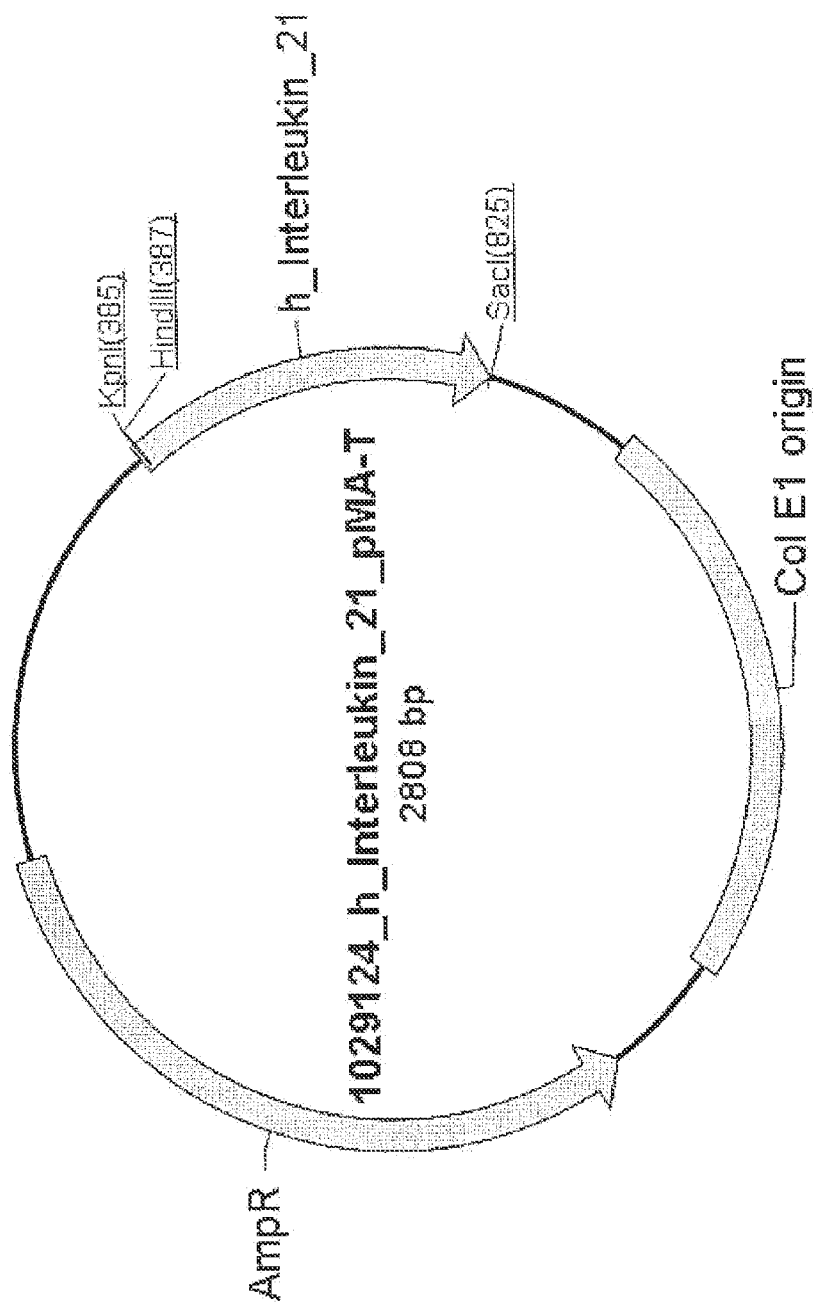

FIG. 52. 0900556_Eb-GP1_pMK vector.
FIG. 53. 0900558_H5_pMK vector.
FIG. 54. 1029127_mouse_interleukin_4_pMA-T vector.
FIG. 55. 0900560_IL-4_Human_pMA vector.
FIG. 56. 1029126_mouse_interleukin_21_pMA-T vector.
FIG. 57. 1029124_Interleukin_21_pMA-T vector.

MATERIALS AND METHODS

Plasmid Construction

The pPPI4 plasmid (Progenics Pharmaceuticals Inc., Tarrytown, N.Y.) containing a codon-optimized stabilized gp140 gene that is based on the subtype B, R5 isolate JR-FL has been described elsewhere (SOSIP.R6 gp140; Binley 2000, Binley 2002, Sanders 2002). To facilitated subsequent cloning steps, we first introduced a BamH1 site at the C-terminus of pPPI4-SOSIP.R6 gp140. This modification changed the most C-terminal amino acid of the natural gp140 protein (Y681I), and added one more amino acid (682L). These changes did not adversely affect the folding and secretion of SOSIP.R6 gp140 proteins (data not shown).

The gene encoding the functional domain (amino acids 118 to 261) of murine CD40L was amplified from the mouse fibroblast cell line J558 (American Type Culture Collection, Rockville, Md.), using the Expand PCR system according to the manufacturer's instructions (Roche, Mannheim, Germany). The PCR was performed with sense and antisense primers (5'mCD40L1BamH1 [5'-CTCATACTCATAG-GATCCTCGATCCTCAAATTGCAGC-3'] (SEQ ID NO:8) and 3'mCD40LSfu1 [5'-CTCATACTCATATTCGAATTA-GAGTTTGAGTAAGCC-3']) (SEQ ID NO:9). The PCR product was cloned downstream of the gp140 ORF in pPPI4-SOSIP.R6 using BamHI and SfuI, creating pPPI4-SOSIP.R6-L1-CD40L. The plasmids pPPI4-SOSIP.R6-L2-CD40L and pPPI4-SOSIP.R6-L3-CD40L were created by PCR amplification using pPPI4-SOSIP.R6-L1-CD40L as the template and the following 5' primers and, in both cases, 3'mCD40LSfu1: 5' mCD40L2BamH1: [5'-CTCATACTCAT- AGGATCCTCGGTGGAGGTAGCGATCCTCAA ATTG-CAGC-3'] (SEQ ID NO:10); 5' mCD40L3BamH1: [5'-CT-CATACTCATAGGATCCTCGGTGGAGGTAGCGGTGGAGG TGATCCTCAAATTGCAGC-3'] (SEQ ID NO:11). The resulting BamH1-Sful fragments containing the linker sequences and amino acids 118-261 from CD40L were then cloned behind the SOSIP.R6 gp140 sequences.

The pPPI4-SOSIP.R6-L4-CD40L plasmid was generated by PCR amplification, with pPPI4-SOSIP.R6-L3-CD40L as the template and primers 5' mCD40L4BamH1: [5'-CTCAT-ACT CATAGGATCCTCGGCGGTGGCGGTAGCG-GTGGTGGAGGTAGC-3'] (SEQ ID NO:12) and 3'mCD40LSful. Plasmid pPPI4-SOSIP.R6-L5-CD40L was generated by PCR amplification using pPPI4-SOSIP.R6-L4-CD40L as a template and primers 5'mCD40L5BamH1: [5'-CTCATACTCATAGGATCCTCGGTGGAG-GTGGAAGCGGCGGTGGCGGT-3'] (SEQ ID NO:13) and 3'mCD40LSful. These steps created the following spacers between SOSIP.R6 and mCD40L: L1: No spacer; L2: GGGS (SEQ ID NO:1); L3: GGGSGGG (SEQ ID NO:2); L4: GGGGSGGGGSGGG (SEQ ID NO:3); L5 GGGGSGGGGSGGGGSGGG (SEQ ID NO:4). To facilitate subsequent cloning steps, the linker region of pPPI4-SOS-IP.R6-L5-CD40L between Env and CD40L was further modified to introduce the restriction sites for Asp718, AgeI, NotI and BstE2 (pPPI4-SOSIP.R6-L5MCS-CD40L), creating the 18 amino acid linker sequence GGGGTGGGGTGGGGRGGG (SEQ ID NO:4) (non-silent changes are underlined). The resulting sequence modifications did not adversely affect the secretion of the SOSIP.R6-L5-CD40L fusion protein (data not shown).

A DNA fragment encoding a codon-optimized isoleucine zipper motif (IZ) based on GCN4 (AGAATGAAGCAGATC-GAGGACAAGATCGAGGAGATCCTGAG-CAAGATCTACCACA TCGAGAACGAGATCGCCA-GAATCAAGAAGCTGATCGGCGAGAGA (SEQ ID NO:14), which encodes the peptide sequence RMKQIEDK-IEEILSKIYHIENEIARIKKLIGER (Harbury 1994)) (SEQ ID NO:15), was annealed using two 5'-sense oligonucleotides, 5'IZAge1Bg12: 5'CCGGTAGAATGAAGCAGATC-GAGGACAAGATCGAGGAGATCCTGAGCAA-3' (SEQ ID NO:16) and 5'IZ2Bg12Not1: 5'-GATCTACCACATC-GAGAAC GAGATCGCCAGAATCAAGAAGCTGATCG-GCGAGAGAGGC-3' (SEQ ID NO:17) and the two antisense oligonucleotides 3'IZ1Age1Bg12: 5'-GATCTTGCTCAG-GATCTCCTCGATCTTGTCCTCGATCT-GCTTCATTCTA-3' (SEQ ID NO:18) and 3'IZ2Bg12Not1: 5'-GGCCGCCTCTCTCGCCGATCAGCTTCTTGATTC TGGCGATCTCGTTCTCGATGTGGTA-3' (SEQ ID NO:19), leading to a double stranded DNA fragment with a 5' AgeI site (single underline), a Bg12 site (double underlined) and a 3' NotI site (dotted underline). This fragment was cloned into pPPI4-SOSIP.R6-L5MCS-CD40L using AgeI and NotI, leaving a linker of 11 amino acids (GGGGTGGGGTG) (SEQ ID NO:6) between the SOSIP gp140 and IZ moieties, and a 6-amino acid linker (GGRGGG) (SEQ ID NO:5) between IZ and CD40L. Finally, we added a C-terminal oligo-histidine tag (HHHHHHHH) (SEQ ID NO:20) using the Quickchange mutagenesis kit (Stratagene, La Jolla, Calif.) as described above, creating the pPPI4-SOSIP.R6-IZ-CD40L-His construct.

We also created a similar plasmid without the sequences encoding CD40L (pPPI4-SOSIP.R6-IZ), by replacing the NotI-SfuI fragment (CD40L-His) by one containing only the oligo-histidine tag. Codon-optimized genes encoding the extracellular domain of the human and mouse versions of CD40L (amino acids 118 to 261) were synthesized (Mr. gene, Regensburg, Germany) and cloned behind SOSIP.R6-IZ using Not1 and Sfu1. The pPPI4-IZ-CD40L plasmid encoding trimeric CD40L without gp140 was constructed by cutting out the Env-encoding sequences from pPPI4-SOSIP.R6-IZ-hCD40L using NarI and AgeI, followed by Klenow blunting and self-ligation.

The sequence integrity of all clones was confirmed prior to use. The amino acid numbering of gp140 is based on HXB2 Env. For the rabbit experiments, codon-optimized rabbit based sequences were used for APRIL and BAFF. Like CD40L, only the active domain of APRIL and BAFF was used, corresponding to amino acids 115-250 and 150-289, respectively.

Codon-optimized sequences encoding amino acids 21 to 128 of mouse surfactant protein A (mSP-A) corresponding to the N-terminal region, the collagen like region and the neck region with AgeI and NotI restriction sites on the 5' and 3'end, respectively, were purchased (Mr Gene). To generate gp140-mSPA-CD40L, the AgeI-NotI fragment was cloned into the gp140-IZ-CD40L construct, replacing IZ and keeping the linkers flanking mSP-A the same those flanking IZ in gp140-IZ-CD40L.

Codon-optimized sequences encoding amino acids 26 to 139 of human granulocyte-macrophage colony-stimulating factor (GM-CSF) were synthesized (Mr Gene) containing a HindIII and BmgBI on either side. The V1V2 domain (amino acids tlnckdvnatnttndsegtmergeiknc-sfnittsirdevqkeyalfykldvvpidnnntsyrliscdTS) (SEQ ID NO:21) was replaced by GM-CSF (KLTPLCVGSGSTQP-WEHVNAIQEARRLLNLSRDTAAEMNETVE VISEM-FDLQEPTC LQTRLELYKQGLRGSLTKLKGPLTM-MASHYKQHCPPTPETSCATQIITFESFKENL KDFLLVIPFDCWGSGSCNTS) (SEQ ID NO:22) using HindIII and BmgBI on the N and C-terminal side of the V1V2 loop, respectively and underlined in the above sequence. The sequence indicated in bold corresponds to amino acids 26-139 of human GM-CSF, flanked by flexible GSG linkers. SCNTS is based on the JR-FL sequence, but an extra putative N-linked glycosylation site (indicated in italic) was inserted, based on previous data suggesting that glycosylation at this position facilitates correct folding of the Env glycoprotein trimer complex. A similar procedure was followed for the insertion of mouse GM-CSF the amino acids (KLTPLCVGS-GVTRPWKHVEAIKEALNLLDDMPVTL-NEEVEVVSNEFSFKKLTCVQT RLKIFEQGLRGNFT-KLKGALNMTASYYQTYCPPTPETDCETQVTTYADFI DSLKTF LTDIPFECKGSGSCNTS) (SEQ ID NO:23).

To generate constructs with a C-terminal sequence based on the Fc part of human IgG1 the following codon-optimized amino acid sequence was synthesized (Mr Gene; GGR-SPQPQPKPQPKPEP-EGSLQGDQGGGGEPKSCDKTHTCPPCPA-PELLGGPSVFLFP PKPKDTLMISRTPEVTCVVVDVSHEDPE-VKFNWYVDGVEVHNAKTKPREEQYNST YRVVSV-LTVLHQDWLNGKEYKCKVSNKALPA-PIEKTISKAKGQPREPQVYTLPPSR DELTKNQVSLTCLVKGFYPSDIA-VEWESNGQPENNYKTTPPVLDSDGSFFLYSKLT VDK-SRWQQGNVFSCSVMHEALHNHYTQKSLSLSPGK-STOP-SfuI) (SEQ ID NO:24). This fragment was cloned at the C-terminus of gp140-IZ, using NotI and SfuI. The locations of both sites are underlined in the sequence above. In bold is indicated the sequence corresponding to amino acids 99 to 330of the constant region of human IgG1. The introduced Fc-tail effectively replaces the 8X His tag which is usually at this location in our constructs.

To create Ebola GP-APRIL and Influenza HA-April, the env sequence of Env-APRIL were replaced by the sequences encoding GP (FIG. 46) and HA (FIG. 47), respectively, using NarI and BamH1 (see also FIGS. 52 and 53). To create Env-IL4 and Env-IL21, the sequences of Env-GMCSF encoding GMSCF were replaced by the sequences encoding mIL4 (FIG. 48), hIL4 (FIG. 49), mIL21 (FIG. 50), and hIL21 (FIG. 51), respectively, using Hind3 and Bmgl (see also FIGS. 54-57).

Rabbit CD40L Isolation

Neither the gene sequence nor the mRNA sequence of rabbit CD40L was known. We therefore isolated it ourselves. Peripheral blood mononuclear cells (PBMCs) were isolated from New Zealand White rabbit blood using Ficoll Paque (GE Healthcare, Diegem, Belgium) using the protocol described by (Liu, Hoyt 1996). Briefly, the blood was diluted 3× in Hanks Balanced Salt Solution (HBSS) after which Ficoll Paque was added. This was spun for 30 minutes at 2200 RPM without brake. The serum was then removed and kept apart, followed by removing of the cells from the Ficoll Paque gradient 3× washing with HBSS, of which the first time with homologous serum added. The cells were then stimulated in RPMI 1640 supplemented with 2 mM L-Glutamine, 40 IU/ml IL-2, 10% FCS, 10% homologous rabbit serum and 2 ug/ml PHA at 37 degrees. After three days, RNA was isolated from these cells using the RNeasy mini kit (Qiagen, Venlo, The Netherlands) according to the manufacturer's instructions.

Earlier attempts at determining the sequence of rabbit mRNA for CD40L enabled us to determine parts of the 3' sequence. This information was used to design a primer (R1) for first strand synthesis, which was performed using the Thermoscript RT-PCR system (Invitrogen, Breda). Almost complete rabbit CD40L cDNA was then amplified using a forward primer based on mouse CD40L mRNA (F1) and the primer used for first strand synthesis. For this the Expand high fidelity kit (Roche, Almere) was used. The resulting PCR product was then sequenced.

Analysis of a protein BLAST using the blastp algorithm showed that the closest known sequence to the amplified rabbit sequence was an mRNA sequence that was 89% homologous to human CD40L. If there would have been contamination, blasting analysis would have shown a sequence identity at 100% or very close to it. Blasting of both the amino acid and cDNA sequence into the database with all rabbit sequences showed no significant similarity to any known rabbit sequence. This can be explained by the fact that the rabbit genome identification project is still in process and large pieces of the genome have not yet been puzzled together. This sequence however was incomplete at the 5' and 3' end. Therefore we determined the location and size of the exons in the mouse CD40L mRNA coding sequence and blasted its corresponding putative rabbit sequence, exon by exon into the database with rabbit genome shotgun sequences. Each individual exon could be found within the rabbit sequences and was an exact match with the sequence we identified. The rabbit exons were located in two pieces of shotgun sequence. The spread and distribution was similar to that found in the mouse and human genome. This allowed us to confirm that the sequence found was actual rabbit sequence and to determine the outer 5' and 3' end of the rabbit CD40L mRNA coding sequence. These ends had high homology with its corresponding mouse homologous sequence. An alignment of rabbit, mouse and human CD40L mRNA sequence can be found in. The sequence of the primers used were ATGATAGAAACATACAGCCAACCTTCC (SEQ ID NO:25) and CAAACACCGAAGCATCCGCTTGC (SEQ ID NO:26).

Cell Culture and Transient Transfection 293T cells were transiently transfected with Env using linear polyethylenimine as described previously (Kirschner 2006). Briefly, DNA encoding Env (or plasmid DNA for mock transfections) was diluted to 0.1× the culture volume and mixed with Dulbecco's Modified Eagle's Medium (Invitrogen, Breda, The Netherlands). A volume of 0.15× the culture volume of a 1 mg/ml solution of linear polyethylenimine (PEI, MW 25,000) was then added and mixed. After incubation for 20 min, the DNA-PEI mix was added to the cells for 4 h before replacement with the same culture medium supplemented with 10% fetal bovine serum (FBS) (HyClone, Perbio, Etten-Leur, The Netherlands), penicillin, streptomycin, and MEM non-essential amino acids (0.1 mM, Invitrogen, Breda, The Netherlands). Env-containing supernatants were harvested 48 h after transfection.

SDS-PAGE, Blue Native PAGE and Western Blotting

SDS-polyacrylamide gel electrophoresis (SDS-PAGE) and western blotting were performed according to established protocols using the anti-gp120 V3 loop MAb PA-1 (1:20,000; final concentration, 50 ng/ml; Progenics) (Trkola 1996) and horseradish peroxidase-labeled goat anti-mouse IgG (1:5,000). Luminometric detection of envelope glycoproteins was performed using the western lightning ECL system (PerkinElmer, Groningen, The Netherlands). Blue Native (BN)-PAGE was carried out with minor modifications to the published method (Sanders 2002; Schuelke 2002). Thus, purified protein samples or cell culture supernatants were diluted with an equal volume of a buffer containing 100 mM 4-(N-morpholino) propane sulfonic acid (MOPS), 100 mM Tris-HCl, pH 7.7, 40% glycerol, 0.1% Coomassie blue, just prior to loading onto a 4 to 12% Bis-Tris NuPAGE gel (Invitrogen). Typically, gel electrophoresis was performed for 2 h at 150V (~0.07A) using 50 mM MOPS, 50 mM Tris, pH 7.7 as running buffer.

Immunoprecipitation Assays

Supernatants were concentrated 25-fold from 293T cells transiently transfected with gp140-IZ, gp140-IZ-BAFF or gp140-IZ-APRIL constructs and incubated overnight at 4° C. with MAbs or CD4-IgG2 in a 500 µl volume containing 100 µl of a 5-fold concentrated RIPA buffer (250 mM Tris-HCl, pH 7.4, 750 mM NaCl, 5% NP-40, 12.5 mM sodium deoxycholate, Complete Protease Inhibitor Cocktail (Roche, Mannheim, Germany)). Next, 50 µl of protein G-coated agarose beads (Pierce Inc./Thermo Fisher Scientific, Etten-Leur, The Netherlands) were added for 2 h rotation-mixing at 4° C. The beads were washed extensively with ice-cold 1×RIPA buffer containing 0.01% Tween 20. Proteins were eluted by heating the beads at 100° C. for 5 min in 50 µl of SDS-PAGE loading buffer supplemented with 100 mM dithiothreitol (DTT). The immunoprecipitated proteins were fractionated on 8% SDS-PAGE gels at 125 V for 2 h. Recombinant mouse CD40/TNFRSF5/Fc chimera, anti-mouse CD40L and recombinant human DC-SIGN/CD209/Fc were acquired from R&D Systems (Abingdon, UK). MAbs 2G12, 4E10 and 2F5 were obtained from Hermann Katinger through the NIH AIDS Research and Reference Reagent Program (ARRRRP); HIVIg was obtained through the ARRRP from NABI and NHLBI. MAb b12 was donated by Dennis Burton (The Scripps Research Institute, La Jolla, Calif.); CD4-IgG2 was a gift from William Olson (Progenics Pharmaceuticals Inc., Tarrytown, N.Y.).

Immunizations (Rabbits)

Plasmid DNA was amplified using DH5a cells and isolated using the EndoFree Plasmid Giga Kit (Qiagen, Venlo, The Netherlands). The immunizations were carried out at Genovac (Freiburg, Germany), under contract. The facilities at Genovac comply with the European Community guidelines for animal housing and in vivo experiments. New Zealand white rabbits were immunized on days 0, 14, 28, 56 with 125

µg of endotoxin-free DNA at the abdominal dermis using gene gun technology. The gp120 protein control group was immunized at the same dates, but instead of plasmid, 30 µg JR-FL gp120 in alum was injected subcutaneously at six sites: twice into the shoulder, abdomen, and hind limb. On day 112, all rabbits were injected with 1 ml PBS containing 30 µg JR-FL SOSIP.R6 protein (Sanders 2002, Beddows 2005) and 60 µg Quil A adjuvant. The injections were performed as follows: 300 µl intradermally (50 µl in each of 6 sites), 400 µl intramuscularly (200 µl into each hind leg) and 300 µl subcutaneously (neck region). Blood samples were obtained on days 0, 14, 28, 42, 56, 84, 112, 126 and the final bleed at day 140. Some animals did not survive until the end of the experiment.

Mice Immunizations (Gene Gun)

Plasmid DNA was amplified using DH5α cells and isolated using the EndoFree Plasmid Giga Kit (Qiagen, Venlo, The Netherlands). The immunizations were carried out at Genovac (Freiburg, Germany), under contract. The facilities at Genovac comply with the European Community guidelines for animal housing and in vivo experiments. Out-bred NMRI mice were immunized on days 0, 12, 28 and 42 with 20 µg of endotoxin-free DNA at the abdominal dermis, using gene gun technology. Blood samples were obtained on days 0, 12, 28, 42 and 56 (terminal bleed).

gp120-Specific and Total Immunoglobulin ELISA

Anti-gp120 antibody titers were measured by ELISA essentially as described previously (Sanders 2002). For measuring total serum immunoglobulin levels goat anti-mouse IgG (Jackson ImmunoResearch, Newmarket, UK) was coated onto the wells overnight (10 µg/ml in 0.1 M NaHCO3, pH 8.6; 100 µl/well). After blocking, serially diluted serum was applied for approximately 2 h. Bound mouse IgG was detected with HRP-labeled goat anti-mouse IgG (Jackson Immunoresearch, Suffolk, England; used at 1:5000 (0.2 µg/ml)), followed by luminometric detection.

Ni-NTA Trimer ELISA

Supernatants from HEK 293T cells transiently transfected with His-tagged Env proteins were diluted 1:3 in TBS/10% FCS and added for 2 h to pre-blocked Ni-NTA HisSorb 96-well plates (Qiagen). After 3 washes using TSM (20 mM Tris, 150 mM NaCl, 1 mM CaCl2, 2 mM MgCl2), various MAbs and polyclonal antibodies diluted in TSM/5% BSA were added for 2 h. When appropriate, Env proteins were pre-incubated with sCD4 for 30 min. The wells were then washed 5 times using TSM/0.05% Tween, followed by a 45 min incubation with the corresponding HRP-labeled secondary antibodies in TSM/5% BSA. After 5 washes in TSM/0.05% Tween, luminometric detection using established protocols.

Neutralization Assays

The TZM-bl reporter cell line stably expresses high levels of CD4 and HIV-1 co-receptors CCR5 and CXCR4 and contains the luciferase and β-galactosidase genes under the control of the HIV-1 long-terminal-repeat promoter. The TZM-bl cell line was obtained through the NIH AIDS Research and Reference Reagent Program, Division of AIDS, NIAID, National Institutes of Health (John C. Kappes, Xiaoyun Wu, and Tranzyme Inc. (Durham, N.C.)). Single-cycle infection experiments and inhibition experiments using TZM-bl cells were performed as described (Eggink 2009).

T Cell Functional Assays

The numbers of T-cells in spleens of immunized mice were determined using standard cell surface staining protocols and an LSR-II flow cytometer (BD Biosciences). The resulting data were analyzed using FlowJo software. All antibodies were purchased from BD Biosciences. Surface staining was carried out in buffer (PBS+10% FBS) for 20 min, followed by 2 washes with the same buffer. Prior to staining for specific cell surface markers, Fc receptors were blocked with an anti-mouse CD16/CD32 antibody (clone 2.4G2). The following labeled antibodies specific for mouse T cell markers were used: TCRβ-APC (clone H57-597), CD3 APC (clone 145-2C11), CD4 PCP (clone RM4-5), CD8 PE (clone 53-6.7).

In vitro re-stimulation of T cells (CD4$^+$ and CD8$^+$ combined) in unfractionated splenocyte cultures was carried out by culturing 5×10$^5$ cells/well with JR-FL gp120 (10 µg/ml) in a final volume of 200 µl/well (RPMI 1640 supplemented with 10% FBS, HEPES, glutamine, sodium pyruvate, penicillin, streptomycin, non-essential amino acids and 2-mercaptoethanol). Positive control wells received an anti-CD3e antibody (2 µg/ml, BD Biosciences, Clone 145-2C11, Cat 553057), negative control wells received media. Supernatants were collected after a 96 h culture at 37° C. in 5% CO2 and stored at −80° C. till further use. Concentrations of IL-2, IL-4, IL-5, IL-10 and IFN$_\gamma$ in the supernatants were measured by a sandwich ELISA, according to the manufacturer's instructions (OptEIA mouse ELISA kits, BD Biosciences), with the use of a TMB substrate kit (BD Biosciences) to provide a colorimetric endpoint at 405 nm. The assay sensitivity limits were approximately 3 pg/ml for IL-2, 8 pg/ml for IL-4, 16 pg/ml for IL-5 and 30 pg/ml for IL-10 and IFN$_\gamma$. Cytokine levels were expressed in pg/ml and graphs plotted to show values for each individual mouse.

Tf-1 Cell Proliferation

TF-1 cells were maintained in RPMI 1640 medium (Invitrogen) supplemented with 10% heat inactivated FCS (Hyclone) and 50 U/ml GMCSF (Schering-plough). Cells were cultured twice a week. Tf-1 cells were plated in 96-wells plate (Greiner) in 100u1 fresh RPMI 1640 medium supplemented with FCS (5.0*10$^4$ cells/well). Supernatant from 293T cells, transfected with various Env expressing plasmids, was added in 3-fold serial dilutions to Tf-1 cells (100 ul/well). After 3 days of culture at 37° C., cells were harvested and washed twice with PBS supplemented with 2% FCS. Cells were resuspended in 200u1 PBS 2%-FCS and the cells were counted in a fixed volume using FACS.

Ni-NTA Immobilization

TALON Dynabeads (invitrogen) were washed three times with washing buffer (50 mM Na-phosphate pH 8.0, 300 mM NaCl, 0.01% Tween-20, 0.015 mM imidazole) according to manufacturer's guidelines. Beads were incubated with polyhistidine tagged Env proteins in the supernatant of transfected 293T cells for 2.5 hrs at 4° C., while rotating. Env-bound beads were washed three times in washing buffer.

Protein G Immobilization

Fc-tagged Env in the supernatant (800 ul) of transiently transfected 293T cells was incubated with protein agarose G beads (20 ul) (Pierce biotechnology) for 2 hrs at RT, while rotating. Beads were centrifuged for 4 min at 2.500 rcf and washed three times with IP buffer (150 mM NaCl, 25 mM Tris/HCl pH 6.8) according to manufacture guidelines.

Statistical Analyses

One-tailed Mann-Whitney U tests were performed for statistical analysis of immunogenicity experiments.

CREATION AND CHARACTERIZATION OF TRIMERIC ENV-APRIL/BAFF/CD40L FUSION CONSTRUCTS

Enhancing SOSIP.R6 gp140 Trimer Formation

We have previously described modifications that improve the stability of soluble, cleaved gp140 trimers based on the R5 subtype B isolate JR-FL (Binley 2000). The amino-acid sequence of gp120 and the gp41 ectodomain was modified as follows (FIG. 2). Briefly, we introduced: (i) a disulfide bond between residues 501 in gp120 and 605 in gp41 (A501C, T605C; Binley00); (ii) a trimer-stabilizing substitution in gp41 (I559P; Sanders 2002); (iii) a sequence-enhanced site for furin cleavage (RRRRRR; Binley 2002) (SEQ ID NO:27). Despite these modifications, the resulting JR-FL SOSIP.R6 gp140 protein is expressed as heterogeneous oligomers, with monomers, dimers and tetramers present as well as the desired trimers. Although trimers based on other HIV-1 sequences (e.g., KNH1144 from subtype A) can be produced more consistently (Beddows 2006), we still wish to learn more about the general influences on gp140 trimer formation. We have therefore assessed the effect of various additional modifications to the JR-FL SOSIP.R6 gp140 sequence (for simplicity, we will use the term gp140, or Env, to describe this particular protein from here on). The addition of heterologous trimerization motifs has been shown to improve gp140 trimer formation (Yang 2000). We therefore introduced a GCN4-based isoleucine zipper (IZ) sequence (Harbury 1994) at the gp140 C-terminus (FIG. 2). In addition, we added an octa-histidine (H8) motif immediately C-terminal to the IZ trimerization domain, with flexible 11 and 6 amino acid linkers placed between the gp140 and IZ sequences, and between IZ and the H8 tag, respectively (FIG. 2). The optimal linker length was determined in concurrent studies (see below). The resulting gp140-IZ and unmodified gp140 proteins were expressed transiently in 293T cells, but without furin co-transfection, and then analyzed by SDS-PAGE and Blue Native (BN)-PAGE. Both gp140 proteins were efficiently expressed (FIG. 2). As expected, the unmodified gp140 was secreted as a mixture in which dimers and trimers predominated (each at ~50% prevalence). The proportion of trimers was markedly greater, however, for the gp140-IZ protein (~90%), presumably because of the impact of the heterologous trimerization domain (FIG. 2).

We next studied the gp140 and gp140-IZ proteins using analytical size exclusion chromatography on a Superose-6 column, compared to standard proteins of defined molecular weight (FIG. 3). Analysis of the eluted Env-protein components by SDS-PAGE and western blotting showed that multiple oligomeric gp140 forms were present (Sanders 2002). We previously reported that SOSIP gp140 monomers, dimers and trimers were eluted from a Superdex-200 size exclusion column at positions corresponding to apparent molecular weights of 240, 410 and 520 kDa, respectively. Here, using Superose-6 columns that allow greater resolution at the higher end of the molecular weight range of interest, we observed that most of the SOSIP gp140 protein forms were eluted in volumes corresponding to apparent molecular weights in the range 150-450 kDa, which is consistent with the presence of monomers and dimers. In contrast, the gp140-IZ protein forms were more homogeneous, with a predominant elution peak of ~580 kDa that is consistent with the presence of trimers. Hence, the gel filtration analysis confirms the SDS-PAGE and BN-PAGE studies and shows that the addition of the IZ motif enhances gp140 trimer formation and/or stability.

Construction of Chimeric gp140-CD40L Fusion Proteins

The extracellular domain of murine CD40L, consisting of amino acids 118 to 261 and including the CD40 binding site, was fused to the C-terminus of gp140 (FIG. 4). To allow the gp140 and the CD40L components to fold independently and the fusion protein to be secreted efficiently, we added flexible linkers between the two elements. Since the optimal linker length could only be established empirically, we compared linkers of 0, 4, 7, 13 and 18 residues (constructs L1-L5; FIG. 4). The different gp140-CD40L fusion proteins were expressed transiently in 293T cells and the supernatants analyzed by SDS-PAGE and western blotting (FIG. 4). Linkers L2-L4 (4-13 residues) allowed the most efficient secretion of gp140-CD40L; having no linker or a longer linker resulted in lower expression levels (FIG. 4). Based on these results, and also cloning considerations, subsequent constructs contained an 11-residue linker between the gp140 and C-terminal components (see below).

Enhancing gp140-CD40L Trimer Formation

Our goal was to create a trimeric gp140-CD40L fusion protein, because the native form of HIV-1 Env is trimeric and CD40L is also optimally functional as either a trimer or a multimer of trimers (Morris 1999, Haswell 2001, Stone 2006). The first gp140-CD40L constructs we evaluated were expressed as a mixture of molecular species, with monomers, dimers and tetramers all present in addition to the desired trimers (FIG. 5). The heterogeneity arises because JR-FL gp140 itself is expressed as multiple oligomeric forms (Sanders 2002), and perhaps also because the globular, extracellular domain of CD40L does not form trimers efficiently in the absence of the membrane-spanning domain (Morris 1999). We showed above that the formation of gp140 trimers is improved by the incorporation of a heterologous GCN4 isoleucine zipper (IZ) trimerization domain at the C-terminus, consistent with a previous report (Yang 2000) (FIG. 2). Moreover, similar modifications have been shown to improve CD40L trimer formation (Morris 1999). We therefore introduced the IZ motif between gp140 and CD40L, using 11 and 6 amino acid linkers, respectively, at the gp140/IZ and IZ/CD40L junctions (FIG. 5). The resulting gp140-IZ-CD40L protein and, for comparison, the gp140-L3-CD40L protein were expressed in 293T cells and analyzed by BN-PAGE. As was observed with gp140 (FIG. 5), the gp140-IZ-CD40L protein formed trimers more efficiently (~95% trimeric) than gp140-L3-CD40L, which lacked the IZ motif (~50% trimeric) (FIG. 5).

APRIL and BAFF Constructs

We further explored the possibilities to design constructs with the B cell activating factors APRIL and BAFF as alternatives to CD40L. The constructs are depicted schematically in FIG. 6. APRIL and BAFF are more specific for B cells. Therefore the extracellular domain of BAFF and APRIL (AA 183-323 and 115-250, respectively (FIG. 7)) were fused to the Env-IZ construct in the same way as CD40L was (see "Construction of chimeric gp140-CD40L fusion proteins"). We have made constructs containing the human, mouse and rabbit sequences of BAFF, APRIL and CD40L.

Transient transfection experiments using these constructs, followed by SDS-PAGE and western blotting of the cell supernatant show that the constructs express well (for the rabbit version see FIG. 10; similar results obtained for the human and mouse version, not shown). Blue Native PAGE followed by western blotting showed that these constructs also form trimers efficiently, albeit slightly less efficiently than Env-IZ (for the rabbit versions see FIG. 11; similar results obtained for the human and mouse version, not shown). We next probed the structure of the fusion constructs with a panel of monoclonal antibodies, including conformational antibodies. In addition we tested a receptor mimetic, CD4-IgG2. Immunoprecipitation experiments show that despite modifications to the C-terminus of Env, the structure of the Env part is intact and well folded, as indicated by the efficient binding of pooled Ig from HIV-infected individuals (HIVIg), b12 (directed to the CD4 binding site), CD4-IgG2 and 2F5 (directed to gp41) (FIG. 8). 17b binds to a conformational epitope that is induced by CD4 binding and overlaps with the co-receptor bindingsite. We observed some binding of 17b to Env-BAFF and En-APRIL in the absence of (soluble) CD4 but 17b binding was increased after addition of soluble CD4, indicating that the Env domain of the constructs is able to undergo CD4-induced conformational changes. Combined these data indicate that the constructs are well-folded (FIGS. 8,10,11).

Env-APRIL and Env-BAFF Elicit Enhanced Antibody Responses in Rabbits

In order to test whether fusion of BAFF or APRIL to Env can provide enhanced immune responses in vivo, we designed an immunization experiment in rabbits (FIG. 9). The immunizations were carried out at Genovac (Freiburg, Germany), under contract. New Zealand white rabbits were immunized on days 0, 14, 28, 56 with 125 μg of endotoxin-free DNA at the abdominal dermis using gene gun technology. Group H was immunized at the same dates as group A-G, but instead of DNA 30 μg JR-FL gp120 in alum was injected subcutaneously at six sites: twice into the shoulder, abdomen, and hind limb.

On day 112, all rabbits were injected with 1 ml PBS containing 30 μg JR-FL SOSIP protein (reference) and 60 μg Quil A adjuvant. The day 112 protein injections were performed as follows: 300 μl intradermally (50 μl in each of 6 sites), 400 μl intramuscularly (200 μl into each hind leg) and 300 μl subcutaneously (neck region). Blood samples were obtained on days 0, 14, 28, 42, 56, 84, 112, 126 and the final bleed at day 140. One animal in the Env-BAFF group did not survive until the end of the experiment: it died of an unknown cause.

Anti-gp120 antibody titers in the rabbit sera were measured by ELISA. The resulting midpoint IgG anti-gp120 binding titers shown in FIG. 12 indicate that Env-APRIL and Env-BAFF induce increased antibody responses compared to the Env DNA construct or the gp120 protein immunization control group. This was significant ($p<0.05$ according to the one-tailed Mann-Whitney test) at days 42, 126 and 140 for Env-APRIL compared to Env and on days 28, 42, 126 and 140 for Env-APRIL compared to gp120.

Since virus-associated Env is trimeric, we also analyzed the antibody responses against trimeric Env. Anti-trimeric gp140 titers were measured by using a gp140 construct which had the epitope which is recognized by the D7324 antibody (APTKAKRRVVQREKR) (SEQ ID NO:28) attached at its C-terminus. The resulting midpoint anti-trimeric Env IgG binding titers are shown in FIG. 13. These data show that at week 18 (day 126), Env-APRIL and Env-BAFF induce the highest IgG anti-trimeric Env binding titers of the tested constructs, even after boosting with trimeric protein. To get a better sense of the quality of the induced immune response we divided the anti-trimer midpoint binding titers by the anti-gp120 midpoint binding titers. The resulting trimer-gp120 ratios are depicted in FIG. 14. At week 18 Env-APRIL and Env-BAFF provided the highest trimer-gp120 ratio's of the tested constructs, indicating that a higher percentage of the induced antibodies are directed against trimeric Env. To rule out that we induced unspecific immune activation by the fusion of co-stimulatory molecules, we measured total IgG levels in the serum. Goat anti-mouse IgG (Jackson ImmunoResearch, Newmarket, UK) was coated overnight (10 μg/ml) in 0.1 M $NaHCO_3$, pH 8.6 (100 μl/well). After blocking, serially diluted serum was applied for approximately 1 hr. Bound mouse IgG was detected with HRP-labeled goat anti-mouse IgG (Jackson Immunoresearch, Suffolk, England); used at 1:5000 dilution followed by luminometric detection. There were no differences in total IgG levels indicating that there was no unspecific immune activation (data not shown).

The analysis of serum IgA and mucosal IgG and IgA responses is in progress. APRIL is important for class-switching to IgA and mucosal B cell response so we expect these responses to be enhanced. Improvement of mucosal responses is of course highly relevant for HIV-1 vaccine design.

Env-ARPIL Induces Enhanced Neutralizing Antibody Responses in Rabbits

Env binding antibodies are not necessarily predictive of antiviral activity and therefore we studied the capacity of the rabbit sera to neutralize two different virus strains. SF162 is a neutralization sensitive virus strain. In our experiment is represents a heterologous challenge since the vaccine Env was from the JR-FL strain. We also tested neutralization of JR-FL, the homologous strain, which is notoriously neutralization resistant.

Sera from rabbits taken at week 12 and week 18 were tested in a standard single cycle TZM-bl based neutralization assay. TZM-bl cells express the HIV receptor and co-receptors and further contain a luciferase reporter gene under control of the HIV-1 LTR. Luciferase activity is directly correlated with virus infection. Serially diluted, heat-inactivated serum was mixed with SF162 or JR-FL pseudovirus and incubated for 1 hr at room temperature, after which the virus-serum mix was added to the TZM-bl cells and incubated for two days at 37° C. The cells were then lysed and luciferase expression was measured. The results revealed that Env-APRIL induced the most potent and most consistent neutralization (not shown). Importantly our in house results were corroborated independently by the NIH reference laboratory for immune monitoring using a panel of different challenge viruses (FIG. 15). The neutralization titers are given in FIG. 15. The heat maps show that the most consistent neutralization of MN, SF162 and BaL is observed with Env-APRIL. In summary, the data indicate that fusion of Env to co-stimulatory molecules APRIL and BAFF, enhances the humoral immune response in rabbits, leading to higher antibody levels, better memory and more efficient virus neutralization.

Env-APRIL and Env-BAFF Induce Improved T Cell Responses in Mice

Since APRIL acts on B cells it is likely that B cells are directly activated by the fusion construct. To test, however, whether the improved antibody response was accompanied by an improved T helper response. We used gene gun methodology to immunize out-bred NMRI mice with plasmids encoding either Env, Env-CD40L, Env-BAFF or Env-APRIL. The plasmids were administered on days 0, 14, 28 and 42 and the T cells responses in the spleens was measured at day 56 (FIGS. 16,17), focusing on the secretion of cytokines relevant for B cell responses. Env-specific responses were analyzed using gp120 as a recall antigen, with culture medium and anti-CD3 stimulation serving as negative and positive controls, respectively. The negative and positive controls performed as expected and are not shown.

FIGS. 16 and 17 show that Env-APRIL and Env-BAFF enhance T cell responses to the gp120 antigen dramatically.

Env-APRIL Activates B Cells in Vitro

Env-APRIL was tested for its capability to activate naïve human B cells. Naïve B cells isolated from human blood were stimulated using a cocktail of IL-4, IL-10 and CD40L to provide a baseline activation. In addition mock, Env, Env-APRIL, Env-BAFF or Env-CD40L were supplied. At day 5 the expression of the cell surface markers HLA-DR, CD40, CD38 and CD86 was measured. The levels of CD86 and CD40 were similar irrespective of the fusion protein, but Env-APRIL induced higher levels of CD38, a plasma cell marker, and this was accompanied by lower expression of HLA-DR (FIG. 41A). At day 14 the secretion of IgM, IgG and IgA was measured (FIG. 41B). Env-CD40L induced enhanced IgM and IgG secretion by B cells compared to mock and unconjugated Env. Env-APRIL also enhanced secretion of IgM and IgG but not as efficiently as Env-CD40L. In contrast, Env-APRIL potently induced IgA secretion, consistent with the role of APRIL in class-switching to IgA and mucosal antibody responses.

Ebola GP-APRIL and Influenza HA-APRIL Activate B Cell in Vitro

To provide evidence that the fusion of APRIL is applicable to other antigens, APRIL was fused to the ebola virus glycoprotein (GP) and the influenza virus hemagglutinin (HA). It was tested whether the fusion constructs are able to activate human B cells. Naïve B cells isolated from human blood were stimulated using a cocktail of IL-4, IL-10 and CD40L to provide a baseline activation. In addition the B cells were incubated with mock, Env-APRIL, GP-APRIL or HA-APRIL. At day 5 the expression of the cell surface markers HLA-DR, CD40, CD80 and CD86 was measured. There were no major changes, except for the enhanced CD38 expression with Env-APRIL as noted above (FIG. 42A). At day 14 we measured the secretion if IgM, IgG and IgA (FIG. 42B). While Env-APRIL induced a pronounced IgA response in particular, HA-APRIL induced high levels of IgM and IgG in addition to IgA. GP-APRIL also induced secretion of IgM, IgG and IgA but not as efficiently as HA-APRIL. These data indicate that fusion to APRIL benefits the antibody response to various antigens.

VARIATIONS AND IMPROVEMENTS

Combination With Co-stimulatory Molecules At A Different Location

Thus far we have described the addition of co-stimulatory molecules at the C-terminus of Env. We choose the C-terminus for the addition of co-stimulatory molecules for mainly two reasons. First, addition to the N-terminus of Env is likely to result in misfolding since the N-terminus is not exposed, but buried in the Env complex. The addition at the exposed C-terminus allows for independent folding of Env and APRIL/BAFF etc. Second, it allows for the addition of trimerization domains or other domains between Env and the co-stimulatory molecule.

We explored the possibility of introducing small co-stimulatory molecules within Env as an alternative to the C-terminus. The possibility of two locations for insertion of co-stimulatory molecules also opens up the possibility of combining co-stimulatory molecules. Our second projected location for the introduction of co-stimulatory motifs is the variable V1V2 domain. Since we previously removed a large number of amino acids (PCT/NL2009/050609), we hypothesized that we could exploit the resulting "gap" and "fill it" with a co-stimulatory molecule. The V1V2 is not required for function and can easily be manipulated to contain heterologous sequences (Law 2007; Pantophlet 2009) and we have extensive experience with modification of the V1V2 domain ourselves (Sanders 2000; Bontjer 2009). We therefore felt confident that we would be able to incorporate heterologous immunostimulatory sequences. We have previously generated functional Env variants that lack the entire V1V2-domain resulting in a 20 kDa reduction in size. Considering the plasticity of Env, in particular in this region, we expected that we could replace the V1V2 domain with cytokine sequences, many of which are of the same size as the V1V2-domains itself. Our initial choice was the cytokine GM-CSF, but to create a more extensive proof of principle we also include IL-2 and IL-4. GM-CSF (size ~14 kDa) recruits and activates DC, but it has pleiotropic effects, also recruiting and activating NK cells, neutrophils and macrophages, which then produce cytokines to create a milieu favorable for the initiation of a potent immune response. GM-CSF is successfully used in a variety of preclinical and clinical settings both for therapeutic use and to augment vaccine responses. Importantly, GM-CSF can enhance anti-HIV responses and has good track record in clinical use.

Based on our studies on our V1V2 deletion studies (Bontjer 2009), we replaced the V1V2 domain (amino acids 128-194) in a stable recombinant and soluble Env trimer construct (JR-FL SOSIP.R6-IZ gp140) by the sequences encoding human IL-2, flanked on both sides by a flexible linker Gly-Ser-Gly (FIGS. 18,19,20). The constructs were then expressed in 293T cells and analyzed by SDS-PAGE and western blot (FIG. 21). The Env-IL-2, Env-IL-4 and Env-GM-CSF constructs were expressed efficiently, indicating that the introduced cytokine sequences did not affect protein folding. The constructs were also recognized efficiently by conformational antibodies and receptor mimics (FIGS. 22,23).

We next investigated whether the IL-4 and GM-CSF components in Env-IL-4 and Env-GM-CSF were functional. The Tf1 cell line requires IL-4 or GM-CSF for proliferation and when neither is present in the culture medium, they do not proliferate (FIG. 24). When recombinant IL-4 or GM-CSF is present in the medium, Tf1 cells proliferate efficiently (FIG. 24). We found that the Tf1 cells also proliferated in the presence of Env-IL-4 or Env-GM-CSF, but not in the presence of Env or Env-dV1V2, demonstrating that the IL-4 and GM-CSF components in the chimeric proteins are well-folded, well-exposed and functional (FIG. 24). Importantly, mice immunized with Env-GM-CSF developed higher Env-specific antibody levels compared to mice immunized with Env alone, indicating that GM-CSF replacing the V1V2 domain exerts adjuvant activity in vivo (FIG. 25). In another experiment it was shown that Env-rGMCSF enhances the antibody response to Env in rabbits (FIG. 43). It is possible to truncate cytokine sequences inserted in Env. We have already made one truncated GM-CSF construct successfully (GM-CSF 1) in which contains 15 amino acids less GM-CSF sequence compared to the first generation Env-GM-CSF. This construct is expressed efficiently and forms trimers efficiently (FIG. 26). As an alternative to rationally designed truncations, the cytokines are placed in the context of full length gp160 and live virus to allow the virus to optimize and accommodate the inserted sequences by virus evolution, similar to what we have done previously with dV1V2 viruses (Bontjer 2009).

Env-IL21 chimera's based on mouse and human IL21 molecules were also efficiently expressed (FIG. 44). These chimera's are especially useful since it is intended to target B cells.

It was investigated whether Env-hIL-4 and Env-hIL21 were able to activate human B cells in vitro. Naïve B cells isolated from human blood were stimulated using a cocktail of IL-4, IL-10 and CD40L to provide a baseline activation. In addition, mock, Env, Env-IL4 or Env-IL21 were added. At day 5 the expression of the cell surface markers HLA-DR, CD40, CD38 and CD86 was measured (FIG. 45A). Compared to unconjugated Env, both Env-IL4 and Env-IL21 induced modestly increased levels of CD38, a marker for plasma cells. Env-IL4 also induced an increase in CD40 expression. At day 14, the secretion if IgM, IgG and IgA was also measured (FIG. 45B). Env-IL4 induced enhanced IgM, IgG and IgA secretion compared to mock or Env alone, but Env-IL21 induced dramatic increases in the secretion of IgM, IgG and IgA. These data first of all confirm that the embedded IL-21 domain is functional, but also show that embedding IL-21 into Env to target and activate B cells is a valid vaccine strategy.

Another location for the introduction of heterologous sequences is the V3 domain. This is a particularly useful site for placing CCR5- and CXCR4-binding chemokines, such as SDF-1. Importantly, Env binds to CCR5 or CXCR4 via its V3 loop and replacement of the V3 by SDF-1, which is also able to bind to CCR5 or XCXR4 results in a functional Env (Yonezawa 2001), providing evidence that our strategy is feasible.

The generation and development of hyperactive cytokines may of course have many future applications. A plethora of cytokines is used in laboratory studies as well as clinical applications and more active cytokine variants could be very valuable. Our lab has a long-standing expertise with the introduction and optimization of heterologous sequences including complete proteins within an HIV-1 backbone (Zhou 2006).

Polytrimeric Fusion Constructs

BAFF and APRIL function when they are trimeric. However, optimal activation is achieved when they are multimeric (i.e. a multitude of trimers). Therefore, multimeric antigen-APRIL/BAFF fusion constructs are created. As an added advantage increased multimerization also contributes to enhanced Env-BCR cross-linking and enhanced B cell activation.

A first strategy is the addition of the sequences encoding the N-terminal domain, the collagen-like domain and the neck domain from surfactant protein A or similar molecules such as adiponectin, collectin, Clq and MBL (FIGS. 27-32). Surfactant protein A forms octadecameric 'bouquet-like' structures consisting of 6 trimers (FIG. 27). The appropriate connection of Env or another antigen with APRIL/BAFF/ using Surfactant protein A (SPA) should results in octadecameric Env-APRIL/BAFF fusion constructs with optimal APRIL/BAFF activity. As an added advantage the increased valence from 3 to 18 contributes to enhanced Env-BCR cross-linking and enhanced B cell activation. Another strategy to 'multimerize' Env and APRIL/BAFF is their immobilization on nanoparticles (FIG. 33). We have already explored methods to immobilize our Env trimers on synthetic microparticles using a C-terminal His tag. Since the His tag is trimerized on Env trimers, the affinity for Ni-NTA is extremely high. When magnetic Ni-NTA coated microparticles were incubated with His-tagged Env trimers, we found that Env trimers were immobilized on these beads extremely efficiently and stably (FIG. 34). Thus, vaccine antigens are improved for instance by immobilizing them in a densely packed array on nanoparticles in combination with immunostimulatory molecules.

A third strategy to enhance the valency of antigens and co-stimulatory molecules is the fusion of Env with a C-terminal trimerization domain to the Fc part of immunoglobulin G. This results in hexameric molecules (FIG. 35). Env-Fc constructs were efficiently expressed (FIG. 36). In addition, we have shown that it is possible to combine this strategy with the inclusion of cytokines in Env (FIG. 36). The Fc tail was functional as we could capture Env-Fc constructs efficiently using protein G (FIG. 37).

REFERENCES

Beddows et al. 2005 J. Virol. 79:8812
Beddows et al. 2006 AIDS Res Hum Retroviruses 22:569
Binley et al. 2000 J. Virol. 74:627
Binley et al. 2002 J. Virol. 76:2606
Bonifaz et al. 2004 J. Exp. Med. 199:815
Bontjer et al. 2009 J. Virol. J. Virol. 83:368
Bower et al. 2004 Virology 328:292
Burton et al. 2004 Nat. Imm. 5:233
Cerutti 2008 Nat. Rev. Imm. 8:421.
Delgado et al. 2009 Nat. Med. 15:34
Dudziak et al. 2007 J. Exp. Med. 204:1095
Eggink et al. 2007, Trends Microbiol. 15: 290-293
Eggink et al. 2009 J. Biol. Chem. 2009 284:26941
Flynn et al. 2005 J. Infect. Dis. 191:654
Gilbert et al. 2005 J. Infect. Dis. 191:666
Harbury et al. 1994 Nature 371:80
Haswell 2001 Eur. J. Immunol. 31:3094
Kimberley et al. 2009 J. Cell Physiol. 218:1
Kirschner et al. 2006 Protein Expr. Purif. 48:61
Koch et al. 2005. Virology 340:277
Kwong & Wilson 2009 Nat. Immunol. 10:573
Lahoud et al. 2009 J. Immunol. 182:7587
Law et al. 2007 J. Virol. 81:4272
Liu et al. 2009. Nature 457:87
Mackay & Schneider 2009. Nat. Rev. Immunol. 9:491
Morris et al. 1999 J. Biol. Chem. 274:418
Pantophlet et al. 2009 J. Virol. 83:1649
Parren et al. 1997 Nat Med. 3:366-7.
Pitisuttithum et al. 2006 J. Infect. Dis. 194:1661.
Reynolds et al. 2008 J. Exp. Med. 205:2537
Sanders et al. 2000 J. Virol. 74:5091
Sanders et al. 2002 J. Virol. 76:8875
Sanders et al. 2002 J. Virol. 76:7293
Schülke et al. 2002 J. Virol. 76:7760
Shattock et al. 2008 PLoS Med. 5:e81
Steinman&Banchereau 2007 Nature. 449:419
Stone 2006 J. Virol. 80:1762
Trkola et al. 1996 384:184.
Yang et al. 2000 J. Virol. 74:5716
Yang et al. 2008, Nat Biotechnol. 26:326
Yonezawa et al. 2001 J. Virol. 75:4258
Xu et al. 2008 J. Immunol. 181:276
Zhou et al. 2006 Gene Ther. 13:1382

The invention claimed is:

1. A fusion protein comprising an antigen and a compound comprising at least the extracellular domain of a proliferation inducing ligand (APRIL), wherein said antigen is an immunogenic part of a microorganism comprising at least 25 amino acids.

2. A fusion protein according to claim 1, wherein said antigen comprises a virus protein of HIV, influenza virus or Ebola virus.

3. A fusion protein according to claim 1, further comprising a multimerizing polypeptide.

4. A fusion protein according to claim 1, wherein said antigen is linked to said ligand via at least one linker comprising an amino acid sequence with a length of from 1 to 20 amino acids.

5. A nucleic acid molecule encoding a fusion protein according to any one of claim 1.

6. A method for producing a fusion protein according to claim 1, said method comprising:
   Generating and/or providing a nucleic acid molecule comprising a nucleotide sequence encoding a fusion protein; and
   allowing expression of said fusion protein from said nucleic acid molecule in a suitable expression system.

7. An oligomeric complex comprising at least 2 fusion proteins according to claim 1.

8. A fusion protein according to claim 1, wherein the antigen comprises an amino acid sequence with a length of at least 300 amino acids with at least 80% sequence identity to SEQ ID NO:85 with a deletion of at least 5 amino acids in the region corresponding to amino acid positions 120-204 of SEQ ID NO:85.

9. An immunogenic composition comprising a fusion protein according to claim 1.

10. A method for obtaining an antibody capable of specifically binding a fusion protein according to claim 1, wherein said method comprises:
    providing a non-human animal with a fusion protein; and
    obtaining from said non-human animal an antibody capable of specifically binding said fusion protein.

11. A fusion protein according to claim 1, wherein said antigen is linked to said ligand via at least one linker comprising an amino acid sequence with a length from 4 to 13 amino acids.

* * * * *